United States Patent
Clarke et al.

(10) Patent No.: US 11,920,193 B2
(45) Date of Patent: Mar. 5, 2024

(54) METHOD OF CHARACTERIZING A POLYNUCLEOTIDE

(71) Applicant: Oxford Nanopore Technologies PLC, Oxford (GB)

(72) Inventors: James Anthony Clarke, Oxford (GB); James White, Oxford (GB); Richard Muscat, Oxford (GB); Jessica Mary May Johnson, Oxford (GB); Ramiz Iqbal Nathani, Oxford (GB); Andrew John Heron, Oxford (GB); Mark John Bruce, Oxford (GB); Lakmal Nishantha Jayasinghe, Oxford (GB); Domenico Caprotti, Oxford (GB); David Jackson Stoddart, Oxford (GB); Rebecca Victoria Bowen, Oxford (GB); Christopher James Wright, Oxford (GB); Paul Richard Moody, Oxford (GB)

(73) Assignee: Oxford Nanopore Technologies PLC, Oxford (GB)

( * ) Notice: Subject to any disclaimer, the term of this patent is extended or adjusted under 35 U.S.C. 154(b) by 308 days.

(21) Appl. No.: 16/972,039

(22) PCT Filed: Jun. 6, 2019

(86) PCT No.: PCT/GB2019/051571
§ 371 (c)(1),
(2) Date: Dec. 4, 2020

(87) PCT Pub. No.: WO2019/234432
PCT Pub. Date: Dec. 12, 2019

(65) Prior Publication Data
US 2021/0363577 A1     Nov. 25, 2021

(30) Foreign Application Priority Data

Jun. 6, 2018   (GB) ...................... 1809323

(51) Int. Cl.
*C12Q 1/6869*     (2018.01)
*G01N 33/487*     (2006.01)

(52) U.S. Cl.
CPC ..... *C12Q 1/6869* (2013.01); *G01N 33/48721* (2013.01)

(58) Field of Classification Search
CPC ................. C12Q 1/6869; G01N 33/48721
See application file for complete search history.

(56) References Cited

U.S. PATENT DOCUMENTS

| | | | |
|---|---|---|---|
| 6,465,193 B2 | 10/2002 | Akeson et al. | |
| 6,916,665 B2 | 7/2005 | Bayley et al. | |
| 8,986,528 B2 | 3/2015 | Denison et al. | |
| 10,246,741 B2 | 4/2019 | Clarke | |
| 11,098,355 B2 | 8/2021 | Heron et al. | |
| 11,466,317 B2 | 10/2022 | Clarke et al. | |
| 2002/0197618 A1 | 12/2002 | Sampson | |
| 2013/0048499 A1 | 2/2013 | Mayer et al. | |
| 2014/0134618 A1 | 5/2014 | Kokoris et al. | |
| 2015/0152492 A1 | 6/2015 | Brown et al. | |
| 2015/0275289 A1 | 10/2015 | Otwinowski et al. | |
| 2015/0344945 A1* | 12/2015 | Mandell ........... G01N 27/44743 204/453 |
| 2016/0041179 A1 | 2/2016 | Ju et al. | |
| 2016/0237488 A1 | 8/2016 | Ke et al. | |
| 2016/0326578 A1 | 11/2016 | Bielas | |
| 2017/0044605 A1 | 2/2017 | Merriman et al. | |
| 2019/0352709 A1 | 11/2019 | Clarke et al. | |
| 2020/0010887 A1 | 1/2020 | Heron et al. | |
| 2021/0148903 A1 | 5/2021 | Fordham | |
| 2022/0090192 A1 | 3/2022 | Heron et al. | |
| 2023/0084931 A1 | 3/2023 | Clarke et al. | |

FOREIGN PATENT DOCUMENTS

| | | |
|---|---|---|
| CN | 1860370 A | 11/2006 |
| CN | 103695530 A | 4/2014 |
| WO | WO 2000/028312 A1 | 5/2000 |
| WO | WO 2000/034527 A2 | 6/2000 |
| WO | WO 2001/042782 A1 | 6/2001 |
| WO | WO 2002/028312 A1 | 4/2002 |

(Continued)

OTHER PUBLICATIONS

PCT/GB2017/053603, Apr. 6, 2018, International Search Report and Written Opinion.
PCT/GB2017/053603, Jun. 13, 2019, International Preliminary Report on Patentability.
PCT/GB2017/051493, Oct. 24, 2017, International Search Report and Written Opinion.
PCT/GB2017/051493, Dec. 6, 2018, International Preliminary Report on Patentability.

(Continued)

*Primary Examiner* — Neil P Hammell
*Assistant Examiner* — Morgan T Lindgren Baltzell
(74) *Attorney, Agent, or Firm* — Wolf, Greenfield & Sacks, P.C.

(57) ABSTRACT

Methods of characterizing an analyte using a detector such as a nanopore and an enzyme are provided. One aspect features methods for characterizing a double-stranded polynucleotide using a detector, e.g., without using a hairpin connecting a template and a complement of the double-stranded polynucleotide. Another aspect features methods for characterizing an analyte using a tag-modified nanopore with increased sensitivity and/or higher throughput. Compositions and systems including, e.g., adaptors for attachment to double-stranded polynucleotides and tag-modified nanopores, which can be used in the methods are also provided.

17 Claims, 44 Drawing Sheets

Specification includes a Sequence Listing.

(56) References Cited

FOREIGN PATENT DOCUMENTS

| | | | |
|---|---|---|---|
| WO | WO 2005/124888 A1 | 12/2005 | |
| WO | WO 2006/100484 A2 | 9/2006 | |
| WO | WO 2008/102120 A1 | 8/2008 | |
| WO | WO 2008/102121 A1 | 8/2008 | |
| WO | WO 2009/035647 A1 | 3/2009 | |
| WO | WO 2009/077734 A2 | 6/2009 | |
| WO | WO 2010/004265 A1 | 1/2010 | |
| WO | WO 2010/004273 A1 | 1/2010 | |
| WO | WO 2010/055307 A1 | 5/2010 | |
| WO | WO 2010/086602 A1 | 8/2010 | |
| WO | WO 2010/086603 A1 | 8/2010 | |
| WO | WO 2010/086620 A1 | 8/2010 | |
| WO | WO 2011/067559 A1 | 6/2011 | |
| WO | WO 2012/003330 A2 | 1/2012 | |
| WO | WO 2012/042226 A1 | 4/2012 | |
| WO | WO 2012/107778 A2 | 8/2012 | |
| WO | WO 2012/164270 A1 | 12/2012 | |
| WO | WO 2013/014451 A1 | 1/2013 | |
| WO | WO 2013/041878 A1 | 3/2013 | |
| WO | WO 2013/057495 A1 | 4/2013 | |
| WO | WO 2013/057498 A1 | 4/2013 | |
| WO | WO 2013/098561 A1 | 7/2013 | |
| WO | WO 2013/098562 A1 | 7/2013 | |
| WO | WO 2013/109970 A1 | 7/2013 | |
| WO | WO 2013/153359 A1 | 10/2013 | |
| WO | WO 2013/185137 A1 | 12/2013 | |
| WO | WO 2014/013259 A1 | 1/2014 | |
| WO | WO 2014/013260 A1 | 1/2014 | |
| WO | WO 2014/013262 A1 | 1/2014 | |
| WO | WO 2014/064443 A1 | 5/2014 | |
| WO | WO 2014/064444 A1 | 5/2014 | |
| WO | WO 2014/074922 A1 | 5/2014 | |
| WO | WO 2014/135838 A1 | 9/2014 | |
| WO | WO 2015/014035 A1 | 2/2015 | |
| WO | WO 2015/022544 A1 | 2/2015 | |
| WO | WO 2015/055981 A1 | 4/2015 | |
| WO | WO 2015/110777 A1 | 7/2015 | |
| WO | WO 2015/110813 A1 | 7/2015 | |
| WO | WO 2015/124935 A1 | 8/2015 | |
| WO | WO 2015/127387 A1 | 8/2015 | |
| WO | WO 2015/150786 A1 | 10/2015 | |
| WO | WO 2015/150787 A1 | 10/2015 | |
| WO | WO-2015150786 A1 * | 10/2015 | ........... C12Q 1/6869 |
| WO | WO 2015/166275 A1 | 11/2015 | |
| WO | WO 2015/176034 A1 | 11/2015 | |
| WO | WO 2016/034591 A2 | 3/2016 | |
| WO | WO 2016/055777 A2 | 4/2016 | |
| WO | WO 2016/059363 A1 | 4/2016 | |
| WO | WO 2016/059375 A1 | 4/2016 | |
| WO | WO 2016/059427 A1 | 4/2016 | |
| WO | WO 2016/059436 A1 | 4/2016 | |
| WO | WO 2016/099673 A1 | 6/2016 | |
| WO | WO 2016/161402 A1 | 10/2016 | |
| WO | WO 2017/125565 A1 | 7/2017 | |
| WO | WO-2017125565 A1 * | 7/2017 | ........... C12N 9/1247 |
| WO | WO 2017/203269 A1 | 11/2017 | |
| WO | WO 2018/100370 A1 | 6/2018 | |

OTHER PUBLICATIONS

PCT/GB2019/051571, Sep. 10, 2019, International Search Report and Written Opinion.
PCT/GB2019/051571, Dec. 17, 2020, International Preliminary Report on Patentability.
U.S. Appl. No. 17/817,065, filed Aug. 3, 2022, Clarke et al.
PCT/GB2018/051190, Jul. 26, 2018, International Search Report and Written Opinion.
PCT/GB2018/051190, Nov. 14, 2019, International Preliminary Report on Patentability.
International Search Report and Written Opinion for Application No. PCT/GB2018/051190, dated Jul. 26, 2018.
International Preliminary Report on Patentability for Application No. PCT/GB2018/051190, dated Nov. 14, 2019.

Anderson, The clinical plasma proteome: a survey of clinical assays for proteins in plasma and serum. Clin Chem. Feb. 2010;56(2):177-85. doi: 10.1373/clinchem.2009.126706. Epub Nov. 2, 2009.
Edwards et al., The role of proteomics in clinical cardiovascular biomarker discovery. Mol Cell Proteomics. Oct. 2008;7(10):1824-37. doi: 10.1074/mcp.R800007-MCP200. Epub Jul. 30, 2008.
Hu et al., Detection and analysis of DNA recapture through a solid-state nanopore. Chinese science bulletin. Dec. 2014;59(35):4953-9.
Jacquet et al., Identification of cardiac myosin-binding protein C as a candidate biomarker of myocardial infarction by proteomics analysis. Mol Cell Proteomics. Dec. 2009;8(12):2687-99. doi: 10.1074/mcp.M900176-MCP200. Epub Aug. 31, 2009.
Jiang et al., miR2Disease: a manually curated database for microRNA deregulation in human disease. Nucleic Acids Res. Jan. 2009;37(Database issue):D98-104. doi: 10.1093/nar/gkn714. Epub Oct. 15, 2008.
Köhler et al., Continuous cultures of fused cells secreting antibody of predefined specificity. Nature. Aug. 7, 1975;256(5517):495-7. doi: 10.1038/256495a0.
Maddox et al., Elevated serum levels in human pregnancy of a molecule immunochemically similar to eosinophil granule major basic protein. J Exp Med. Oct. 1, 1983;158(4):1211-26. doi: 10.1084/jem.158.4.1211.
Patz et al., Panel of serum biomarkers for the diagnosis of lung cancer. J Clin Oncol. Dec. 10, 2007;25(35):5578-83. doi: 10.1200/JCO.2007.13.5392.
International Search Report and Written Opinion for Application No. PCT/GB2017/053603, dated Apr. 6, 2018.
International Preliminary Report on Patentability for Application No. PCT/GB2017/053603, dated Jun. 13, 2019.
International Search Report and Written Opinion for Application No. PCT/GB2017/051493, dated Oct. 24, 2017.
International Preliminary Report on Patentability for Application No. PCT/GB2017/051493, dated Dec. 6, 2018.
International Search Report and Written Opinion for Application No. PCT/GB2019/051571, dated Sep. 10, 2019.
International Preliminary Report on Patentability for Application No. PCT/GB2019/051571, dated Dec. 17, 2020.
Altschul et al., Basic local alignment search tool. J Mol Biol. Oct. 5, 1990;215(3):403-10.
Altschul, A protein alignment scoring system sensitive at all evolutionary distances. J Mol Evol. Mar. 1993;36(3):290-300.
Biswas et al., Click Addition of a DNA Thread to the N-Termini of Peptides for Their Translocation through Solid-State Nanopores. ACS Nano. Oct. 27, 2015;9(10):9652-64. doi: 10.1021/acsnano.5b04984. Epub Sep. 16, 2015.
Braha et al., Designed protein pores as components for biosensors. Chem Biol. Jul. 1997;4(7):497-505.
Case 1:17-cv-00275-LPS Document 18. Notice of subsequent events relating to Oxford's motion to dismiss (D.I. 9). Oct. 18, 2017.
Case 1:17-cv-00275-LPS Document 19. Oxford Nanopore Technologies, Inc.'s response to Pacific Biosciences of California, Inc.'s notice of subsequent events. Oct. 24, 2017.
Case 1:17-cv-00275-RGA Document 10. Oxford's opening brief in support of its motion to dismiss PacBio's complaint for patent infringement. May 8, 2017.
Case 1:17-cv-00275-RGA Document 14. PacBio's response to Oxford's motion to dismiss. Jun. 5, 2017.
Case 1:17-cv-00275-RGA Document 16. Oxford's reply brief in support of its motion to dismiss PacBio's complaint for patent infringement. Jun. 26, 2017.
Case 1:17-cv-01353-LPS Document 13. First Amended Complaint for Patent Infringement. Nov. 30, 2017.
Case 1:17-cv-01353-LPS Document 15. Plaintiff's response to Oxford Nanopore Technologies, Inc.'s Motion to Dismiss and Request for Scheduling Conference. Nov. 30, 2017.
Case 1:17-cv-01353-RGA Document 10. Oxford's opening brief in support of its motion to partially dismiss Pacbio's complaint for patent infringement. Nov. 16, 2017.
Chandler et al., A new microparticle size calibration standard for use in measuring smaller microparticles using a new flow cytometer. J Thromb Haemost. Jun. 2011;9(6):1216-24. doi: 10.1111/j.1538-7836.2011.04283.x.

(56) References Cited

OTHER PUBLICATIONS

Chen et al., High spatial resolution nanoslit SERS for single-molecule nucleobase sensing. Nat Commun. Apr. 30, 2018;9(1):1733. doi: 10.1038/s41467-018-04118-7.
Colas et al., Microscopical investigations of nisin-loaded nanoliposomes prepared by Mozafari method and their bacterial targeting. Micron. 2007;38(8):841-7.
Devereux et al., A comprehensive set of sequence analysis programs for the VAX. Nucleic Acids Res. Jan. 11, 1984;12(1 Pt 1):387-95.
Eliseev et al., Molecular Recognition of Nucleotides, Nucleosides, and Sugars by Aminocyclodextrins. J. Am. Chem. Soc., 1994;116:6081-6088.
Feng et al., Nanopore-based fourth-generation DNA sequencing technology. Genomics Proteomics Bioinformatics. Feb. 2015;13(1):4-16. doi: 10.1016/j.gpb.2015.01.009. Epub Mar. 2, 2015. Erratum in: Genomics Proteomics Bioinformatics. Dec. 2015;13(6):383. Erratum in: Genomics Proteomics Bioinformatics. Jun. 2015;13(3):200-201. Erratum in: Genomics Proteomics Bioinformatics. Dec. 2015; 13(6):383.
Gonzalez-Perez et al., Biomimetic triblock copolymer membrane arrays: a stable template for functional membrane proteins. Langmuir. Sep. 15, 2009;25(18):10447-50. doi: 10.1021/la902417m.
Grant et al., A facile method for attaching nitroxide spin labels at the 5' terminus of nucleic acids. Nucleic Acids Res. 2007;35(10):e77. Epub May 21, 2007.
Heron et al., Simultaneous measurement of ionic current and fluorescence from single protein pores. J Am Chem Soc. Feb. 11, 2009;131(5):1652-3. doi: 10.1021/ja808128s.
Holden et al., Direct introduction of single protein channels and pores into lipid bilayers. J Am Chem Soc. May 11, 2005;127(18):6502-3.
Holden et al., Functional bionetworks from nanoliter water droplets. J Am Chem Soc. Jul. 11, 2007;129(27):8650-5. Epub Jun. 16, 2007.
Hornblower et al., Single-molecule analysis of DNA-protein complexes using nanopores. Nat Methods. Apr. 2007;4(4):315-7. Epub Mar. 4, 2007.
Howorka et al., A Protein Pore with a Single Polymer Chain Tethered within the Lumen. J. Am. Chem. Soc. Feb. 29, 2000;122(11):2411-2416. https://doi.org/10.1021/ja993221h.
Howorka et al., Probing distance and electrical potential within a protein pore with tethered DNA. Biophys J. Dec. 2002;83(6):3202-10.
Howorka et al., Sequence-specific detection of individual DNA strands using engineered nanopores. Nat Biotechnol. Jul. 2001;19(7):636-9.
Ivanov et al., DNA tunneling detector embedded in a nanopore. Nano Lett. Jan. 12, 2011;11(1):279-85. doi: 10.1021/nl103873a. Epub Dec. 6, 2010.
Kocalka et al., Rapid and efficient DNA strand cross-linking by click chemistry. Chembiochem. May 23, 2008;9(8):1280-5. doi: 10.1002/cbic.200800006.
Kolb et al., Click Chemistry: Diverse Chemical Function from a Few Good Reactions. Angew Chem Int Ed Engl. Jun. 1, 2001;40(11):2004-2021.
Kozarewa et al., 96-plex molecular barcoding for the Illumina Genome Analyzer. Methods Mol Biol. 2011;733:279-98. doi: 10.1007/978-1-61779-089-8_20.
Kumar et al., Nonradioactive labeling of synthetic oligonucleotide probes with terminal deoxynucleotidyl transferase. Anal Biochem. Mar. 1988;169(2):376-82. Erratum in: Anal Biochem Sep. 1988;173(2):469.
Langecker et al., Synthetic lipid membrane channels formed by designed DNA nanostructures. Science. Nov. 16, 2012;338(6109):932-6. doi: 10.1126/science.1225624.
Lieberman et al., Processive replication of single DNA molecules in a nanopore catalyzed by phi29 DNA polymerase. J Am Chem Soc. Dec. 22, 2010;132(50):17961-72. doi: 10.1021/ja1087612. Epub Dec. 1, 2010.
Liu et al., Adding new chemistries to the genetic code. Annu Rev Biochem. 2010;79:413-44. doi: 10.1146/annurev.biochem.052308.105824.
Montal et al., Formation of bimolecular membranes from lipid monolayers and a study of their electrical properties. Proc Natl Acad Sci U S A. Dec. 1972;69(12):3561-6.
Nikolov et al., Behavior of giant vesicles with anchored DNA molecules. Biophys J. Jun. 15, 2007;92(12):4356-68. Epub Mar. 23, 2007.
Pfeiffer et al., Bivalent cholesterol-based coupling of oligonucleotides to lipid membrane assemblies. J Am Chem Soc. Aug. 25, 2004;126(33):10224-5.
Smith et al., Capture, Unfolding, and Detection of Individual tRNA Molecules Using a Nanopore Device. Front Bioeng Biotechnol. Jun. 24, 2015;3:91. doi: 10.3389/fbioe.2015.00091.
Soni et al., Synchronous optical and electrical detection of biomolecules traversing through solid-state nanopores. Rev Sci Instrum. Jan. 2010;81(1):014301. doi: 10.1063/1.3277116. 7 pages.
Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.
Stranges et al., Design and characterization of a nanopore-coupled polymerase for single-molecule DNA sequencing by synthesis on an electrode array. Proc Natl Acad Sci U S A. Nov. 1, 2016;113(44):E6749-E6756. doi: 10.1073/pnas.1608271113. Epub Oct. 11, 2016.
Troutt et al., Ligation-anchored PCR: a simple amplification technique with single-sided specificity. Proc Natl Acad Sci U S A. Oct. 15, 1992;89(20):9823-5. Erratum in: Proc Natl Acad Sci U S A Apr. 15, 1993;90(8):3775.
United States District Court for the District of Delaware Order. *Pacific Biosciences of California, Inc.* v. *Oxford Nanopore Technolgoies, Inc.* Civil Action No. 17-275-RGA. Nov. 9, 2017.
Van Lengerich et al., Covalent attachment of lipid vesicles to a fluid-supported bilayer allows observation of DNA-mediated vesicle interactions. Langmuir. Jun. 1, 2010;26(11):8666-72. doi: 10.1021/la904822f.
Wendell et al., Translocation of double-stranded DNA through membrane-adapted phi29 motor protein nanopores. Nat Nanotechnol. Nov. 2009;4(11):765-72. doi: 10.1038/nnano.2009.259. Epub Sep. 27, 2009. Author Manuscript.
Yoshina-Ishii et al., Arrays of mobile tethered vesicles on supported lipid bilayers. J Am Chem Soc. Apr. 2, 2003;125(13):3696-7.
Yusko et al., Controlling the translocation of proteins through nanopores with bioinspired fluid walls. Nat Nanotechnol. Nat Nanotechnol. Apr. 2011; 6(4): 253-260. EPub Feb. 20, 2011. doi: 10.1038/nnano.2011.12 Author manuscript; available in PMC Oct. 1, 2011.
Peng et al., Reverse DNA translocation through a solid-state nanopore by magnetic tweezers. Nanotechnology. May 6, 2009;20(18):185101. doi: 10.1088/0957-4484/20/18/185101. Epub Apr. 14, 2009.

\* cited by examiner

Time (s)

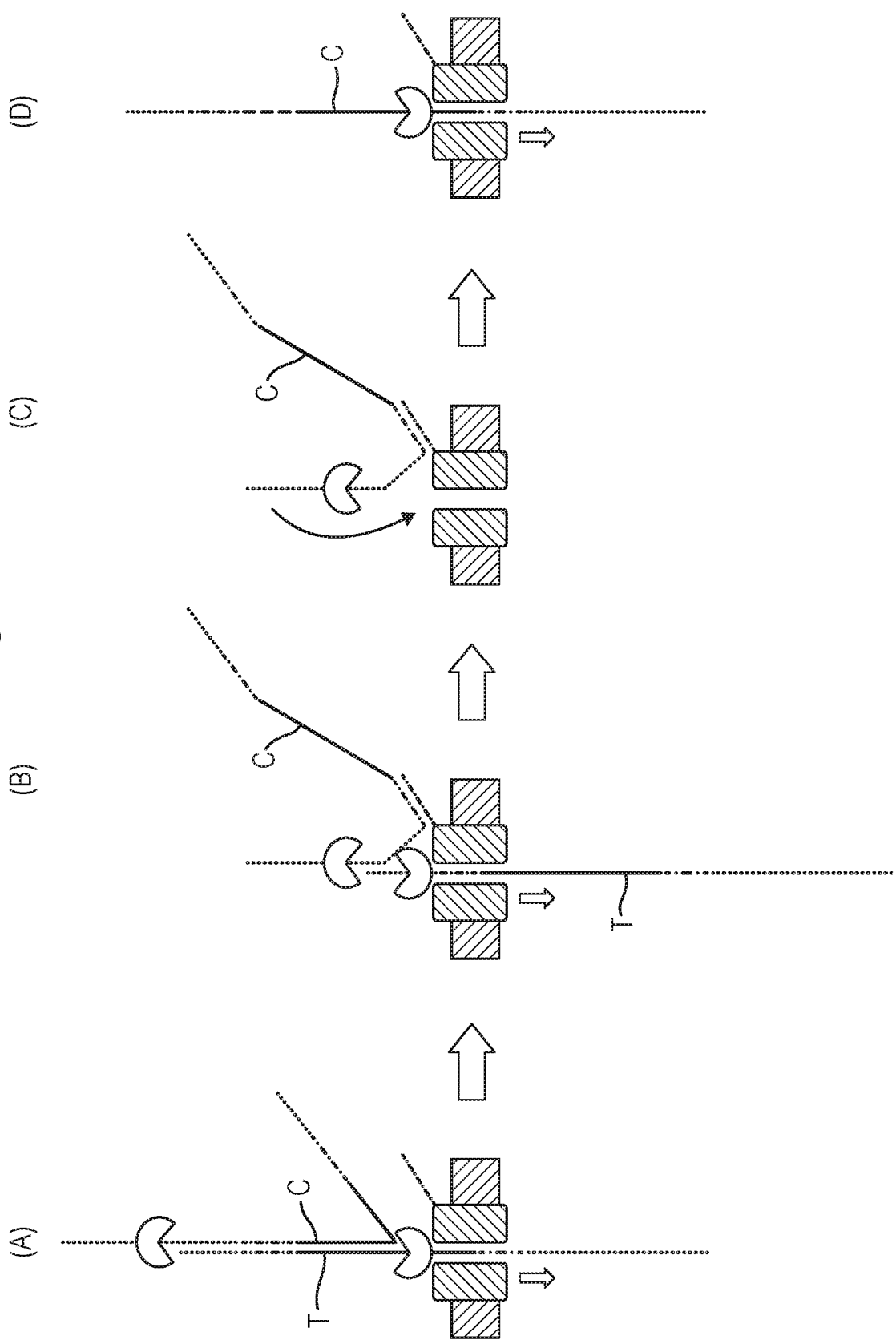

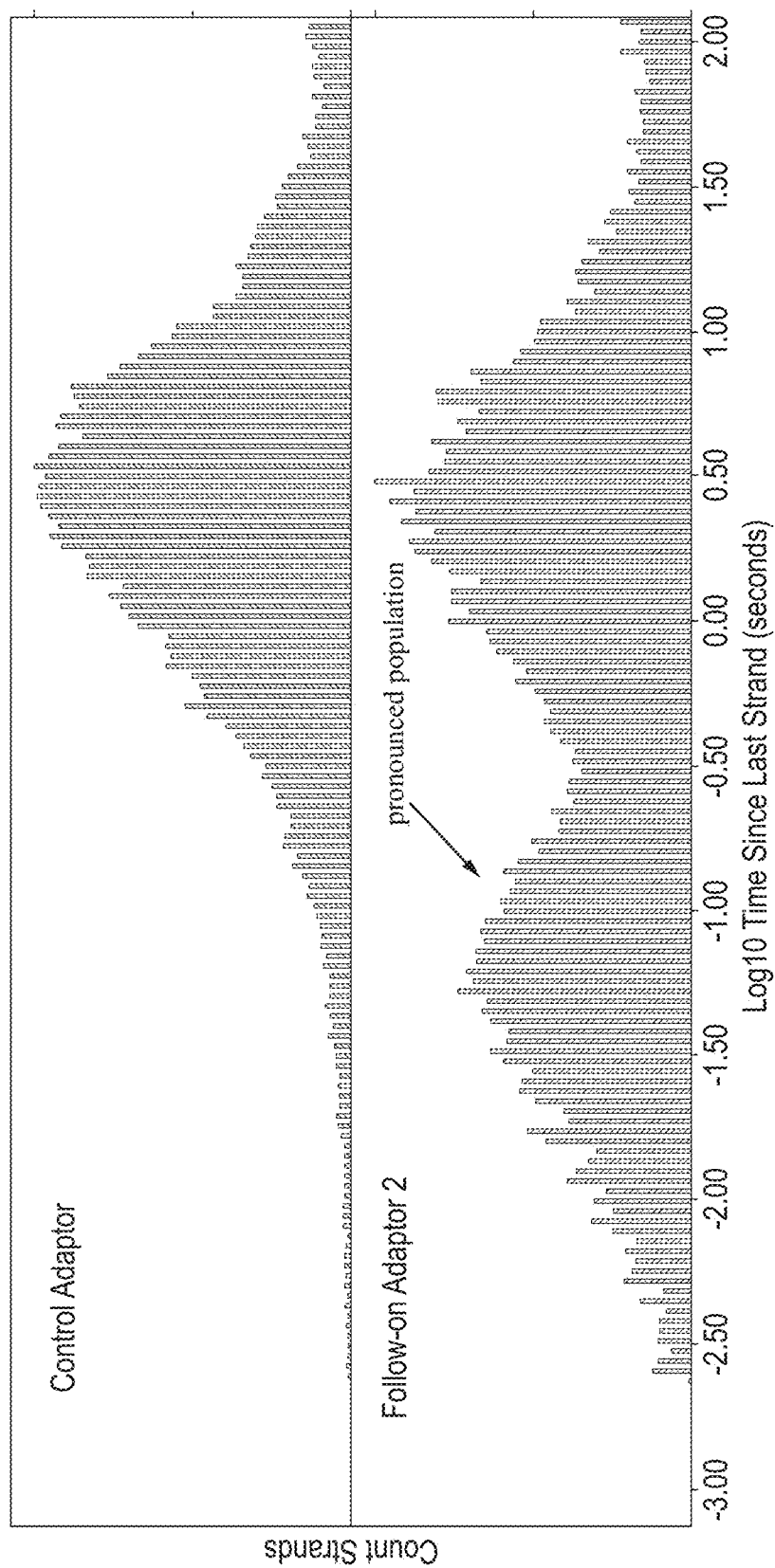

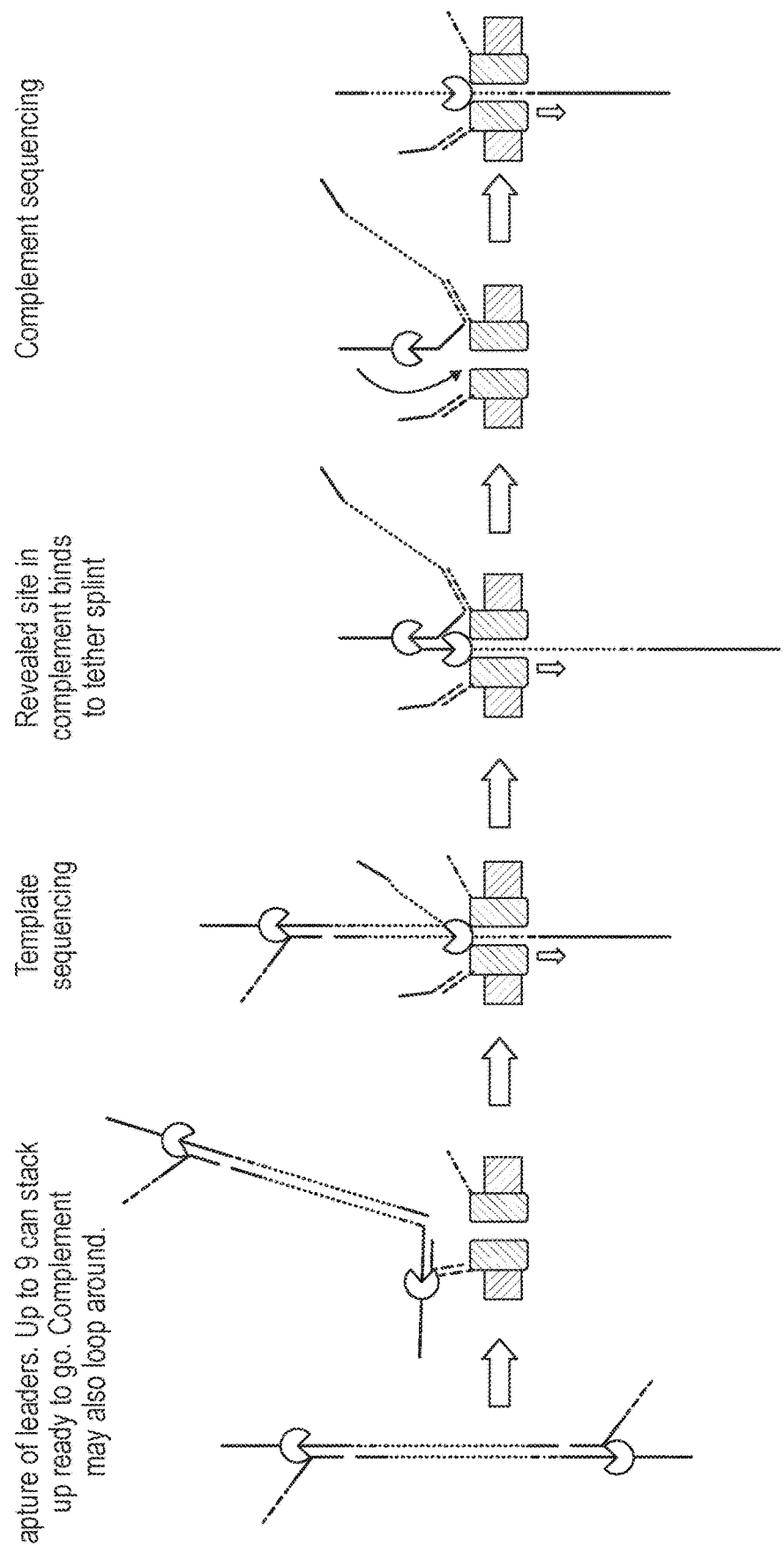

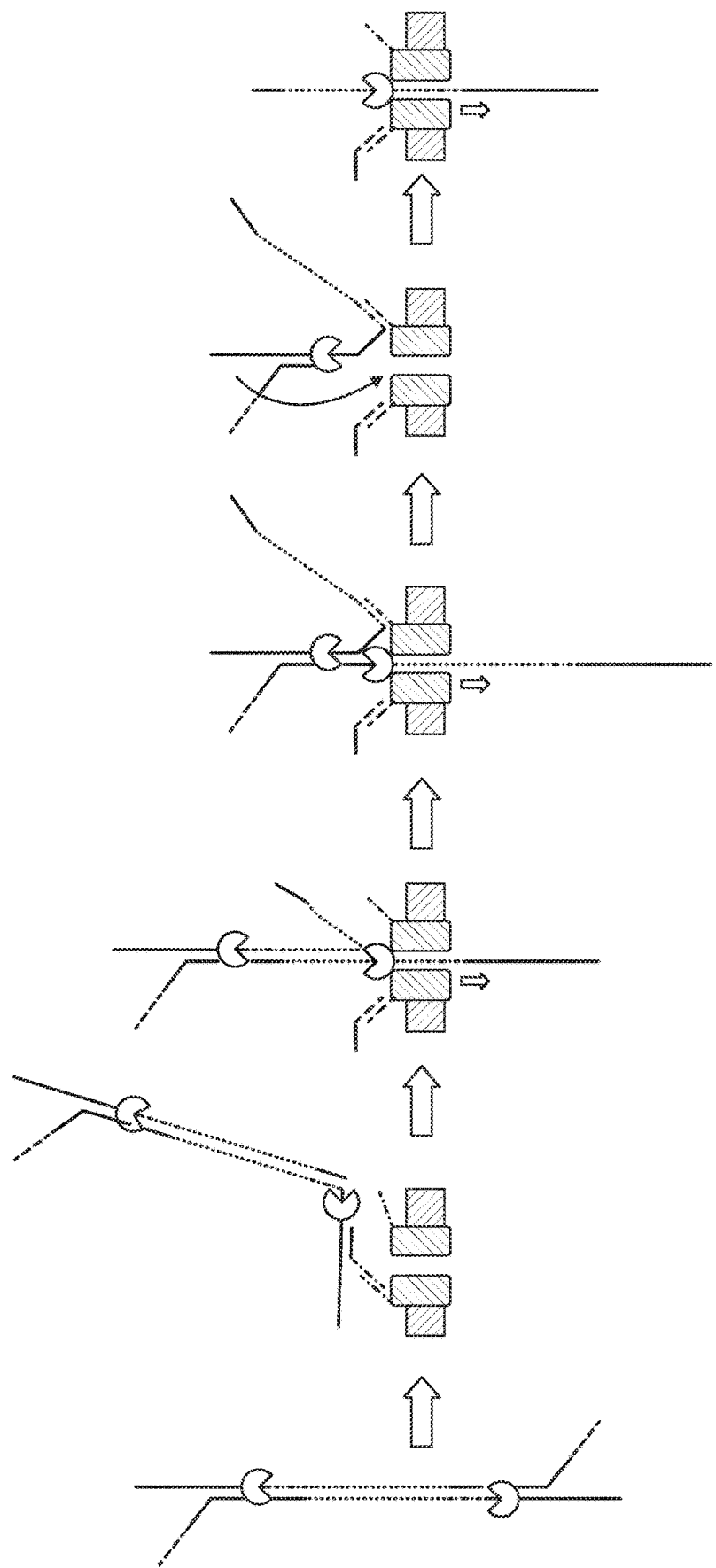

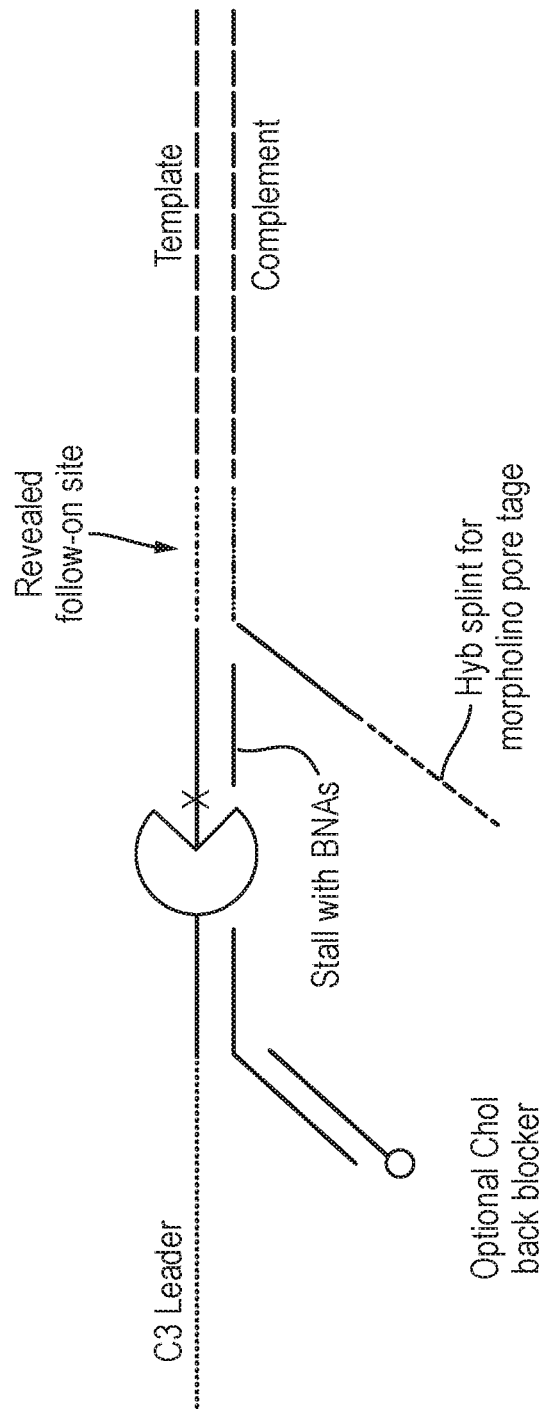

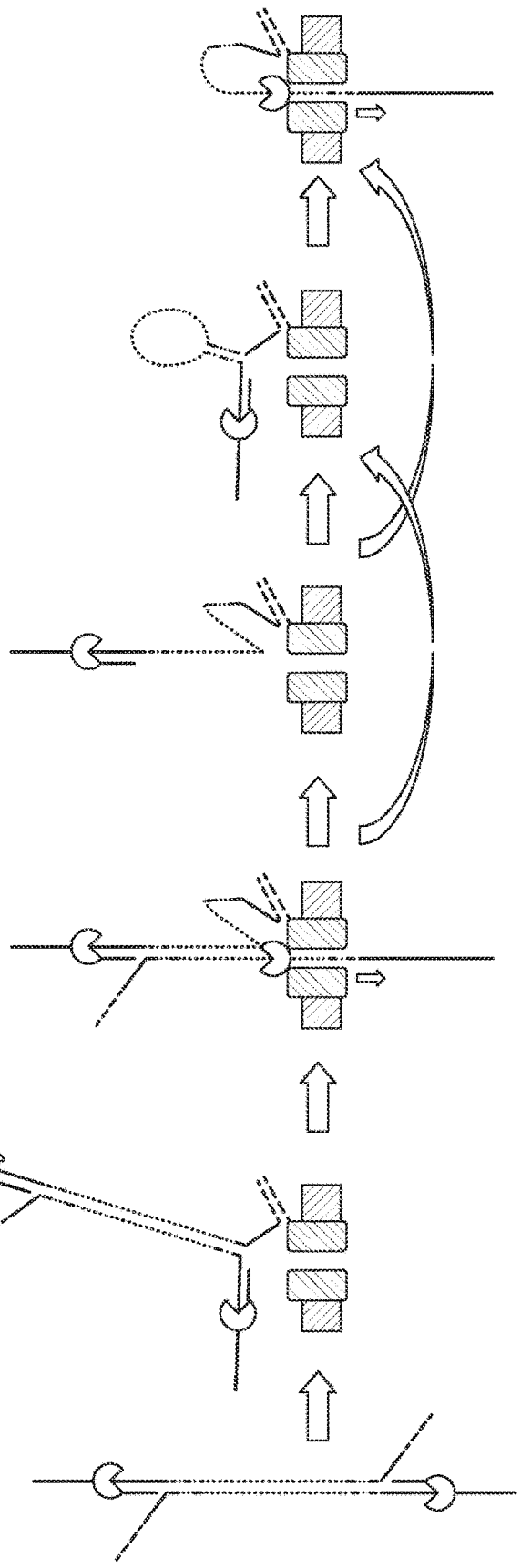

| Sequence | Name | SEQ ID |
|---|---|---|
| /5Phos/GCCCTGCTGAGGTGTTAACC/iSp18//iSp18//iSp18//iSp18/TTTTGTCAGAGTTCCA GTCAGAGTTCCT | P0001 TOP B PoreCap stall | (SEQ ID NO: 5) |
| /5Phos/GCAACCTTCTGACTTGGTGTTAACCGTTCTTTGTCAGAGTTCC/iSp18//iSp18//iSp18/GGTTAACA CCCAAGCAGAGCCAAT | P0002 BOT B PoreCap stall | (SEQ ID NO: 6) |
| /5Phos/GCCCTGCTGAGGTGTTAACCTTCTGACTTTTGTCAGAGTTCAGAGTTCCT | P0003 TOP B PoreCap No stall | (SEQ ID NO: 3) |
| /5Phos/GCAACCTTCTGACTTGGTGTTAACCGTTAAACACCCAAGCAGAGCCAGCAAT | P0004 BOT B PoreCap No stall | (SEQ ID NO: 4) |
| /5Phos/GGTCCTGAAGAAGTTCGGTCTCTTGTGTTAACCT | P0016 POSEN tailattach TOP A | (SEQ ID NO: 29) |
| /5Phos/GGTTAACACAAGAAGACACCAAGAAAGTTCTTGACCAGCAGCCAAT TAAGTCAGAGTTCC | P0017 POSEN tailattach BOT A | (SEQ ID NO: 30) |
| /5Phos/CCAATTGCATCGGTTCGTCTGCGG/8888/TTTTCGGTCTGATGATTCAGAACCAAGAGTCTGCTCGA GTGTTAACCT | P0018 POSEN tailattach TOP B | (SEQ ID NO: 31) |
| /5Phos/GGTTAACACACCCAAGCAGAGCCAAGAAACCAATGTTAACC/8888/CCGCAGACGAACC CACAATTGGAGAGTTCC | P0019 POSEN tailattach BOT B | (SEQ ID NO: 32) |
| /5Phos/GGTTAACACCCAAGCAGAGCCAAGAACTTCTCAGACCAGCCAAAA/8888/CCCCAGAGGAACC | P0020 POSEN tailattach BOT B noside | (SEQ ID NO: 33) |
| /5Phos/GCGGCAAGTAAGGTTAACCGTTAACC/8888/TTTTGGTCTGAGGAAGTTCGGTGTCTTGTGTTAACCT GCAAT TAAGTCAGAGTTCC | P0021 POSEN tailattach TOP C | (SEQ ID NO: 34) |
| /5Phos/GGTTAACACAGGACCAAGCAGAGCCAAGAACTTCTGACCAAGAAAA/8888/GGTTAACCAAGCAGAGCCA | P0022 POSEN tailattach BOT C | (SEQ ID NO: 35) |
| /5Phos/GGCCGTCATGCTGGCTCGTCC/8888/TTTTGGGGCGTCTGACGTTAACT | P0023 POSEN splintagain TOP A | (SEQ ID NO: 36) |
| /5Phos/GGTTAACACCCAAGCAGAGCCTGCTGAGACGCCAAAA/8888/GGAACCACAATTGGACAAT | P0024 POSEN splintagain BOT A | (SEQ ID NO: 37) |
| /5Phos/GCCGTCGTTGGGTGTTAACC/8888/TTTTTGCCCTGCTGGCTGGCTGCACAGCAGCCTTGGCTGTGTTAA CCG | P0025 POSEN splintagain TOP B | (SEQ ID NO: 38) |
| /5Phos/GGTTAACACCCAAGCAGAGCCAGCCTTGATTAACACCAAGCAGAGCCAAAA/8888/CGAACCACAATT GGAGCAAT | P0026 POSEN splintagain BOT B | (SEQ ID NO: 39) |
| /5-Phos/CGGCGTCAGCTGGCTCGTTAACC/8888/TTTTGTCAGACCAGTCCAAGTCGTCGGAGTCGTTCCAAT | P0027 TOP 1sp18 | (SEQ ID NO: 40) |
| /5-Phos/TTGGAACCACCTGCTGCTGCAGACGCCTTCTGACACCGCCAAAA/8/GGTTAACACCCAAGCAGAGCCAAT | P0028 BOT 1sp18 | (SEQ ID NO: 41) |
| /5-Phos/CGGCGTCAGCTGGCTGGCTGTTAACC/8888/TTTTTGTCACAGAGGTTCC | P0029 TOP 1hybsite | (SEQ ID NO: 42) |
| /5-Phos/TTGGAACCACCTGCTGCTGCAGACGCCAAAA/8888/GGTTAACACCCAAGCAGAGCCAGCAAT | P0030 BOT 1hybsite | (SEQ ID NO: 43) |

1- αHL control
2- Modified - αHL control
3- Unmodified - oligmer
4- Modified - oligmer
5- Modified - oligomer
6- Modified - oligomer
7- Unmodified - monomer
8- Modified - monomer
9- Modified - monomer
10- - Modified - monomer

Fig. 27B
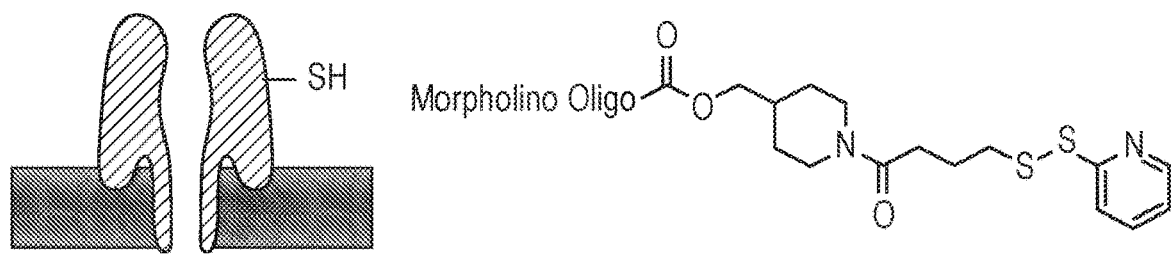
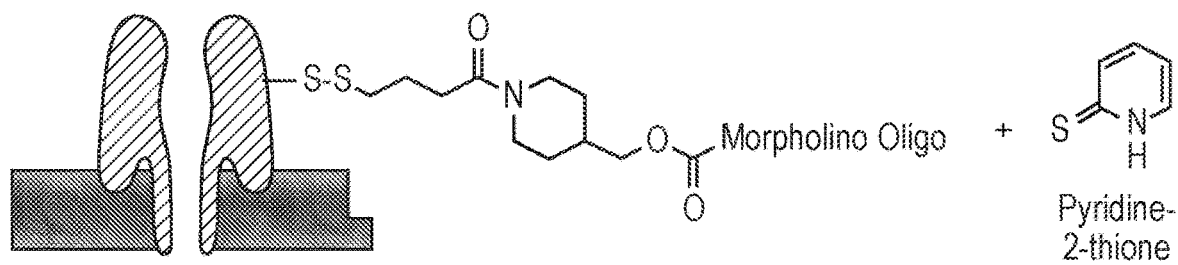
Fig. 28
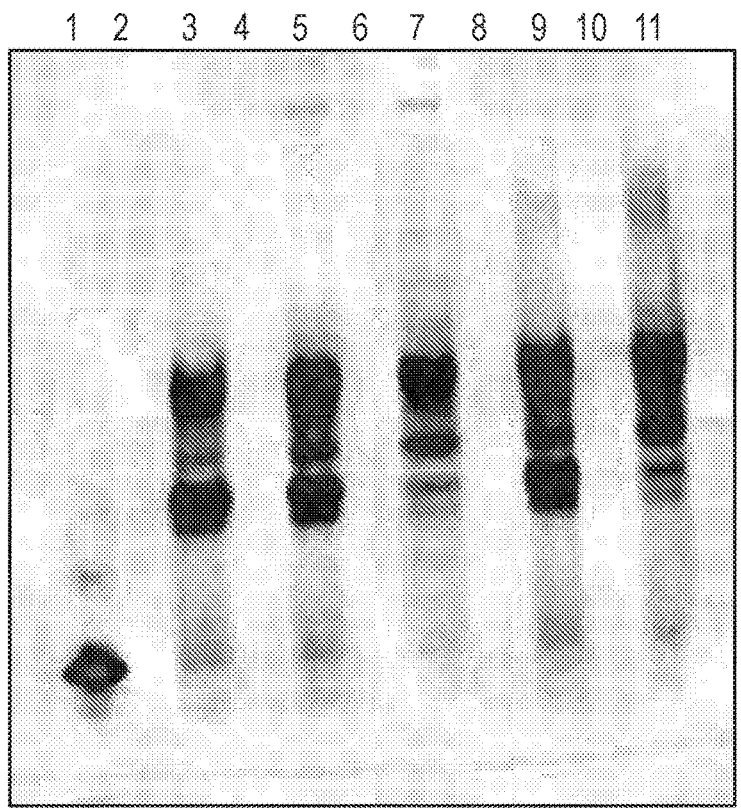

Fig. 31
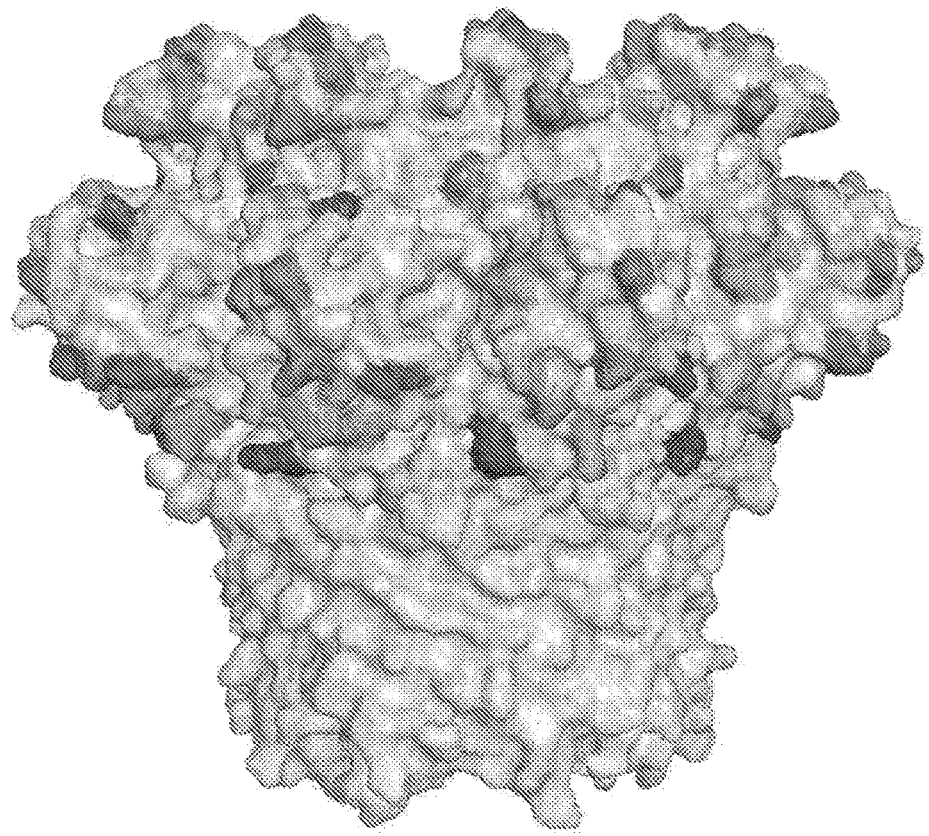
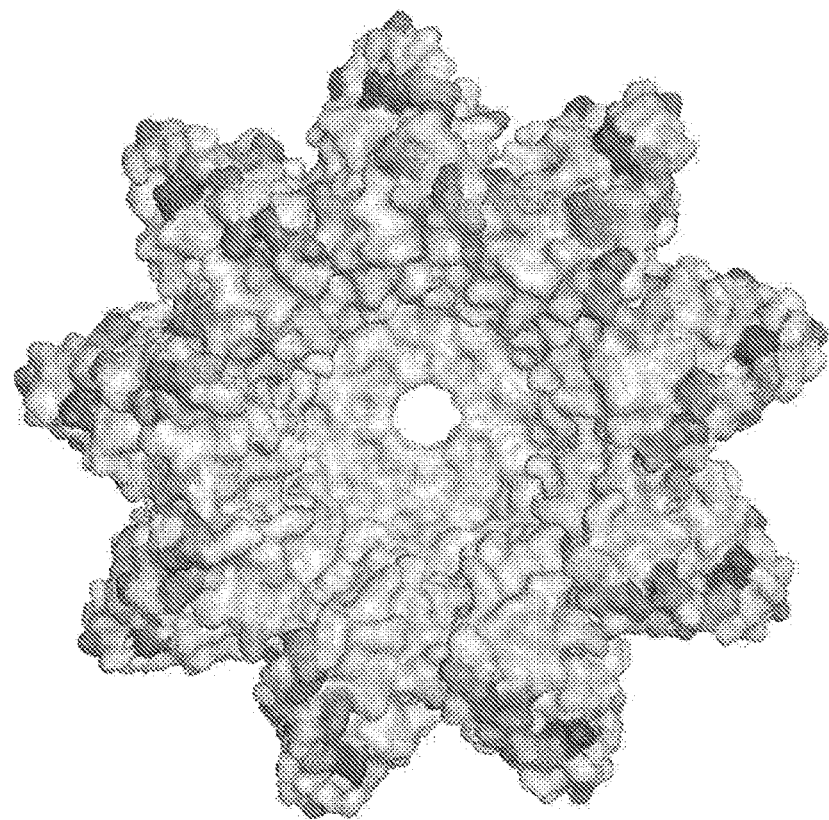

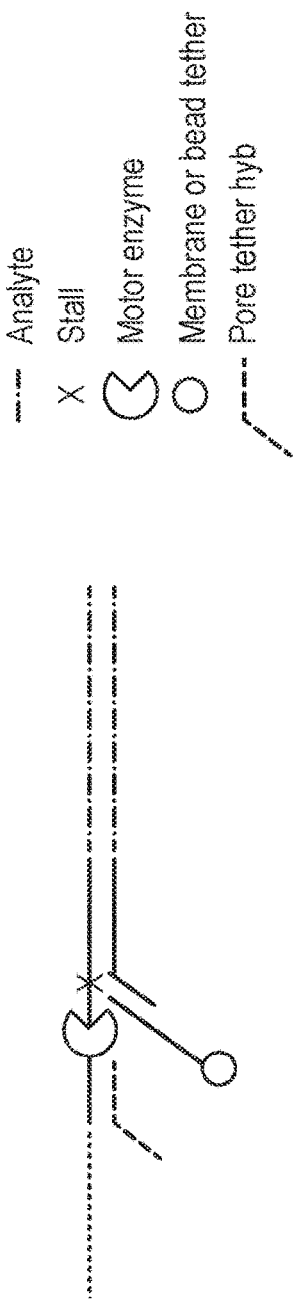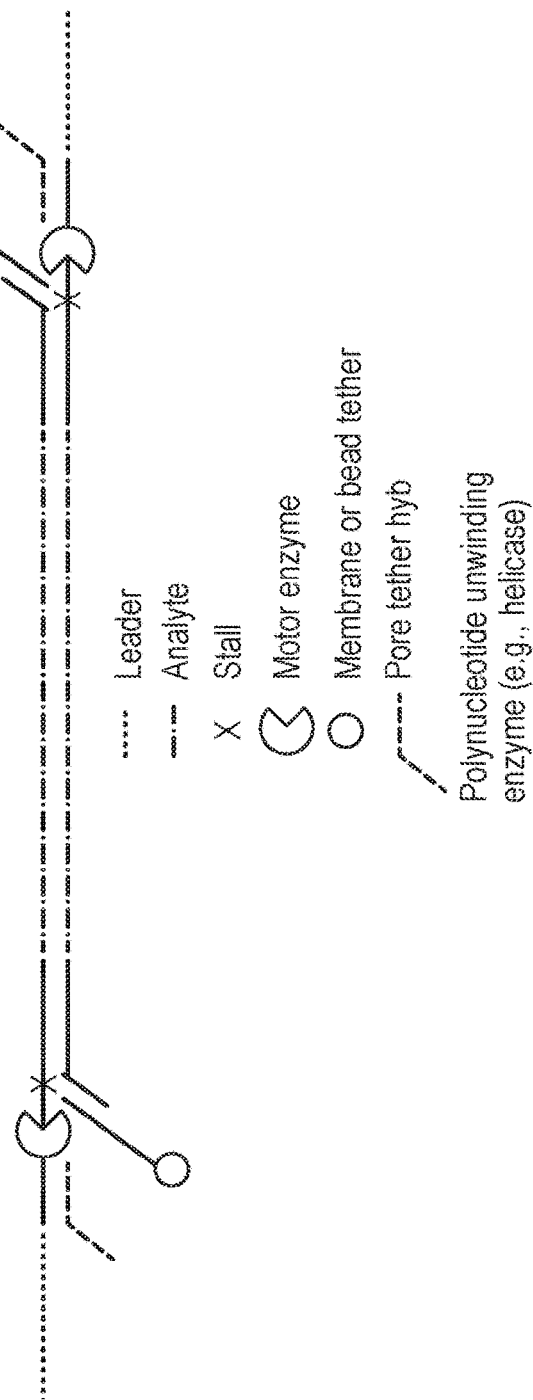

Fig. 38
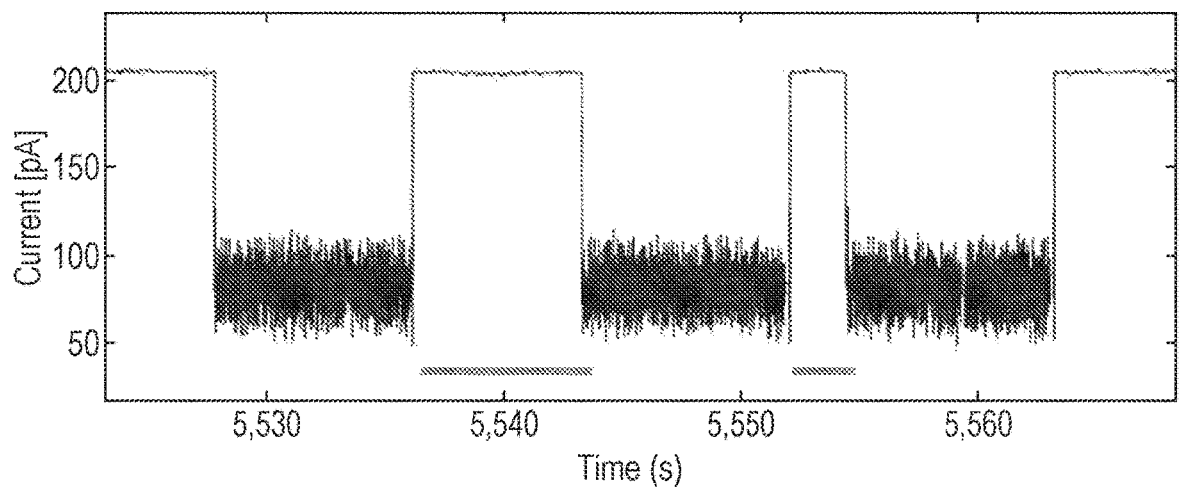
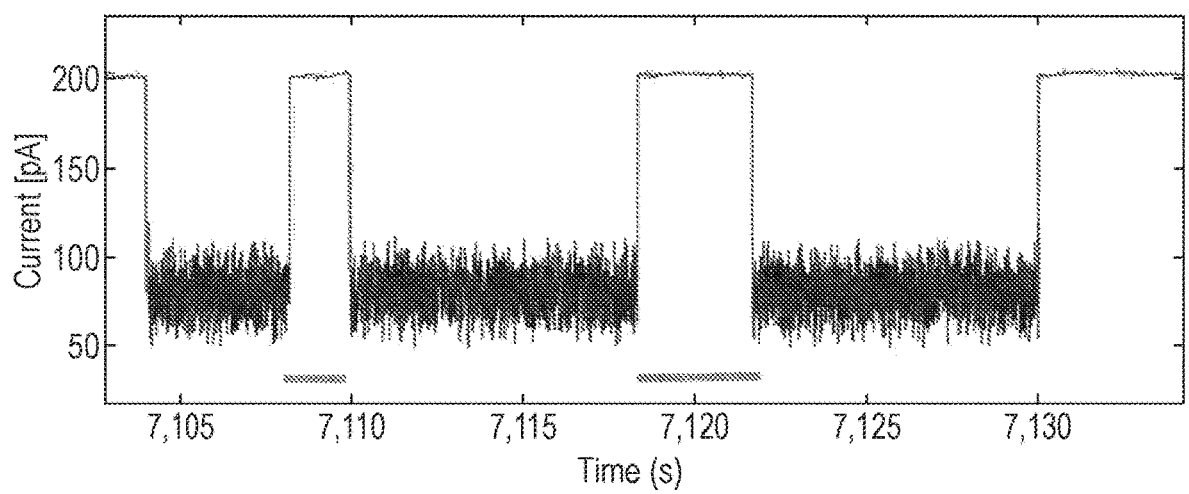

Fig. 39
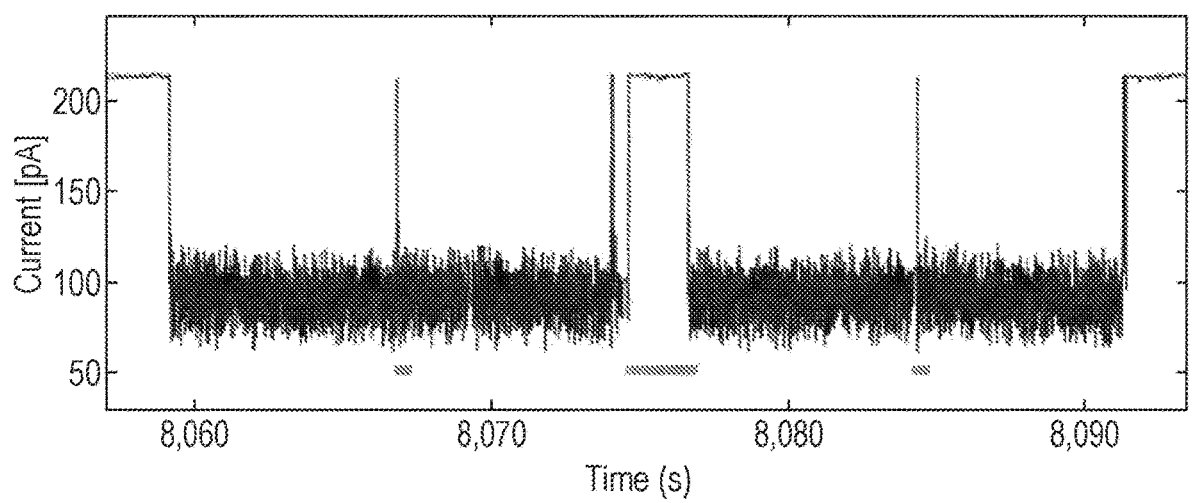
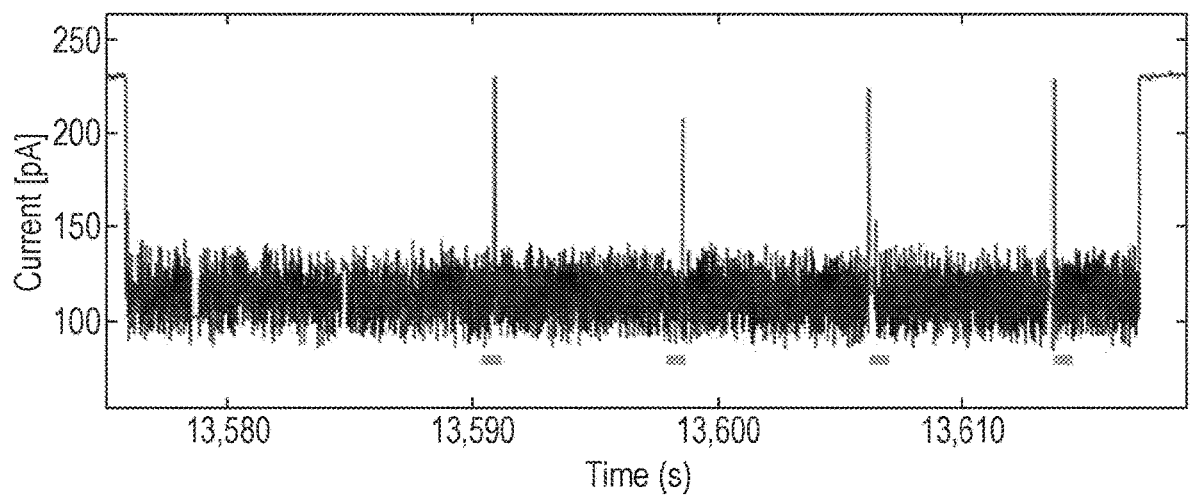

Fig. 42

| Sample | Pore | Strands | Sequencing Pores | Mapped Strands | Follow on Strands | Follow on Strands (%) |
|---|---|---|---|---|---|---|
| 1 | Tethered | 5299 | 101 | 2525 | 195 | 7.7% |
| 2 | Tethered | 5114 | 99 | 2482 | 161 | 6.5% |
| 3 | Tethered | 228185 | 409 | 20517 | 1187 | 5.76% |
| 4 | Tethered | 219216 | 454 | 22369 | 1391 | 6.22% |
| 5 | Tethered | 106680 | 164 | 76097 | 6908 | 9% |
| 6 | Tethered | 103487 | 208 | 74211 | 6045 | 8.1% |
| 7 | Non-Tethered | 19719 | 299 | 11113 | 23 | 0.2% |
| 8 | Non-Tethered | 12566 | 285 | 5483 | 53 | 0.96% |
| 9 | Non-Tethered | 118773 | 341 | 12199 | 28 | 0.23% |
| 10 | Non-Tethered | 69880 | 304 | 4998 | 2 | 0.04% |

SEQUENCE LISTING

```
<160> NUMBER OF SEQ ID NOS: 63

<210> SEQ ID NO 1
<211> LENGTH: 40
<212> TYPE: DNA
<213> ORGANISM: Artificial Sequence
<220> FEATURE:
<223> OTHER INFORMATION: Synthetic

<400> SEQUENCE: 1
aaggttaaca caaagacacc gacaactttc ttcagcacct                        40

<210> SEQ ID NO 2
<211> LENGTH: 45
<212> TYPE: DNA
<213> ORGANISM: Artificial Sequence
<220> FEATURE:
<223> OTHER INFORMATION: Synthetic

<400> SEQUENCE: 2
ggtgctgaag aaagttgtcg gtgtctttgt gttaacctta gcaat                  45

<210> SEQ ID NO 3
<211> LENGTH: 59
<212> TYPE: DNA
<213> ORGANISM: Artificial Sequence
<220> FEATURE:
<223> OTHER INFORMATION: Synthetic

<400> SEQUENCE: 3
ggcgtctgct tgggtgttta accttttgt cagagaggtt ccaagtcaga gaggttcct    59

<210> SEQ ID NO 4
<211> LENGTH: 64
<212> TYPE: DNA
<213> ORGANISM: Artificial Sequence
<220> FEATURE:
<223> OTHER INFORMATION: Synthetic

<400> SEQUENCE: 4
```

```
ggaacctctc tgacttggaa cctctctgac aaaaaggtta acacccaag cagacgccag    60 caat                                                                64
```

<210> SEQ ID NO 5
<211> LENGTH: 59
<212> TYPE: DNA
<213> ORGANISM: Artificial Sequence
<220> FEATURE:
<223> OTHER INFORMATION: Synthetic
<220> FEATURE:
<221> NAME/KEY: misc_binding
<222> LOCATION: (23)..(24)
<223> OTHER INFORMATION: nucleotides separated by 4x iSp18

<400> SEQUENCE: 5

```
ggcgtctgct tgggtgttta accttttgt cagagaggtt ccaagtcaga gaggttcct     59
```

<210> SEQ ID NO 6
<211> LENGTH: 64
<212> TYPE: DNA
<213> ORGANISM: Artificial Sequence
<220> FEATURE:
<223> OTHER INFORMATION: Synthetic
<220> FEATURE:
<221> NAME/KEY: misc_binding
<222> LOCATION: (35)..(36)
<223> OTHER INFORMATION: nucleotides separated by 4x iSp18

<400> SEQUENCE: 6

```
ggaacctctc tgacttggaa cctctctgac aaaaaggtta acacccaag cagacgccag    60 caat                                                                64
```

<210> SEQ ID NO 7
<211> LENGTH: 262
<212> TYPE: PRT
<213> ORGANISM: Escherichia coli

<400> SEQUENCE: 7

```
Cys Leu Thr Ala Pro Pro Lys Glu Ala Ala Arg Pro Thr Leu Met Pro
1               5                   10                  15

Arg Ala Gln Ser Tyr Lys Asp Leu Thr His Leu Pro Ala Pro Thr Gly
            20                  25                  30

Lys Ile Phe Val Ser Val Tyr Asn Ile Gln Asp Glu Thr Gly Gln Phe
        35                  40                  45

Lys Pro Tyr Pro Ala Ser Asn Phe Ser Thr Ala Val Pro Gln Ser Ala
    50                  55                  60

Thr Ala Met Leu Val Thr Ala Leu Lys Asp Ser Arg Trp Phe Ile Pro
65                  70                  75                  80

Leu Glu Arg Gln Gly Leu Gln Asn Leu Leu Asn Glu Arg Lys Ile Ile
                85                  90                  95

Arg Ala Ala Gln Glu Asn Gly Thr Val Ala Ile Asn Asn Arg Ile Pro
            100                 105                 110

Leu Gln Ser Leu Thr Ala Ala Asn Ile Met Val Glu Gly Ser Ile Ile
        115                 120                 125

Gly Tyr Glu Ser Asn Val Lys Ser Gly Gly Val Gly Ala Arg Tyr Phe
    130                 135                 140

Gly Ile Gly Ala Asp Thr Gln Tyr Gln Leu Asp Gln Ile Ala Val Asn
145                 150                 155                 160

Leu Arg Val Val Asn Val Ser Thr Gly Glu Ile Leu Ser Ser Val Asn
                165                 170                 175
```

```
Thr Ser Lys Thr Ile Leu Ser Tyr Glu Val Gln Ala Gly Val Phe Arg
            180                 185                 190

Phe Ile Asp Tyr Gln Arg Leu Leu Glu Gly Glu Val Gly Tyr Thr Ser
        195                 200                 205

Asn Glu Pro Val Met Leu Cys Leu Met Ser Ala Ile Glu Thr Gly Val
    210                 215                 220

Ile Phe Leu Ile Asn Asp Gly Ile Asp Arg Gly Leu Trp Asp Leu Gln
225                 230                 235                 240

Asn Lys Ala Glu Arg Gln Asn Asp Ile Leu Val Lys Tyr Arg His Met
                245                 250                 255

Ser Val Pro Pro Glu Ser
            260

<210> SEQ ID NO 8
<211> LENGTH: 16
<212> TYPE: DNA
<213> ORGANISM: Artificial Sequence
<220> FEATURE:
<223> OTHER INFORMATION: Synthetic

<400> SEQUENCE: 8
ggaacctctc tgacaa                                                        16

<210> SEQ ID NO 9
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_binding
<222> LOCATION: (2)..(3)
<223> OTHER INFORMATION: nucleotides separated by 4x iSp18

<400> SEQUENCE: 9
ttttgaccgc tcgcctc                                                       17

<210> SEQ ID NO 10
<211> LENGTH: 12068
<212> TYPE: DNA
<213> ORGANISM: Artificial Sequence
<220> FEATURE:
<223> OTHER INFORMATION: Synthetic

<400> SEQUENCE: 10
tggtttgtca gagaggttca agtccagggt tccttgcctg tcatctatct tcggcgtctg        60
cttgggtgtt aacgcctctg caccggacgg tccctcgcc ctttgagga gggttaggaa         120 gagaaaaccg cacctgtacc ggatcggtta tttcgcattc ttatcagacc cactgcaacc       180
gctgaatatg caggcataac aggtgcagga tcaccaggca atgcagcagg taaatatcat       240
tgccgtccca gactttggtg gtgaccttat tgtccacgtc cagctcctgc caccgggaac       300
catttcatag tccatccagg tactatgca gtactctccc accatgtttg ataccaggtt        360
tccttggcga tcgccagtat tgacggtgta aacgcgtagg ccgtacccat tgcttcgacg       420
ataggccagc gtacacgttc gcggaccacc ggtttcttc ccagtcaacg acataaacgg        480
ctccgtccgc gccatcggtg cccaggcatc gcgcacggtg gcgttaaacg aacctttggc       540
atcttctagc aacctgctgg tggttgttcg caacgggctt cccagggcca tatggatgta       600
cggcggcatt aaacgccccc attcgatccg gtggcctggt gcactcgggc gcgcggaagc       660
gatgcgccgg gttatctttg ttgtaatccc ggcagccgga ttccactggg tatcagtgtt       720
```

```
cgtgctgccc gataatgatt atttctggcg acatcgtgga tgtcacggaa gccacgcgaa    780
tcgcgcgatc agccattttg tcggtgacgt cataaacaat cgaagcttcc accgcgtgca    840
tattggcatt gccgccgcgg tactcttcga ttttctgaag gcttcgtccc gggattcagg    900
catatcttct tctccagaaa tatttctcga taatttcgta tgggccttaa tcagtagcgc    960
gcttccaggt gaccgtttgg cgacggcgct ggcggcaccc agcggaaaca aagtgttagt   1020
aagccctgtt gcaggcatcc accacgccct ctgatgccgt tcgcacgcgg cgtaccagcc   1080
gccataattt tatccgcacc atcgccgttc atggctttga tgccgtgatc aaccaacgat   1140
ggcgccaggt cagcccatcg ccgcaaccag cgatcgcgtg caacatacga gcggtgatcc   1200
acagatgggt gccatctctc tctttgattt gccctttgtg cctaaccagc catgcagtcg   1260
gcactacgga attttaccaa aatcaaagat gcggtcggtt tcctgttcag ccaacgttg    1320 gcagcagggt gttaaaccat ttcattcata ccatctcatc ttggcggcgt ttagccatca   1380
tttcgtcgac gatatcgcca agttgttgta atttctgatt acaaacgtca cgcagcatca   1440
gctcgttgtc tggtaaaccg acgaccgtct tgaactgcac ggcctgccag gaatccccga   1500
taacccaccg tcgttactgc cacgcgtacg acgcaggaac gattttcgt cgacaccgaa    1560 gagatctcac ccatggcgcc attaatgctg tcattcagac gttgtgaagc acagaaagct   1620
cttgttgcgg accttttgcca taaagcggca ttttcagctt tgtgaaggtc agcgccactt  1680
tctcgcccgg ctctttgagc acggcatcga tgatcagcaa ccgcgatcga atttatgctc   1740
acggcacaac ggtgggcgga cgctggttcg tgatgcttac cagaccgtga gtggcacagt   1800
tcgttgaact cttttcaccat atcgaagacg ttgctgcgca tcttcatcac tacgccacag  1860
caccagcagt tttaggcttt gccaccgtct tgtttgatct tgtggattga ttttgcggtc   1920
agcaaccacg ctatcgtgga gattcgttct gggaatgaac tttcatcggc ggcgaccgca   1980
atcatggcgc aactttgtaa tcgcattttg ctcaaccacc tggcggtaac cgtgacgatc   2040
taccaagtcc ttgagcataa ggcgaagacg cgccgccggc gttaacacga aatccagtta   2100
aaacgctact cctgagcttc tggaagggcg gtgcccagc cgcggcaaac atcatgcacg    2160
ctaaacttct gcgctgatcg acctgctgcg tagcaaaacc gccgatgcgc gtaatgtcgt   2220
tgatggtgtg cttattcatt catttattcc ttttatccga tcgttacatt ttactttggc   2280
agtcatccca gcgcgacacg gacctgttca agaatggcgg accgatctgg cgacccgcga   2340
cccgctgcgc gcctggctat aaacctccca tcgggcagcc cagcggcatt ggcacatgca   2400
gctggttggc gacatcaagg gcgatgcaag attcttctgg gcaagatcga tcatgaaggc   2460
gggaaaagat ctccgctgag gactttgttt ggccaggaag tggtgaagtg acctttaccg   2520
gcagcatttg ctttcatcgc gacggcaaca tcgaggaagt tagggcttcg cacaaacggc   2580
aacttctgcc gaaagcacgc caggcgcaat gcctcgccag ttgttgatga gcaacgcgga   2640
tccccatgcg cggaccgcca gcgttgatca actcactgcc gctcaccatc ggatcggtgt   2700
ggcacgtcca actgttcaac ggtgccgcca gccagccagt aacagagtac cggtaatggc   2760
atttgcagaa gtacggccta ccggtgggtg tcatcatact gaaactgcgg caccatcggc   2820
aatcaattcg gttttgcagc ggatggatgg tggacatatc aatgaccaac acatggtgat   2880
aaagccttcg caaaacgccg tttcaccgaa caacacgttg cgcaccagat cgccattcgg   2940
caacatggta tgataaattc ggcatcttta gcggcctgcc ggttggcggc ggggtcacgc   3000
tgtctaccag atactacacc ttcggcgttc acatcaaaga cgcgaagttg atgcccttgc   3060
```

```
tgcaataaat tgctcaccgg tggcggacca tttgtcctaa accgataaac gcgattgctg    3120
ccgcaaccct cctcctagaa tatggtgtgc tcacttttgt catttatgac atgctttgct    3180
tgtctgtttt gatcgtattt gtaatttatc gtcaagattg acagccgtca ccccaaacaa    3240
ttggtgaggt ggtagacgca tcccaaatca ctgagaatga ccatgattca ttgttgccaa    3300
tggccaagta ccaaccgtga tggatcgcat ctattacgtg gaaggaatac cgacggagag    3360
cgtgaaaccg tggcgaggta tactggagag ttggtggcgg ccagcggcg acggcggcgg    3420 ttgcggcagc aggctgcgag cgcaaggtc atttattggt cacgtgggtg atggcggctg    3480
gtggcaacct gctggcagag ctggaatcct gggcgttaac acccgttacg caaacgagca    3540
taaccaggcg aaatattgca atcaccatca tggtggatac aaggcgagcg ataatcatt    3600 aactaccccc atgccggatc ctgctgcctg acagagtggt tggagaattg atttctctcc    3660
ggtgggatgt tggctggcag atgtacgctg gcacgacgag cgctaaaagc cttcgccctg    3720
gccgtcaggc gggtgtgatg accgttctgg acggggacga tgcgccgcag gaccatccgg    3780
tgaaactggt ggcattaagc gatcacgcgg cctttcagaa ccggtctggc agcaacgggc    3840
gtgaagatgg cttggtgcgc taaaacaggc acaaacgctc taaatggtca tgtctatgtg    3900
accagggtag ccgcgagctg cgatagctgg aaaatggtgg gcgtcgcatc gtagccttca    3960
aagttgatgt ggtagatacc acaggtgcgg gtgatgtttt cacggcgcgc acagcggtgg    4020
cactggctgg caacaagtgg ggatttagcg agtcggtcca actacgtaac agtgtggcaa    4080
cgttaaaata cgtcggtgga cgaccgggat ctgactgtga tcaaacccga tctttgtcac    4140
ttttgtatga aatgccaggg gtgatggttt cgaggaattt tcgcaggcct taccgaacta    4200
accggtaacc cgcagcgacc aactcctcct gctgatcgcc gagcgggtat atgaatattg    4260
atgagctggc aaatcgctgg atgtctccac acagacggtc cgcgggatat tcgtagtcat    4320
gagcaggctg attacgcact gcagctcacg gtggcgcggt cagctcgcat cagtgtgacg    4380
ttcggcagcg tgaggtttcg caagctcgag aaaaacgttg ccgaagcggt ggcgaactat    4440
attcctgatg gttcaacaat atttatcacc agtggtacgg cttctattcg acgtatttgc    4500
ccaggcgttg ccaaccataa tcatttacgg ataatctacc agcttgaagc ctcgtgtggc    4560
gcatattgct acaacccgcg ctttgaagtg gtgcccggcg gtacgttgcg ctctcgccaa    4620
tggcgggatc attggccttc cggcggcgtc gctgtggccg atttcgtgcg cgattatcgg    4680
taacaagcgt tgccggccgg tgagcgatgg cgcgttgatg gagtttgata agcagaaact    4740
aacggctggg tgaaaacgat gatggcgcac ccgaaatatt ctggtcgccg atcacacaag    4800
tatcatgcct tcggcagcgg ttgaaattga taacgtggca caggtcactg cgctcttacc    4860
gacgagctgc cgcccgctgc gctaaatcac gcttacaaga caataggtaa atcattcttc    4920
cccaggagag acgcgcgtta cgaccgttaa cctggccata ccttgccaca acccaaaccc    4980
atcctttcca ctacagttaa tttcttgtgg cgcgaaagac acaaatactc tatatctttg    5040
atttgagtaa tgtgattatc aatgtcaaca ccaacgtgtg ctggggcctg ggcgattgcg    5100
catgttactt cagcatcgct taagaagagt ttattgctgg gagcgtttca tctggcatgg    5160
gcattgaaat tagcgacaag cgttcacaga gagcgctgta tgtctgaatg gctctaccac    5220
taagctacga cagttctctc acggctggcg acagtgtttg ttgcgctacg ccggaagtga    5280
tcgccgtaat gcataaaacta cctgcgtgac aggggcatcg tggtggtgct ttccaatacc    5340
aacctgcata ccaccttcta gcccggaaga atacccgaaa ttcgtgatgc tgctattata    5400
tctatctgtc gcagatctgg ggatgcgcaa acctgaagca cgaatttacc agcatgtttt    5460
```

```
gcaggcggaa ggttttcacc cagcgatacg gtctttcgac gataacgccg ataatatgaa    5520
gggcaatcaa ctgggcatta ccggtgttcg gtgaagataa accaccatcc aagctatttc    5580
gcagtgttat gtaaaaacca ttcaggacaa aactaaggca ccatgccatc cactattggg    5640
cctggcacaa aactactctg gcagcacgta ttgaggacaa catgacaacc tggcggtaac    5700
cttgcctatg catttatgct ctcggctaat tcgccgctgg ttgccgttgt tttgcgcttt    5760
tcgccgcttt tcccatgttt tccgacgtca gcattcagtt acgtcacttt attatttgt    5820 aactttctgc ctgctgcagc gatgttattc agcggtatat gaacaatttg ttgccaattc    5880
aacaagatga ccgccgttgg ggctgatggg ctgatcgtca ccgcgttatt gttgatgtac    5940
tccatccgat agcgcgttga ataccatctg gcgcagtaag taagcgcgac caaaatttac    6000
tcgttcaccg tcactggtgg attttaacac taaagacccg cttctggcaa gggccagtct    6060
ggcgatcagt tcctgttgct ctccctgcgc tgggcgaaac gtctcgctct gtcatcgata    6120
acgtgcgtat ttttcccgtt gctgttgtcg tggatctctc cttctggttg ccagctggca    6180
ttgttctacc atccgtacct aaccgcggcg cgattgtcag cgtttgtcgc cacactcctg    6240
ttcgaagcag gaaggtttc gcgcatatct acatgttccc gtctatcagc tcatttatgg    6300
tgtgcggcgg tgatccccat tctttgtttg ggtctactgg acatggtgta tcgtcttcgc    6360
agcgccgaag tactgtcact ctcgggaata ccgcaaaagc taaaacaagc agcttcgaca    6420
agaagacgac gaaccatgat tgcattaatt caacgcgtaa cccgtgccag cgtcaccgtg    6480
gagagaagtg ggcgagggag tagctgggac tttgcggtgt tattagcggt gctcaaaggt    6540
gtgaacgaaa gcaaaccatc tgtgcgagca ttaacagcta ccgcatcttt atgatgcgag    6600
gcagatgaat ctccagcgat gcaacgggcg cggcagtgt gctggtggtt tcccagttta    6660
ccctcgccac cagatattct gaacagggga tacttaagtt tctctcaggt gcatcacgga    6720
tcgcgcaggg cgttatatga ctatttcgtc gaacgctgcc gtcggcaaga gatgaacaca    6780
ccgacaggcc gcttcgctgc ggatatgcag gtatctggtc agccggccag ccccatgtga    6840
cattctgtga tttgcagtgc tgagccagct tccggttgt cacgggaaac gaaagtatcg    6900
ctatgtatct gccaggttcc acaaacagaa gaagaattga gagcgttact atcagtttcg    6960
ctggaaatgt tgcgcccttc atcaacaggt tcggaacacg cgcgtgggat gcgatggcgc    7020
atcgcagatg gtcacgtcga cgacagggta atctcggtaa cggtaaactg cgactgtata    7080
ttgtctaccg acaatgaagc gtccattcaa catggccgtt catcccggcg tgcgggacaa    7140
gggttaggcg ctgatggcga tgaccacagg tcggtggcgc gtcaggaaga gcgttaagcg    7200
catgactaac agcgcccgtg aagacgcggt gcggagtttt cgccagcggg tttgtgtcag    7260
ggagaaatca ccacataacc acgccgattc gccattttg atgattaagc ccgtcgcctc    7320
gttgacattc accgcatcgc ggcgactggt gcgcctggct gtgggcggta cgaacatatc    7380
gcgggtgaaa aatgggcgtg cgcattcagc aatataccgg gcaaaattta tcactaccat    7440
gccgaaaccg gcaatcaagt ccgcaccata cgctgtttac cgaagacatt tctcggcgac    7500
gctcactgga ctgggacttt atctgtgata cgcgtgaacg ccacctcggc gaacgattat    7560
tcttgcggat acgcatatcc acttcaacca gccgattggc ggtaaacctc gtgcggtacg    7620
ccgacctcgg tatacgcaag cggcgatctc gaccgtcgcg cgcggacgaa agcaggtgca    7680
gatgcaggtc gaaatctttg gcaacagggc taccgggtgc agtgtttgaa ggcacgtatg    7740
tcgttctgct tgcccgcgaa agccatttgg cccgtatgaa ggcgggcgag tagctgatgg    7800
```

-continued

```
aaggcgaaca cctctctctc ttcaggtgca ttatgataga tcgccaagct atttcagttg    7860
ctgtaaataa gaactctata agttacgcat tcttcttcgt tggctccatg cggtgtcttg    7920
ccacatcact gttcaggagc atttaaataa tactttagcg aactggtggc aattatcacg    7980
ccgaatagcg cttattccat catcttagtt catgtttgag cgattttga  tagtcaaaac    8040
cccactctgg tgccatactt ttctcttaaa tactttaaaa tctatagcta acaaacaata    8100
tacaaagata atggatagct cgtcagtatc aaccatttac cctttcttgt gttatgaata    8160
ttatgttgta tgtttgctct taaaccgtgg gaaggaggct ataatggttg ccaatataat    8220
ctatttctgt gaaagttatt ctgttgttaa tttgaaaaca actttcccag actgttacca    8280
acaaaattat atgatgaaca agtaaagacc ggttggtggc agtactacaa ccgatgcgat    8340
gaagattaat ttcaccgcca aatcctggtg ctgttaggat gctggcgttt tcggctacac    8400
cattcaagat tatgcaaata atatctcaga ccaacaatat attcttaaca cccataattc    8460
atctgagcga tactaaacca ttttgagtaa taagtaaaca gctacagcac tcttattatt    8520
tctggaaaac gcctcgcaaa aacaaaacat aaaatccgct ttttaaatga ttttccggcg    8580
ccattttcgc gccacattaa tgagtaatat aatgagtatt agtaatgtgt gtatgcggtt    8640
ttcttcattt acatcgaaga accgttaaac ggctgaacaa gcttcggggc tggcgtaagg    8700
tttctgatca atttacgcga agcggtagag caatatctgg aacgtcagca attcccgaat    8760
acgtaaaaca aaggagagca ggcaaaaggg aggtagttgg tgttgatgat cgttaggagc    8820
ataagggaat gacaagaatt ttgttcttga atataaaaac agatgcccct attctggtat    8880
taatgaggct gtttgcgaac ttataataac tgcaactgtt acatcatatc tggaaacgcc    8940
tcgcaaataa aaatgatgca ataaatagag cttt cttcaa gattcggcaa ggtacttttc    9000
tctccatgtg gattcaaaat gatattggcg gtgttatgaa ctctctggca gtacagatat    9060
gggcgggaat tttactcgat ttatcgaatg gggtgattca aagcaacttg atgatctcga    9120
aggtgcagcg caatgtttcc tcgtgcggac ctattaaggg aagcggtaga tcatacctga    9180
taatcaaatc aaacaagcaa gaaccaatgt tcctggcatc tggcaaggaa ggtgcagaag    9240
atgattatcg aatatcggcg taagctgcgc gagaatggtg tgggaaaatg atgtcaatca    9300
gattgctgac aacgtgcccg ttgttcgaaa tgccggatgc ggcgtgaacg ccttatccgg    9360
cctacaaagt cagtataaat tcaatgtatt gcagtttatt ggtaggcctg atggctggcg    9420
catcaggcaa tcttgctgtc atcggtctca tgcccataac cttattgatg tgggtggtgg    9480
gtaaattggt aaaccggcac tggcggcatg gcggtgttaa cgcggaatac gagatggtgt    9540
cgtcaccacc taacgagctg taatccgggc gacctgcgcc accggaaaac gtcggggtac    9600
tcttcacccg gaaacaggaa cgggttgatg gaatgcgaac tcttcttctt gtattcgtgc    9660
gtccaaagta ccaagaggcg aaggtcatct actacggctt cgttttggtc tttttcctga    9720
taagaaggta ctggtagtgt cgctggtcat cgcagctttc tggctttaat gcccggccta    9780
tttcgtcatc agcagccagt attacggttt gccgctctct gcggattgct gcattcccgc    9840
gcactacgtg ccattcagtt tcacgggtta cggtgcagta acaccttcgg tggtgccaat    9900
ttgcaccatg ctggacttcg gcagcagaac cacaaaccgg gcaatattga cgttgctcgc    9960
caaacattca gcgcgggctt tgccggatca ggtcggccat gcgcccggta ggcgacagtg   10020
cagccagata aacggcgctt tatcgctgct gacggacgag aaaatcagga gcaaacagcg   10080
cgctggccat atcttccagc tcctgagtca ttaccttctc cagattctca atcactgcca   10140
ccagcgccgg gccgctcatt tcaggtttca gctcggcaat cagcgccatc aagcagcttt   10200
```

```
ccggtgctta tcgcacggca ggcggaatat ccagcgggct tgccttgtgc gctggcttct   10260
ttaatgcgcc tgcagtcaga tccatctcca gcgcacgatt tgttcgtaca gcaccacttc   10320
ctgggcggta aggcgtcagc tttgtaaagc gcaggtaatc gcagaggatt tattttctgc   10380
cagctcgcgc agacgctcgg cgcggcggtt gtataaattc ttgagccgag gaacaataac   10440
ggcggaatcg catatccacc gtacgtttct cgcgaaccca gctcatcttg cggattatgc   10500
gaatattcag ctctttccgt tgtcttgcag ttccgcattt tctgctgccg ggtgatgttt   10560
cttcgccctg gcattgtatc cttccaccat ggcattgtcg tgcctttcac ccaagggtga   10620
atgccaccat gataaccctg aataacgcca cctgcggcaa atagatgcaa cacgtgctgt   10680
agaatcggat caccggattg aaagcaaggc gcaaaataag gacgccagat aatcacgcgc   10740
tcgcagcagc agaaccggga aaataatcgc accgccgaa gaaacgcatt tcggccgaag   10800
ttataacgcc cgtatactca cctcctcgtt gacgacgatc ttacgaatat tcttcttcaa   10860
aagatagcat catccccgat tgattggttg tgatgcccag taacgaaaaa acggtgatga   10920
accctgagac aaaacataaa ccacgcaccg acaaacgggt gcagaattct acatatacag   10980
ctgcgaatac cgcggttgca tcaaccagtt gaaggacggg gcaaaagccg ctcaccgccg   11040
ccggggatga agcggccacg gtgatccagt ggttgatacg ttccagcgcg gtgcagcgca   11100
cggtggtgtc gtcgtttcat ttgcgctctc gtcttctctt cgtgcagatt attctcttcc   11160
tcatcaccac ggttcaggcc gacaccccat agtagaagat actggccgca agggccagcc   11220
gcaaaataac agccgcgagc ggtttcgat gcctttcaga atttgcggtt tcttcccggt   11280
tcgggttctc cggcaaacca tgatactgaa tttggcttgt caacgtggtg caacacatta   11340
cgtgtactac cgacataccg gatcgtacag acccacattg tcgtaaccac caggttttca   11400
gctcagcaac gcgctcgctc tttccaacgt tttcatcaaa ctcgtacaag tgaatccgcg   11460
cccgttgggc aggtcttcac ctgagctgaa gttctaccaa ccaccgcacg gatcgacgaa   11520
gcgtacattg gcgaacacgg ttgtcagcgc aggtttgagc gcggggtaat gaacggacag   11580
cctggtacat gccaccaacc aatgcactgc tcggctgaag tcgacattac cgttgacacc   11640
tgaataattg cacgctacac caggcacgcc ttcaggcagc ctggatggaa cagtacgcca   11700
cagccgtctt tgcggatcaa agccattcag tttgtctggc tgtccacttc gagcgcatta   11760
ccgtccacga tttggcgcta aatcattggg gttgtcgtac accccaatgt tattgccgac   11820
attgtatcgc agtgtcgttc cctctgaaca cgccaccaca accgggcttt acagccgata   11880
caggtggtaa cgtcgatgag tttcgcccac ttcttcctgg aagtcccgcg cctgaggcgc   11940
ggggtcgaac attagtcgcg gaacgacgaa taagttaaac atgacagacg ccgagataga   12000
gcgacgagca aagtaaggaa ccccgcctct ctgacttgga acctcgttcc agcagtacag   12060
ccaacttg                                                              12068
```

<210> SEQ ID NO 11
<211> LENGTH: 11605
<212> TYPE: DNA
<213> ORGANISM: Artificial Sequence
<220> FEATURE:
<223> OTHER INFORMATION: Synthetic

<400> SEQUENCE: 11

```
cactttgata agaggttcca agtcattcct actgcctgtc gctctatctt cggcgtctgc     60
ttggtgttta acctattcgt cgttccgcga ctaacggtct gaccccgcgc ctccaggcgc    120
```

```
ggaacttcag aaaagtggcg aaactcatcg acgttaccac cagctctggc tgtaaacccc      180
tgtcaaaggt ggcgtgttca agtggaacga cattcgcgac cgtcgtaata acattggggt      240
gtacgacaac cccaatgatt taaacgcacc aaatcgtgga cggtaatgcg cgctatcggt      300
gaacagaacg acaaactgga atggctgatc caccaagacg gcagcgtact gttcgatcag      360
gctgcctggg cgtgccggcg gaagattacc agtgtcagta tggcctcgtc gacttcagtc      420
ccaggcggtg cggtggcatg cggattgtgc gacaccgcgg gctgtccgtt cgacattccg      480
cgcggaagac aaccgcgtct acaatgtgcc gctgtgcgtc gaccgcgtgg tggttgggcg      540
aaccagcctg cgtgaagacc accgcgcggg cgcgattcac ttcggtacga aagagtcggt      600
aaacgctggc gaaacgagcg ttgctgagct gaaaacccgc ggttacgaca atgcgggtct      660
gtacgatcca gcgagaacgt cggtggtacg tcatgtacac gtgccgcacc atgctgaaac      720
tgaccaaatc tgtatcgcga agcacaggag actaatcagc gaaaccgcaa ttctggaagg      780
cctcctggaa gccgctcgcg gctgttggct tgcggctacc cttgcggcca gtatgtcccg      840
ccgtggtgtc ggtcgaaccg tgcggatgag aagaaataat cctgcacgag aaagacgggc      900
gcaaatgaac gacgtgacct gtcgtgcgct actgcgcgcc ggaacgctat ccaaccactg      960
gatcaccgcc ttcttcatcc tggcggcggt gagcgggctg ggctttattt cccgtccctt     1020
caactggttg atccaccaaa tcgccattta ccgcaactgg cgttctgcac ccgtttgtca     1080
gcgtggttca tttgcctcgt tcatcatcat gttttccgtt gccagcatct ggcttcatca     1140
atcgggtaat cttttggcga agaatattcg tagatcgtcg tcaacgaagt aggtgacacc     1200
gggcgttata actggtcaga aatgcgtttt cctgggcggc gattattttt ctggttctgc     1260
tgctggtgag cggcgtgatt atcagcgatc atatttacgc ctgctttctc cgtagtgatc     1320
gattcgcgtt aatgctgcca ttcatttacc agtggcgaca gccagcggat tatcatggtg     1380
catatctgcg ccgccctttg ggtgaaaggc acgatgccgc catgaaggat gtaccagcgc     1440
ctgtgggcga acatcgcac ccgcgctgat gccgtgaggt ccgcaagaca acggaaagcc     1500
aatcagtatt cgcataatcc tggaatgagc tgggtcaagc ggcttgtacg gcgagatatg     1560
attccgccgt tattgttcct cggctcaaaa ttaaccgcgc cgagctgtct gcgcgagctg     1620
gcgaaataat cctctggtga ttacctgcgc tttgctgcgc ttatcgcccg ccaggaaagt     1680
ggtgctgtac gaccatccac tggagatggt ctgtgcgcgc ataaaagcca gcgcacaagg     1740
caagcccgca gatattcacg ttctgccgcg tgataagcac tggcaaaaac tgctgatggc     1800
gctgattgct ggcgctgaaa ccacaaatag gcccggcgct ggcggtgaag tctggaggca     1860
tcgactcagg gctggaagac cagcccagcg cctcctgatt tctcgtccgc gtccgtgctg     1920
ataaaacgcc gttgtatcct gggctacgca atcgctctac tggctgaatg gccaatctca     1980
gtcaacaaag cccgcgctga gccacgacga gcaacgtcag ccttgcccgg tttgtggttt     2040
atgccggtgt ccaaagcata agttaccgtg gcaccactcg gaactacgac ctgcactgca     2100
actattgtga aactgaatag cacgtggtgc gcagccatca acaactgcga gcaggcgaca     2160
aacccattac cattcgctgg atgacgagca aacgcgataa agccaaagct gcgtgacgac     2220
gcctgaaaat tctctatcgg aaaagtccag aaatcaagcc gtaacgggtg gcctcctctg     2280
gtactggacg cacgaatggg caagaggcta tgcccgcagt tccatcaacc gttcacattt     2340
ccgggtgaag gtaatctccc gacgttttcg ggtaacaggt cgcccggatt acagcgctca     2400
tggggtgtga cgacaccatc tctcgtattc gttaccacct caaactgtgc cgccggtgcc     2460
agtttgactc aatttcacca catcaataag gaccttggcg gggcggtgac aagcgtagat     2520
```

```
tgcctgatgc gctgcgcgct tatcaggcct accaataaac tgcaatacga tgaatttata   2580
cgactttggc aaggccagat ggcgttcgcc gcatccggca tgaacaacgc gttgtcagca   2640
actcgattga catcatttta ttgttcctcg cgcaacccca cgctgatatt cgacaccatc   2700
ttcacaccgc ctgccagatg ccgggaacac tggttcttgc tgttgcgttg atttatggtg   2760
atgatccagc ttccttaatg ggtccgcacg gaagattaca tttgcctcga gatcatcgtt   2820
gtaatcacct cattcgtcgt caggtaaaat tctgcccata tctatacctg ccaaagttca   2880
ccaatatcac ttcaatatca ttttgaatct ggaaaagtac cctgccgaat ctttaaaaac   2940
tcatttacac ttatcatttt attttgcgag gcgttttcag atatggtcat ggcagttgcg   3000
gattatattc aagtaaaaca accttgtatt aataccagaa taagggcatc tgtactatgt   3060
tcaaaattga aaattttgtc attccttatg ctcttacact gatcatcata ccaactacct   3120
ccccctttgc ctgctcctta cagcactggg aattactgac gttcagatat tgctctacca   3180
cttcgcatcc attgcagatc gtgaaaccca cgccagcaag cgttccgtgt tagtgcctct   3240
tctgataaat gaaaaaccgt atacatcgcc attaataccet tgtattactc agccaatgct   3300
gtgcgaaagt atggaaaatc atttaagcgg attttgcatg ttgttttgtt gcgaggcgtt   3360
ttccatatgc tctatagagt gttgcgttgt ttcatttatt actcaaatgg ttagttatcg   3420
ctaaagtgga ttatgattac tatgaatata ttatattcag aatgttgttg cataatctga   3480
atggtgtaac tgaaaaacat atcagcatcc taacagcacc ggattttaaa ttgaaattaa   3540
tctttcatct gaaccggtca gtactgccgc aaccggtctt tacttgctct atattctata   3600
tttgtggtaa tgattcagga aggattgttt tctaaattaa caacagaata actttcttgt   3660
ttaatgagat taatgtggca accattataa taccacggtt tagagcaaac atacaacata   3720
ttattcataa catacagagc agtaaatgaa tgatactgac aatgatgcta gtccattatc   3780
tttgcataat attttattgct ataatttaaa aatatttatg agaaagtatg gcacagagaa   3840
cgactatcaa gtatcagcaa actaagatga tggtggcatt atctgcgata aaattgccac   3900
tcagttctac aaataatatt taaatatact gaacagtgat ctgtgaacgt aagacccaac   3960
gagaataaaa atttatagag ttcttgtttt aatataacga aaccgggacc agcaaatgac   4020
ctgaataggg agaacgcttg cctatgccat cagctactct tcttcgttcc tcctcttctt   4080
accgggccaa atagctgcgc caggcgaacg atacgtgcct tcaaacagct gcacccggcg   4140
tctcgtcgcc aagattttcg acctgcatct gccgcggcca gcgccgtcgc gcgccagacg   4200
gtcgagatcg ccgctgagca ccgaggtcgg ctaccgcatg agtttaccgc tatcggcctt   4260
ggcggcggtt aagccgcatc ccatcacgaa caagtcgttc cgccggggtg tggcgaccgc   4320
agcatcggcc agataagtcc caaccagtga gcgtcgccag tgaataaact cccgaaacaa   4380
aaccgccgta tggtgcagtt cctgattacg gttctggcat ggtagtgacc gtacgcccgg   4440
tatgataccc gaatgcgcgc catttttcact ggcgcgaat atgttcgtac cacgcctgtt   4500
cgctgcgcgc accgccgcga tgcggtcatc cagagtggcg acgggcttaa tcgtggcgaa   4560
tcggcgtgtg gttggcgtgg tgatttctcc cagtgctcgg caacggcgaa aaactcaccg   4620
cgtcttcacg ggcgctacag gtcgcacgcc aacgccttcc tgacgccacc gactccaggt   4680
catcgccatc ggcgcccttc atcctgcgtc gggatgaacg gccataaagc aaatggacgc   4740
ttcattgtcg gcattaatat acggcctacc gccagattac cctgctcgtc gacgaccatc   4800
tggtgatgcg ccatcgcatc ccacgcgtcg cgttcagaac cttttggttg atgcgagcac   4860
```

```
gacatttcag cagagcctga taacgcatac aattcttcct gcacggaacc gaaggtgata   4920
cgccagcgta ctctcttgtt tcccgtgacg accctgaaac ttcagctcgc ctgcaaccaa   4980
gaatgtcacg ggccatcgtg ataacgatac cctgcatatc ccgcagcgaa gcgtgtttgc   5040
gtgttcatct cttgcggcgg cggcgttcga cgaaatagtc atataacgcc tctgcgcgat   5100
ccggtgatgc acctttgggc ttgggctttg tcccgttcag tatcacggcg agggctgaaa   5160
ccaccagcct gccgccgcct gttgcgttga gattcatctt gcttcggcat cgctaaaatc   5220
cggtatgagc acgtgattct cctttcgaca cccaataaca aggtccgcgc caatttcgcc   5280
cgtcgcctat cctctacatt tgggattacg cgttaattaa tgcaatcatg gttcgtcatt   5340
cttgttcttc ttgctggttg cggtattccc cgagtggtaa tttcgcgcca agcagacgta   5400
caccatgtca gtgttaaaac gaagagaatg gtcaccgcca gcacaccata atgagctga    5460
tatgagcgga acatgatgta aacgcaaacc tttcttctgc tgattaagtg cggcgacaaa   5520
acgcgccaaa cgataaatcg cggttaggta cgcggatgg taggaacaat gctgtacagc    5580
aaccagagat ccccgacaac aggaaaaata cgcagcacgt tgtcggtaac cgtattgatc   5640
ctcgccagcg caggagaagg caatgaactg atcgccagac tggcccctac cagcattcgc   5700
aaatcatcca gtacgaacag taaattttgg tcgcgctcgt ttaccacgcc agatggtatt   5760
caacgctatc gatggagtac atcagcaaca ataacgcggt gacgtcagcc cgcacgcccc   5820
aacggcggtc atcttgttgg gtggcaacaa attgttcgat ataccgctgg taacatcgcc   5880
agtagcaggc gaagttgctt aaagtagtga cggcttgaat gctgacgtcg aaaacatggg   5940
aaaagcgacg ctttaaaagc aacggcagcc agcggcacta atgaacaacg acccttgagc   6000
aaggttacct gccagggttg tcatgttgtc ctctcaatgc gttggtagtt tgctttcgac   6060
cttggacggg tacggtgcct ggctttgtct gaatggtttt aacaacacta gcgaaacggt   6120
ccgggatcag gtggttgctc gctactgatg ctggtaatgc ccggctgatt ggctccttct   6180
atgacccatc ggcgttatcg tcgaaagacc ttatcgctgg gtgaaaacgc cttccgccgc   6240
aaacatgctg ttaattcagc cttttcggga cgcatctaga tcttgcgaca gatagatatg   6300
attgtagcat cacaatttc cgggtattct ccggcagaag gtggtatgcg agcggttgtg    6360
gaagcaccac ccgcatgata cctgctcacg cagtttgtgc atgatgtggc gatcacttcc   6420
gggcgcagcg cagcaaacac cgcctgccag ccgtgagaga cgctgctcg tagcttggct    6480
gagccaaatc tcgtgacaca cgcctctgc gaacgcttcg tcataatttc cccacactca    6540
tgctgatgaa acactaccat atgaaaactc ttcttaagcg atgccagcgg aatacgcgtt   6600
gaaatcatca ggctcccaac acggttaaag tcgatatcga caacattacc taaatcaaga   6660
tatagagcat tttgcctcct ttcgcgccac aagaagtgct gtagcaggaa aggatgggtt   6720
taactatgtg gcaagtgtaa accaggttaa cggtcacaaa atctacgcgt cttcctggga   6780
aaatgatttc gttggctgtc tcccaaccga aaacgtgatt ttagcgccgg cgagcggcaa   6840
ctcgtcggta agagcgcagt gacctgtgcc acgttaccaa tttcaaaaac ctgccaagca   6900
tgatgccgtg tgatcggcga ccagcagggc tgttctcgcg tacgccatca tgtttcacca   6960
cgccgctgaa cacatcaact ccatcaacgc gccatcctct aatcgctaac cttacattca   7020
ataatcggca caatcataca aaggacgcgc tgaagggcca atgatcccgc tattatgagg   7080
cgcaacgtac cgccgggcac tatcgcttta aacgcgggtt gcggtaaaga ataatgcgcc   7140
gcgcaggctt cggtggtgat tatccgcaaa tgattatggt tcgtaacgcg gcaacatgct   7200
caacagtcat gccaatggtg ataatattgt tgaatataag acctggtctg ccaccgctgc   7260
```

```
ggcaatcgct ttttctcggt ttgcgaaacc tcgctgctcg aacgccgtat taacgacact   7320
ggaagcccga cccgcgccac cgtgatggcg cgtaatcaga actgccgctc atggtgaata   7380
tccccagcgg accgtctgcg tggagacatc caacgaattt gccaacaata tcataaatat   7440
accacgctcg acacgatcaa cactggtggt cgtgccgcgg gttaccggtt agttcagtgg   7500
gctgtgaaaa attcctcgaa aaccatcacc ctggcatttt gccaaaaggt gacaaaaaga   7560
tcgggtttga tcggtcactg gggatcccga agcaaatccc gccggatgat gtcgtttgcc   7620
cgctacccgc tggcgaagcg gactgactcg cttcatccca ccacttgttg ccagcgccac   7680
cgccaaagcg ccgtgaaaac atcacccgca gtacatcacc accacctcgg ctttgaaggc   7740
cggttgatgc tggcgcccac caccagtagt cgcagcctgc acgctaccct gggtcatagg   7800
catgacaaat ttagccaggc gacatgcctg ttttggcgct gtctcttttc gcccgttaag   7860
cgcgccagac ccggttctga ggccgcgcga tcgcgaaacg ctactacccg gctcacgccg   7920
atatcctgcg gcgtaatccc cgtccagaac aggtcatcac cgcctgacgg tggggtgaag   7980
aacttttagc gccgtctgcc agcgtacgtc tgccagcaca acatcccgca ggaaatcgat   8040
ttcctcaacc gcctctgcat catcaggcag cagatccggg ctggggtggt taatgattat   8100
ccgctctgct agcggtatcc gcatgatggc cggattgccg aagatttcgc ctggttatac   8160
cgtttggtgt aacgggtgtt aacgcccagg attccagctc tgccagcagg ctgttgccga   8220
tgtctgtcat cacctacgta tgcatcgacc ctgcgcccac aacctttacc cgccaccaac   8280
cgctaccgtc gccgctggcc tgcaacttcc gtataatttc tcgccacatg cccaccgctc   8340
tcgtcgtgtc cttccacgta atagatgcga tcctgtccac gtttatacct acacaagcag   8400
atcatggtca ttctccttaa acattgcggg atgcgttcat tttaattcac cagtgtttaa   8460
aagtgacggc tacatcaatt ttgactgtcg atacaaacca gtcaaacgaa caaagcaaag   8520
catgtcataa atgacaaaaa gtgacataac tgtattcagg agggttatgg caacaatcac   8580
cgacctcgtt ttacggacaa tgggtccgcc aatggcgagc aatttattgc agcaagaacg   8640
taacttcgcg tcttgatgtg aacgccgaag ctgccgacat ctggtgaaca aggtgcgact   8700
cgccgccaac cggcgcagac cactaaagat gaatttatca ttactgttct tgaatggcga   8760
tctggtgcgc aacattgttc tgattgaaaa cggcgtttgc gaaggcttat ctgttcgctg   8820
gtcgttgata tgtccacctc atgcaaaccg ataaattcgt tgccgatata cagcaaaggc   8880
ttcagcatga tggatgttcc gacgaaaccg tacttctgca aatgccatta ccggtactct   8940
gttactgctg atggcggcct gaaccgttga acgatgccac gcccgtccca ccggtggcga   9000
tgggcggtgg ttgatcgcgc tggcggtccg ggcatgggga tcacgttagc tcatcagcaa   9060
ctacatgagc atcgcgctca atgcgctctg acggaaaccg ccgtttgtga ccctggatct   9120
tccgtgttgc cgcaaagtga tgagcgcacg ccgcaagtaa gatcttcacc gcttcggcaa   9180
acaagtctcg gcgagatct tctccgccat actcatgatc gatcttgccg cagaatccca   9240
gcatcgcctt gatgtcgcca accaaagctg catcgtgcca atgctggggc cgcctcgcag   9300
ggttgtaact gagcgcgcgg cgatcgcgat cgccaggacg gtccgccatt ctggagcagg   9360
tcgtgtcagg tctgggatgg ctaccagtaa aaatgtaacg actggataaa ggaataaatg   9420
aatgaataag tacaccatca acgacattac gcgcgcatcg gcggttttg ccatactggc   9480
ggtcgatcag caagccatgc cgcaatgttt accacagctg gggcacctgc tcggtagccg   9540
tgggcacaac gatttcaaag ttaacactgc aaggccctct cgccttgtcc tcggcgattc   9600
```

-continued

```
tggtagatca gcaattcgcc accgccaggt ggttgagcaa acgcgttata gcaggacgcg      9660
ccatgattgt catgccgatg agttcattct acagcagcag tattccggtc gatagcatgg      9720
tgtcgaccgc aaaatcaatc gctacagatc aaacaagacg gtggcaagcg gcaaaactgc     9780
tggtgctgtg gcgtgatgaa gatgcgcagc agcgtctgga tatggtgaag agttcggcga      9840
actgtgccac tcacacggtg ttgagccagt cattccgccc accgcgtcgt ggcgataaat      9900
tcgatcgcga acaagcgatc atcgataccg ccagagctgg gcgacggtgg cgctgacctc      9960
tcaaagttga aatgccgctt tatggcaggt ccgcaacaga acttctgctt cacaacgtca     10020
gaccgagcca catcaatatg ccatgcgggt gatctctctt ccggtgtctc gtaagctgtt     10080
cccgcattgc cgtacgcgtg gcaatgacgg cgggcgcatc ggacctggca ggccgtgcgg     10140
tctgggcatc ggtcgtcggt ttaccagaca acgagctgat gctgcgtgac gtttgcaccg     10200
aagtacaaca acagcgacat cgtcagcaaa ccaatggcta aacgccgcta tgaatgagga     10260
taaagatggt ttaacaccta agcttacaac cgttggctgg aacggaaacc gaccatcttt     10320
gattttggta aaaattccgt agtgccgact ggtttggctg gttaggcaat aaaggcaaat     10380
caaagagatg ggcaccatct gtggatcacc gctcattgcg tttattccgt tgccacggcg     10440
tgggtcgacc tggcgcttac tcgttggttg atcacggtat caagccatga gcgtgataaa     10500
tatggcggct gagccatgcc tgcacgtgaa tgacggggcg tggtggatgc ctcgagcaga     10560
tatcaacgct aacagcatgc cagcacgggt gcctgccagc gccgtcacgg cagattttcc     10620
aggcgctcgt tacaccattg aaattatcca gaaatatttc tgaacgaaga aggcagatgt     10680
gctggagtcc tgggacgaag ccttccagca aaaccgaaga gtaccgcgac ggcaatgcca     10740
tatgcacgcg gtggaaactt ctcttgattg tttatgacgt cactcacgac aaaaatgagc     10800
tggatcgcgc gattcgcgtg gcttccccgc gatatccggc aatcgccgaa ataatcatta     10860
tcgcgttaac gaacacttcg atacccgtgg aatccgctgc cggattacaa caaagatcgc     10920
cggcacgtcg cttccgcgcg ttcgggtaca ccaggccact ggatcgaatg gggccgttta     10980
atgctgcaca tcatgctgcc tggaagcccg ttgcgaacaa ccagcgtaac gctgaagata     11040
ccaaggtctg tttaacgcca ccgtgcgcga tgcctgggca cccgatgcg cggacgggat     11100 tgcgacatac cgttgactgg gaaggaaaac cggtggtccg cgaacgatgt acgttggcct     11160
atcaagcaat ggtacggcct acgcgctcca ccgtcactgg cgatcgccag tatgaaaccc     11220
tggtatcaaa catggtgggg tgcattgagt acctgatgga ctatgaaaat ggttcctggt     11280
ggcggagctg gatgcagtta atggtcctac aaagtctggg acgctaaaca ggatattatc     11340
acctgctgca ttgcctgagt gatcccacgt atcccgttag cgcccggcat gctccagcag     11400
tttgcagcag attactggat aataatgcga aataactgat ctgaaaatag gtgcgggttt     11460
cctctaaccc tctccccaaa ggggcgaggg gacgtccggt gcagaaggtt aaacgcaagc     11520
agacgccgaa gatagagcat tgagcaagga acactctcgt ttggaacatc tggcaaacgc     11580
gaagcagacg ccagcaatac gtaac                                          11605
```

<210> SEQ ID NO 12
<211> LENGTH: 61
<212> TYPE: DNA
<213> ORGANISM: Artificial Sequence
<220> FEATURE:
<223> OTHER INFORMATION: Synthetic
<220> FEATURE:
<221> NAME/KEY: misc_binding
<222> LOCATION: (1)..(1)
<223> OTHER INFORMATION: nucleotides preceded by 1x 5SpC3 and 29x iSpC3

```
<220> FEATURE:
<221> NAME/KEY: misc_binding
<222> LOCATION: (33)..(34)
<223> OTHER INFORMATION: Synthetic

<400> SEQUENCE: 12
ggcgtctgct tgggtgttta acctttttt tttaatgtac ttcgttcagt tacgtattgc    60
t                                                                   61

<210> SEQ ID NO 13
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(1)
<223> OTHER INFORMATION: 5BNA-G
<220> FEATURE:
<221> NAME/KEY: modified_base
<222> LOCATION: (2)..(2)
<223> OTHER INFORMATION: iBNA-G
<220> FEATURE:
<221> NAME/KEY: modified_base
<222> LOCATION: (3)..(3)
<223> OTHER INFORMATION: iBNA-T
<220> FEATURE:
<221> NAME/KEY: modified_base
<222> LOCATION: (4)..(4)
<223> OTHER INFORMATION: iBNA-T
<220> FEATURE:
<221> NAME/KEY: modified_base
<222> LOCATION: (5)..(5)
<223> OTHER INFORMATION: iBNA-A

<400> SEQUENCE: 13
ggttaaacac ccaagcagac gcctaagtca gagaggttcc                         40

<210> SEQ ID NO 14
<211> LENGTH: 45
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (23)..(23)
<223> OTHER INFORMATION: iBNA-A
<220> FEATURE:
<221> NAME/KEY: modified_base
<222> LOCATION: (24)..(24)
<223> OTHER INFORMATION: iBNA-meC
<220> FEATURE:
<221> NAME/KEY: modified_base
<222> LOCATION: (25)..(25)
<223> OTHER INFORMATION: iBNA-A
<220> FEATURE:
<221> NAME/KEY: modified_base
<222> LOCATION: (26)..(26)
<223> OTHER INFORMATION: iBNA-T
<220> FEATURE:
<221> NAME/KEY: modified_base
<222> LOCATION: (27)..(27)
<223> OTHER INFORMATION: iBNA-T

<400> SEQUENCE: 14
gcaatacgta actgaacgaa gtacattttt gaggcgagcg gtcaa                   45

<210> SEQ ID NO 15
<211> LENGTH: 41
<212> TYPE: DNA
```

```
<213> ORGANISM: Artificial Sequence
<220> FEATURE:
<223> OTHER INFORMATION: Synthetic

<400> SEQUENCE: 15
ggttaaacac ccaagcagac gcctttgagg cgagcggtca a                    41

<210> SEQ ID NO 16
<211> LENGTH: 47
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (23)..(23)
<223> OTHER INFORMATION: iBNA-A
<220> FEATURE:
<221> NAME/KEY: modified_base
<222> LOCATION: (24)..(24)
<223> OTHER INFORMATION: iBNA-meC
<220> FEATURE:
<221> NAME/KEY: modified_base
<222> LOCATION: (25)..(25)
<223> OTHER INFORMATION: iBNA-A
<220> FEATURE:
<221> NAME/KEY: modified_base
<222> LOCATION: (26)..(26)
<223> OTHER INFORMATION: iBNA-T
<220> FEATURE:
<221> NAME/KEY: modified_base
<222> LOCATION: (27)..(27)
<223> OTHER INFORMATION: iBNA-T

<400> SEQUENCE: 16
gcaatacgta actgaacgaa gtacattttt taagtcagag aggttcc              47

<210> SEQ ID NO 17
<211> LENGTH: 80
<212> TYPE: DNA
<213> ORGANISM: Artificial Sequence
<220> FEATURE:
<223> OTHER INFORMATION: Synthetic
<220> FEATURE:
<221> NAME/KEY: misc_binding
<222> LOCATION: (44)..(45)
<223> OTHER INFORMATION: nucleotides separated by 4x iSp18

<400> SEQUENCE: 17
taacgaggtt gtttctatct cggcgtctgc ttgggtgttt aaccttttg tcagagaggt    60 tccaagtcag agaggttcct                                              80

<210> SEQ ID NO 18
<211> LENGTH: 123
<212> TYPE: DNA
<213> ORGANISM: Artificial Sequence
<220> FEATURE:
<223> OTHER INFORMATION: Synthetic
<220> FEATURE:
<221> NAME/KEY: misc_binding
<222> LOCATION: (35)..(36)
<223> OTHER INFORMATION: nucleotides separated by 4x iSp18
<220> FEATURE:
<221> NAME/KEY: misc_binding
<222> LOCATION: (98)..(99)
<223> OTHER INFORMATION: nucleotides separated by 4x iSp18

<400> SEQUENCE: 18
ggaacctctc tgacttggaa cctctctgac aaaaaggtta acacccaag cagacgccga    60 gatagaaaca acccatcaga ttgtgtttgt tagtcgctag cgactaacaa acacaatctg   120
``` atg                                                                    123

<210> SEQ ID NO 19
<211> LENGTH: 70
<212> TYPE: DNA
<213> ORGANISM: Artificial Sequence
<220> FEATURE:
<223> OTHER INFORMATION: Synthetic
<220> FEATURE:
<221> NAME/KEY: misc_binding
<222> LOCATION: (15)..(16)
<223> OTHER INFORMATION: nucleotides separated by 15x iSpC3
<220> FEATURE:
<221> NAME/KEY: misc_binding
<222> LOCATION: (48)..(49)
<223> OTHER INFORMATION: nucleotides separated by 1x iSp18

<400> SEQUENCE: 19
ggttgtttct atctcggcgt ctgcttgggt gtttaacctt ttttttttaa tgtacttcgt    60
tcagttacgt                                                            70

<210> SEQ ID NO 20
<211> LENGTH: 41
<212> TYPE: DNA
<213> ORGANISM: Artificial Sequence
<220> FEATURE:
<223> OTHER INFORMATION: Synthetic

<400> SEQUENCE: 20
ggttaaacac ccaagcagac gcctttgagg cgagcggtca a                         41

<210> SEQ ID NO 21
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (24)..(24)
<223> OTHER INFORMATION: iBNA-A
<220> FEATURE:
<221> NAME/KEY: modified_base
<222> LOCATION: (25)..(25)
<223> OTHER INFORMATION: iBNA-meC
<220> FEATURE:
<221> NAME/KEY: modified_base
<222> LOCATION: (26)..(26)
<223> OTHER INFORMATION: iBNA-A
<220> FEATURE:
<221> NAME/KEY: modified_base
<222> LOCATION: (27)..(27)
<223> OTHER INFORMATION: iBNA-T
<220> FEATURE:
<221> NAME/KEY: modified_base
<222> LOCATION: (28)..(28)
<223> OTHER INFORMATION: iBNA-T

<400> SEQUENCE: 21
tcgttaacgt aactgaacga agtacatt                                        28

<210> SEQ ID NO 22
<211> LENGTH: 71
<212> TYPE: DNA
<213> ORGANISM: Artificial Sequence
<220> FEATURE:
<223> OTHER INFORMATION: Synthetic
<220> FEATURE:
<221> NAME/KEY: misc_binding
<222> LOCATION: (1)..(1)

```
<223> OTHER INFORMATION: nucleotides preceded by 1 x 5SpC3 and 14 x
      iSpC3
<220> FEATURE:
<221> NAME/KEY: misc_binding
<222> LOCATION: (16)..(17)
<223> OTHER INFORMATION: nucleotides separated by 15 x iSpC3
<220> FEATURE:
<221> NAME/KEY: misc_binding
<222> LOCATION: (49)..(50)
<223> OTHER INFORMATION: nucleotides separated by 1 x iSp18

<400> SEQUENCE: 22
ttgtcagaga ggttccggcg tctgcttggg tgtttaacct ttttttttta atgtacttcg    60
ttcagttacg t                                                        71

<210> SEQ ID NO 23
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (18)..(18)
<223> OTHER INFORMATION: iBNA-A
<220> FEATURE:
<221> NAME/KEY: modified_base
<222> LOCATION: (19)..(19)
<223> OTHER INFORMATION: iBNA-meC
<220> FEATURE:
<221> NAME/KEY: modified_base
<222> LOCATION: (20)..(20)
<223> OTHER INFORMATION: iBNA-A
<220> FEATURE:
<221> NAME/KEY: modified_base
<222> LOCATION: (21)..(21)
<223> OTHER INFORMATION: iBNA-T
<220> FEATURE:
<221> NAME/KEY: modified_base
<222> LOCATION: (22)..(22)
<223> OTHER INFORMATION: iBNA-T

<400> SEQUENCE: 23
acgtaactga acgaagtaca tt                                            22

<210> SEQ ID NO 24
<211> LENGTH: 100
<212> TYPE: DNA
<213> ORGANISM: Artificial Sequence
<220> FEATURE:
<223> OTHER INFORMATION: Synthetic

<400> SEQUENCE: 24
ttgtcagaga ggttcctttt tttttttttt tttttttttt ttttggttgt              60
ttctgttggt gctgatattg ctttttttgac cgctcgcctc                       100

<210> SEQ ID NO 25
<211> LENGTH: 31
<212> TYPE: DNA
<213> ORGANISM: Artificial Sequence
<220> FEATURE:
<223> OTHER INFORMATION: Synthetic
<220> FEATURE:
<221> NAME/KEY: misc_binding
<222> LOCATION: (29)..(30)
<223> OTHER INFORMATION: nucleotides separated by 6x iSp18

<400> SEQUENCE: 25
gcaatatcag caccaacaga aacaaccttt t                                  31
```

<210> SEQ ID NO 26
<211> LENGTH: 3587
<212> TYPE: DNA
<213> ORGANISM: Artificial Sequence
<220> FEATURE:
<223> OTHER INFORMATION: Synthetic

<400> SEQUENCE: 26

| | | | | | |
|---|---|---|---|---|---|
| gccatcagat | tgtgtttgtt | agtcgctgcc | atcagattgt | gtttgttagt | cgcttttttt | 60 |
| ttttggaatt | ttttttttgg | aattttttttt | ttgcgctaac | aacctcctgc | cgttttgccc | 120 |
| gtgcatatcg | gtcacgaaca | aatctgatta | ctaaacacag | tagcctggat | tgttctatc | 180 |
| agtaatcgac | cttattccta | attaaataga | gcaaatcccc | ttattggggg | taagacatga | 240 |
| agatgccaga | aaacatgac | ctgttggccg | ccattctcgc | ggcaaaggaa | caaggcatcg | 300 |
| gggcaatcct | tgcgtttgca | atggcgtacc | ttcgcggcag | atataatggc | ggtgcgttta | 360 |
| caaaaacagt | aatcgacgca | acgatgtgcg | ccattatcgc | ctagttcatt | cgtgaccttc | 420 |
| tcgacttcgc | cggactaagt | agcaatctcg | cttatataac | gagcgtgttt | atcggctaca | 480 |
| tcggtactga | ctcgattggt | tcgcttatca | aacgcttcgc | tgctaaaaaa | gccggagtag | 540 |
| aagatggtag | aaatcaataa | tcaacgtaag | gcgttcctcg | atatgctggc | gtggtcggag | 600 |
| ggaactgata | acggacgtca | gaaaaccaga | atcatggtt | atgacgtcat | tgtaggcgga | 660 |
| gagctattta | ctgattactc | cgatcaccct | cgcaaacttg | tcacgctaaa | cccaaaactc | 720 |
| aaatcaacag | gcgccggacg | ctaccagctt | ctttcccgtt | ggtgggatgc | ctaccgcaag | 780 |
| cagcttggcc | tgaaagactt | ctctccgaaa | agtcaggacg | ctgtggcatt | gcagcagatt | 840 |
| aaggagcgtg | gcgctttacc | tatgattgat | cgtggtgata | ccgtcaggc | aatcgaccgt | 900 |
| tgcagcaata | tctgggcttc | actgccgggc | gctggttatg | gtcagttcga | gcataaggct | 960 |
| gacagcctga | ttgcaaaatt | caaagaagcg | ggcggaacgg | tcagagagat | tgatgtatga | 1020 |
| gcagagtcac | cgcgattatc | tccgctctgg | ttatctgcat | catcgtctgc | ctgtcatggg | 1080 |
| ctgttaatca | ttaccgtgat | aacgccatta | cctacaaagc | ccagcgcgac | aaaaatgcca | 1140 |
| gagaactgaa | gctggcgaac | gcggcaatta | ctgacatgca | gatgcgtcag | cgtgatgttg | 1200 |
| ctgcgctcga | tgcaaaatac | acgaaggagt | tagctgatgc | taaagctgaa | aatgatgctc | 1260 |
| tgcgtgatga | tgttgccgct | ggtcgtcgtc | ggttgcacat | caaagcagtc | tgtcagtcag | 1320 |
| tgcgtgaagc | caccaccgcc | tccggcgtgg | ataatgcagc | ctcccccga | ctggcagaca | 1380 |
| ccgctgaacg | ggattatttc | accctcagag | agaggctgat | cactatgcaa | aaacaactgg | 1440 |
| aaggaaccca | gaagtatatt | aatgagcagt | gcagatagag | ttgcccatat | cgatgggcaa | 1500 |
| ctcatgcaat | tattgtgagc | aatacacacg | cgcttccagc | ggagtataaa | tgcctaaagt | 1560 |
| aataaaaccg | agcaatccat | ttacgaatgt | ttgctgggtt | tctgttttaa | caacattttc | 1620 |
| tgcgccgcca | caaatttgg | ctgcatcgac | agtttctct | tgcccaattc | cagaaacgaa | 1680 |
| gaaatgatgg | gtgatggttt | cctttggtgc | tactgctgcc | ggtttgtttt | gaacagtaaa | 1740 |
| cgtctgttga | gcacatcctg | taataagcag | ggccagcgca | gtagcgagta | gcattttttt | 1800 |
| catggtgtta | ttcccgatgc | tttttgaagt | tcgcagaatc | gtatgtgtag | aaaattaaac | 1860 |
| aaaccctaaa | caatgagttg | aaatttcata | ttgttaatat | ttattaatgt | atgtcaggtg | 1920 |
| cgatgaatcg | tcattgtatt | cccggattaa | ctatgtccac | agccctgacg | ggaacttct | 1980 |
| ctgcgggagt | gtccgggaat | aattaaaacg | atgcacacag | ggtttagcgc | gtacacgtat | 2040 |
| tgcattatgc | caacgccccg | gtgctgacac | ggaagaaacc | ggacgttatg | atttagcgtg | 2100 |

```
gaaagatttg tgtagtgttc tgaatgctct cagtaaatag taatgaatta tcaaaggtat    2160
agtaatatct tttatgttca tggatatttg taacccatcg gaaaactcct gctttagcaa    2220
gattttccct gtattgctga aatgtgattt ctcttgattt caacctatca taggacgttt    2280
ctataagatg cgtgtttctt gagaatttaa catttacaac cttttttaagt ccttttatta   2340 acacggtgtt atcgttttct aacacgatgt gaatattatc tgtggctaga tagtaaatat    2400
aatgtgagac gttgtgacgt tttagttcag aataaaacaa ttcacagtct aaatcttttc    2460
gcacttgatc gaatatttct ttaaaaatgg caacctgagc cattggtaaa accttccatg    2520
tgatacgagg gcgcgtagtt tgcattatcg tttttatcgt ttcaatctgg tctgacctcc    2580
ttgtgttttg ttgatgattt atgtcaaata ttaggaatgt tttcacttaa tagtattggt    2640
tgcgtaacaa agtgcggtcc tgctggcatt ctggagggaa atacaaccga cagatgtatg    2700
taaggccaac gtgctcaaat cttcatacag aaagatttga agtaatattt taaccgctag    2760
atgaagagca agcgcatgga gcgacaaaat gaataaagaa caatctgctg atgatccctc    2820
cgtggatctg attcgtgtaa aaaatatgct taatagcacc atttctatga gttaccctga    2880
tgttgtaatt gcatgtatag aacataaggt gtctctggaa gcattcagag caattgaggc    2940
agcgttggtg aagcacgata ataatatgaa ggattattcc ctggtggttg actgatcacc    3000
ataactgcta atcattcaaa ctatttagtc tgtgacagag ccaacacgca gtctgtcact    3060
gtcaggaaag tggtaaaact gcaactcaat tactgcaatg ccctcgtaat taagtgaatt    3120
tacaatatcg tcctgttcgg agggaagaac gcgggatgtt cattcttcat cacttttaat    3180
tgatgtatat gctctctttt ctgacgttag tctccgacgg caggcttcaa tgacccaggc    3240
tgagaaattc ccggacccctt tttgctcaag agcgatgtta atttgttcaa tcatttggtt   3300
aggaaagcgg atgttgcggg ttgttgttct gcgggttctg ttcttcgttg acatgaggtt    3360
gccccgtatt cagtgtcgct gatttgtatt gtctgaagtt gtttttacgt taagttgatg    3420
cagatcaatt aatacgatac ctgcgtcata attgattatt tgacgtggtt tgatggcctc    3480
cacgcacgtt gtgatatgta gatgataatc attatcactt tacgggtcct ttccggtgaa    3540
aaaaaaggta ccaaaaaaaa catcgtcgtg agtagtgaac cgtaagc                  3587

<210> SEQ ID NO 27
<211> LENGTH: 41
<212> TYPE: DNA
<213> ORGANISM: Artificial Sequence
<220> FEATURE:
<223> OTHER INFORMATION: Synthetic

<400> SEQUENCE: 27
acgtaactga acgaagtaca ttttttgaggc cgagcggtca a                        41

<210> SEQ ID NO 28
<211> LENGTH: 40
<212> TYPE: DNA
<213> ORGANISM: Artificial Sequence
<220> FEATURE:
<223> OTHER INFORMATION: Synthetic

<400> SEQUENCE: 28
ggttaaacac ccaagcagac gcctaagtca gagaggttcc                           40

<210> SEQ ID NO 29
<211> LENGTH: 38
<212> TYPE: DNA
```

```
<213> ORGANISM: Artificial Sequence
<220> FEATURE:
<223> OTHER INFORMATION: Synthetic

<400> SEQUENCE: 29
ggtgctgaag aaagttgtcg gtgtctttgt gttaacct                              38

<210> SEQ ID NO 30
<211> LENGTH: 60
<212> TYPE: DNA
<213> ORGANISM: Artificial Sequence
<220> FEATURE:
<223> OTHER INFORMATION: Synthetic

<400> SEQUENCE: 30
ggttaacaca agacaccga caactttctt cagcaccagc aattaagtca gagaggttcc       60

<210> SEQ ID NO 31
<211> LENGTH: 77
<212> TYPE: DNA
<213> ORGANISM: Artificial Sequence
<220> FEATURE:
<223> OTHER INFORMATION: Synthetic
<220> FEATURE:
<221> NAME/KEY: misc_binding
<222> LOCATION: (23)..(24)
<223> OTHER INFORMATION: nucleotides separated by 4x iSp18

<400> SEQUENCE: 31
ccaatttgtg ggttcgtctg cggttttttgg cgtctgcttg ggtgtttaac caaggcgtct    60
gcttgggtgt ttaacct                                                    77

<210> SEQ ID NO 32
<211> LENGTH: 99
<212> TYPE: DNA
<213> ORGANISM: Artificial Sequence
<220> FEATURE:
<223> OTHER INFORMATION: Synthetic
<220> FEATURE:
<221> NAME/KEY: misc_binding
<222> LOCATION: (53)..(54)
<223> OTHER INFORMATION: nucleotides separated by iSp18

<400> SEQUENCE: 32
ggttaaacac ccaagcagac gccttggtta acacccaag cagacgccaa aaaccgcaga      60
cgaacccaca aattggagca attaagtcag agaggttcc                            99

<210> SEQ ID NO 33
<211> LENGTH: 82
<212> TYPE: DNA
<213> ORGANISM: Artificial Sequence
<220> FEATURE:
<223> OTHER INFORMATION: Synthetic
<220> FEATURE:
<221> NAME/KEY: misc_binding
<222> LOCATION: (53)..(54)
<223> OTHER INFORMATION: nucleotides separated by 4x iSp18

<400> SEQUENCE: 33
ggttaaacac ccaagcagac gccttggtta acacccaag cagacgccaa aaaccgcaga      60
cgaacccaca aattggagca at                                              82

<210> SEQ ID NO 34
<211> LENGTH: 66
<212> TYPE: DNA
<213> ORGANISM: Artificial Sequence
```

```
<220> FEATURE:
<223> OTHER INFORMATION: Synthetic
<220> FEATURE:
<221> NAME/KEY: misc_binding
<222> LOCATION: (23)..(24)
<223> OTHER INFORMATION: nucleotides separated by 4x iSp18

<400> SEQUENCE: 34
ggcgtctgct tgggtgttta acctttttgg tgctgaagaa agttgtcggt gtctttgtgt    60
taacct                                                               66

<210> SEQ ID NO 35
<211> LENGTH: 88
<212> TYPE: DNA
<213> ORGANISM: Artificial Sequence
<220> FEATURE:
<223> OTHER INFORMATION: Synthetic
<220> FEATURE:
<221> NAME/KEY: misc_binding
<222> LOCATION: (42)..(43)
<223> OTHER INFORMATION: nucleotides separated by 4x iSp18

<400> SEQUENCE: 35
ggttaacaca aagacaccga caactttctt cagcaccaaa aaggttaaac acccaagcag    60
acgccagcaa ttaagtcaga gaggttcc                                       88

<210> SEQ ID NO 36
<211> LENGTH: 44
<212> TYPE: DNA
<213> ORGANISM: Artificial Sequence
<220> FEATURE:
<223> OTHER INFORMATION: Synthetic
<220> FEATURE:
<221> NAME/KEY: misc_binding
<222> LOCATION: (15)..(16)
<223> OTHER INFORMATION: nucleotides separated by 4x iSp18

<400> SEQUENCE: 36
ccaatttgtg gttccttttt ggcgtctgct tgggtgttta acct                     44

<210> SEQ ID NO 37
<211> LENGTH: 49
<212> TYPE: DNA
<213> ORGANISM: Artificial Sequence
<220> FEATURE:
<223> OTHER INFORMATION: Synthetic
<220> FEATURE:
<221> NAME/KEY: misc_binding
<222> LOCATION: (28)..(29)
<223> OTHER INFORMATION: nucleotides separated by 4x iSp18

<400> SEQUENCE: 37
ggttaaacac ccaagcagac gccaaaaagg aaccacaaat tggagcaat                49

<210> SEQ ID NO 38
<211> LENGTH: 69
<212> TYPE: DNA
<213> ORGANISM: Artificial Sequence
<220> FEATURE:
<223> OTHER INFORMATION: Synthetic
<220> FEATURE:
<221> NAME/KEY: misc_binding
<222> LOCATION: (15)..(16)
<223> OTHER INFORMATION: nucleotides separated by 4x iSp18

<400> SEQUENCE: 38
ccaatttgtg gttccttttt ggcgtctgct tgggtgttta accaaggcgt ctgcttgggt    60
``` gtttaacct                                                              69

<210> SEQ ID NO 39
<211> LENGTH: 74
<212> TYPE: DNA
<213> ORGANISM: Artificial Sequence
<220> FEATURE:
<223> OTHER INFORMATION: Synthetic
<220> FEATURE:
<221> NAME/KEY: misc_binding
<222> LOCATION: (53)..(54)
<223> OTHER INFORMATION: nucleotides separeted by 4x iSp18

<400> SEQUENCE: 39
ggttaaacac ccaagcagac gccttggtta aacacccaag cagacgccaa aaaggaacca      60
caaattggag caat                                                        74

<210> SEQ ID NO 40
<211> LENGTH: 61
<212> TYPE: DNA
<213> ORGANISM: Artificial Sequence
<220> FEATURE:
<223> OTHER INFORMATION: Synthetic
<220> FEATURE:
<221> NAME/KEY: misc_binding
<222> LOCATION: (23)..(24)
<223> OTHER INFORMATION: nucleotides separated by 1x iSp18

<400> SEQUENCE: 40
ggcgtctgct tgggtgttta accttttttgt cagagaggtt ccaagtcaga gaggttccaa     60
t                                                                      61

<210> SEQ ID NO 41
<211> LENGTH: 66
<212> TYPE: DNA
<213> ORGANISM: Artificial Sequence
<220> FEATURE:
<223> OTHER INFORMATION: Synthetic
<220> FEATURE:
<221> NAME/KEY: misc_binding
<222> LOCATION: (37)..(38)
<223> OTHER INFORMATION: nucleotides separated by 1x iSp18

<400> SEQUENCE: 41
ttggaacctc tctgacttgg aacctctctg acaaaaaggt taaacaccca agcagacgcc      60
agcaat                                                                 66

<210> SEQ ID NO 42
<211> LENGTH: 45
<212> TYPE: DNA
<213> ORGANISM: Artificial Sequence
<220> FEATURE:
<223> OTHER INFORMATION: Synthetic
<220> FEATURE:
<221> NAME/KEY: misc_binding
<222> LOCATION: (23)..(24)
<223> OTHER INFORMATION: nucleotides separated by 4x iSp18

<400> SEQUENCE: 42
ggcgtctgct tgggtgttta accttttttgt cagagaggtt ccaat                     45

<210> SEQ ID NO 43
<211> LENGTH: 50
<212> TYPE: DNA
<213> ORGANISM: Artificial Sequence
<220> FEATURE:
<223> OTHER INFORMATION: Synthetic

```
<220> FEATURE:
<221> NAME/KEY: misc_binding
<222> LOCATION: (21)..(22)
<223> OTHER INFORMATION: nucleotides separated by 4x iSp18

<400> SEQUENCE: 43
ttggaacctc tctgacaaaa aggttaaaca cccaagcaga cgccagcaat            50

<210> SEQ ID NO 44
<211> LENGTH: 40
<212> TYPE: DNA
<213> ORGANISM: Artificial Sequence
<220> FEATURE:
<223> OTHER INFORMATION: Synthetic

<400> SEQUENCE: 44
ggttaaacac ccaagcagac gcctaagtca gagaggttcc                       40

<210> SEQ ID NO 45
<211> LENGTH: 14
<212> TYPE: DNA
<213> ORGANISM: Artificial Sequence
<220> FEATURE:
<223> OTHER INFORMATION: Synthetic

<400> SEQUENCE: 45
ggaacctctc tgac                                                   14

<210> SEQ ID NO 46
<211> LENGTH: 47
<212> TYPE: DNA
<213> ORGANISM: Artificial Sequence
<220> FEATURE:
<223> OTHER INFORMATION: Synthetic

<400> SEQUENCE: 46
gcaatacgta actgaacgaa gtacattttt taagtcagag aggttcc               47

<210> SEQ ID NO 47
<211> LENGTH: 59
<212> TYPE: DNA
<213> ORGANISM: Artificial Sequence
<220> FEATURE:
<223> OTHER INFORMATION: Synthetic

<400> SEQUENCE: 47
ggcgtctgct tgggtgttta accttttgt cagagaggtt ccaagtcaga gaggttcct   59

<210> SEQ ID NO 48
<211> LENGTH: 64
<212> TYPE: DNA
<213> ORGANISM: Artificial Sequence
<220> FEATURE:
<223> OTHER INFORMATION: Synthetic

<400> SEQUENCE: 48
ggaacctctc tgacttggaa cctctctgac aaaaggtta aacacccaag cagacgccag  60
caat                                                              64

<210> SEQ ID NO 49
<211> LENGTH: 44
<212> TYPE: DNA
<213> ORGANISM: Artificial Sequence
<220> FEATURE:
<223> OTHER INFORMATION: Synthetic
```

-continued

<400> SEQUENCE: 49
gcaatacgta acgtaacgaa gtacatttaa gtcagagagg ttcc    44

<210> SEQ ID NO 50
<211> LENGTH: 39
<212> TYPE: DNA
<213> ORGANISM: Artificial Sequence
<220> FEATURE:
<223> OTHER INFORMATION: Synthetic

<400> SEQUENCE: 50
acgtaacgta acgaagtaca tttaagtcag agaggttcc    39

<210> SEQ ID NO 51
<211> LENGTH: 439
<212> TYPE: PRT
<213> ORGANISM: enterobacteria phage T4

<400> SEQUENCE: 51

Met Thr Phe Asp Asp Leu Thr Glu Gly Gln Lys Asn Ala Phe Asn Ile
1               5                   10                  15

Val Met Lys Ala Ile Lys Glu Lys Lys His Val Thr Ile Asn Gly
        20                  25                  30

Pro Ala Gly Thr Gly Lys Thr Thr Leu Thr Lys Phe Ile Ile Glu Ala
        35                  40                  45

Leu Ile Ser Thr Gly Glu Thr Gly Ile Ile Leu Ala Ala Pro Thr His
        50                  55                  60

Ala Ala Lys Lys Ile Leu Ser Lys Leu Ser Gly Lys Glu Ala Ser Thr
65              70                  75                  80

Ile His Ser Ile Leu Lys Ile Asn Pro Val Thr Tyr Glu Glu Asn Val
                85                  90                  95

Leu Phe Glu Gln Lys Glu Val Pro Asp Leu Ala Lys Cys Arg Val Leu
            100                 105                 110

Ile Cys Asp Glu Val Ser Met Tyr Asp Arg Lys Leu Phe Lys Ile Leu
        115                 120                 125

Leu Ser Thr Ile Pro Pro Trp Cys Thr Ile Ile Gly Ile Gly Asp Asn
    130                 135                 140

Lys Gln Ile Arg Pro Val Asp Pro Gly Glu Asn Thr Ala Tyr Ile Ser
145                 150                 155                 160

Pro Phe Phe Thr His Lys Asp Phe Tyr Gln Cys Glu Leu Thr Glu Val
                165                 170                 175

Lys Arg Ser Asn Ala Pro Ile Ile Asp Val Ala Thr Asp Val Arg Asn
            180                 185                 190

Gly Lys Trp Ile Tyr Asp Lys Val Val Asp Gly His Gly Val Arg Gly
        195                 200                 205

Phe Thr Gly Asp Thr Ala Leu Arg Asp Phe Met Val Asn Tyr Phe Ser
    210                 215                 220

Ile Val Lys Ser Leu Asp Asp Leu Phe Glu Asn Arg Val Met Ala Phe
225                 230                 235                 240

Thr Asn Lys Ser Val Asp Lys Leu Asn Ser Ile Ile Arg Lys Lys Ile
                245                 250                 255

Phe Glu Thr Asp Lys Asp Phe Ile Val Gly Glu Ile Val Met Gln
            260                 265                 270

Glu Pro Leu Phe Lys Thr Tyr Lys Ile Asp Gly Lys Pro Val Ser Glu
        275                 280                 285

Ile Ile Phe Asn Asn Gly Gln Leu Val Arg Ile Ile Glu Ala Glu Tyr

```
                290                 295                 300
Thr Ser Thr Phe Val Lys Ala Arg Gly Val Pro Gly Glu Tyr Leu Ile
305                 310                 315                 320

Arg His Trp Asp Leu Thr Val Glu Thr Tyr Gly Asp Asp Glu Tyr Tyr
                325                 330                 335

Arg Glu Lys Ile Lys Ile Ile Ser Ser Asp Glu Glu Leu Tyr Lys Phe
            340                 345                 350

Asn Leu Phe Leu Gly Lys Thr Ala Glu Thr Tyr Lys Asn Trp Asn Lys
        355                 360                 365

Gly Gly Lys Ala Pro Trp Ser Asp Phe Trp Asp Ala Lys Ser Gln Phe
    370                 375                 380

Ser Lys Val Lys Ala Leu Pro Ala Ser Thr Phe His Lys Ala Gln Gly
385                 390                 395                 400

Met Ser Val Asp Arg Ala Phe Ile Tyr Thr Pro Cys Ile His Tyr Ala
                405                 410                 415

Asp Val Glu Leu Ala Gln Gln Leu Leu Tyr Val Gly Val Thr Arg Gly
            420                 425                 430

Arg Tyr Asp Val Phe Tyr Val
        435
```

<210> SEQ ID NO 52
<211> LENGTH: 69
<212> TYPE: DNA
<213> ORGANISM: Artificial Sequence
<220> FEATURE:
<223> OTHER INFORMATION: Synthetic

<400> SEQUENCE: 52
ccaatttgtg gttccttttt ggcgtctgct tgggtgttta accaaggcgt ctgcttgggt    60
gtttaacct                                                            69

<210> SEQ ID NO 53
<211> LENGTH: 74
<212> TYPE: DNA
<213> ORGANISM: Artificial Sequence
<220> FEATURE:
<223> OTHER INFORMATION: Synthetic

<400> SEQUENCE: 53
ggttaaacac ccaagcagac gccttggtta acacccaag cagacgccaa aaaggaacca    60
caaattggag caat                                                      74

<210> SEQ ID NO 54
<211> LENGTH: 49
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (28)..(29)
<223> OTHER INFORMATION: nucleotides separated by 4x iSp18

<400> SEQUENCE: 54
ggttaaacac ccaagcagac gccaaacagg aaccacaaat tggagcaat               49

<210> SEQ ID NO 55
<211> LENGTH: 69
<212> TYPE: DNA
<213> ORGANISM: Artificial Sequence
<220> FEATURE:

<223> OTHER INFORMATION: Synthetic
<220> FEATURE:
<221> NAME/KEY: misc_feature
<222> LOCATION: (54)..(55)
<223> OTHER INFORMATION: nucleotides separated by 4x iSp18

<400> SEQUENCE: 55
ccaatttgtg gttcgttttt ggcgtctgct tgggtgttta accaaggcgt ctgcttgggt    60
gtttaacct    69

<210> SEQ ID NO 56
<211> LENGTH: 44
<212> TYPE: DNA
<213> ORGANISM: Artificial Sequence
<220> FEATURE:
<223> OTHER INFORMATION: Synthetic

<400> SEQUENCE: 56
gcaatacgta actgaacgaa gtacatttaa gtcagagagg ttcc    44

<210> SEQ ID NO 57
<211> LENGTH: 39
<212> TYPE: DNA
<213> ORGANISM: Artificial Sequence
<220> FEATURE:
<223> OTHER INFORMATION: Synthetic

<400> SEQUENCE: 57
acgtaactga acgaagtaca tttaagtcag agaggttcc    39

<210> SEQ ID NO 58
<211> LENGTH: 4
<212> TYPE: PRT
<213> ORGANISM: Artificial Sequence
<220> FEATURE:
<223> OTHER INFORMATION: Synthetic

<400> SEQUENCE: 58

Ser Gly Ser Gly
1

<210> SEQ ID NO 59
<211> LENGTH: 6
<212> TYPE: PRT
<213> ORGANISM: Artificial Sequence
<220> FEATURE:
<223> OTHER INFORMATION: Synthetic

<400> SEQUENCE: 59

Ser Gly Ser Gly Ser Gly
1               5

<210> SEQ ID NO 60
<211> LENGTH: 8
<212> TYPE: PRT
<213> ORGANISM: Artificial Sequence
<220> FEATURE:
<223> OTHER INFORMATION: Synthetic

<400> SEQUENCE: 60

Ser Gly Ser Gly Ser Gly Ser Gly
1               5

<210> SEQ ID NO 61
<211> LENGTH: 10
<212> TYPE: PRT

```
<213> ORGANISM: Artificial Sequence
<220> FEATURE:
<223> OTHER INFORMATION: Synthetic

<400> SEQUENCE: 61

Ser Gly Ser Gly Ser Gly Ser Gly Ser Gly
1               5                   10

<210> SEQ ID NO 62
<211> LENGTH: 16
<212> TYPE: PRT
<213> ORGANISM: Artificial Sequence
<220> FEATURE:
<223> OTHER INFORMATION: Synthetic

<400> SEQUENCE: 62

Ser Gly Ser Gly Ser Gly Ser Gly Ser Gly Ser Gly Ser Gly Ser Gly
1               5                   10                  15

<210> SEQ ID NO 63
<211> LENGTH: 12
<212> TYPE: PRT
<213> ORGANISM: Artificial Sequence
<220> FEATURE:
<223> OTHER INFORMATION: Synthetic

<400> SEQUENCE: 63

Pro Pro Pro Pro Pro Pro Pro Pro Pro Pro Pro Pro
1               5                   10
```

METHOD OF CHARACTERIZING A POLYNUCLEOTIDE

RELATED APPLICATIONS

This application is a national stage filing under 35 U.S.C. § 371 of international application number PCT/GB2019/051571, filed Jun. 6, 2019, which claims the benefit of Great Britain application number GB 1809323.7, filed Jun. 6, 2018, the entire contents of each of which are herein incorporated by reference.

REFERENCE TO A SEQUENCE LISTING SUBMITTED AS A TEXT FILE VIA EFS-WEB

This application contains a Sequence Listing which has been submitted in ASCII format via EFS-Web and is hereby incorporated by reference in its entirety. Said ASCII copy, created on Jun. 13, 2023, is named 0036670107US00-SUBSEQ-CBD and is 58,964 bytes in size.

FIELD

Provided herein are methods of characterizing a polynucleotide analyte using a detector such as a nanopore and an enzyme. Compositions and systems including, e.g., adaptors for attachment to a double-stranded polynucleotide, and tag-modified nanopores, which can be used in the methods are also provided. In some embodiments, methods of sequencing one or more target polynucleotides using a transmembrane pore are provided herein.

BACKGROUND

There is currently a need for rapid and cheap polynucleotide (e.g. DNA or RNA) sequencing and identification technologies across a wide range of applications.

Transmembrane pores (e.g., nanopores) have been used to identify small molecules or folded proteins and to monitor chemical or enzymatic reactions at the single molecule level. Transmembrane pores (e.g., nanopores) have great potential as direct, electrical biosensors for polymers and a variety of small molecules. In particular, recent focus has been given to nanopores as a potential DNA sequencing technology and biomarker recognition.

Ion flow through the nanopore may be measured under a potential difference applied across the nanopore. Interaction of an analyte with the nanopore can give rise to a characteristic change in ion flow and measurement of the resultant signal can be used to characterize the analyte. For example the measured signal may be current and may for example be used to determine the sequence of a polynucleotide. A polynucleotide strand may be caused to translocate through the pore and the identities, such as the sequence, of the nucleotides may be derived from the measured signal. Such sequencing methods are disclosed for example in WO0142782, WO2016034591, WO2013041878, WO2014064443 and WO2013153359.

Methods for sequencing a double-stranded polynucleotide have been developed, e.g., involving translocation of both the template and complement strands connected by a hairpin. Strand sequencing typically involves the use of a polynucleotide binding protein such as a helicase to control the movement of the polynucleotide through the nanopore. Such methods are disclosed for example in WO2013057495. The dimensions of a nanopore may be such that it only permits translocation of single stranded polynucleotides. Double stranded polynucleotides may be determined by separating the strands to provide single stranded polynucleotides prior to translocation through the nanopore. A polynucleotide binding protein such as a helicase may be used to simultaneously separate the double stranded polynucleotide and control the rate of translocation of the resultant single strand through the nanopore. The two strands of the double stranded polynucleotide may be linked by a bridging moiety such as a hairpin loop and methods for preparing such a construct are described for example in WO2013057495. This ensures that translocation of the forward (template) strand is followed by translocation of the reverse (complement) strand. Measurement of both strands in this way is advantageous as information from the two complementary linked strands can be combined and used to provide higher confidence observations than may be achieved from measurement of template strands only. However, preparation of such a hairpin linked polynucleotide can increase sample preparation time and result in a loss of valuable analyte. Further, translocation of a hairpin linked template and complement polynucleotide strands through a nanopore can give rise to rehybridization of the strands on the other (trans) side of the nanopore. This can alter the rate of translocation giving rise to a lower sequencing accuracy. Further, due to the differences in current-time data for the template and complement strands, two algorithms are used for computation, which makes the computation more complex and intensive.

Accordingly, there is a need for improved methods of characterizing an analyte, e.g., a double stranded polynucleotide, with increased accuracy and higher efficiency/throughput.

SUMMARY

In its broadest aspect, the disclosure relates to any sensing method that uses an enzyme to process a polynucleotide analyte near a sensor/detector. More particularly, the disclosure is concerned with the sequential processing of both strands of a double stranded polynucleotide analyte without the need to covalently link the two strands via a bridging moiety such as a hairpin loop. In the described methods, the first strand of the double stranded polynucleotide analyte is sequenced in close proximity to the detector such that the processing enzyme can function to process the analyte. As the first strand is sequenced the two strands of the double stranded polynucleotide are partially separated and the second strand of the double stranded polynucleotide analyte becomes localized to the detector. In particular the second strand of the double stranded polynucleotide is localised to the detector via a hybridisation tag. After the first strand has been sequenced in close proximity to the detector the second strand is then sequenced in close proximity to the detector. The sequential processing of the two strands of the analyte may be achieved via any method, for example methods that involve direct interaction with a detector such as such as strand sequencing methods or exonuclease methods. Alternatively or additionally the sequential processing of the analyte may involve detection of the by-products of a polymerase reaction.

The disclosure generally relates to methods for characterizing a polynucleotide analyte using a detector (for example, a nanopore) and compositions, e.g., adaptors and nanopores, that can be used in the methods described herein. The present disclosure is, in part, based on the unexpected finding that both strands of a double stranded polynucleotide can be sequentially processed by enzymes for example a polymerase and the by-products of such processing detected e.g. by being translocated through a nanopore to provide sequence information, without the need to covalently link the two strands via a bridging moiety such as a hairpin loop. For example, in some embodiments, an adaptor with a duplex stem comprising a capture sequence that is complementary to a pore tag conjugated to a detector (e.g. a nanopore) can be provided to each end of a double stranded polynucleotide, wherein the capture sequence is only revealed upon unwinding of the strand. Thus, as a first strand of a double-stranded polynucleotide is processed, the duplex stem of the adaptor is unzipped to expose the capture sequence on a second strand of the double-stranded polynucleotide, which is then captured by the pore tag of the detector. Such method not only keeps the second strand held close to the detector, it also shortens the time delay between processing the first and second strands, thereby improving the overall accuracy and efficiency of the sequencing method. It was also found that capture of multiple analytes at a nanopore that are subsequently processed can enhance sensitivity and/or throughput of characterizing the analytes.

The present inventors have also found that when an enzyme for example a polymerase is used to process one of the two strands of a double stranded polynucleotide, the second strand may remain in the vicinity of a pore and, subsequent to the processing of the first strand through the pore, the second strand may be captured by the pore and a polymerase may be used to process the second strand.

Accordingly, one aspect of the present invention provides a method of sequencing a target polynucleotide, comprising:
  (a) contacting a transmembrane pore with:
    (i) a double stranded polynucleotide comprising the target polynucleotide and a polynucleotide complementary to the target polynucleotide; and
    (ii) at least one polymerase capable of processing the strands of the double stranded polynucleotide;
    wherein at least one tag that binds to a portion of the double stranded polynucleotide is conjugated to the transmembrane pore;
  (b) detecting a signal corresponding to ion flow through the pore to detect the translocation of the by-products of the processing reactions through the pore;
  (c) identifying a signal corresponding to translocation of the by-products of the processing of the target polynucleotide by the polymerase and a sequential signal corresponding to the separate translation of the by-products of the processing of the polynucleotide complementary to the target polynucleotide by the polymerase;
  (d) analyzing the signals identified in (c),
  thereby sequencing the target polynucleotide.

In this aspect, a double stranded barcode sequence may be attached to one or both ends of the target double stranded polynucleotide, a leader sequence may be comprised in an adaptor, the adaptor may comprise a double stranded region and at least one single stranded region, the adaptor may comprise a double stranded barcode sequence, the adaptor may comprise a membrane-tether or a pore-tether, leader sequences attached to the two ends of the target double stranded polynucleotide may be different, the double stranded polynucleotide may have a different adaptor at each end thereof and/or the polymerase may be bound to the leader sequence. Where a polymerase is bound to the leader sequence, activity of the polymerase may be stalled until the polynucleotide contacts the transmembrane pore. Where a double stranded barcode sequence is attached to one or both ends of the target double stranded polynucleotide, a unique barcode sequence may be attached to each double stranded polynucleotide in a sample. In this aspect, the double stranded polynucleotides may be attached to microparticles and/or the pore may be modified to enhance capture of the polynucleotide. For example, one or more molecules that attract or bind the polynucleotide or adaptor may be linked to the pore. Such molecules may be selected from, for example, a PNA tag, a PEG linker, a short oligonucleotide, a positively charged amino acid and an aptamer. In this aspect, the transmembrane pore may be, for example, a protein pore, such as a pore derived from or based on Msp, α-hemolysin (α-HL), lysenin, CsgG, ClyA, Spl or FraC, or a solid state pore and/or the membrane may be an amphiphilic layer or a solid state layer.

The method is advantageous over the known methods of sequencing double stranded polynucleotides in which the two strands are linked using a bridging moiety such as a hairpin loop. The method is also advantageous over the known methods of measuring template polynucleotide strands only. In particular, the method of the invention combines the both the advantages the template strand only method and the hairpin loop method without the mentioned drawbacks of the hairpin loop method.

For example, the method disclosed in WO2013/014451 uses multiple adaptors and only some of the double stranded polynucleotides in a sample will have a Y adaptor added at one end and an adaptor comprising a bridging moiety at the other end, with the other polynucleotides in the sample being discarded. The method of the invention can be performed using a single leader sequence or adaptor that can be added to both ends of the double stranded polynucleotide. When using such a single leader sequence/adapter system, less of the sample, if any, needs to be discarded.

In the method, either end of the double stranded target polynucleotide can be captured by the pore. This improves sensitivity compared to the method disclosed in WO2013/014451, where only the end of the double stranded polynucleotide that does not comprise the bridging moiety can be captured by the pore.

Also described herein is a population of adaptors comprising a double stranded barcode sequence, a single stranded leader sequence and a polynucleotide binding protein capable of separating the strands of a double stranded polynucleotide and controlling the movement of a polynucleotide through a transmembrane pore, wherein the barcode sequence in each adaptor in the population is unique.

Another aspect provided herein relates to a method of characterizing a polynucleotide. The polynucleotide may comprise DNA or RNA. The method comprising:
  (i) combining in a solution:
    (a) a construct comprising a double-stranded polynucleotide, having a template strand and a complement strand, wherein the template strand and the complement strand are not covalently linked, with
    (b) a detector, wherein at least one tag that binds to a portion of the construct is conjugated to the detector; and
    (c) a polymerase and nucleotides;
  and
  (ii) providing a condition so as to permit the template strand of the construct to be processed by the polymerase and the products and/or by-products of the processing reaction to be detected by the detector, thereby detecting the addition of a nucleotide by the polymerase to the polynucleotide strand;

wherein as the template strand of the double-stranded polynucleotide is processed, the complement strand becomes bound to the detector via the at least one tag conjugated to the detector.

In some embodiments, detecting the products and/or by-products of the processing reaction involves measuring a property indicative of the products and/or by-products of the processing reaction; and the polynucleotide is characterized based on the measured property of the products and/or by-products of the processing reaction.

In some embodiments, after processing of the template strand of the construct by the polymerase, the polymerase dissociates from the template strand. In some embodiments, after processing of the template strand by the polymerase, the complement strand of the construct is processed by a polymerase and the products and/or by-products of the processing reaction are detected by the nanopore.

In some embodiments, characterizing the polynucleotide comprises detecting the nucleotide sequence of the polynucleotide. In some embodiments, the nucleotide sequence of the polynucleotide is determined based on the order in which the products and/or by-products of the processing reaction are detected by the detector. In some embodiments, the nucleotides in the solution are labelled. In some embodiments, each type of nucleotide in the solution is distinguishably labelled according to the type of nucleotide. In some embodiments, the nucleotides in the solution are labelled with optical labels and/or polymer tags. In some embodiments, the polymer tags are charged polymer tags.

In some embodiments, the method comprises:
(i) combining in a solution:
  a) a construct comprising a double-stranded polynucleotide, having a template strand and a complement strand, wherein the template strand and the complement strand are not covalently linked, with
  b) a detector, wherein at least one tag that binds to a portion of the construct is conjugated to the detector; and
  c) a polymerase and nucleotides;
and
(ii) providing a condition so as to permit the template strand of the construct to be processed by the polymerase and the by-products of the processing reaction to be detected by the detector, thereby detecting the addition of a nucleotide by the polymerase to the polynuceotide strand;
wherein as the template strand of the double-stranded polynucleotide is processed, the complement strand becomes bound to the detector via the at least one tag conjugated to the detector.

In some embodiments, the products and/or by-products of the processing reaction(s) are sequentially released as nucleotides are sequentially added by the polymerase to the polynuceotide strand. In some embodiments, the by-products of the processing reaction(s) are labelled phosphate species. In some embodiments, the by-products of the processing reaction(s) are distinguishably labelled according to the type of nucleotide being added by the polymerase to the polynuceotide strand. In some embodiments, the by-products of the processing reaction(s) are labelled with optical labels and/or polymer tags. In some embodiments, the polymer tags are charged polymer tags.

In some embodiments, the method comprising detecting a product of the sequential addition of polynucleotides by the polymerase to the nucleic acid strand. In some embodiments, the product of the sequential addition of polynucleotides by the polymerase to the nucleic acid strand is a change in one or more properties of the polymerase. In some embodiments, the product of the sequential addition of polynucleotides by the polymerase to the nucleic acid strand is a change in the conformation of the polymerase. In some embodiments, step (ii) of the method comprises processing of the the template strand of the construct by the polymerase and detection of the products of the processing reaction by the detector, thereby detecting the addition of a nucleotide by the polymerase to the polynuceotide strand; wherein the sequential addition of nucleotide(s) by the polymerase to the polynuceotide strand causes a change in the conformation of the polymerase and wherein the detected product of the processing reaction is the conformationally-changed polymerase.

In some embodiments, the detector is selected from (i) a zero-mode waveguide, (ii) a field-effect transistor, optionally a nanowire field-effect transistor; (iii) an AFM tip; (iv) a nanotube, optionally a carbon nanotube and (v) a nanopore. In some embodiments, the detector is a nanopore. In some embodiments, the nanopore also functions to unwind the polynucleotide. In some embodiments, the nanopore is a motor protein nanopore, optionally which is phi29.

In some embodiments, the polymerase functions to unwind the polynucleotide. In other words, the polymerase may have strand displacement activity.

In some embodiments, an adapter is attached to one or both of the two ends of the double-stranded polynucleotide prior to processing of the construct by the polymerase. In some embodiments, an adapter is attached to each of the two ends of the double-stranded polynucleotide prior to processing of the construct by the polymerase.

In some embodiments, each adaptor comprises a duplex stem and a first single strand extending from the duplex stem, wherein the first single strand of one adaptor is contiguous with the template strand and the first single strand of the other adaptor is contiguous with the complement strand. In some embodiments, each adaptor comprises a second single strand extending from the duplex stem, wherein the second single strand of the one adaptor is contiguous with the complement strand and/or the second single strand of the other adaptor is contiguous with the template strand.

In some embodiments, the or each adapter comprises a polymerase. In some embodiments, the polymerase is pre-bound to the or each adaptor.

In some embodiments, the detector is a nanopore and the polymerase is located at a site in close proximity to the opening of the barrel or channel of the nanopore. The polymerase may be provided within the lumen of the nanopore. In some embodiments, the active site of the polymerase is orientated towards the opening of the nanopore.

In some embodiments, the detector is a nanopore and at least one tag that binds to a portion of the construct is conjugated to an outer rim of the nanopore. In some embodiments, one or more tags that bind to a portion of the adaptor is conjugated to the nanopore. In some embodiments, the one or more tags that bind to a portion of the adaptor are conjugated to the outer rim of the nanopore.

In some embodiments, at least one of the one or more tags that bind to a portion of the construct is a nucleic acid having sequence complementarity to the portion of the construct. In some embodiments, at least one of the one or more tags that bind to a portion of the adaptor is a nucleic acid having sequence complementarity to the portion of the adaptor. The nucleic acid may be uncharged, including e.g. but not limited to PNA or morpholino.

In some embodiments, processing of the template strand by the polymerase reveals a portion of the complement strand for hybridization with a tag.

In some embodiments, an adapter comprising a duplex stem and a first single strand extending from the duplex stem is attached to at least one end of the double-stranded polynucleotide such that the first single strand of the adaptor is contiguous with the complement strand; and the condition is maintained for a sufficient time to permit processing of the template strand of the construct to an extent that the portion of the adaptor that has its first single strand contiguous with the complement strand is available for hybridization with a tag.

In some embodiments, the method comprises maintaining the conditions for a sufficient time to permit the complement strand to be processed by a polymerase and thereby characterized following processing and characterization of the template strand.

In some embodiments, the detector is a nanopore and the nanopore comprises a first tag and a second tag, and the first tag and the second tag bind to a portion of the first single strand of an adaptor that is contiguous with the template strand and to a portion of the first single strand of an adaptor that is contiguous with the complement strand, respectively.

In some embodiments, the detector is a nanopore and the condition is a potential difference across the nanopore. In some embodiments, step (ii) comprises applying a potential difference across the nanopore so as to permit the by-products of the processing reaction to enter the nanopore; and the potential difference is maintained across the nanopore for a sufficient period of time so as to permit translocation of at least a portion of the by-products of the processing reaction through the nanopore.

In some embodiments, the detector is a nanopore and the solution is ionic and the measured property is ion current flow through the nanopore. The method may thus comprise measuring a change in ionic current flow through the nanopore as the by-products of the processing reaction translocate through the nanopore. The polynucleotide may be characterized based on the change in ionic current flow through the nanopore measured as the by-products of the processing reaction translocate through the nanopore. Data indicative of the measured properties indicative of the products and/or by-products of processing of the template strand and the complement strand of the double-stranded polynucleotide may be obtained and used to characterize the polynucleotide. The template strand data may be compared to or combined with the complement strand data to characterize the polynucleotide.

In some embodiments, the polynucleotide comprises RNA and/or DNA.

In some embodiments, the method further comprises
determining a sequence of the template strand based on changes measured in a property indicative of the by-products of the processing of the template strand by the polymerase,
determining a sequence of the complement strand based on changes measured in a property indicative of the by-products of the processing of the complement strand by a polymerase, and
comparing the sequence of the template strand with the sequence of the complement strand to establish a sequence of the polynucleotide.

A system for characterizing a polynucleotide, e.g., which can be used in any aspects of the methods described herein, is also provided. The system comprises: (i) a construct comprising a polynucleotide having a template strand and a complement strand, wherein the template strand and the complement strand are not covalently linked; (ii) a detector, wherein at least one tag that binds to a portion of the construct is conjugated to the detector; and (iii) a polymerase and nucleotides. The detector may be a nanopore disposed in a membrane, wherein the at least one tag that binds to a portion of the construct is conjugated to the nanopore.

In some embodiments, an adaptor is attached to both of the two ends of the polynucleotide, each adaptor comprising a duplex stem and a first single strand extending from the duplex stem. The first single strand of one adaptor may be contiguous with the template strand and the first single strand of the other adaptor may be contiguous with the complement strand. For each adaptor, a polymerase may be bound to the first single strand extending from the duplex stem.

In some embodiments, each adaptor can comprise a second single strand extending from the duplex stem, wherein the second single strand of the one adaptor is contiguous with the complement strand and the second single strand of the other adaptor is contiguous with the template strand.

In some embodiments, the at least one tag that is conjugated to the nanopore (a) has sequence complementarity with a portion of the adaptor that is within the duplex stem on a strand contiguous with the first single strand, and (b) has further sequence complementarity with a portion of the adaptor that is within the second single strand.

In some embodiments, the detector is a nanopore and at least two tags are conjugated to the nanopore, wherein one of the at least two tags has sequence complementarity with a portion of the adaptor that is within the duplex stem on a strand contiguous with the first single strand, and wherein the other of the at least two tags has sequence complementarity with a portion of the adaptor that is within the second single strand. In some embodiments, at least two tags may be conjugated to the outer rim of the nanopore.

A further aspect relates to a method for preparing a system for characterizing a polynucleotide. The method comprises: (i) obtaining a construct comprising a polynucleotide having a template strand and a complement strand, wherein the template strand and the complement strand are not covalently linked, and (ii) combining the construct with (a) a nanopore disposed in a membrane and (b) a polymerase and nucleotides; under conditions in which the construct is exposed to an outer rim of the nanopore, wherein at least one tag having sequence complementarity with a portion of the construct is conjugated to the outer rim of the nanopore.

In some embodiments, an adaptor may be attached at each of two ends of the polynucleotide, each adaptor comprising a duplex stem and a first single strand extending from the duplex stem, wherein the first single strand of one adaptor is contiguous with the template strand and the first single strand of the other adaptor is contiguous with the complement strand. For each adaptor, a polymerase may be bound to the first single strand extending from the duplex stem.

Complexes comprising two or more components formed in any aspects of the methods described herein are also within the scope of the disclosure. In some embodiments, a complex comprises: (i) a nanopore having a tag, (ii) a complement polynucleotide strand bound to the nanopore via the tag, and (iii) a template polynucleotide strand partially hybridized with the complement polynucleotide strand, wherein at least one by-product of the processing of the template polynucleotide by a polymerase is disposed within the lumen of the nanopore. In any embodiment of the complexes described herein, the tag can be at an outer rim external to its lumen.

In another aspect, a method for determining a characteristic of a polynucleotide using a nanopore comprises: (i) providing the polynucleotide; (ii) causing the polynucleotide to bind to a tag conjugated to an outer rim of a nanopore external to the lumen of the nanopore, and (iii) obtaining measurements of by-products of processing of the polynucleotide by a polymerase while moving the by-products with respect to the nanopore, wherein the measurements are indicative of one or more characteristics of the polynucleotide; and (iv) characterizing the polynucleotide based on the measurements obtained in step (iii).

A method for sequentially detecting two non-covalently bound molecules through a nanopore is also provided. The method comprises: contacting a pair of non-covalently bound molecules to a nanopore under conditions that promote processing of a first member of the pair of non-covalently bound molecules by a polymerase and detection of the by-products of the processing reaction by the nanopore, wherein a binding site on a second member of the pair is exposed during processing of the first member by the polymerase, and wherein the binding site reversibly binds to a tag that is present on the nanopore.

In some embodiments, the non-covalently bound molecules are complementary nucleic acid strands. In some embodiments, the pair of non-covalently bound molecules may comprise a target nucleic acid attached to an adaptor, and the binding site may be present on the adaptor.

In some embodiments, the tag on the nanopore can be an oligonucleotide, and the binding site on the second member can be a portion of a nucleic acid that has a sequence that is complementary to the tag.

Also provided herein is a method of characterising a polynucleotide comprising: contacting a pair of non-covalently bound molecules to a nanopore under conditions that promote processing of a first member of the pair of non-covalently bound molecules by a polymerase and detection of the by-products of the processing reaction by the nanopore sequentially followed by processing of a second member of the pair of non-covalently bound molecules by a polymerase and detection of the by-products of the processing reaction by the nanopore; measuring a property indicative of the by-products of the processing reactions, and obtaining data indicative of the measured property; and determining the characteristic based upon the obtained data of both the first and second members.

Also provided herein is a method of characterizing a polynucleotide, the method comprising:
(i) combining in a solution:
  a) a construct comprising a double-stranded polynucleotide, having a template strand and a complement strand, wherein the template strand and the complement strand are not covalently linked, with
  b) a detector, wherein at least one tag that binds to a portion of the construct is conjugated to the detector; and
  c) an exonuclease;
and
(ii) providing a condition so as to permit the template strand of the construct to be processed by the exonuclease so that the exonuclease digests an individual nucleotide from one end of the construct and the individual nucleotide interacts with the detector;
(iii) repeating step (ii) at the same end of the construct and thereby determining the sequence of the construct;

wherein as the template strand of the double-stranded polynucleotide is processed, the complement strand becomes bound to the detector via the at least one tag conjugated to the detector.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein.

For illustration purposes only, the strands in the figures described herein are labeled as "Template" and "Complement" according to which ends are captured. The first strand that passes through the nanopore is labeled as the template and the complementary strand that follows the first strand is labeled as the complement. The actual template and complement of a double-stranded polynucleotide are determined after analyzing the sequence information obtained from the first strand and the second strand.

FIG. 1A is a schematic representation of the polynucleotide (e.g., DNA) construct translocating through a nanopore under the control of an enzyme. The template enters the nanopore and the same enzyme proceeds around the hairpin to control movement of the complement that follows the template. Once the hairpin region translocates through the nanopore, the hairpin may reform on the trans side of the nanopore. FIG. 1B shows peaks representing the accuracy of the sequence information obtained from translocation of the template, from translocation of the complement and when the sequence information obtained from translocation of the template and translocation of the complement was combined algorithmically.

FIG. 2A is a schematic representation of a double stranded polynucleotide (e.g., DNA) construct translocating through the nanopore under enzyme control. Template and complement of the double-stranded polynucleotide are not covalently linked, and each strand has an enzyme loaded on the adaptor. After the template strand has passed through the nanopore (and the enzyme is dissociated), the complement strand is separately captured by the pore and sequenced. In the absence of a hairpin joining the template to the complement there is little or no secondary hairpin structure formed on the trans side of the nanopore. FIG. 2B shows peaks representing the accuracy of the sequence information obtained from translocation of the template, from translocation of the complement and when the sequence information obtained from translocation of the template and translocation of the complement was combined algorithmically.

FIG. 3A is a schematic representation of the enzyme-loaded adaptor. The labels represent the following: (1) spacers (e.g., a leader sequence); (2) a polynucleotide binding protein (e.g., polynucleotide unwinding enzyme, e.g., polymerase);

(3) a spacer; and (4) an anchor such as a cholesterol anchor. The other solid lines represent polynucleotide sequences. FIG. 3B shows the adaptor attached to each end of a double-stranded polynucleotide such as a fragment of genomic DNA, with a polynucleotide binding protein (e.g., polynucleotide unwinding enzyme, e.g., polymerase) loaded on each adaptor.

FIG. 9A is a schematic representation of the enzyme-loaded adaptor. The labels represent the following: (1) spacers (e.g., a leader sequence); (2) a polynucleotide binding protein (e.g., polynucleotide unwinding enzyme, e.g., polymerase); (3) a spacer; (4) an anchor such as a cholesterol anchor, which is optional; and (5) a duplex stem positioned on the opposite end of the (1) spacers (e.g., a leader sequence), the duplex stem comprising a capture sequence on a strand that is aligned with the (1) spacers (e.g., a leader sequence), wherein the capture sequence is complementary to a tag (e.g., a capture polynucleotide) conjugated to an outer rim of a nanopore. The other solid lines represent polynucleotide sequences. FIG. 9B shows the construct when the adaptor is attached to each end of a double stranded polynucleotide, with a polynucleotide binding protein (e.g., polynucleotide unwinding enzyme, e.g., polymerase) loaded on each adaptor.

FIG. 10 (panels A-D) illustrates a schematic representation of a method of sequencing a double-stranded polynucleotide using a nanopore according to one method disclosed herein. The method involves providing (i) a double-stranded polynucleotide with each end attached to an adaptor (e.g., as illustrated in FIG. 9A without the anchor (4)) and a polynucleotide binding protein (e.g., polynucleotide unwinding enzyme) loaded on the adaptor, and (ii) a nanopore with a capture polynucleotide conjugated to an outer rim of the nanopore. The second strand (complement) of the double-stranded polynucleotide is coupled to the nanopore by binding the capture sequence of the adaptor that is attached to the second strand to the tag (e.g., a capture polynucleotide) conjugated to the outer rim of a nanopore.

FIG. 11A shows an example section of strand data, which shows that the open-pore level with no strand blocking the current is at approximately 200 pA. When strands are captured, the current is reduced to the 50-100 pA range, dependent on sequence composition. As strands finish passing through the pore the current returns to open-pore level at 200 pA. The separate strands are labeled as $T_n$ (e.g., $T_1$, $T_2$, . . . ) and $C_1$ (e.g., $C_1$, C2, . . . ) for the pairs of template and complement strands, and as T for the strands where the T is not followed by its complement pair. The labels and data correspond to the data in Table 4. FIG. 11A illustrates that the complementary second strand of a pair typically immediately follows the template, with a very short time between strands. FIG. 11B shows a zoomed in section of the electrical trace, highlighting one of the follow-on pairs, labeled $Template_1$ and $Complement_1$.

FIG. 12A shows a further example electrical trace of a follow-on template-complement pair. FIGS. 12B, 12C, and 12D show zooms of the trace in FIG. 12A, with stars marking the sp18 spacers in the duplex stem (e.g., complementary tags sections) that were added to the strands to enable coupling to a pore-tag (e.g., a capture polynucleotide conjugated to the outer rim of a nanopore). FIG. 12B shows the sp18s at the start of the template strand. FIG. 12C shows the sp18s at the end of the template and start of the complement, and FIG. 12D shows the sp18 at the end of the complement. These markers can be used to demonstrate that the dsDNA substrate had enzyme-adapters attached to both ends of the dsDNA, and measure the efficiency of the attachment.

FIG. 13 shows a histogram of the distribution of open-pore times between subsequent strands (x-axis) as sequential strands pass through the pores (aggregated from all channels on a MinION chip). The top panel, Control Adapter (as described in Example 2), shows that the distribution of times is on average approximately 3 seconds between strands when sequencing without a capture sequence in the polynucleotide construct that can couple to the pore tag (e.g., a capture polynucleotide). The bottom panel, Follow-On Adapter 2 (as described in Example 4), shows that when the strands contain a capture sequence in the complement that can couple to the pore tag (e.g., a capture polynucleotide), a new population at approximately 50 milliseconds is observed. The short 50 ms population is from the fast capture of the complement strand soon after its template pair. Capture is fast because the complement strand is held very close to the pore via the binding of the complement to the pore tag and is thus not allowed to diffuse away. The arrow indicates a pronounced population within the data from Example 4, using the follow-on adapter as described in the Example.

FIG. 16 is a schematic illustration of how nanopores with two different tag types can be used to capture strands from solution (for improved sensitivity). The adaptor that is attached to an end of a double-stranded polynucleotide comprises a capture sequence (e.g., forming a non-complementary arm of a Y-adaptor) that is available to couple to a first pore tag, while a separate capture sequence within the duplex stem that is only revealed when unzipped permits the complement to bind to a second pore tag and thus enables complement capture for follow-on sequencing.

FIG. 17A is a schematic illustration of how the same capture sequence can be used in two locations of an adaptor, one revealed to allow strands to bind to a pore tag of a nanopore out of solution for improved sensitivity, and the other initially unrevealed and exposed when template unzips through the pore, becoming available to bind to another of the multiple tags on a pore (a pore with only one type of tag) to enable follow-on sequencing.

FIG. 18 shows a schematic of an adapter design that enables follow-on sequencing and increased sensitivity. The pore binding sequence (labeled as "Hyb splint for morpholino pore tag" in FIG. 18) is exposed to a surrounding solution and initially available for binding to the pore tag, so it improves sensitivity. The pore binding site is also contiguous with the complement strand when attached, so that when the template strand has passed through the pore or has been processed the complement strand remains bound to pore. This process is shown schematically in FIG. 19.

FIG. 19 is a schematic illustration showing a double stranded polynucleotide with an adaptor of FIG. 18 attached to each end. A strand is coupled to a nanopore from solution via an exposed pore binding site, thus improving the sensitivity of subsequent capture of the nearby template strand. The binding site is also contiguous with the complement strand, so that when the template has passed through the nanopore the complement remains bound to the nanopore. The complement might proceed to a number of possible conformations as shown, before ultimate capture and sequencing to enable follow-on sequencing. In FIG. 19, the green and yellow complementary segments attached to both ends of a strand to be detected, respectively, could bind together to form a hairpin structure comprising the strand, facilitating the sequencing process by bringing the strand closer to the nanopore for increased sequencing efficiency. It can be particularly beneficial when the strand to be detected is a long strand.

FIG. 21 is a schematic illustration showing a double stranded polynucleotide with an adaptor of FIG. 20 attached to each end. The dsDNA strand binds to a pore as shown via a binding site on a side-arm attached to the adapter as described in FIG. 20. When the template is captured in the pore, the side-arm sequence is unzipped and remains bound to the pore-tag as shown. Later into template unzipping the second site with the same sequence is revealed to bind to the side-arm (itself still bound to pore-tag). In this way, a single tag on a pore can be used to improve capture sensitivity, and can re-used to later enable follow-on of the complement of the substrate. At the end, the pore-tag retains the side-arm sequence, but the side-arm itself is captured by the pore and stripped from the pore-tag to free the pore-tag for another cycle.

Figure 23:
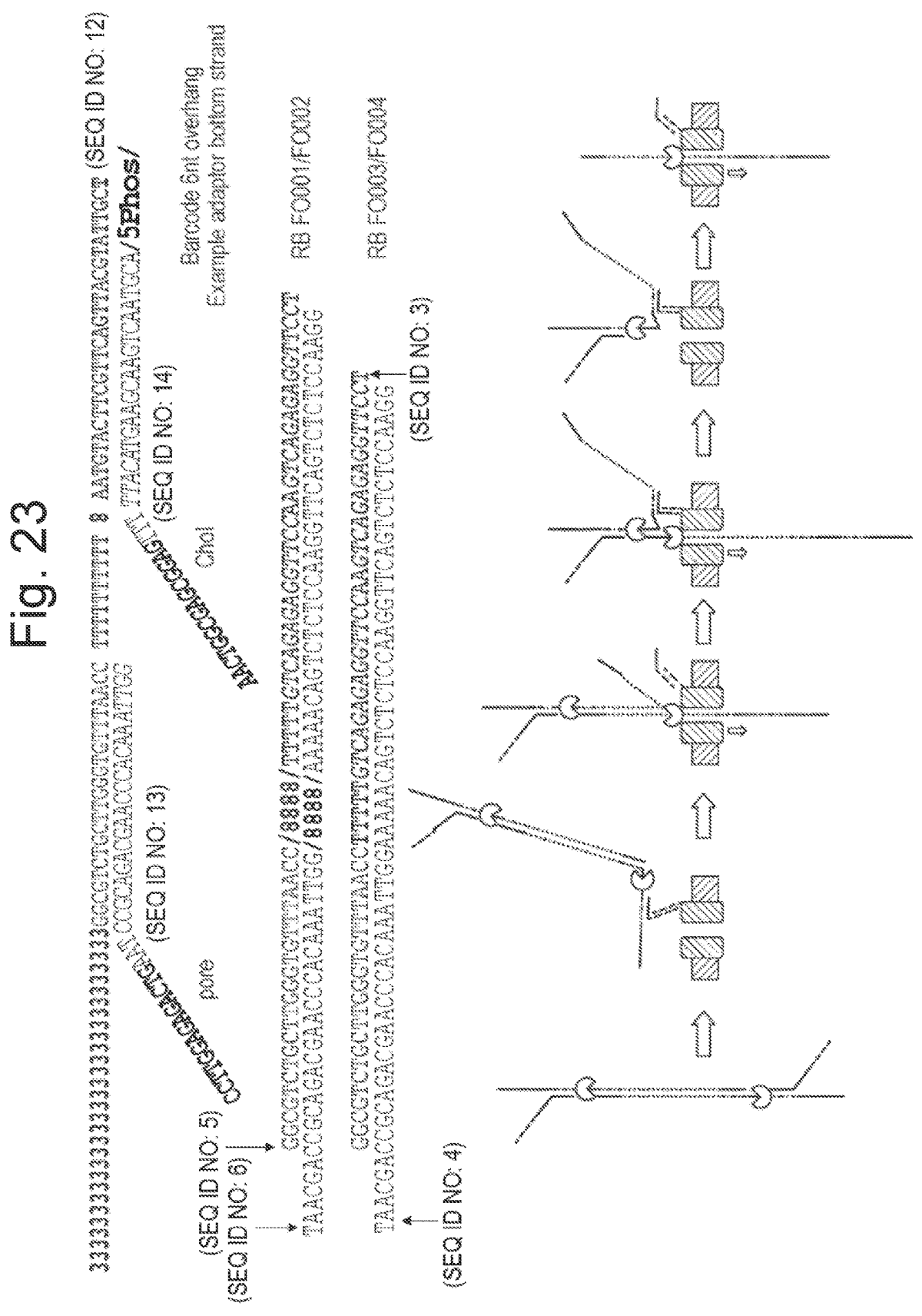

FIG. 23 provides example adapters/sequences that can enable the method disclosed in FIG. 21.

FIG. 26 provides example sequences of the components that make up the adapters described in the above figures.

FIG. 27B shows a schematic representation of a nanopore modified with a pyridyl-dithio morpholino.

FIG. 28 shows a Cy3 Florescent gel showing hybridization of an analyte to pyridyl-dithio morpholino modified pore.

FIG. 31 illustrates a diagram showing a computer rendering of a nanopore (e.g., a CsgG nanopore) highlighted with positions at which a cysteine can be added for conjugation to a pore tag. The pore tag can be conjugated to the external surface of a nanopore, e.g., on cis-side or trans-side of a membrane, when the nanopore is disposed in a membrane.

FIG. 32A shows an embodiment of a Y adapter design, which includes two hybridization sites, one for the pore tether (red) and the other for the membrane or bead tether (blue). In this design the pore tether is next to the leader sequence. FIG. 32B shows a ligated analyte, e.g., a double stranded polynucleotide, with a Y adapter on either end.

FIG. 38 shows example traces of sequential strands translocating through a nanopore without a pore tag that can bind to a strand to allow follow-on sequencing. The time between strands is indicated by the red bars, in these examples the time between strands ranges from 2-5 seconds.

FIG. 39 shows example traces of sequential strands translocating a modified pore according to one method disclosed herein. The time between strands is indicated by the red bars, in these examples the time between strands ranges from 0.02-3 seconds.

FIG. 42 shows a data table from *E. coli* runs showing an increase in the number of follow on strands with the tethered pore.

FIG. 46 is a schematic representation of a double stranded nucleic acid being processed under enzyme control so that sequence of both strands of a double stranded nucleic acid are determined. Sense and antisense strands of the double stranded nucleic acid are not covalently linked. As the first strand of the double stranded nucleic template is being processed information indicative of the sequence of the first strand is obtained by the detector, and the antisense strand becomes localised to the detector via a capture tag conjugated to the detector. After the first strand of the double stranded nucleic acid has been processed, the second strand is separately processed and information indicative of the sequence of the second strand is obtained by the detector.

FIG. 47 represents an example of the method shown in FIG. 46. FIG. 47 is a schematic representation of a double stranded DNA template being processed under polymerase control so that the by-products of a sequencing reaction are detected. Sense and antisense strands of the double stranded template are not covalently linked, and each strand has a polymerase loaded on the adaptor. As the sense strand of the double stranded DNA template is being processed and the by-products of the sequencing by synthesis reaction are detected by the nanopore, the antisense strand becomes localised to the nanopore via a capture polynucleotide conjugated to an outer rim of the nanopore. After the sense strand of the DNA template has been processed (and the enzyme has dissociated), the antisense strand is separately sequenced and the by-products of the sequencing by synthesis reaction are detected by the nanopore.

DETAILED DESCRIPTION OF THE INVENTION

Figure 1A:
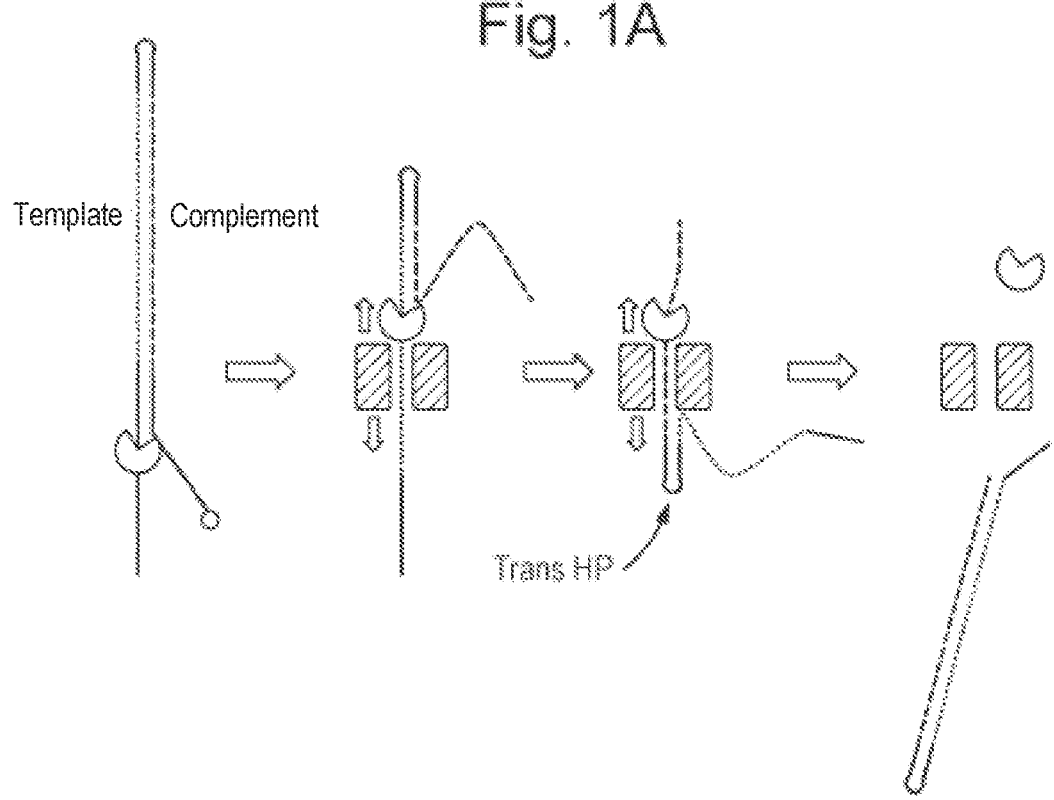
FIGS. 1A-1B illustrate a prior art method of sequencing a double stranded polynucleotide (e.g., DNA) construct, in which the template and complement strands are attached via a hairpin loop and the template strand comprises a 5' leader sequence, using a transmembrane pore.

While detectors for example transmembrane pores (e.g., protein nanopores or solid state nanopores) are useful as sensors to detect or characterize a biopolymer, there are still challenges of increasing the accuracy and/or efficiency of the detection method using detectors such as transmembrane pores. For example, there are various drawbacks of translocation of both the template and complement strands of a double stranded polynucleotide connected by a hairpin through a nanopore. While measurement of both strands in this way is advantageous as information from the two complementary linked strands can be combined and used to provide higher accuracy than may be achieved from measurement of template strands only, preparation of such a hairpin linked polynucleotide is more involved and time consuming and can result in a loss of valuable analyte. Further, translocation of a hairpin linked template and complement polynucleotide strands through a nanopore can give rise to rehybridization of the strands on the other (trans) side of the nanopore. This can alter the rate of translocation giving rise to a lower sequencing accuracy. A strand with a hairpin structure is also more difficult to translocate as fast as a single linear strand. Additionally, due to the differences in current-time data for the template and complement strands, two algorithms are used for computation, which makes the computation more complex and intensive. There is thus a need for improved methods of characterizing an analyte e.g. a polynucleotide.

For analyte detection, there is typically a time delay between translocation of one analyte and translocation of the next one. This delay can be of the order of seconds to minutes, which can result in slower characterization, in a higher pore open current which depletes the reference electrode more quickly, and/or in an increased likelihood of a nanopore getting blocked when the pore is open. Accordingly, there is a need to develop methods and compositions that improve the accuracy and/or efficiency or throughput of characterizing analytes using a nanopore.

The present disclosure is, in part, based on the unexpected discovery that both strands of a double stranded polynucleotide can be sequentially processed e.g. by an enzyme such as a polymerase to provide sequence information without the need to covalently link two strands via a bridging moiety such as a hairpin loop. For example, in one aspect, the present inventors have discovered that when a polynucleotide binding protein (e.g., a polymerase) is used to process the first of the two strands of a double stranded polynucleotide, the second strand may remain in the vicinity of a detector for example a pore and, subsequent to the processing of the first strand, the second strand may be captured by the detector and a polynucleotide binding protein e.g. a polymerase may be used to process the second strand.

In another aspect, the present inventors have discovered that an adaptor with a duplex stem comprising a capture sequence that is complementary to a tag conjugated to a detector for example a nanopore, can be provided to each end of a double stranded polynucleotide, wherein the capture sequence is only revealed upon processing of the strand. Thus, as a first strand of a double-stranded polynucleotide is processed e.g. by a polynucleotide binding protein (e.g., a polymerase), the duplex stem of the adaptor is unzipped to expose the capture sequence on a second strand of the double-stranded polynucleotide, which is then captured by the pore tag of the nanopore. Such method keeps the second strand, which would otherwise typically diffuse away, close to the detector (e.g. nanopore) for sequencing following the template being sequenced. In particular, the methods described herein can significantly increase the likelihood of a follow-on processing of a complement after a template processing to at least about 60% of the time, as compared to 0.1%-1% of the time that is typically observed in typical nanopore sequencing.

It was also discovered that modification of a nanopore to comprise multiple binding sites for multiple analytes such that one or more analytes can bind to the nanopore via the binding sites, while an analyte is being characterized by the nanopore, can enhance sensitivity and/or throughput of characterizing the analytes. Without wishing to be bound by theory, coupling or capture of analytes at the outer rim of the nanopore can enhance the local concentration of the analytes at the pore. Further, at least one or more analytes in the vicinity of the nanopore can readily enter the nanopore one following another for characterization, thus decreasing time delay and thus the open-pore current time between each analyte characterization.

Accordingly, various aspects herein relate to methods of characterizing one or more analytes using a detector for example a nanopore, as well as composition and systems including, e.g., adaptors and nanopores, that can be used in the methods described herein. Some aspects feature methods and compositions for characterizing a double-stranded polynucleotide using a nanopore, e.g., without using a hairpin connecting a template and a complement of the double-stranded polynucleotide. Other aspects features methods and compositions for characterizing an analyte using a tag-modified nanopore with increased sensitivity and/or higher throughput.

Accordingly, provided herein is a method which provides a means of sequencing a nucleic acid strand by detecting the products and/or by-products of a sequencing reaction, such as a sequencing by synthesis reaction. The by-products may be detected and/or characterised by detecting and analysing signals using a polymerase in close proximity to a detector. Nucleoside phosphates (nucleotides) may be labelled so that a phosphate labelled species is released upon the addition of a nucleotide to a synthesised nucleic acid strand that is complementary to the template strand, and the phosphate labelled species is detected. Suitable labels may be optical labels that are detected using a nanopore, or a zero mode wave guide, or by Raman spectroscopy, or other detectors. Suitable labels may be non-optical labels e.g. polymer tags (e.g. charged polymer tags) that are detected using a nanopore, or other detectors. In another approach, nucleoside phosphates (nucleotides) are not labelled and upon the addition of a nucleotide to a synthesised nucleic acid strand that is complementary to the template strand, a natural by-product species is detected. Suitable detectors may be ion-sensitive field-effect transistors, or other detectors. These methods are described in more detail herein.

The detection of the by-products of processing double-stranded polynucleotides by an enzyme can be readily achieved by those skilled in the art. The detection of certain by-products of enzyme processing has previously been described by Stranges et al, "*Design and characterization of a nanopore-coupled polymerase for single-molecule DNA sequencing by synthesis on an electrode array*", Proc Natl Acad Sci USA. 2016 Nov. 1; 113(44): E6749-E6756, and such methods may be applied in the methods provided herein.

Methods for Characterizing an Analyte (e.g., a Double Stranded Polynucleotide)

In one aspect, the disclosure provides a method of sequencing a target polynucleotide, comprising:
(a) contacting a transmembrane pore with:
  (i) a double stranded polynucleotide comprising the target polynucleotide and a polynucleotide complementary to the target polynucleotide; and
  (ii) at least one polymerase capable of processing the strands of the double stranded polynucleotide;
  wherein at least one tag that binds to a portion of the double stranded polynucleotide is conjugated to the transmembrane pore;
(b) detecting a signal corresponding to ion flow through the pore to detect the translocation of the by-products of the processing reactions through the pore;
(c) identifying a signal corresponding to translocation of the by-products of the processing of the target polynucleotide by the polymerase and a sequential signal corresponding to the separate translation of the by-products of the processing of the polynucleotide complementary to the target polynucleotide by the polymerase; and
(d) analyzing the signals identified in (c),
thereby sequencing the target polynucleotide.

The method may further comprise before step (a) a step of attaching single stranded leader sequences to the target and complementary polynucleotides. The method may further comprise before step (a) a step of digesting one end of the target polynucleotide to produce a leader sequence on the complementary strand and/or digesting one end of the complementary polynucleotide to produce a leader sequence on the target strand. The method may still further comprise binding a polynucleotide binding protein (e.g., polynucleotide unwinding enzyme) to the leader sequences.

In this aspect, a polynucleotide binding protein (e.g., polynucleotide unwinding enzyme) is typically a polymerase. In this aspect, a first polynucleotide binding protein (e.g., polynucleotide unwinding enzyme, e.g., polymerase) separates the target and complementary strands of the double stranded polynucleotide and processes either the target polynucleotide or the complementary polynucleotide. A second polynucleotide binding protein (e.g., polynucleotide unwinding enzyme, e.g., polymerase), which may be another protein of the same type as the first polynucleotide binding protein (e.g., polynucleotide unwinding enzyme, e.g., polymerase), or may be a different type of polynucleotide binding protein (e.g., polynucleotide unwinding enzyme, e.g., polymerase), processes either the target polynucleotide, where the complementary polynucleotide has already been processed, or the complementary polynucleotide, where the target polynucleotide has already been processed. The second polynucleotide binding protein (e.g., polynucleotide unwinding enzyme, e.g., polymerase) does not need to separate the target polynucleotide and the complementary polynucleotide because separation of the two strands of the double stranded polynucleotide will already have occurred (the first polynucleotide binding protein (e.g., polynucleotide unwinding enzyme, e.g., polymerase) will have separated the two strands whilst processing one of the strands). The first polynucleotide binding protein (e.g., polynucleotide unwinding enzyme, e.g., polymerase) is typically one that processes a double stranded polynucleotide. The second polynucleotide binding protein (e.g., polynucleotide unwinding enzyme, e.g., polymerase) is typically one that processes a single stranded polynucleotide. The first and/or second polynucleotide binding protein (e.g., polynucleotide unwinding enzyme, e.g., polymerase) may be capable of processing a double stranded polynucleotide and a single stranded polynucleotide.

Also disclosed herein is a method for sequentially translocating two non-covalently bound molecules through a nanopore. The method comprises: contacting a pair of non-covalently bound molecules to a nanopore under conditions that promote translocation of a first member of the pair of non-covalently bound molecules through the nanopore, wherein a binding site on a second member of the pair is exposed during translocation of the first member through the nanopore, and wherein the exposed binding site binds to a tag or tether that is present on the nanopore. The binding site on the second member is not exposed (or is shielded) prior to translocation of the first member through the nanopore.

Also provided is a method for sequentially detecting two non-covalently bound molecules with a nanopore. The method comprises: contacting a pair of non-covalently bound molecules to a nanopore under conditions that promote processing of a first member of the pair of non-covalently bound molecules by a polymerase and detection of the by-products of the processing reaction by the nanopore. The binding site on a second member of the pair is exposed during processing of the first member of the pair by the polymerase, and the binding site reversibly binds to a tag that is present on the nanopore.

As used herein, the term "non-covalently bound molecule" refers to a molecule comprising a first a member and a second member, wherein the first member and the second member are associated with each other by means of non-covalent attachment and can be separated from each other as individual entities. The separation and binding process between the first member and the second member are reversible. Examples of means of non-covalent attachment include, but are not limited to complementary base-pairing, ionic interaction, hydrophobic interaction, and/or Van der Waals' interaction.

In some embodiments, the non-covalently bound molecules comprise complementary polynucleotide strands.

In some embodiments, the tag on the nanopore is an oligonucleotide, and the binding site on the second member is a portion of a nucleic acid that has a sequence complementary to the tag.

In some embodiments, the pair of non-covalently bound molecules comprise a target nucleic acid (e.g., a target double stranded polynucleotide) coupled to an adaptor nucleic acid, and wherein the binding site is present on the adaptor nucleic acid.

Figure 9A:
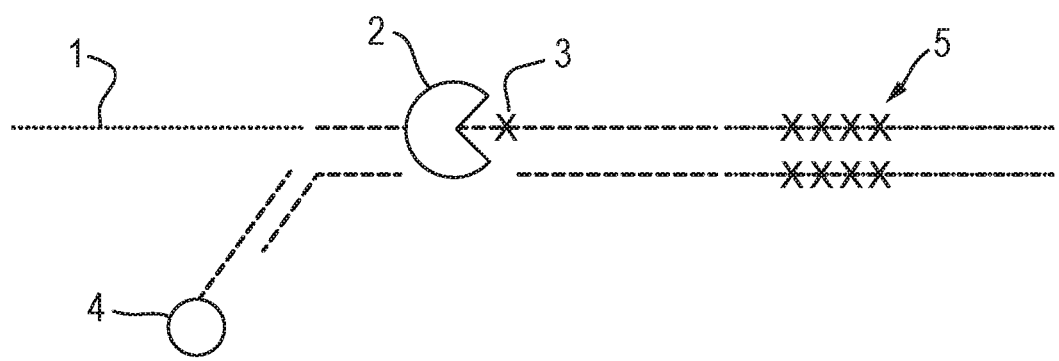
FIGS. 9A-9B illustrate the structure of an enzyme-loaded adaptor according to one embodiment described herein.
Figure 9B:
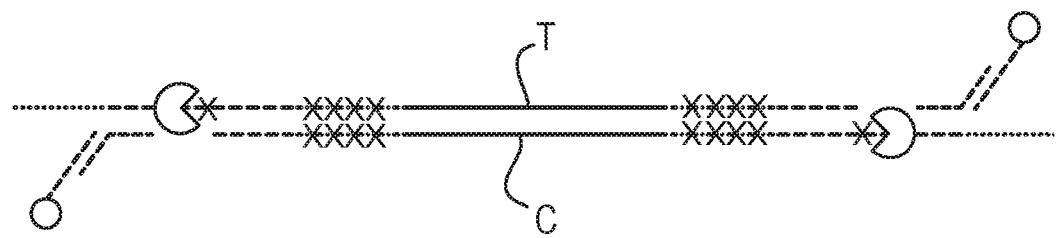

As an example only, FIG. 9B shows a non-covalently bound molecule, which comprises complementary polynucleotide strands (e.g., a template strand and a complement strand) and an adaptor (e.g., an adaptor nucleic acid) attached to each end. The adaptor, as shown in FIG. 9A, comprises a duplex stem (5) and a first single stranded polynucleotide (1) extending from a template strand of the duplex stem. The duplex stem (5) comprises a capture sequence on a strand that is aligned with the first single stranded polynucleotide (1), wherein the capture sequence is complementary to a tag (e.g., a capture polynucleotide) conjugated to an outer rim of a nanopore. In some embodiments, the first single stranded polynucleotide (1) can further comprise a leader sequence. While FIG. 9A shows a second single stranded polynucleotide extending from a complementary strand (e.g., the complement strand) of the duplex stem, it is not required. However, in some embodiments, it may be desirable to have one or more second single stranded polynucleotides comprising one or more tethers for a solid substrate, e.g., a membrane or a bead, and/or a nanopore. When the second single stranded polynucleotide is not complementary to the first single strangled polynucleotide, a Y-adaptor is formed, e.g., as shown in FIG. 9A.

Figure 15:
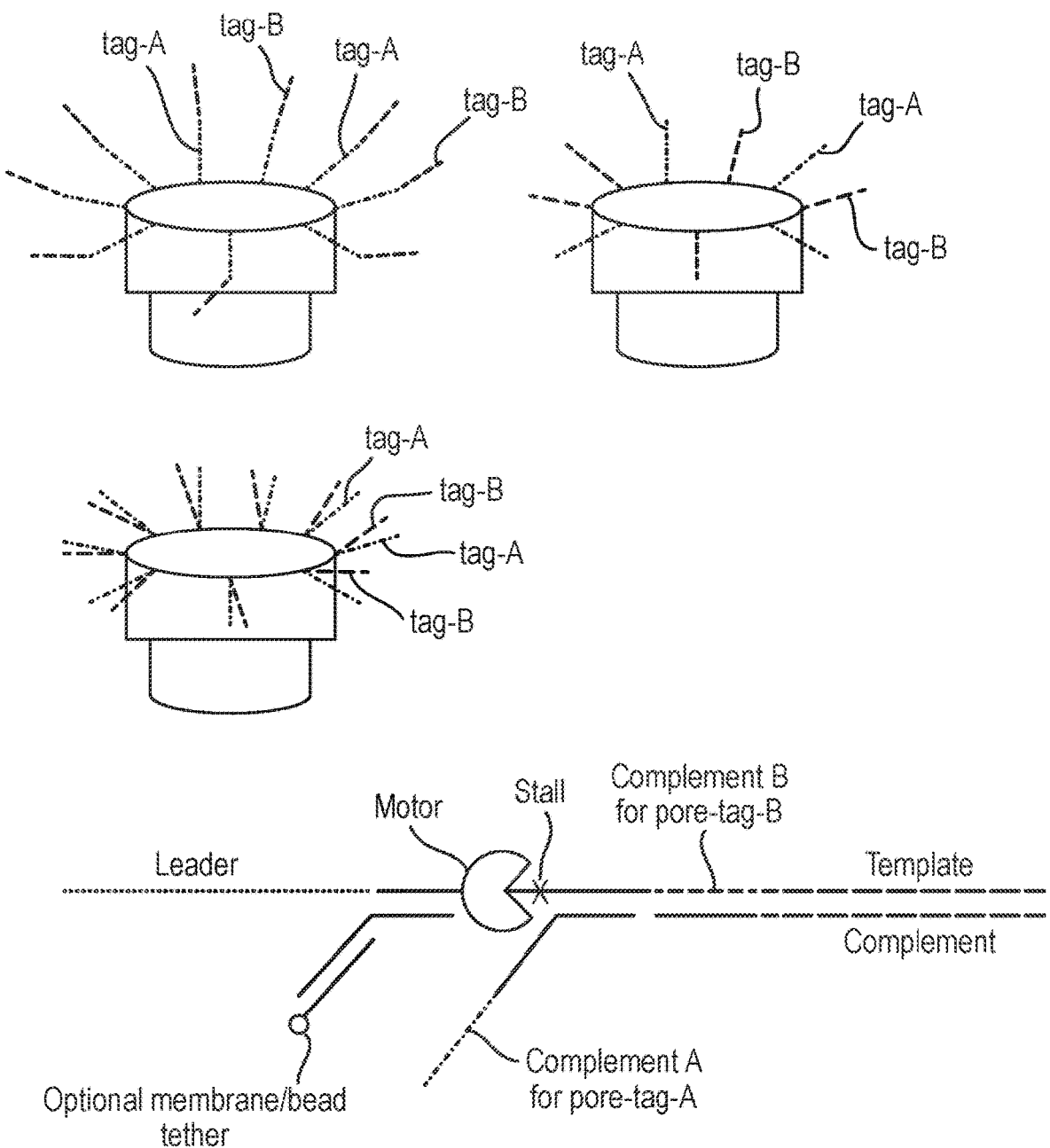
FIG. 15 shows example embodiments of nanopores having two or more types of tags. For example, one tag can be provided to increase the sensitivity of a method for characterizing an analyte ("sensitivity tag"), while another tag can be provided to increase the likelihood of sequencing of a complement strand following a template strand of a double-stranded polynucleotide ("follow-on tag"). The pore tags can be configured in any number of ways. For example, each monomer of an oligomeric pore can have the same type of tag configuration (e.g., with multiple binding sites, as illustrated by Tag-A and Tag-B). Tag-A and Tag-B can be combined to form a single tag, and each monomer comprises the Tag-A/Tag-B combined tag. Alternatively, an oligomeric pore can comprise mixed monomers with different tags attached such that at least one monomer has a different tag configuration from the other monomers. In another example, Tag-A and Tag-B can remain as separate tags and each monomer can comprise both individual tags. Sensitivity and follow-on tags can be separately combined if they are complementary to unique sequences used in the adaptor as illustrated in the bottom panel of a schematic adaptor design.
Figure 36:
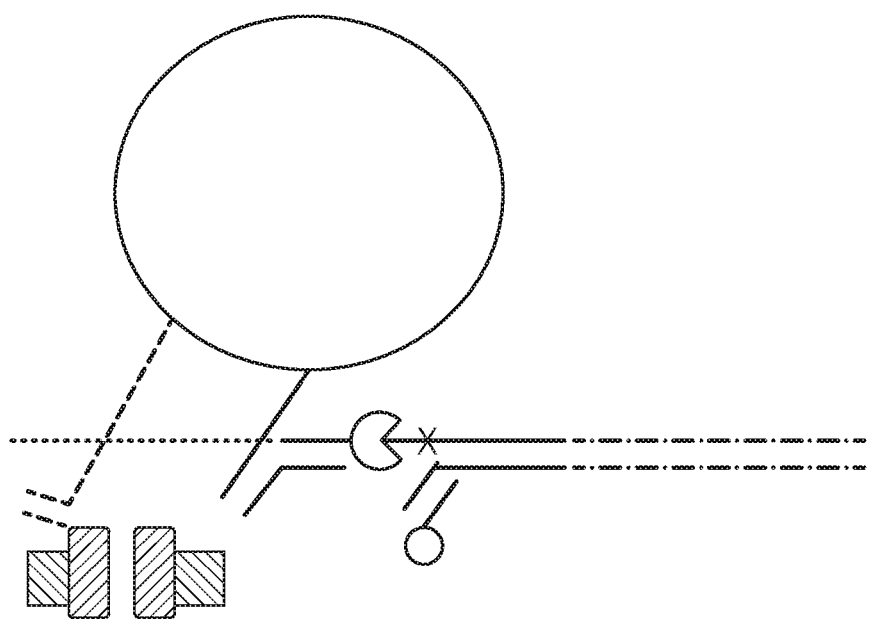
FIG. 36 is a schematic diagram showing an alternative embodiment of a Y adapter design, which includes two hybridization sites, one for a bead tether and the other for the membrane tether. In this design the bead has two different tethers, one to the analyte (blue) and the other to the pore (red).
Figure 37:
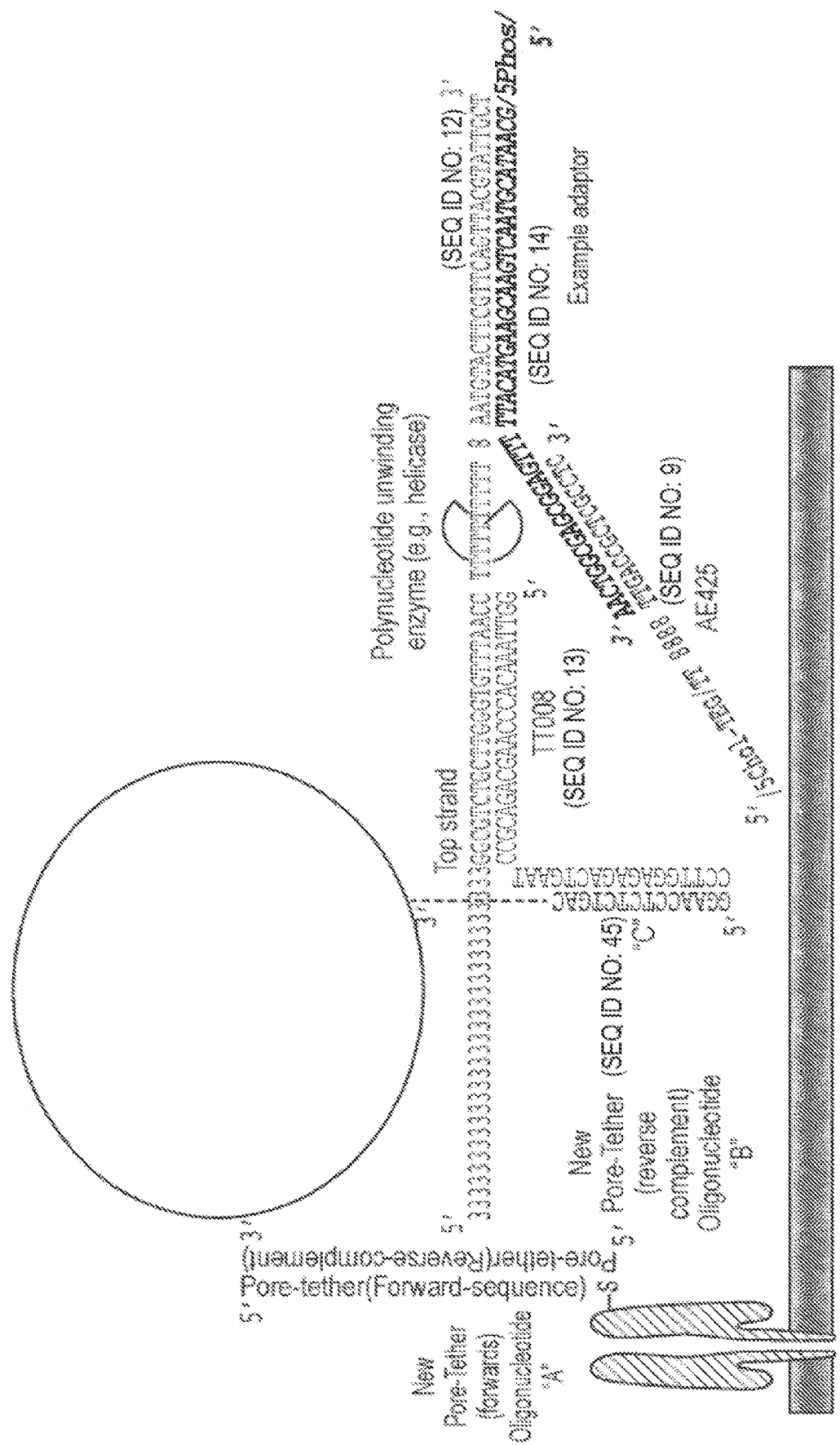
FIG. 37 is a schematic diagram showing example sequences of a Y adapter design illustrated in FIG. 36 and showing indirect attachment of the analyte to the pore.

FIG. 9A shows an example adaptor comprising at least one anchor for a solid substrate, e.g., a membrane or a bead, while FIG. 15 shows an example adaptor comprising at least two anchors, wherein a first anchor is capable of tethering to a solid substrate, e.g., a membrane or a bead, and a second anchor is capable of tethering to a nanopore. The second anchor for the nanopore can be configured to bind to a tag conjugated to the nanopore. In some embodiments, the second anchor for the nanopore can be configured to directly bind to a tag conjugated to the nanopore. For example, the second anchor for the nanopore can comprise a sequence that is complementary to the capture polynucleotide tag conjugated to the nanopore. In alternative embodiments, the second tether for the nanopore can be configured to indirectly bind to a tag conjugated to the nanopore. For example, FIG. 36 shows that an adaptor attached to an analyte can be coupled to a tag on the nanopore via a microparticle, which is further described in detail in the "Microparticles" section below.

It should be noted that the adaptors described herein can be attached to either or both ends of a double stranded polynucleotide. In some embodiments, the same adaptors are attached to both ends of a double stranded polynucleotide. In some embodiments, different adaptors can be attached to the ends of a double stranded polynucleotide. Attachment of different adaptors to the ends of double stranded polynucleotides can be achieved, for example, by mixing two or more populations of different adaptors together with the double stranded polynucleotides. Typically, a mixture of double stranded polynucleotides attached with different adaptors is formed, but there are also methods to achieve a desired hetero-adapter mixture (e.g., through purification or by controlling the attachment of adaptors to the ends of double stranded polynucleotides).

In some embodiments, a double stranded polynucleotide can have an adaptor to its 3' end or 5' end.

Blunt ended double stranded polynucleotides can be captured by a detector such as a nanopore and unzipped or otherwise processed e.g. by a polymerase. Accordingly, in some embodiments, a blunt ended construct without an adaptor (e.g., one as described herein) can be used in any aspects of the methods described herein. While not necessary, in some embodiments, it is desirable to have a leader sequence coupled to at least one end of a double stranded polynucleotide, e.g., to increase the efficiency of processing by a polymerase.

In some embodiments where the adaptor is attached to both ends of a double stranded polynucleotide, one of ordinary skill in the art will readily recognize that when the first single-stranded polynucleotide of an adaptor is coupled to a template strand at one end of the double-stranded polynucleotide, the first single-stranded polynucleotide of another adaptor is coupled to a complement strand at the opposite end of the double-stranded polynucleotide.

In some embodiments, the adaptors can have a pre-bound polynucleotide binding protein (e.g., polynucleotide unwinding enzyme, e.g., polymerase) at each end of the target polynucleotide. In some embodiments, the method can further comprising adding a polynucleotide binding protein (e.g., polynucleotide unwinding enzyme, e.g., polymerase) in solution such that it bounds to the adaptor at each end of the target polynucleotide.

In the disclosed method illustrated in FIG. 10, each end of a double-stranded polynucleotide is attached to an adaptor as described herein and a polynucleotide binding protein (e.g., polynucleotide unwinding enzyme) is loaded on the adaptor, wherein the adaptor comprises a duplex stem with a capture sequence complementary to a tag conjugated to a nanopore (see, e.g., FIG. 9A as an example adaptor). A single-stranded polynucleotide (which may optionally comprise a leader sequence) extending from the construct that comprises a double-stranded polynucleotide enters the nanopore (Panel A). The first strand that enters the nanopore is labeled as template (T), and the reverse complement of the first strand captured is labeled as complement (C). As the first template strand passes through the pore under the control of the polynucleotide binding protein (e.g., polynucleotide unwinding enzyme such as a helicase motor), the complement is gradually unzipped. Panel B shows that towards the end of the template strand, the capture sequence within the duplex stem on the complement is exposed by the unzipping, and thus couples to the tag (e.g., capture polynucleotide) on the nanopore. In Panel C, when the template strand finally passes through the nanopore, and the enzyme dissociates, the complement strand remains coupled to the nanopore via the binding to the tag (e.g., capture polynucleotide) on the nanopore. At some time later the complement strand is captured by its leader sequence. In Panel D, the complement strand passes through the nanopore under the control of the second loaded polynucleotide binding protein, e.g., polynucleotide unwinding enzyme such as helicase motor. As the complement strand passes through the nanopore, the capture sequence will at some point be unzipped from the nanopore's tag (e.g., a capture polynucleotide), thus freeing up the nanopore's tag (e.g., a capture polynucleotide) so that it is available for the next strand. In this disclosed method, both polynucleotide binding proteins (e.g., polynucleotide unwinding enzymes) are capable of processing double-stranded polynucleotides. In some methods, the polynucleotide binding proteins (e.g., polynucleotide unwinding enzymes) loaded at both ends can be the same or different.

While FIG. 10 (Panel B) illustrates that exposing the capture sequence (for binding to a tag on a nanopore) within the duplex occurs toward the end of translocation of the template strand (e.g., capturing far end adapter thus holding it local to pore), more generally, strands can be designed so that binding of a double stranded polynucleotide (e.g., via an end or tail portion) to a nanopore can occur right at the beginning of the unzipping process. In this instance, the capture sequence can be positioned in the adaptor (e.g., as a non-complementary arm of a Y-adaptor portion) such that it is exposed for binding to a nanopore for the entire duration of the unzipping or even before the unzipping process.

In some embodiments, instead of having a polynucleotide binding protein (e.g., polynucleotide unwinding enzyme, e.g., polymerase) bound onto the adaptors attached to the target polynucleotide, a polynucleotide binding protein (e.g., polynucleotide unwinding enzyme, e.g., polymerase) can be immobilized within the lumen of a nanopore such that a single polynucleotide binding protein (e.g., polynucleotide unwinding enzyme, e.g., polymerase) can be used to process both strands.

In some embodiments, the unwinding or separation of the strands as one strand is processed is controlled by a polynucleotide binding protein (e.g., polynucleotide unwinding enzyme, e.g., polymerase). Unwinding or separation of the strands can occur in the absence of a polynucleotide binding protein (e.g., polynucleotide unwinding enzyme). Such enzyme-free methods to control the movement and/or separation of both strands of a polynucleotide are known in the art. For example, certain nanopores themselves can provide the force to unwind a polynucleotide such as a motor protein nanopore, including, e.g., phi29 motor protein nanopore, e.g., as described in Wendell et al. "Translocation of double-stranded DNA through membrane-adapted phi29 motor protein nanopores" *Nat Nanotechnol,* 4 (2009), pp. 765-772, and/or nanopores as described in the U.S. Pat. No. 8,986, 528, the contents of each which are incorporated herein by reference in their entireties.

As used herein, the term "translocate" or "translocation" refers to movement along at least a portion of a nanopore. In some embodiments, translocation is moving from a cis-side of a nanopore to a trans-side of a nanopore.

The target polynucleotide is typically present in a sample comprising multiple copies of the target polynucleotide and/or in a sample comprising multiple different polynucleotides. In some embodiments, the method of any aspects described herein may comprise determining the sequence of one or more target polynucleotides in a sample. The method may comprise contacting the pore with two or more double stranded polynucleotides. For example, the method may comprise contacting the pore with a sample in which substantially all the double stranded polynucleotides have a single stranded leader sequence on each of their two strands. In some embodiments, the double stranded polynucleotides are coupled to each other only via complementary base pairing. In these embodiments, the double stranded polynucleotides can have four free ends, wherein a free end is the end of a polynucleotide strand. The end of the polynucleotide strand may be single stranded, e.g. a single stranded overhang, or base paired to another polynucleotide strand. In some embodiments, the two strands of the double stranded polynucleotides being sequenced are not covalently attached (e.g., no hairpin or other covalent attachment). However, a moiety that does not bridge the template and complement polynucleotides may be added to one or more of the free ends.

In some embodiments of various aspects described herein, the method may further comprise a step of generating or attaching single stranded leader sequences to both strands of substantially all double stranded polynucleotides in a sample, prior to contacting with a detector such as a nanopore. The leader sequences added may have one or more polynucleotide binding proteins (e.g., polynucleotide unwinding enzymes, e.g., polymerase) attached thereto, such that a population of double stranded polynucleotides each comprises a leader sequence with a polynucleotide binding protein (e.g., polynucleotide unwinding enzyme, e.g., polymerase) attached thereto at one end of each of its two strands.

The double stranded polynucleotide comprising the target polynucleotide (e.g., a template) and a polynucleotide complementary to the target polynucleotide (e.g., a complement) may have an adaptor comprising a single stranded leader sequence attached at each end thereof. In some embodiments where the method of various aspects involves a polynucleotide binding protein (e.g., a polynucleotide unwinding enzyme, e.g., polymerase), the method may comprise contacting the pore with two or more polynucleotide binding proteins (e.g., polynucleotide unwinding enzymes, e.g., polymerase) that may be the same or different. The different polynucleotide binding proteins (e.g., polynucleotide unwinding enzymes) may be bound to separate leader sequences, that may be the same or different. For example, a polynucleotide binding protein (e.g., polynucleotide unwinding enzyme) that works in the 5' to 3' direction may be bound to a leader sequence at the 5' end of the target polynucleotide and/or at the 5' end of a complementary polynucleotide. A polynucleotide binding protein (e.g., polynucleotide unwinding enzyme) that works in the 3' to 5' direction may be bound to a leader sequence at the 3' end of the target polynucleotide and/or at the 3' end of a complementary polynucleotide.

Figure 17B:
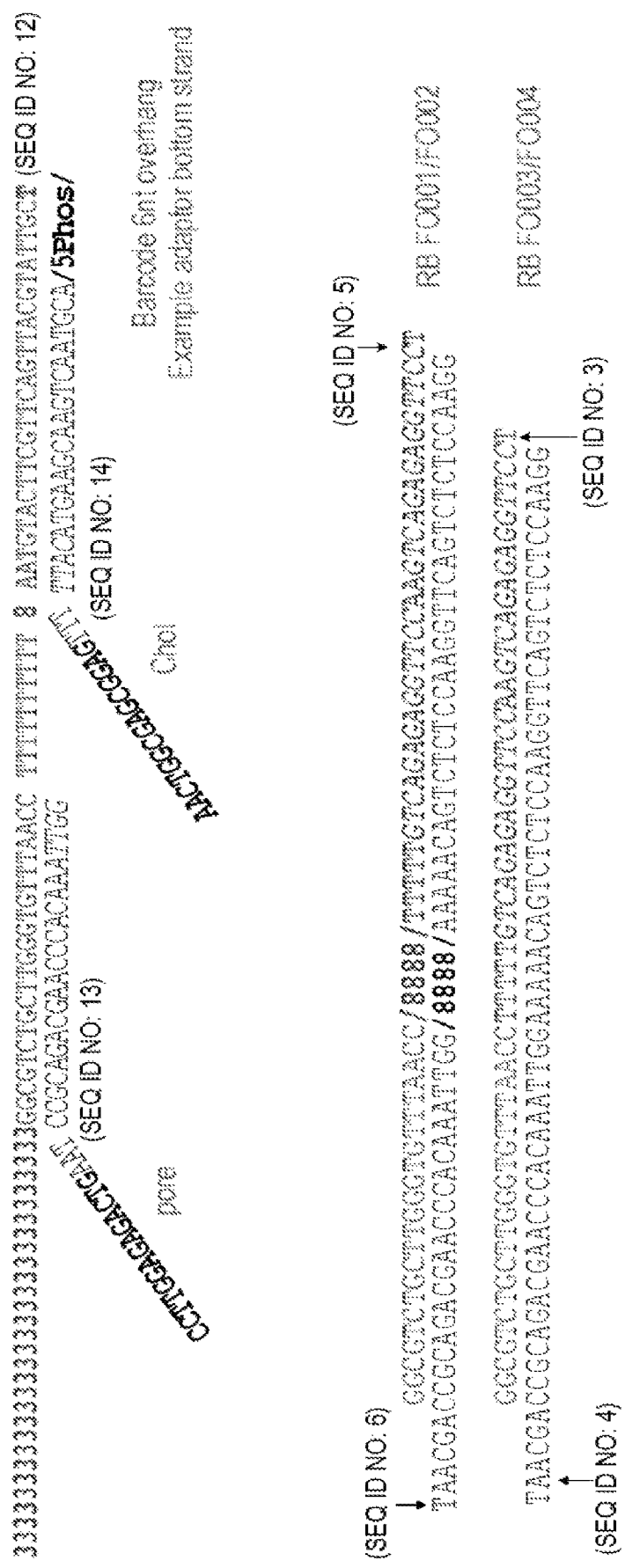
FIG. 17B provide some example sequences that can be used for such purposes. The top construct shows a portion of an example Y adaptor. The "FO001/FO002" and "FO003/FO004" sequences are examples of a duplex stem that can be ligated to the example Y adapter to create a single adaptor construct that can enable the method according to one or more embodiments described herein. The light-blue sequences in the "FO001/FO002" and "FO003/FO004" sequences have the same sequence as the purple sequence, which is a binding sequence site for a nanopore. The same binding sequence site for a nanopore can be used more than once (e.g., twice) within the duplex stem of the adaptor, wherein the light-blue sequences are not exposed.
Figure 20:
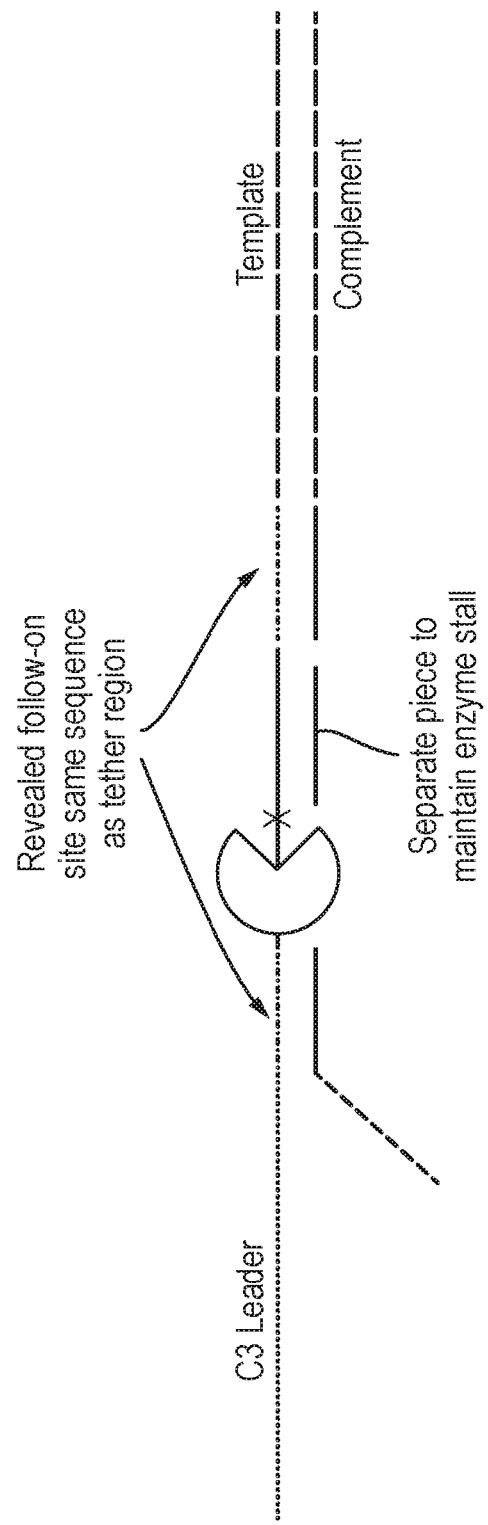
FIG. 20 shows a schematic illustration of an adapter design where the same sequence (green) within a duplex stem is repeated at a different location of the adaptor as shown to enable a follow-on method e.g.
Figure 21:
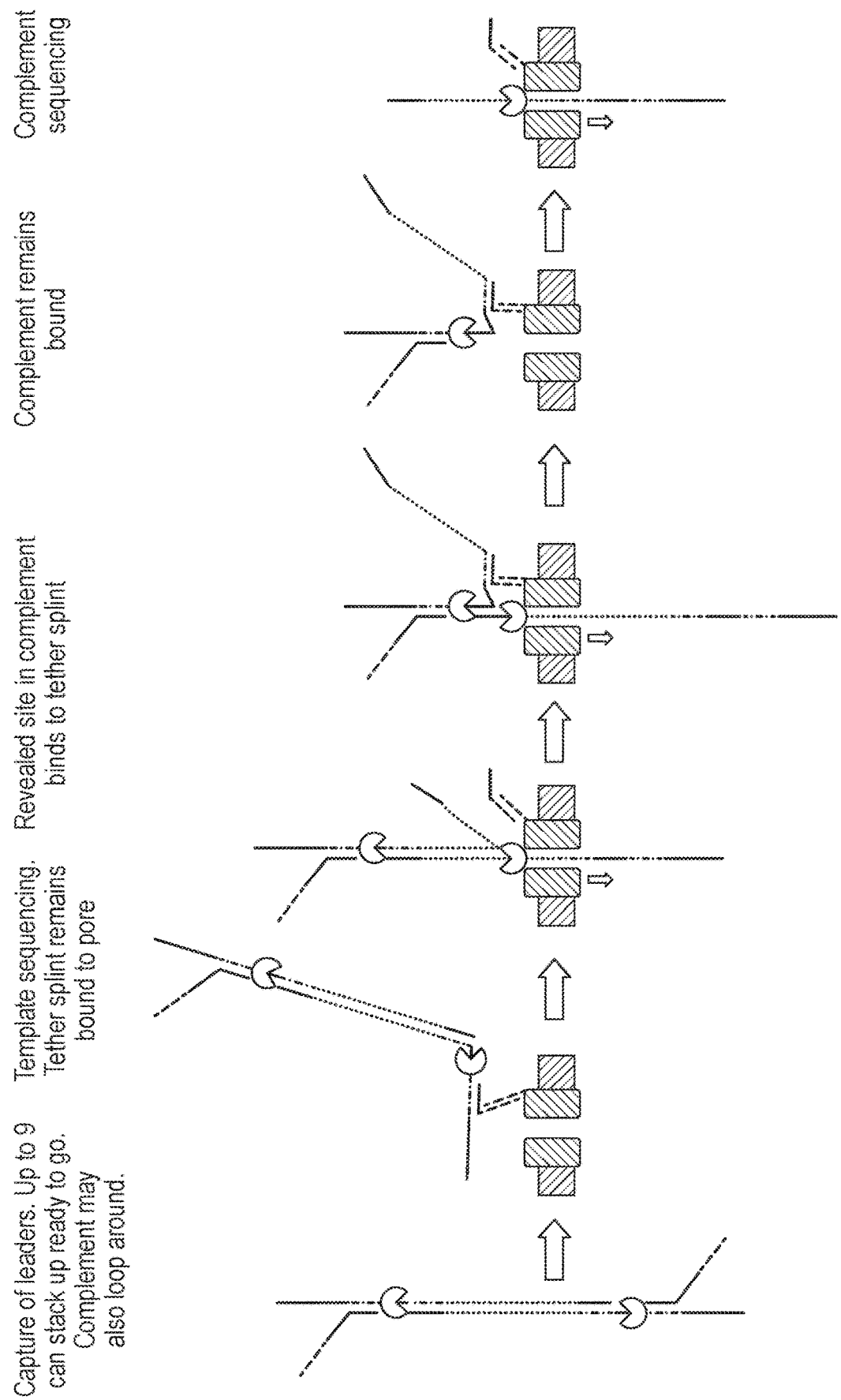
as shown in FIG. 21.
Figure 22:
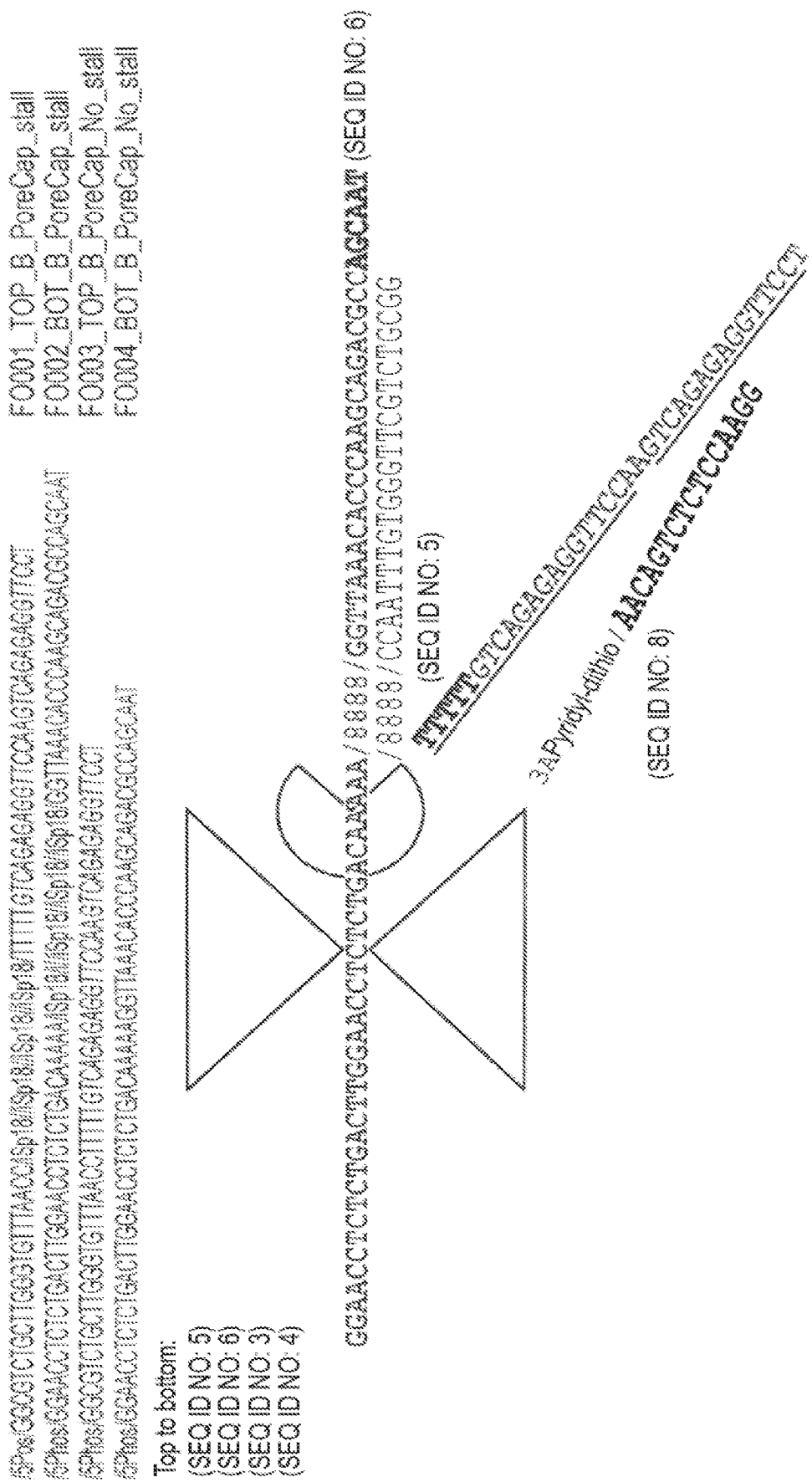
FIG. 22 shows how the revealed sequences are exposed for coupling to the pore-tag as the template-enzyme nears the end of the template strand. Efficiency of the follow-on process can be increased, for example, by including spacers (e.g., 4 sp18 spacers, e.g., hexaethyleneglycol, in the sequence shown) or similar features that briefly pause the enzyme, which allows more time for coupling, or features with optimized geometry or flexibility. A double binding site in the revealed section also improves the chances of coupling to pore-tag.
Figure 24:
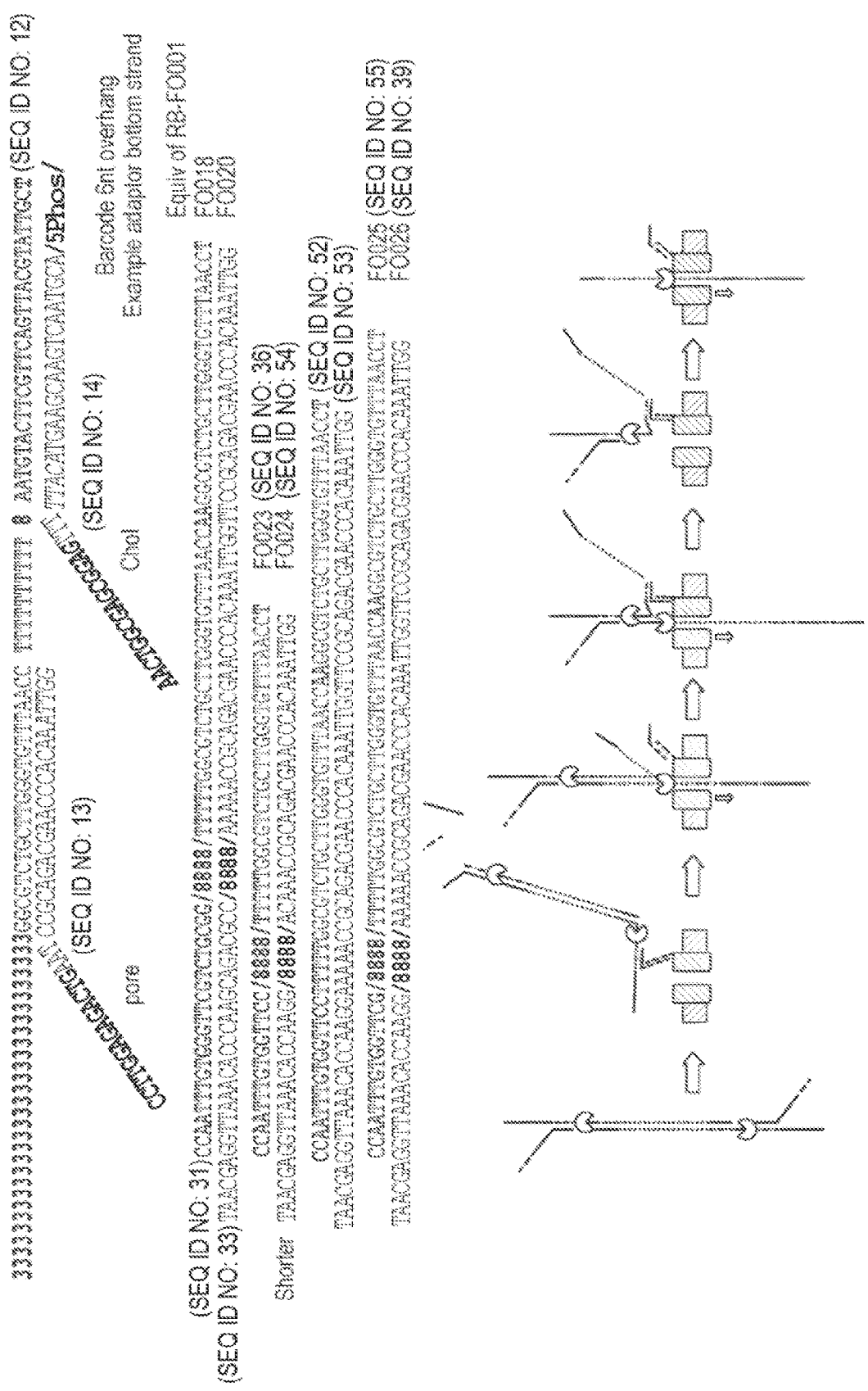
FIG. 24 provides further adapters/sequences that can enable the method disclosed in FIG. 21 and are more optimized in terms of pausing the enzyme.
Figure 25:
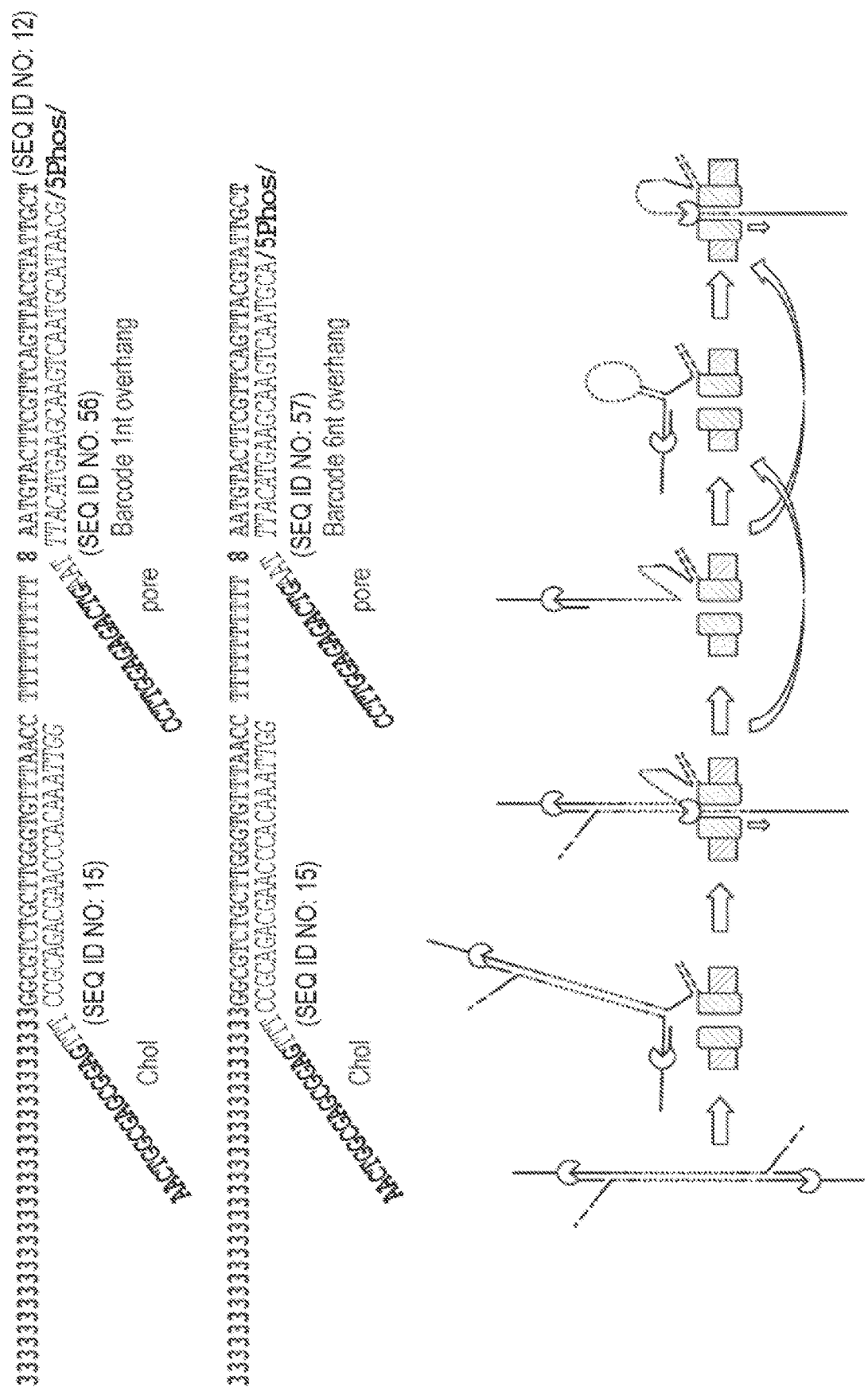
FIG. 25 provides example adapters/sequences that can enable the method disclosed in FIG. 19.

The adaptors used in the methods of various aspects described herein may be further configured to permit binding of an analyte (e.g., a target polynucleotide or a non-covalently bound molecule) to a nanopore for improved sensitivity and/or throughput of the characterization method. This is different in purpose from an embodiment in which a capture sequence within the duplex stem of an adaptor is exposed to allow binding of a second member of a non-covalently bound molecule (e.g., a complement strand of a double-stranded polynucleotide), e.g., as illustrated in FIG. 10 for increasing the likelihood of a complement translocation following a template translocation, thus increasing accuracy of sequencing information. As illustrated in FIG. 16, an adaptor may be further configured to include a tether for binding to a nanopore, e.g., to facilitate capture of the analyte. Thus, the analyte binds to a first tag conjugated to a nanopore before a first member of the analyte (e.g., a template strand of a double stranded polynucleotide) enters the nanopore. As the first member translocates through the pore and unzips the duplex stem to expose a capture sequence on the second member, the second member binds to the a second tag conjugated to the nanopore such that the second member is held close to the nanopore for subsequent characterization after the first member. The first tag and the second tag on the nanopore can be different (e.g., as shown in FIG. 16), or they can be the same (e.g., as shown in FIG. 17A), depending on the design of the adaptors.

Accordingly, a further method disclosed herein involves determining a characteristic of an analyte using a nanopore comprising: (a) providing a nanopore that is modified to comprise at least two or more tags external to the lumen of the nanopore, wherein the tags provide binding sites for at least two or more analytes; and (b) contacting a plurality of analytes to the nanopore under conditions such that at least one or more (e.g., at least one, at least two, at least three, at least four, at least five, at least six, at least seven, at least eight, at least nine, or more) analytes bind to the tags on the nanopore, while an analyte from the plurality is translocating through the nanopore.

Unlike nanopores that are modified to improve interaction of a nanopore with a target analyte, e.g., by altering charges and/or hydrophobicity of the amino acids within the nanopore lumen, the nanopores described herein are modified to provide multiple tags for capture of a plurality of analytes while an analyte is being processed for characterization. This cuts down pore-open time between each analyte characterization and also increases the local concentration of the analytes, thereby increasing the sensitivity of the method. In some embodiments, a tag-modified nanopore as described in the Section "Tag- or Tether-modified nanopores (e.g., for enhancing analyte capture such as polynucleotide capture)" below can be used to achieve such a purpose.

In some embodiments, the analytes may be modified to bind to the tags on the detector (e.g. a nanopore). In some embodiments, the analyte comprises an adaptor as described herein, e.g., an adaptor comprising an anchor for the nanopore.

The interaction between a tag on a detector (e.g. a nanopore) and the binding site on an analyte (e.g., the binding site present in an adaptor attached to an analyte, wherein the binding site can be provided by an anchor or a leader sequence of an adaptor or by a capture sequence within the duplex stem of an adaptor) may be reversible. For example, an analyte can bind to a tag on a nanopore, e.g., via its adaptor, and release at some point, e.g., during characterization of the analyte by the nanopore. A strong non-covalent bond (e.g., biotin/avidin) is still reversible and can be useful in some embodiments of the methods described herein. For example, to ensure processing of a complement of a double-stranded polynucleotide following the processing of a template, it may be desirable to design the the pair of pore tag and analyte adaptor to provide a sufficient interaction between the complement of a double stranded polynucleotide (or a portion of an adaptor that is attached to the complement) and the nanopore such that the complement is held close to the nanopore (without detaching from the nanopore and diffusing away during the translocation of the template) but is able to release from the nanopore as it is processed.

Accordingly, in some embodiments, the pair of pore tag and analyte adaptor used in the methods described herein can be configured such that the binding strength or affinity of a binding site on an analyte (e.g., the binding site present in an adaptor attached to an analyte, wherein the binding site can be provided by an anchor or a leader sequence of an adaptor or by a capture sequence within the duplex stem of an adaptor) to a tag on a nanopore is sufficient to maintain the coupling between the nanopore and analyte for a period of time until an applied force is placed on it to release the bound analyte from the nanopore. In some embodiments where the analyte is a double stranded polynucleotide, the applied force may be processing of a complement strand e.g., by a polymerase.

Figure 11A:
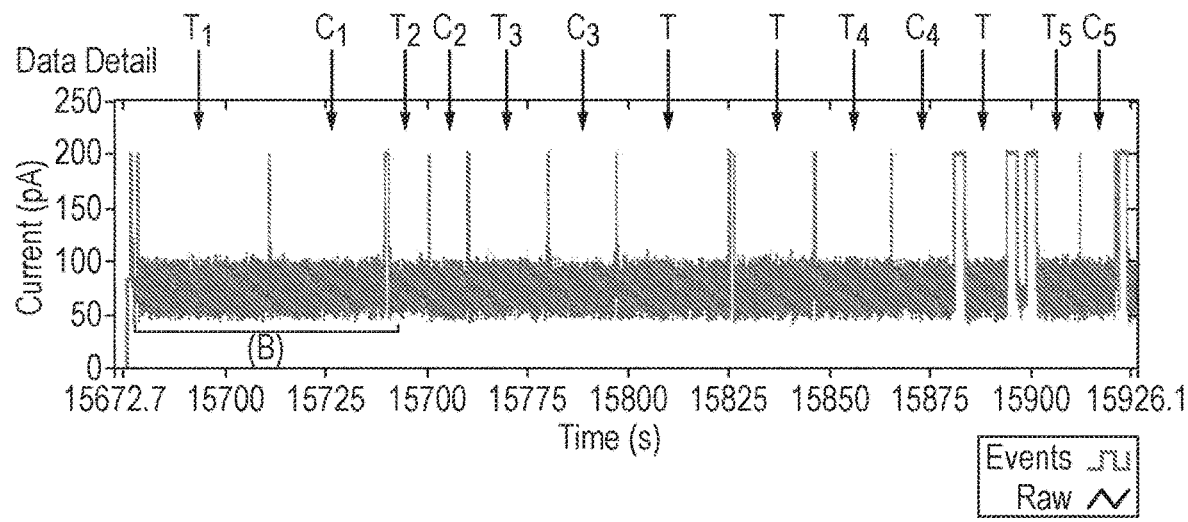
FIGS. 11A-11B show an example section of strand data acquired using the method according to one method disclosed herein. The strand data shows the current (pA) vs time (seconds) of electrical data of a single channel.
Figure 11B:
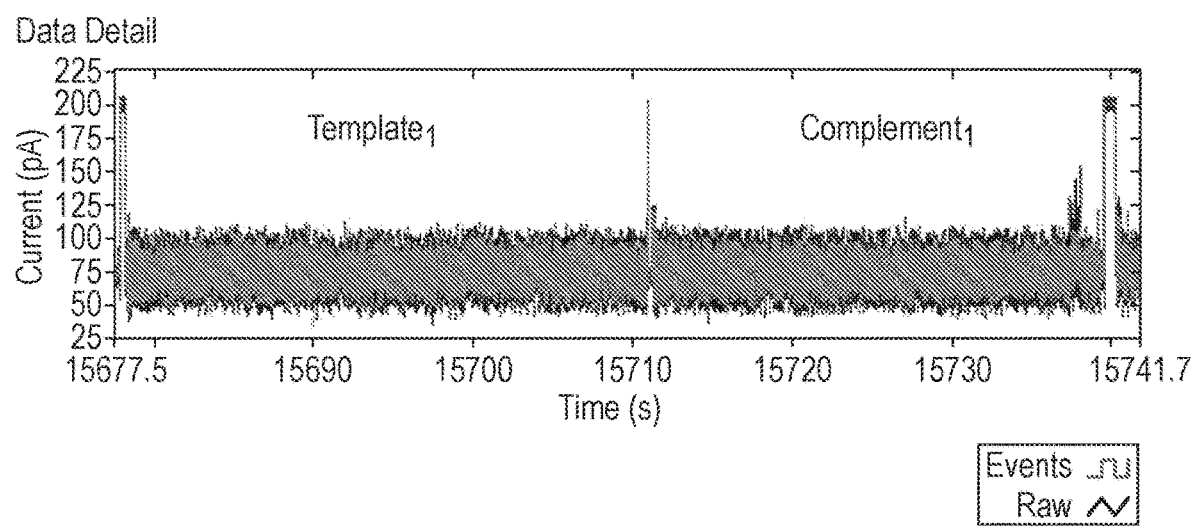

In some embodiments of various aspects described herein, the method may further comprise, upon application of a potential across a membrane, detecting a signal in response to an analyte (e.g., the by-products of the processing of a polynucleotide by a polymerase) passing through the nanopore. In some embodiments, a potential difference can be driven by osmotic imbalance providing ion flow. In some embodiments, a potential difference may be applied across the nanopore between two electrodes positioned on either side the nanopore. The signal may be an electrical measurement and/or an optical measurement. Possible electrical measurements include: current measurements, impedance measurements, tunneling or electron tunneling measurements (Ivanov A P et al., Nano Lett. 2011 Jan. 12; 11(1): 279-85), and FET measurements (International Application WO 2005/124888), e.g., voltage FET measurements. In some embodiments, the signal may be electron tunneling across a solid state nanopore or a voltage FET measurement across a solid state nanopore. Optical measurements may be combined with electrical measurements (Soni G V et al., Rev Sci Instrum. 2010 January; 81(1):014301). The measurement may be a transmembrane current measurement such as measurement of ionic current flowing through the pore. FIGS. 11A-11B show a typical current signal measured over time during sequencing double stranded polynucleotides through a nanopore under the control of a polynucleotide binding protein (e.g., polynucleotide unwinding enzyme) using methods disclosed herein.

Alternatively the measurement may be a fluorescence measurement indicative of ion flow through the channel such as disclosed by Heron et al, J. Am. Chem. Soc., 2009, 131 (5), 1652-1653 or measurement of a voltage across the membrane using a FET. In some embodiments, the method may further comprise, upon application of a potential across the membrane, detecting an ionic current flow through the nanopore as a polynucleotide is processed. In some embodiments, the methods may be carried out using a patch clamp or a voltage clamp. In some embodiments, the methods may be carried out using a voltage clamp. Electrical measurements may be made using standard single channel recording equipment as describe in Stoddart D et al., Proc Natl Acad Sci, 12; 106(19):7702-7, Lieberman K R et al, J Am Chem Soc. 2010; 132(50):17961-72, and International Application WO 2000/28312. Alternatively, electrical measurements may be made using a multi-channel system, for example as described in International Application WO 2009/077734 and International Application WO 2011/067559.

An array of nanopores may be provided to increase the throughput and therefore the measurement of polynucleotide strands, such as a disclosed in International Application WO2014/064443, the content of which is incorporated herein by reference.

As will be apparent from the above discussion, methods provided herein may comprise providing a condition so as to permit the template strand of the construct to be processed by a polymerase and the products of the processing reaction to be detected by the detector, thereby detecting the addition of a nucleotide by the polymerase to the polynuceotide strand.

A probe may comprise an enzyme such as polymerase or a reverse transcriptase suitable for interacting with individual double-stranded polynucleotides, such as DNA or RNA target molecules. Enzymes that catalyze the template-dependent incorporation of nucleotide bases into a growing oligonucleotide strand undergo conformational changes in response to sequentially encountering template strand nucleic acid bases and/or incorporating template-specified natural or analog bases (i.e., an incorporation event). Such conformational changes can modulate electrical current through a bridge molecule to which the probe is coupled, thereby provide a sequence-specific signal pattern in a manner that is dependent on the template molecule.

The method may thus involve detecting the product of the sequential addition of polynucleotides by an enzyme such as a polymerase to the nucleic acid strand, wherein the product is a change in one or more properties of the enzyme such as in the the conformation of the enzyme. Such methods may thus comprise subjecting an enzyme such as polymerase or a reverse transcriptase to a double-stranded polynucleotide under conditions such that the template-dependent incorporation of nucleotide bases into a growing oligonucleotide strand causes conformational changes in the enzyme in response to sequentially encountering template strand nucleic acid bases and/or incorporating template-specified natural or analog bases (i.e., an incorporation event), detecting the conformational changes in the enzyme in response to such incorporation events, and thereby detecting the sequence of the template strand. Such methods may involve detecting and/or measuring incorporation events using methods known to those skilled in the art, such as those described in US 2017/0044605.

Analysis of Signal Measurements

Any suitable signal can be used to detect the processing of a polynucleotide by an enzyme in accordance with the methods provided herein. Various detection methods suitable for use in the methods provided herein are known to those skilled in the art. By way of non-limiting example, the products and/or byproducts of the processing reaction can be detected using a nanopore, or by spectroscopic (e.g. Raman spectroscopy, such as Surface-Enhanced Raman Spectroscopy) or microscopic techniques (e.g. Atomic Force Microscopy). The use of Surface-Enhanced Raman Spectroscopy to detect nucleobases has been descrived in Chen, Li, Kerman, Neutens, Willems, Carnelissen, Lagae, Stakenborg and Van Dorpe ("*High spatial resolution nanoslit SERS for single-molecule nucleobase sensing*", Nature Communications, (2018)9:1733) and are suitable for use in the methods provided herein. Accordingly, in some embodiments, the products and/or by-products of the processing reaction are detected using a spectroscopic or microscopic technique, preferably SERS.

In some other embodiments, the method comprises detecting a signal corresponding to ion flow through a pore indicative of the interaction, for example the processing of polynucleotides by a polymerase. In some embodiments, a potential difference can be driven by osmotic imbalance providing ion flow. In some embodiments, a potential difference may be applied across a transmembrane pore between two electrodes positioned on either side of the pore. Alternatively the measurement may be a fluorescence measurement indicative of ion flow through the channel such as disclosed by Heron et al, J. Am. Chem. Soc., 2009, 131 (5), 1652-1653. An array of nanopores may be provided to increase the throughput and therefore the measurement of polynucleotide strands, such as a disclosed by WO2014064443.

Figure 4:
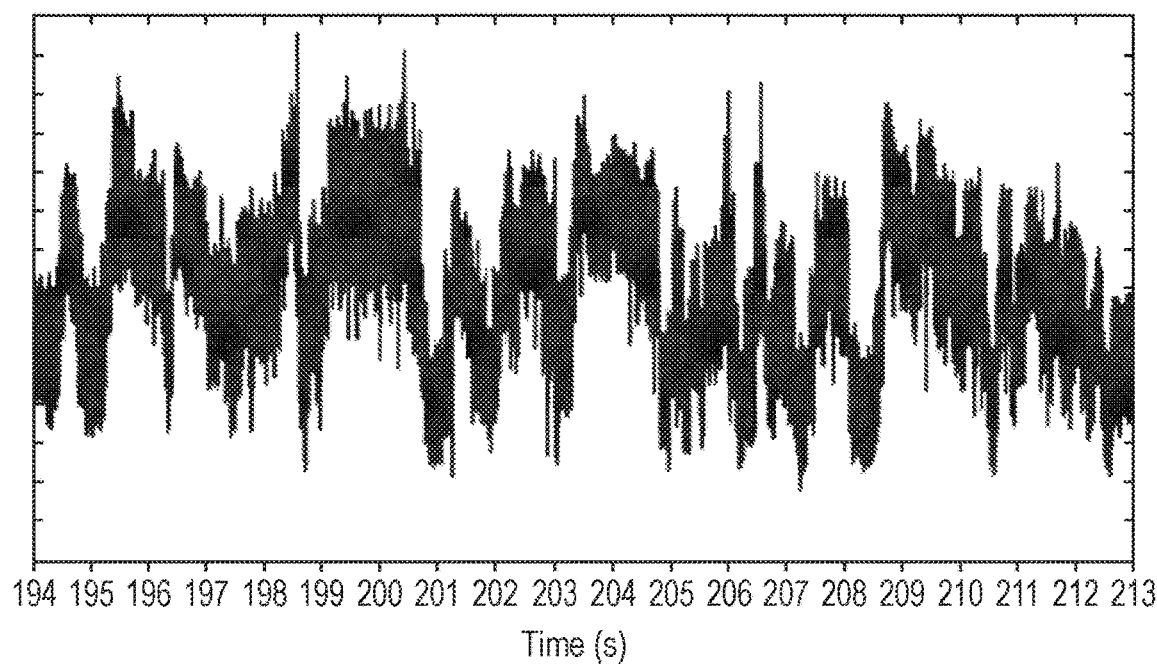
FIG. 4 is a schematic illustration of a current signal measured over time during translocation of a polynucleotide strand through a nanopore.
Figure 5:
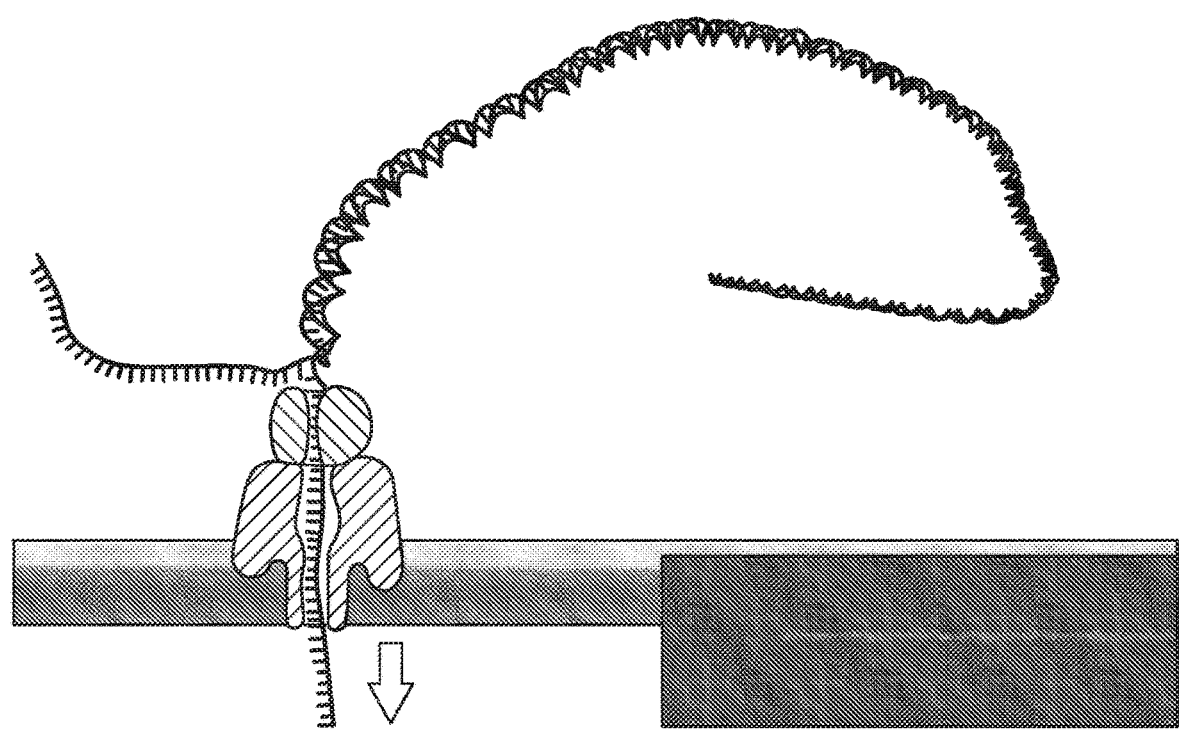
FIG. 5 is an illustration of the separation of a double stranded polynucleotide at the nanopore interface and the subsequent translocation of a single stranded polynucleotide through the nanopore.

FIG. 4 shows a typical current signal measured over time during translocation of a polynucleotide through a nanopore under enzyme control in a disclosed method. When the polynucleotide to be translocated is joined by a hairpin, non-nucleotides or modified nucleotides may be provided in the hairpin to provide a signal indicative of the hairpin. The current signal over reflects the sequence of the polynucleotide as it translocates the nanopore. Thus it is possible to determine which parts of the signal are indicative of the template and complement. Typically the enzyme ratchets the polynucleotide through the nanopore giving rise to characteristic current levels. The magnitude of the signal over time depends upon the nature of the nanopore, and more than one nucleotide can influence the current at any particular time.

In some disclosed methods, the number of nucleotides that influence the current at any particular time may be dependent on a group of k nucleotide units, where k is a plural integer, hereinafter referred to as a 'k-mer'. This might be thought of conceptually as the nanopore having a "blunt reader head" that is bigger than the polymer unit being measured. In such a situation, the number of different k-mers to be resolved increases to the power of k. For example, if there are n possible polymer units, the number of different k-mers to be resolved is $n^k$. With high numbers of k-mers, it can become difficult to resolve the measurements produced by different k-mers, to the detriment of estimating the underlying sequence of polymer units.

Figure 6:
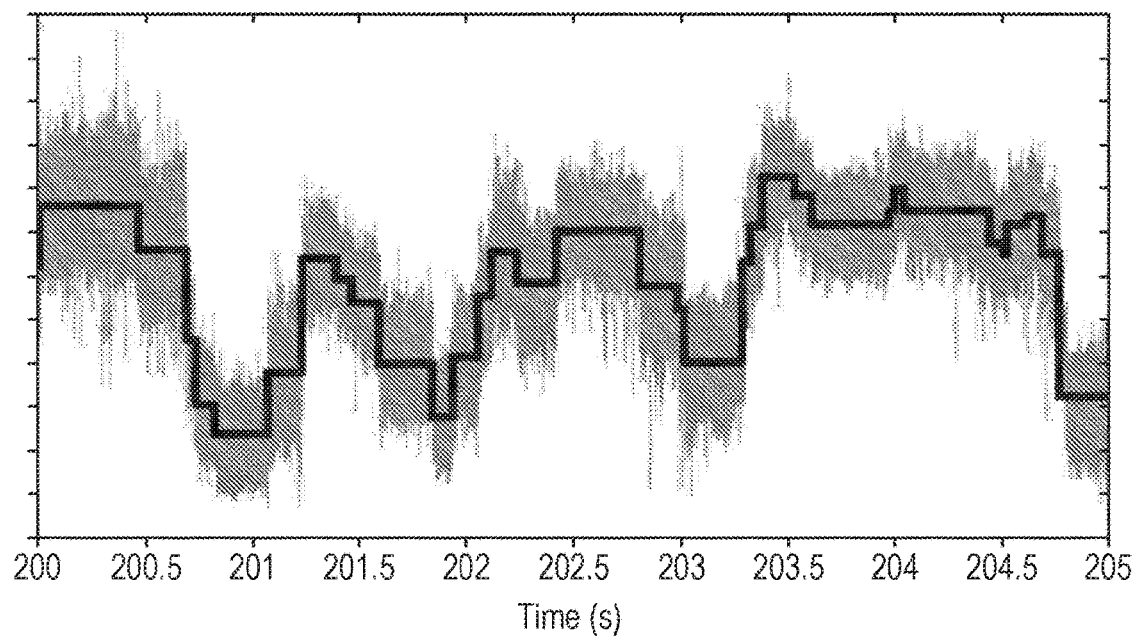
FIG. 6 is an illustration of event detection of a portion of the current time signal of FIG. 4 during sequencing a polynucleotide.

The current vs time sampled data points may be associated into contiguous groups by carrying out a known analytical technique such as a running 't-test' which attempts to find changes in the local mean of the signal. These groups are referred to as events. Events indicative of a particular k-mer may be determined as shown in FIG. 6. An event is represented with a few summary features (mean current of the data points within an associated group and a standard deviation about the mean current).

Figure 7:
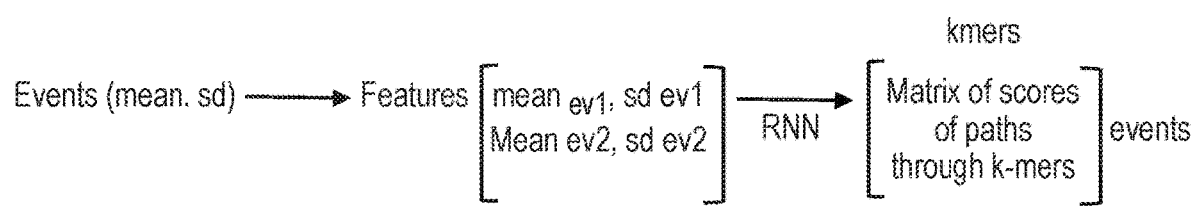
FIG. 7 is a schematic illustration of analysis of signal measurements using an recurrent neural network (RNN) model.
Figure 8:
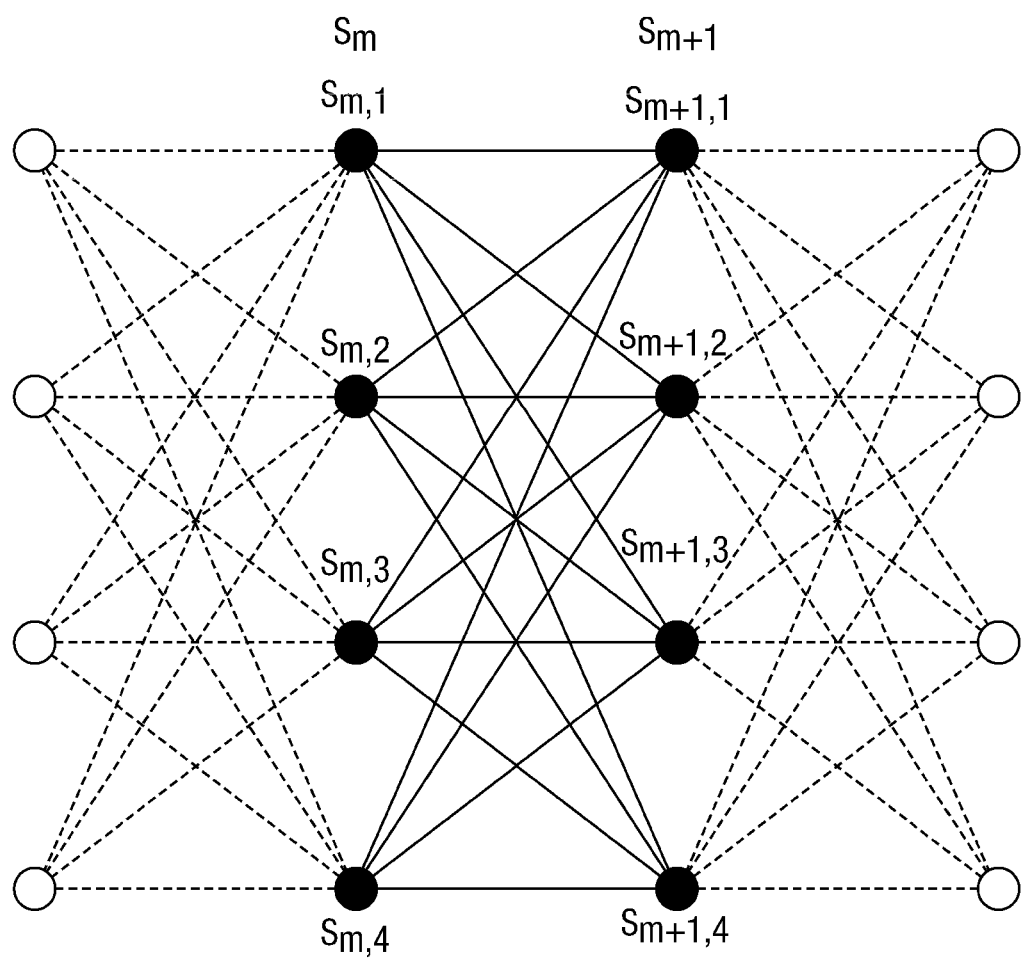
FIG. 8 is an illustration of how a Viterbi algorithm is employed to determine the path through the possible transitions with the highest likelihood.

In order to determine a polynucleotide sequence, in some disclosed methods a model may be referred to which takes into account the number of possible transitions between k-mers and which also takes into the account the current level. Such analytical techniques are disclosed in WO2013041878 hereby incorporated by reference, wherein reference to a probabilistic analytical technique such as a hidden Markov model (HMM) is used to determine the total number of possible transitions and wherein the most likely transition is subsequently determined by an analysis technique such as a Viterbi algorithm. A recurrent neural network (RNN) may be employed as an alternative to an HMM and provides more freedom of mathematical expression over an HMM in for example describing the potential relationship between events and the number of nucleotides that give rise to an event. Such a method employing an RNN is illustrated by example in FIG. 7, wherein from the events, features are derived which incorporate information from other neighboring events. This provides extra information to the RNN, a mathematical model whose output depends upon previous calculations of a sequence of data. An example of how a Viterbi algorithm is employed to determine the path through the possible transitions with the highest likelihood is shown schematically and naively in FIG. 8.

The most likely transition between k-mers may be used to determine a k-mer sequence and thus a nucleotide sequence of a nucleotide strand. Due to the nature of the mathematical methods employed, nucleotide sequence is often stated in terms of % accuracy.

In methods involving measurement of template strands only, the above method may be used to determine the template sequence. However in the case whereby a template and its reverse complement are measured, the pairing relationship between template and its complement may provide added power to sequencing measurement. An example of a particular technique which takes advantage of this relation is disclosed in WO2013041878 whereby the two matrices of template events $t_i$ vs possible k-mer states sk and complement events $c_j$ vs possible k-mer states are combined to form a three dimensional matrix (2D) model. The 2D model finds the most likely alignment of the two series of events, together with the k-mers which explain these observations. This model considers the combination of the template and complement sequences.

In principle a 2D basecaller must examine all triples of $(t_i, c_j, s_k)$ and the number of possible associations between template events, complement paths and k-mers. In practice a full 2D calculation becomes computationally impractical at long read lengths and a useful approximation is therefore to constrain the 2D model, as disclosed in WO201514035.

Alternatively a determination of a nucleotide sequence could be made by comparing the template and complement event data or nucleotide sequences and determining the optimal association between the template and complement. However this method would not provide the improved accuracy of a 2D model as it does not consider the highest likelihood of the combination between the template and complement strands. Example of consensus methods that compare template and complement base-calls is disclosed Unlike the case where the template and complement strands are connected by a hairpin, the complement strand may not always be processed following the template strand in sequential order. For example following the processing of the template strand of the double stranded construct, there exists the possibility that a template strand from a second double-stranded construct may be processed. Furthermore, following the processing of the template (first) strand, there exists the possibility that the complement (second) strand may not be captured by the binding site of the detector (e.g. nanopore). This may be due to for example that the one or more binding sites of the detector (e.g. nanopore) are already occupied by one or more complement strands and therefore a binding site is not available to a complement strand. Any complement strand not captured by the detector (e.g. nanopore) will likely diffuse away from the nanopore and not be captured by the nanopore. Thus in order to make use of the added power of template and complement strands it is first necessary to determine whether the signal measurements correspond to the template and its corresponding complement.

In some embodiments of various aspects described herein, the method may further comprising identifying a signal corresponding to processing of the target polynucleotide and a sequential signal corresponding to the separate processing of the polynucleotide complementary to the target polynucleotide and analysis of the signals thus identified. For those signals thus identified the above mathematical methods may be used to determine the nucleotide sequence of the target wherein the methods make use of both the information of the target (template) and the complement with its associated advantages.

In order to identify whether the signals (e.g., sequential signals) corresponding to the target and its complement, the events may be aligned to each other in order to determine the degree of alignment. Depending on the degree of alignment a determination may be made whether the signals in fact correspond to the target and its complement. The % alignment used to make a positive correlation may be arbitrarily chosen and may for example be greater than 95%. A known pairwise alignment method such a Smith-Waterman or Needleman-Wunsch algorithm may be employed. Suitable example of methods of alignment which may be used are disclosed in WO2015/140535 or WO 2016/059427.

It has been observed that generally, the complement strand either follows its template strand in sequential order or diffuses away from the detector, e.g. the nanopore. There is a much lower chance that the complement strand follows its template strand after a further strand unassociated with that particular complement strand. There are unique characteristics of pairs of template and complement. For example, a template/complement pair generally tends to share the same length of nucleotides (number of events). In addition, a follow-on strand of the pair may be processed much quicker than a new strand, and/or sequencing of a complement tends to be faster, etc. One or more these characteristics can be used to identify template/complement pairs without complicated computational analysis.

In some embodiments, in order to reduce the computational demands, alignments may be restricted to neighboring measurements of strands. Once a template-complement relationship between strands has been established, determination of a sequence can either make use of the measurements of a template or complement strand or the measurements of the template and the complement strand. For example, the sequence of a template strand may be determined, wherein the sequencing accuracy is not considered sufficiently high enough. Under such circumstances, the method may choose determine the sequence from consideration of both the template and complement sequence data to provide a sequence accuracy which is higher than that obtained by determination of the template sequence alone. Alternatively, the sequence accuracy of a template strand may be considered to be sufficiently good enough such that consideration of both the template and complement sequence data isn't considered necessary. Factors determining whether the template sequence data is used or whether both the template and complement sequence data is used may be for example whether the underlying sequence has bases or groups of bases that are difficult to call precisely or for example whether a particular base is a single-nucleotide polymorphism variant.

In the event that no sequential relationship is determined, the sequence of that particular strand may be determined in the same way as would be carried for measurement of a template only strand. In the event that a sequential relationship is determined, the sequence of that particular strand may be determined in the same way as would be carried for measurement of template and complement strand. This information may be combined to provide an overall sequence determination.

Some disclosed methods further comprises analyzing the signal produced when a first strand (e.g., a target polynucleotide) translocates through a transmembrane pore in conjunction with the signal produced when a second strand complementary to the first strand translocates through the same nanopore. The first strand (e.g., a target polynucleotide) and its complement (the second strand) are connected by base pairing. Therefore, once the first polynucleotide binding protein (e.g., polynucleotide unwinding enzyme) has moved along the length of the double stranded polynucleotide the first and the second strands are no longer connected. See, e.g., FIG. 10. The translocation of the second strand through the nanopore is therefore a separate event to the translocation of the first strand through the nanopore, e.g., as shown in FIG. 11, in which the open-pore current (with no strand blocking the current) of about 200 pA was observed between translocation of the first strand and the second strand. While not necessary, it is desirable that translocation of the second strand takes place as soon as, e.g., immediately (e.g., less than 1 second) following translocation of the first strand. See, for example, FIG. 13.

The disclosed method comprises a step of identifying signals corresponding to sequential translocation of the target polynucleotide and the polynucleotide complementary to the target polynucleotide. Sequential translocation includes where the complementary polynucleotide is translocated through the same pore as the target polynucleotide. The target polynucleotide and complementary polynucleotide may be translocated through the pore in either order. Other polynucleotides, such as 1, 2, 3, 4 or 5 to about 10 polynucleotides may pass through the pore between the target polynucleotide and the complementary polynucleotide. Preferably, the target polynucleotide and complementary polynucleotide pass through the pore consecutively, in either order. The pore preferably returns to an open state between the translocation of the first of the target polynucleotide and complementary polynucleotide through the pore and the translocation of the second of the target polynucleotide and complementary polynucleotide through the pore.

In some embodiments, the consecutive processing of the target and complementary polynucleotides may be facilitated by tethering the target polynucleotide and/or the complementary polynucleotide to the membrane and/or to the pore. Other methods of facilitating consecutive processing of the two strands of the double stranded polynucleotide include attaching the target polynucleotide and/or the complementary polynucleotide to microparticles and/or modifying the pore to increase/enhance polynucleotide capture.

Identification of a signal corresponding to processing of the target polynucleotide and a sequential signal corresponding to the separate processing of the polynucleotide complementary to the target polynucleotide may be facilitated using a barcode. Typically, a double stranded barcode is included in or attached to the double stranded polynucleotide. When the target polynucleotide and the complementary polynucleotide are separated (by the polynucleotide binding protein (e.g., polynucleotide unwinding enzyme)) the barcode is retained in both the target polynucleotide and the complementary polynucleotide. Characterisation of the barcode by the transmembrane pore will create a signal characteristic of that barcode. The second and subsequent detection of the barcode by the pore can be used to determine that a target polynucleotide and its complement have been sequentially determined by the pore. The signals corresponding to the target polynucleotide and separately the polynucleotide complementary to the target polynucleotide may thereby be identified.

Tag- or Tether-Modified Nanopores (e.g., for Enhancing Analyte Capture Such as Polynucleotide Capture)

Detectors for use in the methods described herein are modified to comprise one or more binding sites for binding to one or more analytes.

When the detector is a nanopore, the nanopores for use in the methods described herein are modified to comprise one or more binding sites for binding to one or more analytes. In some embodiments, the nanopores may be modified to comprise one or more binding sites for binding to an adaptor attached to the analytes. For example, in some embodiments, the nanopores may bind to a leader sequence of the adaptor attached to the analytes. In some embodiments, the nanopores may bind to a single stranded sequence in the adaptor attached to the analytes. In some embodiments, the nanopores may bind to a capture sequence within a duplex stem of the adaptor attached to the analytes, wherein the capture sequence is revealed only upon unwinding of the duplex stem.

In some embodiments, a nanopore may be modified to comprise one or more binding sites for binding to an adaptor attached to a first strand or second strand of a double stranded oligonucleotide, e.g., to facilitate the sequential processing of the first strand and the second strand by a polymerase.

A nanopore may be modified to comprise one or more tags or tethers, each tag or tether comprising a binding site for the analyte.

In some embodiments, nanopores are modified to comprise two or more tags or tethers. For example, one tag or tether can be provided to increase the sensitivity of a method for characterizing an analyte such as a polynucleotide ("sensitivity tag"), while another tag or tether can be provided to increase the likelihood of sequencing of a complement strand following a template strand of a polynucleotide ("follow-on tag"). As shown in FIG. 15, the pore tags can be configured in any number of ways. By way of example only, in some embodiments, each monomer of an oligomeric pore can have the same type of tag configuration (e.g., with multiple binding sites, as illustrated by Tag-A and Tag-B). Tag-A and Tag-B can be combined to form a single tag, and at least one or more monomers comprises the Tag-A/Tag-B combined tag. Alternatively, an oligomeric pore can comprise mixed monomers with different tags attached such that at least one monomer has a different tag configuration from the other monomers. In another example, Tag-A and Tag-B can remain as separate tags and at least one or more monomers can comprise both individual tags. Sensitivity and follow-on tags can be separately combined if they are complementary to unique sequences used in the adaptors as described herein.

FIG. 16 is a schematic illustration of how nanopores with two different tag types can be used to capture strands from solution (for improved sensitivity). The adaptor that is attached to an end of a double-stranded polynucleotide comprises a capture sequence (e.g., forming a non-complementary arm of a Y-adaptor) that is available to couple to a first pore tag, while a separate capture sequence within the duplex stem that is only revealed when unzipped permits the complement to bind to a second pore tag and thus enables complement capture for follow-on sequencing.

The interaction between a tag on a nanopore and the binding site on an analyte (e.g., the binding site present in an adaptor attached to an analyte, wherein the binding site can be provided by an anchor or a leader sequence of an adaptor or by a capture sequence within the duplex stem of an adaptor) may be reversible. For example, an analyte can bind to a tag on a nanopore, e.g., via its adaptor, and release at some point, e.g., during characterization of the analyte by the nanopore and/or during processing by the polymerase. A strong non-covalent bond (e.g., biotin/avidin) is still reversible and can be useful in some embodiments of the methods described herein. For example, to ensure processing of a complement of a double-stranded polynucleotide following the processing of a template, it may be desirable to design the the pair of pore tag and analyte adaptor to provide a sufficient interaction between the complement of a double stranded polynucleotide (or a portion of an adaptor that is attached to the complement) and the nanopore such that the complement is held close to the nanopore (without detaching from the nanopore and diffusing away) but is able to release from the nanopore as it is processed.

Accordingly, in some embodiments of various aspects described herein, the pair of pore tag and analyte adaptor can be configured such that the binding strength or affinity of a binding site on an analyte (e.g., the binding site present in an adaptor attached to an analyte, wherein the binding site can be provided by an anchor or a leader sequence of an adaptor or by a capture sequence within the duplex stem of an adaptor) to a tag on a nanopore is sufficient to maintain the coupling between the nanopore and analyte until an applied force is placed on it to release the bound analyte from the nanopore. In some embodiments where the analyte is a double stranded polynucleotide, the applied force may be processing of a complement strand by a polymerase.

In some embodiments, the tags or tethers are uncharged. This can ensure that the tags or tethers are not drawn into the nanopore under the influence of a potential difference.

One or more molecules that attract or bind the polynucleotide or adaptor may be linked to the detector (e.g. the pore). Any molecule that hybridizes to the adaptor and/or target polynucleotide may be used. The molecule attached to the pore may be selected from a PNA tag, a PEG linker, a short oligonucleotide, a positively charged amino acid and an aptamer. Pores having such molecules linked to them are known in the art. For example, pores having short oligonucleotides attached thereto are disclosed in Howarka et al (2001) Nature Biotech. 19: 636-639 and WO 2010/086620, and pores comprising PEG attached within the lumen of the pore are disclosed in Howarka et al (2000) J. Am. Chem. Soc. 122(11): 2411-2416.

A short oligonucleotide attached to the detector (e.g. a transmembrane pore), which oligonucleotide comprises a sequence complementary to a sequence in the leader sequence or another single stranded sequence in the adaptor may be used to enhance capture of the target polynucleotide and/or complementary polynucleotide in a method of any aspects described herein.

In some embodiments, the tag or tether may comprise or be an oligonucleotide (e.g., DNA, RNA, LNA, BNA, PNA, or morpholino). The oligonucleotide (e.g., DNA, RNA, LNA, BNA, PNA, or morpholino) can have about 10-30 nucleotides in length or about 10-20 nucleotides in length. An exemplary oligonucleotide (e.g., DNA, RNA, LNA, BNA, PNA, or morpholino) may comprise a sequence as set forth in SEQ ID NO: 8. In some embodiments, the oligonucleotide (e.g., DNA, RNA, LNA, BNA, PNA, or morpholino) for use in the tag or tether can have at least one end (e.g., 3'- or 5'-end) modified for conjugation to other modifications or to a solid substrate surface including, e.g., a bead. The end modifiers may add a reactive functional group which can be used for conjugation. Examples of functional groups that can be added include, but are not limited to amino, carboxyl, thiol, maleimide, aminooxy, and any combinations thereof. The functional groups can be combined with different length of spacers (e.g., C3, C9, C12, Spacer 9 and 18) to add physical distance of the functional group from the end of the oligonucleotide sequence. In some embodiments, the tag or tether may be an oligonucleotide (e.g., DNA, RNA, LNA, BNA, PNA, or morpholino) having a sequence as set forth in SEQ ID NO: 8 with a 5'-malemide modification. In some embodiments, the tag or tether may be an oligonucleotide (e.g., DNA, RNA, LNA, BNA, PNA, or morpholino) having a sequence as set forth in SEQ ID NO: 8 with a 3'-malemide modification. In some embodiments, the tag or tether may be an oligonucleotide (e.g., DNA, RNA, or PNA) having a sequence as set forth in SEQ ID NO: 8 with a 5'-C9-Thiol modification. In some embodiments, the tag or tether may be an oligonucleotide (e.g., DNA, RNA, LNA, BNA, PNA, or morpholino) having a sequence as set forth in SEQ ID NO: 8 with a 3'-C9-Thiol modification. In some embodiments, the tag or tether may be an oligonucleotide (e.g., DNA, RNA, LNA, BNA, PNA, or morpholino) having a sequence as set forth in SEQ ID NO: 8 with a 5'-Thiol modification. In some embodiments, the tag or tether may be an oligonucleotide (e.g., DNA, RNA, LNA, BNA, PNA, or morpholino) having a sequence as set forth in SEQ ID NO: 8 with a 3'-Thiol modification.

In some embodiments, the tag or tether may comprise or be a morpholino oligonucleotide. The morpholino oligonucleotide can have about 10-30 nucleotides in length or about 10-20 nucleotides in length. An exemplary morpholino oligonucleotide may comprise a sequence as set forth in SEQ ID NO: 8. The morpholino oligonucleotides can be modified or unmodified. For example, in some embodiments, the morpholino oligonucleotide can be modified on the 3' and/or 5' ends of the oligonucleotides. Examples of modifications on the 3' and/or 5' end of the morpholino oligonucleotides include, but are not limited to 3' affinity tag and functional groups for chemical linkage (including, e.g., 3'-biotin, 3'-primary amine, 3'-disulfide amide, 3'-pyridyl dithio, and any combinations thereof); 5' end modifications (including, e.g., 5'-primary ammine, and/or 5'-dabcyl), modifications for click chemistry (including, e.g., 3'-azide, 3'-alkyne, 5'-azide, 5'-alkyne), and any combinations thereof. In some embodiments, the tag or tether may be a morpholino oligonucleotide having a sequence as set forth in SEQ ID NO: 8 with a 5'-azide modification. In some embodiments, the tag or tether may be a morpholino oligonucleotide having a sequence as set forth in SEQ ID NO: 8 with a 3'-azide modification. In some embodiments, the tag or tether may be a morpholino oligonucleotide having a sequence as set forth in SEQ ID NO: 8 with a 5'-alkyne modification. In some embodiments, the tag or tether may be a morpholino oligonucleotide having a sequence as set forth in SEQ ID NO: 8 with a 3'-alkyne modification. In some embodiments, the tag or tether may be a morpholino oligonucleotide having a sequence as set forth in SEQ ID NO: 8 with a 3'-pyridyl dithio modification.

In some embodiments, the tag or tether may further comprise a polymeric linker, e.g., to facilitate coupling to a detector e.g. a nanopore. An exemplary polymeric linker includes, but is not limited to polyethylene glycol (PEG). The polymeric linker may have a molecular weight of about 500 Da to about 10 kDa (inclusive), or about 1 kDa to about 5 kDa (inclusive). The polymeric linker (e.g., PEG) can be functionalized with different functional groups including, e.g., but not limited to maleimide, NHS ester, dibenzocyclooctyne (DBCO), azide, biotin, amine, alkyne, aldehyde, and any combinations thereof. In some embodiments, the tag or tether may further comprise a 1 kDa PEG with a 5'-maleimide group and a 3'-DBCO group. In some embodiments, the tag or tether may further comprise a 2 kDa PEG with a 5'-maleimide group and a 3'-DBCO group. In some embodiments, the tag or tether may further comprise a 3 kDa PEG with a 5'-maleimide group and a 3'-DBCO group. In some embodiments, the tag or tether may further comprise a 5 kDa PEG with a 5'-maleimide group and a 3'-DBCO group.

Other examples of a tag or tether include, but are not limited to His tags, biotin or streptavidin, antibodies that bind to analytes, aptamers that bind to analytes, analyte binding domains such as DNA binding domains (including, e.g., peptide zippers such as leucine zippers, single-stranded DNA binding proteins (SSB)), and any combinations thereof.

The tag or tether may be attached to the external surface of a nanopore, e.g., on the cis side of a membrane, using any methods known in the art. For example, one or more tags or tethers can be attached to the nanopore via one or more cysteines (cysteine linkage), one or more primary amines such as lysines, one or more non-natural amino acids, one or more histidines (His tags), one or more biotin or streptavidin, one or more antibody-based tags, one or more enzyme modification of an epitope (including, e.g., acetyl transferase), and any combinations thereof. Suitable methods for carrying out such modifications are well-known in the art. Suitable non-natural amino acids include, but are not limited to, 4-azido-L-phenylalanine (Faz) and any one of the amino acids numbered 1-71 in FIG. 1 of Liu C. C. and Schultz P. G., Annu. Rev. Biochem., 2010, 79, 413-444.

In some embodiments where one or more tags or tethers are attached to a nanopore via cysteine linkage(s), the one or more cysteines can be introduced to one or more monomers that form the nanopore by substitution. In some embodiments, the nanopore may be chemically modified by attachment of (i) Maleimides including diabromomaleimides such as: 4-phenylazomaleinanil, 1.N-(2-Hydroxyethyl)maleimide, N-Cyclohexylmaleimide, 1.3-Maleimidopropionic Acid, 1.1-4-Aminophenyl-1H-pyrrole,2,5,dione, 1.1-4-Hydroxyphenyl-1H-pyrrole,2,5,dione, N-Ethylmaleimide, N-Methoxycarbonylmaleimide, N-tert-Butylmaleimide, N-(2-Aminoethyl)maleimide, 3-Maleimido-PROXYL, N-(4-Chlorophenyl)maleimide, 1-[4-(dimethylamino)-3,5-dinitrophenyl]-1H-pyrrole-2,5-dione, N-[4-(2-Benzimidazolyl)phenyl]maleimide, N-[4-(2-benzoxazolyl)phenyl]maleimide, N-(1-NAPHTHYL)-MALEIMIDE, N-(2,4-XYLYL)MALEIMIDE, N-(2,4-DIFLUOROPHENYL) MALEIMIDE, N-(3-CHLORO-PARA-TOLYL)-MALEIMIDE, 1-(2-Amino-ethyl)-pyrrole-2,5-dione hydrochloride, 1-cyclopentyl-3-methyl-2,5-dihydro-1H-pyrrole-2,5-dione, 1-(3-aminopropyl)-2,5-dihydro-1H-pyrrole-2,5-dione hydrochloride, 3-methyl-1-[2-oxo-2-(piperazin-1-yl)ethyl]-2,5-dihydro-1H-pyrrole-2,5-dione hydrochloride, 1-benzyl-2,5-dihydro-1H-pyrrole-2,5-dione, 3-methyl-1-(3,3,3-trifluropropyl)-2,5-dihydro-1H-pyrrole-2,5-dione, 1-[4-(methylamino)cyclohexyl]-2,5-dihydro-1H-pyrrole-2,5-dione trifluroacetic acid, SMILES O=C1C≡CC(=O)N1CC=2C≡CN=CC2, SMILES O=C1C≡CC(=O)N1CN2CCNCC2, 1-benzyl-3-methyl-2,5-dihydro-1H-pyrrole-2,5-dione, 1-(2-fluorophenyl)-3-methyl-2,5-dihydro 1H-pyrrole-2,5-dione, N-(4-PHENOXYPHENYL)MALEIMIDE, N-(4-NITROPHENYL)MALEIMIDE (ii) Iodocetamides such as: 3-(2-Iodoacetamido)-PROXYL, N-(cyclopropylmethyl)-2-iodoacetamide, 2-iodo-N-(2-phenylethyl) acetamide, 2-iodo-N-(2,2,2-trifluoroethyl)acetamide, N-(4-ACETYLPHENYL)-2-IODOACETAMIDE, N-(4-(AMINOSULFONYL)PHENYL)-2-IODOACETAMIDE, N-(1,3-BENZOTHIAZOL-2-YL)-2-IODOACETAMIDE, N-(2,6-DIETHYLPHENYL)-2-IODOACETAMIDE, N-(2-benzoyl-4-chlorophenyl)-2-iodoacetamide, (iii) Bromoacetamides: such as N-(4-(ACETYLAMINO)PHENYL)-2-BROMOACETAMIDE, N-(2-ACETYLPHENYL)-2-BROMOACETAMIDE, 2-BROMO-N-(2-CYANOPHENYL)ACETAMIDE, 2-BROMO-N-(3-(TRIFLUOROMETHYL)PHENYL)ACETAMIDE, N-(2-benzoylphenyl)-2-bromoacetamide, 2-bromo-N-(4-fluorophenyl)-3-methylbutanamide, N-Benzyl-2-bromo-N-phenylpropionamide, N-(2-BROMO-BUTYRYL)-4-CHLORO-BENZENESULFONAMIDE, 2-Bromo-N-methyl-N-phenylacetamide, 2-bromo-N-phenethyl-acetamide,2-ADAMANTAN-1-YL-2-BROMO-N-CYCLOHEXYL-ACETAMIDE, 2-bromo-N-(2-methylphenyl)butanamide, Monobromoacetanilide, (iv) Disulphides such as: ALDRITHIOL-2, ALDRITHIOL-4, ISOPROPYL DISULFIDE, 1-(Isobutyldisulfanyl)-2-methylpropane, Dibenzyl disulfide, 4-AMINOPHENYL DISULFIDE, 3-(2-Pyridyldithio)propionic acid, 3-(2-Pyridyldithio)propionic acid hydrazide, 3-(2-Pyridyldithio)propionic acid N-succinimidyl ester, am6amPDP1-βCD and (v) Thiols such as: 4-Phenylthiazole-2-thiol, Purpald, 5,6,7,8-TETRAHYDRO-QUINAZOLINE-2-THIOL.

In some embodiments, the tag or tether may be attached directly to a nanopore or via one or more linkers. The tag or tether may be attached to the nanopore using the hybridization linkers described in WO 2010/086602. Alternatively, peptide linkers may be used. Peptide linkers are amino acid sequences. The length, flexibility and hydrophilicity of the peptide linker are typically designed such that it does not to disturb the functions of the monomer and pore. Preferred flexible peptide linkers are stretches of 2 to 20, such as 4, 6, 8, 10 or 16, serine and/or glycine amino acids. More preferred flexible linkers include $(SG)_1$, $(SG)_2$ (SEQ ID NO: 58), $(SG)_3$ (SEQ ID NO: 59), $(SG)_4$ (SEQ ID NO: 60), $(SG)_5$ (SEQ ID NO: 61) and (SG)s (SEQ ID NO: 62) wherein S is serine and G is glycine. Preferred rigid linkers are stretches of 2 to 30, such as 4, 6, 8, 16 or 24, proline amino acids. More preferred rigid linkers include $(P)_{12}$ (SEQ ID NO: 63) wherein P is proline.

A transmembrane pore may be modified to enhance capture of polynucleotides and/or of by-products of the processing reaction by the polymerase. For example, the pore may be modified to increase the positive charges within the entrance to the pore and/or within the barrel of the pore. Such modifications are known in the art. For example, WO 2010/055307 discloses mutations in α-hemolysin that increase positive charge within the barrel of the pore.

Modified MspA, lysenin and CsgG pores comprising mutations that enhance polynucleotide capture are disclosed in WO 2012/107778, WO 2013/153359 and WO 2016/034591, respectively. Any of the modified pores disclosed in these publications may be used herein.

In some embodiments, a CsgG nanopore may be modified to comprise one or more tags or tethers as described herein. One or more tags or tether(s) can be attached to one or more monomers (e.g., 1, 2, 3, 4, 5, 6, 7, 8, 9, or more) of a CsgG nanopore by amino acid modifications at one or more of the following: T3, K7, R11, Q19, K22, A29, T31, R76, N102, G103, N108, R110, Q114, E170, C215, L216, D238, A243, D248, and H255 of SEQ ID NO: 7. In some embodiments, one or more tag(s) or tether(s) can be attached to one or more monomers (e.g., 1, 2, 3, 4, 5, 6, 7, 8, 9, or more) of a CsgG nanopore by amino acid substitutions at one or more of the following: T3C, K7C, R11C, Q19C, K22C, A29C, T31C, R76C, E170C, D238C, A243C, D248C, H255C, C215A/T/S/M/G/I/L, L216V of SEQ ID NO: 7.

In some embodiments, the CsgG nanopore can be further modified to improve capture and/or translocation of analyte (e.g. by-products of the processing reaction by the polymerase) through the nanopore, to improve analyte recognition or discrimination, to improve interaction with a polynucleotide unwinding enzyme, and/or to improve signal-to-noise ratios. For example, in some embodiments, at least one of the monomers that form a CsgG nanopore can comprise one or more mutations as disclosed in WO 2016/034591.

In some embodiments, the CsgG nanopore can comprise one of the following combinations of amino acid substitutions (referenced to SEQ ID NO: 7): (T3C); (K7C); (R11C); (Q19C); (K22C); (A29C); (T31C); (R76C); (E170C); (D238C); (A243C); (D248C); (H255C); (C215A); (C215T); (C215S); (C215M); (C215G); (C215I); (C215L); (C215A, L216V); (A29C, C215T); (T31C, C215T); (R76C, C215T); (T3C, C215A); (K7C, C215A); (R11C, C215A); (Q19C, C215A); (K22C, C215A); (A29C, C215A); (T31C, C215A); (R76C, C215A); (E170C, C215A); (C215A, D238C); (C215A, A243C); (C215A, D248C); (C215A, H255C); (R76C, N91R, C215A); (R76C, N91R, C215A); (R76C, C215A); and (R76C, C215T).

Polynucleotide

The polynucleotide can be a nucleic acid, such as deoxyribonucleic acid (DNA) or ribonucleic acid (RNA). The polynucleotide can comprise one strand of RNA hybridized to one strand of DNA. The polynucleotide may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains. The PNA backbone is composed of repeating N-(2-aminoethyl)-glycine units linked by peptide bonds. The GNA backbone is composed of repeating glycol units linked by phosphodiester bonds. The TNA backbone is composed of repeating threose sugars linked together by phosphodiester bonds. LNA is formed from ribonucleotides as discussed above having an extra bridge connecting the 2' oxygen and 4' carbon in the ribose moiety.

The polynucleotide is preferably DNA, RNA or a DNA or RNA hybrid, most preferably DNA. The target polynucleotide may be double stranded. The target polynucleotide may comprise single stranded regions and regions with other structures, such as hairpin loops, triplexes and/or quadruplexes. The DNA/RNA hybrid may comprise DNA and RNA on the same strand. Preferably, the DNA/RNA hybrid comprises one DNA strand hybridized to a RNA strand.

In some embodiments, the target polynucleotide does not comprise a hairpin structure or any covalent linkage to connect a template and a complement. In some embodiments, the target polynucleotide (e.g., template) and polynucleotide complementary to the target polynucleotide (e.g., complement) are not linked by a bridging moiety, such as a hairpin loop.

In some disclosed methods, a single strand (e.g., template or complement) is translocated through a nanopore, and the strand itself can form a hairpin structure due to the interaction of the adaptors on its both ends. See, e.g., FIG. 19. Such adaptor design can be beneficial for characterizing a long polynucleotide, e.g., by maintaining the other end of the strand close to the nanopore.

In some embodiments, the target polynucleotide can be any length. For example, the polynucleotides can be at least 10, at least 50, at least 100, at least 150, at least 200, at least 250, at least 300, at least 400 or at least 500 nucleotides or nucleotide pairs in length. The target polynucleotide can be 1000 or more nucleotides or nucleotide pairs, 5000 or more nucleotides or nucleotide pairs in length or 100000 or more nucleotides or nucleotide pairs in length or 500,000 or more nucleotides or nucleotide pairs in length, or 1,000,000 or more nucleotides or nucleotide pairs in length, 10,000,000 or more nucleotides or nucleotide pairs in length, or 100,000,000 or more nucleotides or nucleotide pairs in length, or 200,000,000 or more nucleotides or nucleotide pairs in length, or the entire length of a chromosome. The target polynucleotide may be an oligonucleotide. Oligonucleotides are short nucleotide polymers which typically have 50 or fewer nucleotides, such 40 or fewer, 30 or fewer, 20 or fewer, 10 or fewer or 5 or fewer nucleotides. The target oligonucleotide is preferably from about 15 to about 30 nucleotides in length, such as from about 20 to about 25 nucleotides in length. For example, the oligonucleotide can be about 15, about 16, about 17, about 18, about 19, about 20, about 21, about 22, about 23, about 24, about 25, about 26, about 27, about 28, about 29 or about 30 nucleotides in length.

The target polynucleotide may be a fragment of a longer target polynucleotide. In this embodiment, the longer target polynucleotide is typically fragmented into multiple, such as two or more, shorter target polynucleotides. The method of the invention may be used to sequence one or more, such as 2, 3, 4, 5 or more of those shorter target polynucleotides.

In some embodiments, the method of various aspects described herein may be used to sample multiple target polynucleotides, such as 2, 3, 4 or 5 to 10, 15, 20 or more polynucleotides, within a sample.

In some embodiments, the method of various aspects described herein may be used to sequence polynucleotides that are present in double stranded form in a sample.

In some embodiments, the method of various aspects described herein may be used to sequence single stranded polynucleotides by first synthesizing the complement of the single stranded polynucleotide to produce a double stranded polynucleotide. For example, the single stranded polynucleotide may be a RNA, such as mRNA and the complementary cDNA strand may be synthesized to produce a double stranded polynucleotide for sequencing in a method of the invention. For example, the single stranded polynucleotide may be a DNA and the complementary strand may be synthesized to produce a double stranded DNA polynucleotide for sequencing in a method of the invention.

Figure 43:
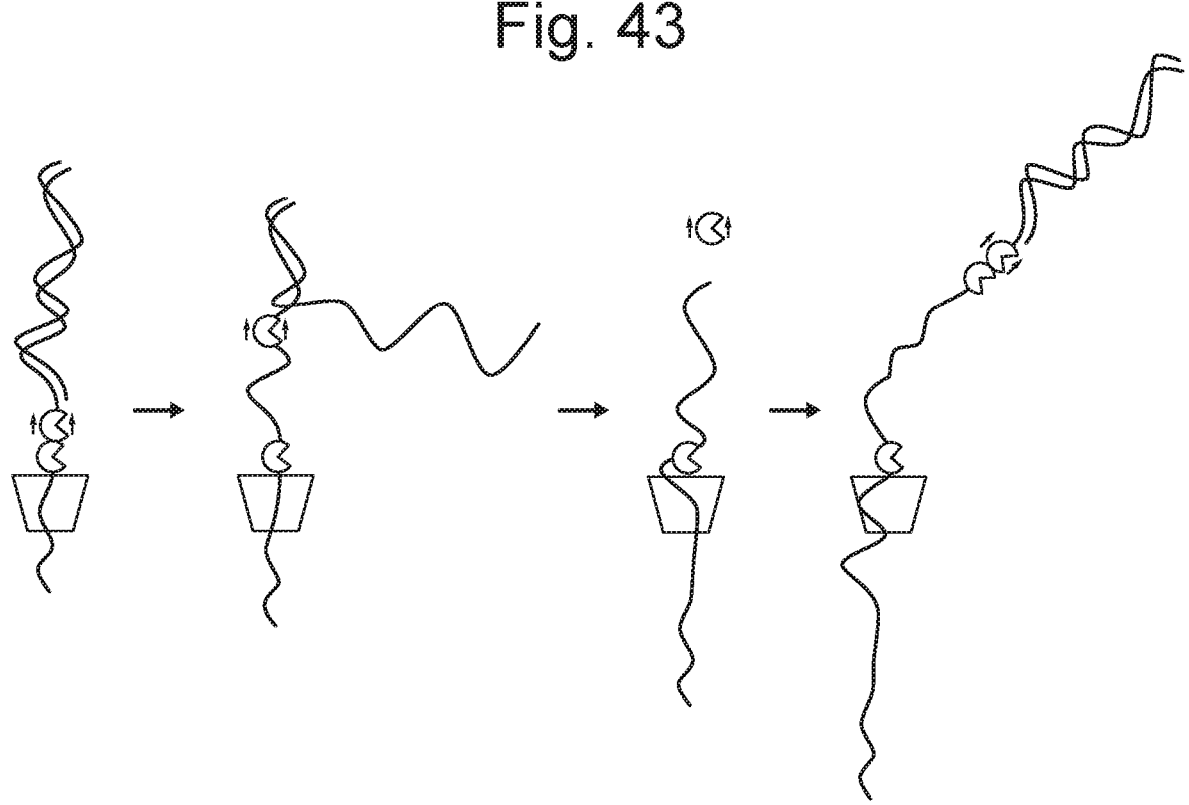
FIG. 43 shows a method that can be used for concatenating both single and double stranded nucleic acids.

In some embodiments the polynucleotide may be a concatenated polynucleotide. Methods of concatenating polynucleotides are described in PCT/GB2017/051493. In one embodiment, the method of attachment used to join the polynucleotides together is click chemistry. In this embodiment, a template (first strand captured) and complement (reverse complement of the first strand) of a first double stranded polynucleotide are characterised using a nanopore when the template and complement are not covalently linked. As the template and complement are separated, a sequence complementary to a pore tether in a follow-on adapter ligated to the first double stranded polynucleotide is exposed in the complement and the complement binds to a pore tether attached to the nanopore. In this embodiment, a concatenation adapter is also ligated to the first double stranded polynucleotide so that the complementary strand can be concatenated to a second double stranded polynucleotide In some disclosed aspects, a concatenation adapter complex that contains a motor protein and a release protein may be prepared. This concatenation adapter may be ligated to both ends of a target polynucleotide. Both the motor protein and the release protein may be stalled on the ligated adapter complex until a polynucleotide is captured by the pore. Once the first polynucleotide has been captured, the blocking chemistry is overcome by both proteins and the motor protein controls the interaction of the polynucleotide with the pore as previously. The release protein, which can translocate quicker than the motor protein, reaches the 3' of the first polynucleotide to release a hybridisation site, complementary to a 5' nucleic acid sequence of the leader strand of the concatenation adapter complex. With this hybridization site revealed, a second polynucleotide can then hybridise to the revealed site and covalent coupling of the 3' end of the first polynucleotide to the 5' of a second polynucleotide can occur (FIG. 43). This process then repeats for further concatenation of target polynucleotides.

In one embodiment, a method of characterising and concatenating double stranded target polynucleotides is provided, where the method of attachment is non-covalent. In this embodiment, the complement strand of the first double stranded target polynucleotide recruits a second double stranded target polynucleotide and brings it into a local concentration to the pore. In turn, as the first complement strand is sequenced the recruited second double stranded target polynucleotide becomes dehybridised from the complement strand and instead hybridises to a pore tether. This enables the first and second (and subsequent, third, fourth, fifth, etc, etc,) double stranded target polynucleotides to be sequentially processed with minimal time between strands. This is especially useful when the concentration of double strand target polynucleotides is low as the second target polynucleotide can be recruited while the first is being sequenced.

In another embodiment, the method of characterising and concatenating double stranded target polynucleotides, e.g. where the method of attachment is non-covalent, may be carried out using a two component fishing tether that provides a second hybrisidation site for the follow-on sequences and for the pore tether, to increase the proportion of events seen.

Figure 44:
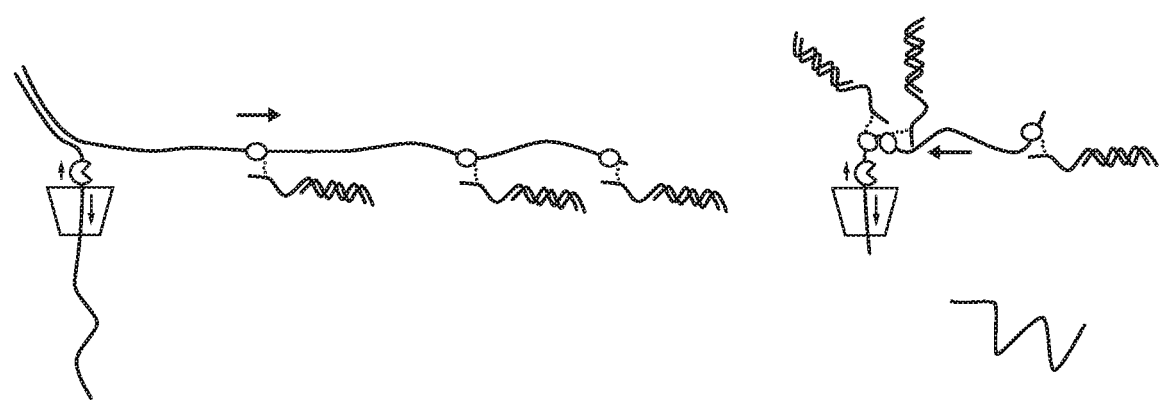
FIG. 44 shows a method a method of characterising and concatenating many double stranded target polynucleotides, where the complement strand of a first double stranded target polynucleotide recruits a many other double stranded target polynucleotides and brings them into a local concentration of the pore. This provides a higher local concentration around the pore than in the general bulk solution and so double stranded target polynucleotides follow one another through the open pore with minimal time between strands. This is especially useful when the concentration of double strand target polynucleotides is low. A tether consisting of an oligo coupled to a single stranded binding protein is used. As the template strand of the first double strand target polynucleotide is sequenced the complement strand is released into solution as ssDNA. The single stranded binding proteins of the other double stranded target polynucleotides are able to bind to the ssDNA. As the complement strand is sequenced the 3' of the complement strand is drawn back towards the pore. The single stranded binding proteins on the ssDNA complement strand are displaced from the complement strand when they encounter the motor protein and so are deposited around the pore increasing the local concentration.
Figure 45:
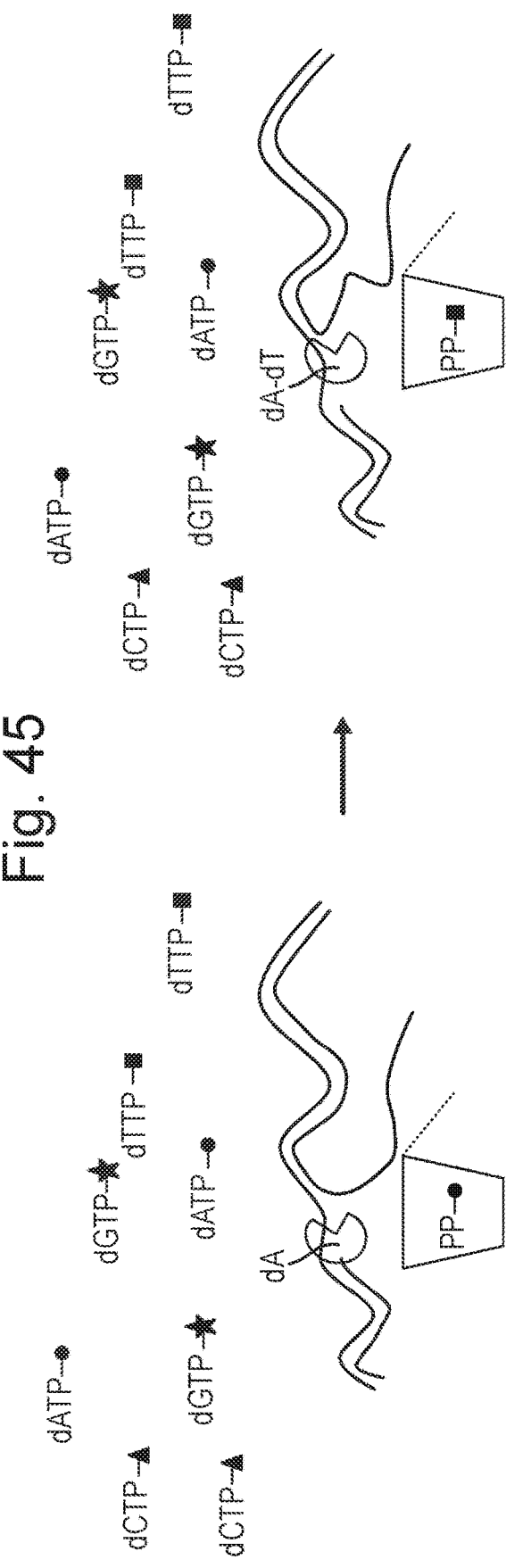
FIG. 45 illustrates one method of sequencing a nucleic acid construct according to the methods provided herein, in which the by-products of a sequencing reaction are detected. The left panel of FIG. 45 shows a schematic representation of a DNA template being processed under polymerase control, as part of a sequencing by synthesis reaction, such that a phosphate labelled species is released and detected by a nanopore when incorporation of a nucleotide complementary to the base of the DNA construct occurs. The right panel of FIG. 45 shows the sequential processing of the DNA template and the subsequent detection of the released phosphate labelled species from incorporation of the next complementary nucleotide of the DNA template.
Figure 46:
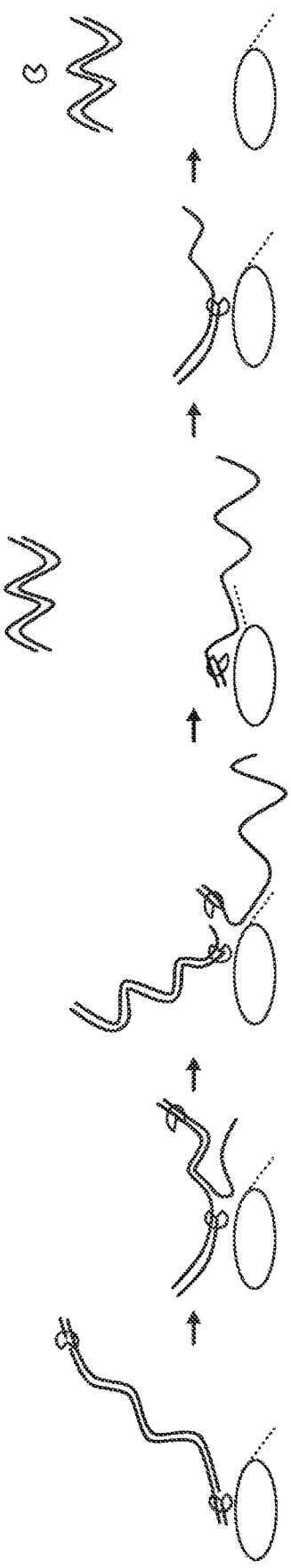
FIGS. 46 and 47 illustrates a method of "follow-on" sequencing of a double stranded nucleic acid construct without the use of a hairpin according to one embodiment of the methods provided herein. Both the sense and antisense strands of the double stranded nucleic acid construct comprise an adaptor at each end.
Figure 47:
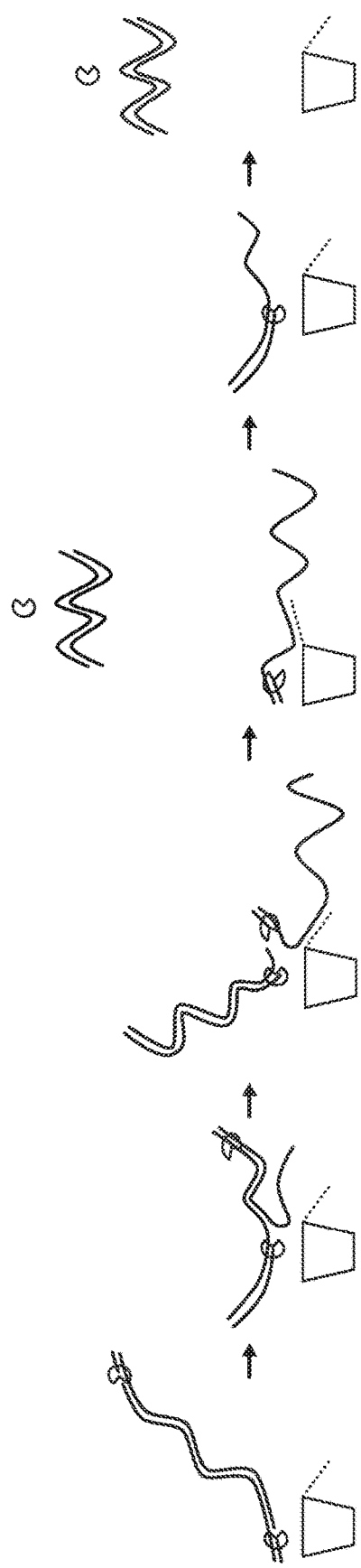
Figure 48:
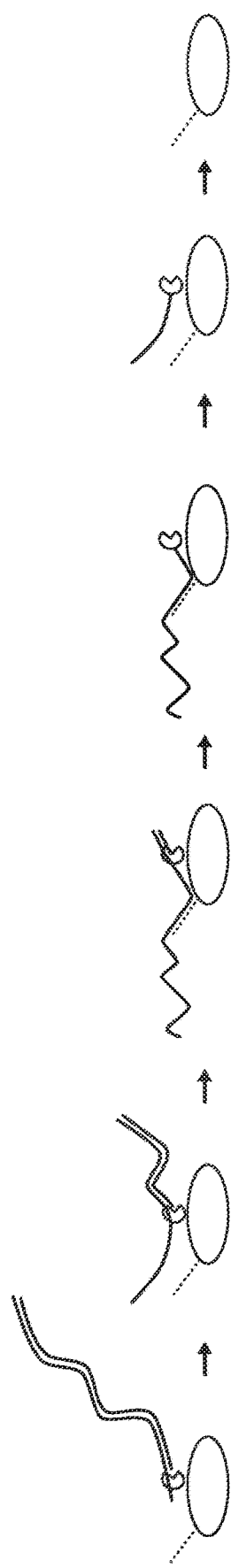
FIG. 48 is a schematic representation of a further method provided herein. A double stranded DNA template is processed under exonuclease control so that the products of the processing reaction are detected. Sense and antisense strands of the double stranded template are not covalently linked. An exonuclease (grey) processes the sense strand with the products of the exonuclease reaction being detected by a detector for example a nanopore (e.g. a transmembrane protein nanopore). As the sense strand is processed by the exonuclease, the antisense strand becomes localised to the detector via a capture tag conjugated to the detector. After the sense strand of the DNA template has been processed by the exonuclease, the antisense strand is separately processed by an exonuclease (black), which may be the same or different exonuclease to the exonuclease that processes the sense strand (grey). The products of the exonuclease reaction are detected by the detector thus allowing information indicative of the sequence of the DNA template to be obtained by the detector.

In one embodiment, the method of characterising and concatenating many double stranded target polynucleotides, e.g. where the method of attachment is non-covalent, may be used to bring multiple, such as from 2 to 20, e.g. 4, 5, 6, 8, 10, 12 or 15, double stranded target polynucleotides to the pore. The complement strand of the first double stranded target polynucleotide may recruit other double stranded target polynucleotides and concentrate them in the vicinity of the pore. This provides a higher local concentration around the pore than in the general bulk solution and so double stranded target polynucleotides are sequentially processed with minimal time between strands. This is especially useful when the concentration of double strand target polynucleotides is low. In this embodiment, a tether consisting of an oligo coupled to a single stranded binding protein may be used. As the template strand of the first double strand target polynucleotide is sequenced the complement strand is released into solution as ssDNA. The single stranded binding proteins of the other double stranded target polynucleotides are able to bind to the ssDNA. As part of the follow-on process, as the complement strand is sequenced the 3' of the complement strand is drawn back towards the pore. The single stranded binding proteins on the ssDNA complement strand are displaced from the complement strand when they encounter the protein controlling processing of the complement and so are deposited around the pore increasing the local concentration. This is depicted in FIG. 44. If the sequence of the target polynucleotide is known, such analyte trawling can be carried out but with complementary sequences also added to the 3' of the pore tether, which can be used to tile sections of the complement strand.

Sample

The analytes (including, e.g., proteins, peptides, molecules, polypeptide, polynucleotides) may be present in a sample. The sample may be any suitable sample. The sample may be a biological sample. Any embodiment of the methods described herein may be carried out in vitro on a sample obtained from or extracted from any organism or microorganism. The organism or microorganism is typically archaean, prokaryotic or eukaryotic and typically belongs to one of the five kingdoms: plantae, animalia, fungi, monera and protista. In some embodiments, the methods of various aspects described herein may be carried out in vitro on a sample obtained from or extracted from any virus.

The sample is preferably a fluid sample. The sample typically comprises a body fluid. The body fluid may be obtained from a human or animal. The human or animal may have, be suspected of having or be at risk of a disease. The sample may be urine, lymph, saliva, mucus, seminal fluid or amniotic fluid, but is preferably whole blood, plasma or serum. Typically, the sample is human in origin, but alternatively it may be from another mammal such as from commercially farmed animals such as horses, cattle, sheep or pigs or may alternatively be pets such as cats or dogs.

Alternatively a sample of plant origin is typically obtained from a commercial crop, such as a cereal, legume, fruit or vegetable, for example wheat, barley, oats, canola, maize, soya, rice, bananas, apples, tomatoes, potatoes, grapes, tobacco, beans, lentils, sugar cane, cocoa, cotton, tea or coffee.

The sample may be a non-biological sample. The non-biological sample is preferably a fluid sample. Examples of non-biological samples include surgical fluids, water such as drinking water, sea water or river water, and reagents for laboratory tests.

The sample may be processed prior to being assayed, for example by centrifugation or by passage through a membrane that filters out unwanted molecules or cells, such as red blood cells. The sample may be measured immediately upon being taken. The sample may also be typically stored prior to assay, preferably below −70° C.

In some embodiments, the sample may comprise genomic DNA. The genomic DNA may be fragmented or any of the methods described herein may further comprise fragmenting the genomic DNA. The DNA may be fragmented by any suitable method. For example, methods of fragmenting DNA are known in the art. Such methods may use a transposase, such as a MuA transposase or a commercially available G-tube.

Leader Sequence

The leader sequence typically comprises a polymer. The polymer is preferably negatively charged. The polymer is preferably a polynucleotide, such as DNA or RNA, a modified polynucleotide (such as abasic DNA), PNA, LNA, polyethylene glycol (PEG) or a polypeptide. The leader preferably comprises a polynucleotide and more preferably comprises a single stranded polynucleotide. The single stranded leader sequence most preferably comprises a single strand of DNA, such as a poly dT section. The leader sequence preferably comprises the one or more spacers.

The leader sequence can be any length, but is typically 10 to 150 nucleotides in length, such as from 20 to 150 nucleotides in length. The length of the leader typically depends on the transmembrane pore used in the method.

The leader sequence may thread into the transmembrane pore and thereby facilitate the movement of polynucleotide towards the pore. The leader sequence can also be used to link the polynucleotide to the one or more anchors as discussed herein.

Typically, a leader sequence is present at one end of the target polynucleotide and at one end of the polynucleotide complementary to the target polynucleotide. Leader sequences may be present at the 5'end of the target polynucleotide and at the 5' end of the complement of the target polynucleotide. Alternatively, leaders sequence may be present at the 3' end of the target polynucleotide and at the 3' end of the complement of the target polynucleotide.

A leader sequence may be present at the 5' end of the target polynucleotide and at the 3' end of the complementary polynucleotide, or vice versa. In these disclosed embodiments, two different polynucleotide binding proteins (e.g., polynucleotide unwinding enzyme)s are typically used, wherein a first polynucleotide binding protein (e.g., polynucleotide unwinding enzyme) moves along the polynucleotide in a 5' to 3' direction and a second polynucleotide binding protein (e.g., polynucleotide unwinding enzyme) moves along the polynucleotide in a 3' to 5' direction.

The leader sequence may be attached to the double stranded polynucleotide by any suitable method. For example, the leader sequence may be ligated to the target polynucleotide and/or to the complement thereof. Alternatively, the leader sequence may be generated by digesting one strand of the double stranded polynucleotide to produce a single stranded overhang on the other strand.

A polynucleotide binding protein (e.g., polynucleotide unwinding enzyme, e.g., polymerase) may be bound to the leader sequence prior to its attachment to the target polynucleotide or complement thereof. A polynucleotide binding protein (e.g., polynucleotide unwinding enzyme, e.g., polymerase) may be bound to a leader sequence present in the double stranded polynucleotide. The activity of the polynucleotide binding protein (e.g., polynucleotide unwinding enzyme, e.g., polymerase) bound to the leader sequence may be stalled until the polynucleotide contacts the transmembrane pore. Methods of stalling polynucleotide binding proteins (e.g., polynucleotide unwinding enzymes, e.g., polymerases) are known in the art, for example in WO 2014/135838.

Adaptor

The leader sequence may be present in an adaptor, wherein the adaptor comprises a double stranded region (e.g., a duplex stem) and at least one single stranded region. At least one of the single stranded regions may be a leader sequence. The adaptor may comprise at least one non-polynucleotide region. The adaptors attached to the two ends of the target double stranded polynucleotide may be the same or different. Preferably, the adaptors in the pair are the same.

The leader sequence is preferably present in a first single stranded region at the 5' end (or 3' end) of one strand of the adaptor. A second single stranded region may be present at the 3' end (or 5' end) of the other strand of the adaptor. The first and second single stranded regions are not complementary. In this embodiment, the adaptor may be referred to as a Y adaptor.

A Y adaptor typically comprises (a) a double stranded region (e.g., a duplex stem) and (b) a single stranded region or a region that is not complementary at the other end. A Y adaptor may be described as having an overhang if it comprises a single stranded region. The presence of a non-complementary region in the Y adaptor gives the adaptor its Y shape since the two strands typically do not hybridise to each other unlike the double stranded portion. The Y adaptor may comprise one or more anchors.

In some embodiments, the adaptor may comprise one or more (e.g., at least one, at least two, at least three or more) binding sites for one or more (e.g., at least one, at least two, at least three or more) tags on the nanopore. In some embodiments, the binding site for the tag on the nanopore may be within the double stranded region (e.g., a duplex stem) such that the binding site is exposed upon separation of the two strands of the double stranded region. See, e.g., FIG. 10. Additionally or alternatively, the binding site for the tag on the nanopore may be on a single stranded portion of the adaptor. By way of example only, FIG. 9A shows an example adaptor comprising at least one anchor for a solid substrate, e.g., a membrane or a bead, while FIG. 15 shows an example adaptor comprising at least two anchors, wherein a first anchor is capable of coupling to a solid substrate, e.g., a membrane or a bead, and a second anchor is capable of coupling to a nanopore. The second anchor for the nanopore can be configured to bind to a tag conjugated to the nanopore.

The Y adaptor comprises a leader sequence which may thread into the pore.

The Y adaptor may be attached to the polynucleotide using any method known in the art. For example, one or both of the adaptors may be ligated using a ligase, such as T4 DNA ligase, *E. coli* DNA ligase, Taq DNA ligase, Tma DNA ligase and 9° N DNA ligase.

In a preferred embodiment, the double stranded polynucleotide, for example the double stranded polynucleotides in the sample are modified so that they comprise Y adaptors at both ends. Any manner of modification can be used. The method may comprise modifying the double stranded target polynucleotide by adding the adaptors.

The double stranded polynucleotide may be provided with adaptors, such as Y adaptors, or anchors by contacting the polynucleotide with a MuA transposase and a population of double stranded MuA substrates. The transposase fragments the double stranded polynucleotide and ligates MuA substrates to one or both ends of the fragments. This produces a plurality of modified double stranded polynucleotides comprising an adaptor or anchor. The modified double stranded polynucleotides may then be investigated using the method of the invention.

These MuA based methods are disclosed in WO 2015/022544 and WO 2016/059363. They are also discussed in detail in WO2015/150786.

The adaptor may further comprise an anchor to tether the double stranded polynucleotide comprising the target polynucleotide and/or its complement to the transmembrane pore or to the membrane comprising the pore, i.e. the adaptor may further comprise a membrane-tether or a pore-tether. The anchor is preferably attached to the single stranded region that is not the leader sequence.

The polynucleotide binding protein (e.g., polynucleotide unwinding enzyme, e.g., polymerase) may be bound to the leader sequence in the adaptor, or the polynucleotide binding protein (e.g., polynucleotide unwinding enzyme, e.g., polymerase) may be added after the adaptor has been attached to the double stranded polynucleotide. The activity of the polynucleotide binding protein (e.g., polynucleotide unwinding enzyme, e.g., polymerase) bound to the leader sequence may be stalled until the polynucleotide contacts the transmembrane pore.

The leader sequence or adaptor may be attached to the double stranded polynucleotide by any suitable method. For example, the leader sequence may be ligated to the target polynucleotide and/or to the complement thereof or the adaptor may be ligated to the double stranded polynucleotide.

In some embodiments, a double stranded barcode sequence may be ligated to one or both ends of the target double stranded polynucleotide. The barcode sequence may be added to the double stranded polynucleotide before the leader sequence or adaptor is added. For example, the barcode sequence may be located between the end of the target double stranded polynucleotide and the adaptor. Preferably, the barcode sequence is comprised in the adaptor.

A unique barcode sequence may be attached, for example ligated, to each double stranded polynucleotide in a sample. The barcode sequence may be used to identify signals corresponding to sequential translocation through the pore of the by-products of processing of the target polynucleotide and the polynucleotide complementary to the target polynucleotide by the polymerase.

The adaptor can comprise one or more spacers to prevent pre-bound polynucleotide binding protein (e.g., a polynucleotide unwinding enzyme) from processing a double stranded polynucleotide. These spacers prevent movement of the polynucleotide binding protein (e.g., a polynucleotide unwinding enzyme) until the polynucleotide binding protein (e.g., a polynucleotide unwinding enzyme) is located at the pore and a potential difference is applied across the pore. The additional force provided by the potential difference pushes the polynucleotide binding protein (e.g., a polynucleotide unwinding enzyme) over the spacers and allows it to process the polynucleotide. Thus movement by the polynucleotide binding protein (e.g., a polynucleotide unwinding enzyme) may only occur when the polynucleotide is in the nanopore and not before. Examples of spacers and methods for preventing pre-bound polynucleotide binding protein (e.g., a polynucleotide unwinding enzyme) from processing a double stranded polynucleotide until the polynucleotide is in a nanopore are described, for example, in WO2015/110813, the contents of which are incorporated herein by reference in its entirety.

Barcode

Polynucleotide barcodes are well-known in the art (Kozarewa, I. et al., (2011), *Methods Mol. Biol.* 733, p 279-298). A barcode is a specific sequence of polynucleotide that affects the current flowing through the pore in a specific and known manner.

The barcode may comprise a nucleotide sequence. A nucleotide typically contains a nucleobase, a sugar and at least one phosphate group. The nucleobase is typically heterocyclic. Nucleobases include, but are not limited to, purines and pyrimidines and more specifically adenine, guanine, thymine, uracil and cytosine. The sugar is typically a pentose sugar. Nucleotide sugars include, but are not limited to, ribose and deoxyribose. The nucleotide is typically a ribonucleotide or deoxyribonucleotide. The nucleotide typically contains a monophosphate, diphosphate or triphosphate. Phosphates may be attached on the 5' or 3' side of a nucleotide.

Nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), 5-methylcytidine monophosphate, 5-methylcytidine diphosphate, 5-methylcytidine triphosphate, 5-hydroxymethylcytidine monophosphate, 5-hydroxymethylcytidine diphosphate, 5-hydroxymethylcytidine triphosphate, cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP), 5-methyl-2'-deoxycytidine monophosphate, 5-methyl-2'-deoxycytidine diphosphate, 5-methyl-2'-deoxycytidine triphosphate, 5-hydroxymethyl-2'-deoxycytidine monophosphate, 5-hydroxymethyl-2'-deoxycytidine diphosphate and 5-hydroxymethyl-2'-deoxycytidine triphosphate. The nucleotides in the adaptor are preferably selected from AMP, TMP, GMP, UMP, dAMP, dTMP, dGMP or dCMP. The nucleotides may be abasic (i.e., lack a nucleobase). The nucleotides may contain additional modifications. In particular, suitable modified nucleotides include, but are not limited to, 2'amino pyrimidines (such as 2'-amino cytidine and 2'-amino uridine), 2'-hyrdroxyl purines (such as, 2'-fluoro pyrimidines (such as 2'-fluorocytidine and 2'fluoro uridine), hydroxyl pyrimidines (such as 5'-α-P-borano uridine), 2'-O-methyl nucleotides (such as 2'-O-methyl adenosine, 2'-O-methyl guanosine, 2'-O-methyl cytidine and 2'-O-methyl uridine), 4'-thio pyrimidines (such as 4'-thio uridine and 4'-thio cytidine) and nucleotides have modifications of the nucleobase (such as 5-pentynyl-2'-deoxy uridine, 5-(3-aminopropyl)-uridine and 1,6-diaminohexyl-N-5-carbamoylmethyl uridine).

A barcode may comprise one or more different nucleotide species. For instance, T k-mers (i.e. k-mers in which the central nucleotide is thymine-based, such as TTA, GTC, GTG and CTA) typically have the lowest current states. In some disclosed methods, modified versions of T nucleotides may be introduced into a modified polynucleotide to reduce the current states further and thereby increase the total current range seen when the barcode moves through the pore.

G k-mers (i.e. k-mers in which the central nucleotide is guanine-based, such as TGA, GGC, TGT and CGA) tend to be strongly influenced by other nucleotides in the k-mer and so modifying the G nucleotides in the modified polynucleotide may help them to have more independent current positions.

Including three copies of the same nucleotide species instead of three different species may facilitate characterization because it is then only necessary to map, for example, 3-nucleotide k-mers in the modified polynucleotide. However, such modifications do reduce the information provided by the barcode.

One or more abasic nucleotides may be included in the barcode. Using one or more abasic nucleotides results in characteristic current spikes. This allows the clear highlighting of the positions of the one or more nucleotide species in the barcode.

The nucleotide species in the barcode may comprise a chemical atom or group such as a propynyl group, a thio group, an oxo group, a methyl group, a hydroxymethyl group, a formyl group, a carboxy group, a carbonyl group, a benzyl group, a propargyl group or a propargylamine group. The chemical group or atom may be or may comprise a fluorescent molecule, biotin, digoxigenin, DNP (dinitrophenol), a photo-labile group, an alkyne, DBCO, azide, free amino group, a redox dye, a mercury atom or a selenium atom.

The barcode may comprise a nucleotide species comprising a halogen atom. The halogen atom may be attached to any position on the different nucleotide species, such as the nucleobase and/or the sugar. The halogen atom is preferably fluorine (F), chlorine (Cl), bromine (Br) or iodine (I). The halogen atom is most preferably F or I.

Anchor

The target polynucleotide may be coupled to the membrane using an anchor (membrane-tether). One or more anchors may be used to couple the target polynucleotide to the membrane. Typically, one or more anchors are attached to each strand of the target polynucleotide. The anchor may be part of the adaptor(s).

If the membrane is an amphiphilic layer, such as a triblock copolymer membrane, the one or more anchors preferably comprise a polypeptide anchor and/or a hydrophobic anchor that can be inserted into the membrane. The hydrophobic anchor is preferably a lipid, fatty acid, sterol, carbon nanotube, polypeptide, protein or amino acid, for example cholesterol, palmitate or tocopherol. In preferred embodiments, the one or more anchors are not the pore.

The components of the membrane, such as the amphiphilic molecules, copolymer or lipids, may be chemically-modified or functionalized to form the one or more anchors. Examples of suitable chemical modifications and suitable ways of functionalizing the components of the membrane are discussed in more detail below. Any proportion of the membrane components may be functionalized, for example at least 0.01%, at least 0.1%, at least 1%, at least 10%, at least 25%, at least 50% or 100%.

The one or more anchors preferably comprise a linker. The one or more anchors may comprise one or more, such as 2, 3, 4 or more, linkers.

Preferred linkers include, but are not limited to, polymers, such as polynucleotides, polyethylene glycols (PEGs), polysaccharides and polypeptides. These linkers may be linear, branched or circular. For instance, the linker may be a circular polynucleotide. The target polynucleotide may hybridize to a complementary sequence on the circular polynucleotide linker.

The one or more anchors or one or more linkers may comprise a component that can be cut or broken down, such as a restriction site or a photo-labile group.

Functionalized linkers and the ways in which they can couple molecules are known in the art. For instance, linkers functionalized with maleimide groups will react with and attach to cysteine residues in proteins.

Cross-linkage of polynucleotides can be avoided using a "lock and key" arrangement. Only one end of each linker may react together to form a longer linker and the other ends of the linker each react with the polynucleotide or membrane respectively. Such linkers are described in WO 2010/086602.

The use of a linker is preferred in the sequencing methods of the invention. If a polynucleotide is permanently coupled directly to the membrane in the sense that it does not uncouple when interacting with the pore and/or with the polymerase, then some sequence data will be lost as the sequencing run cannot continue to the end of the polynucleotide due to the distance between the membrane and the pore. If a linker is used, then the polynucleotide can be processed to completion.

The coupling may be permanent or stable. In other words, the coupling may be such that the polynucleotide remains coupled to the membrane when interacting with the pore and/or with the polymerase.

The coupling may be transient. In other words, the coupling may be such that the polynucleotide may decouple from the membrane when interacting with the pore. For polynucleotide sequencing, the transient nature of the coupling is preferred. If a permanent or stable linker is attached directly to either the 5' or 3' end of a polynucleotide and the linker is shorter than the distance between the membrane and the channel of the transmembrane pore, then some sequence data will be lost as the sequencing run cannot continue to the end of the polynucleotide. If the coupling is transient, then when the coupled end randomly becomes free of the membrane, then the polynucleotide can be processed to completion. Chemical groups that form permanent/stable or transient links are discussed in more detail below. The target polynucleotide and/or its complement may be transiently coupled to a membrane such as an amphiphilic layer e.g. triblock copolymer membrane or lipid membrane using cholesterol or a fatty acyl chain. Any fatty acyl chain having a length of from 6 to 30 carbon atom, such as hexadecanoic acid, may be used.

In preferred embodiments, anchor couples the target polynucleotide and/or its complement to an amphiphilic layer such as a triblock copolymer membrane or lipid bilayer. Coupling of nucleic acids to synthetic lipid bilayers has been carried out previously with various different tethering strategies. These are summarized in Table 1 below.

TABLE 1

| Anchor comprising | Type of coupling | Reference |
| --- | --- | --- |
| Thiol | Stable | Yoshina-Ishii, C. and S. G. Boxer (2003). "Arrays of mobile tethered vesicles on supported lipid bilayers." *J Am Chem Soc* 125(13): 3696-7. |
| Biotin | Stable | Nikolov, V., R. Lipowsky, et al. (2007). "Behavior of giant vesicles with anchored DNA molecules." *Biophys J* 92(12): 4356-68 |
| Cholesterol | Transient | Pfeiffer, I. and F. Hook (2004). "Bivalent cholesterol-based coupling of oligonucleotides to lipid membrane assemblies." *J Am Chem Soc* 126(33): 10224-5 |

TABLE 1-continued

| Anchor comprising | Type of coupling | Reference |
| --- | --- | --- |
| Surfactant (e.g. Lipid, Palmitate, etc.) | Stable | van Lengerich, B., R. J. Rawle, et al. "Covalent attachment of lipid vesicles to a fluid-supported bilayer allows observation of DNA-mediated vesicle interactions." *Langmuir* 26(11): 8666-72 |

Synthetic polynucleotides and/or linkers may be functionalized using a modified phosphoramidite in the synthesis reaction, which is easily compatible for the direct addition of suitable anchoring groups, such as cholesterol, tocopherol, palmitate, thiol, lipid and biotin groups. These different attachment chemistries give a suite of options for attachment to polynucleotides. Each different modification group couples the polynucleotide in a slightly different way and coupling is not always permanent so giving different dwell times for the polynucleotide to the membrane.

Coupling of polynucleotides to a linker or to a functionalized membrane can also be achieved by a number of other means provided that a complementary reactive group or an anchoring group can be added to the polynucleotide. The addition of reactive groups to either end of a polynucleotide has been reported previously. A thiol group can be added to the 5' of ssDNA or dsDNA using T4 polynucleotide kinase and ATPTS (Grant, G. P. and P. Z. Qin (2007). "A facile method for attaching nitroxide spin labels at the 5' terminus of nucleic acids." *Nucleic Acids Res* 35(10): e77). An azide group can be added to the 5'-phosphate of ssDNA or dsDNA using T4 polynucleotide kinase and γ-[2-Azidoethyl]-ATP or γ-[6-Azidohexyl]-ATP. Using thiol or Click chemistry a tether, containing either a thiol, iodoacetamide OPSS or maleimide group (reactive to thiols) or a DIBO (dibenzocyclooxtyne) or alkyne group (reactive to azides), can be covalently attached to the polynucleotide. A more diverse selection of chemical groups, such as biotin, thiols and fluorophores, can be added using terminal transferase to incorporate modified oligonucleotides to the 3' of ssDNA (Kumar, A., P. Tchen, et al. (1988). "Nonradioactive labeling of synthetic oligonucleotide probes with terminal deoxynucleotidyl transferase." *Anal Biochem* 169(2): 376-82). Streptavidin/biotin and/or streptavidin/desthiobiotin coupling may be used for any other polynucleotide. It may also be possible that anchors may be directly added to polynucleotides using terminal transferase with suitably modified nucleotides (e.g. cholesterol or palmitate).

The one or more anchors may couple the target polynucleotide and/or its complement to the membrane via hybridization. The hybridization may be between the one or more anchors and the target polynucleotide and/or its complement, within the one or more anchors or between the one or more anchors and the membrane. Hybridization in the one or more anchors allows coupling in a transient manner as discussed above. For instance, a linker may comprise two or more polynucleotides, such as 3, 4 or 5 polynucleotides, hybridized together. The one or more anchors may hybridize to the target polynucleotide or the polynucleotide complementary to the target polynucleotide. The one or more anchors may hybridize directly to a Y adaptor and/or leader sequence attached to the target polynucleotide and/or its complement. Alternatively, the one or more anchors may be hybridized to one or more, such as 2 or 3, intermediate polynucleotides (or "splints") which are hybridized to the polynucleotide, to a Y adaptor and/or leader sequence attached to the target polynucleotide and/or its complement.

The one or more anchors may comprise a single stranded or double stranded polynucleotide. One part of the anchor may be ligated to a single stranded or double stranded polynucleotide analyte. Ligation of short pieces of ssDNA have been reported using T4 RNA ligase I (Troutt, A. B., M. G. McHeyzer-Williams, et al. (1992). "Ligation-anchored PCR: a simple amplification technique with single-sided specificity." Proc Natl Acad Sci USA 89(20): 9823-5). Alternatively, either a single stranded or double stranded polynucleotide can be ligated to a double stranded polynucleotide and then the two strands separated by thermal or chemical denaturation. To a double stranded polynucleotide, it is possible to add either a piece of single stranded polynucleotide to one or both of the ends of the duplex, or a double stranded polynucleotide to one or both ends. For addition of single stranded polynucleotides to the double stranded polynucleotide, this can be achieved using T4 RNA ligase I as for ligation to other regions of single stranded polynucleotides. For addition of double stranded polynucleotides to a double stranded polynucleotide then ligation can be "blunt-ended", with complementary 3' dA/dT tails on the polynucleotide and added polynucleotide respectively (as is routinely done for many sample preparation applications to prevent concatemer or dimer formation) or using "sticky-ends" generated by restriction digestion of the polynucleotide and ligation of compatible adapters. Then, when the duplex is melted, each single strand will have either a 5' or 3' modification if a single stranded polynucleotide was used for ligation or a modification at the 5' end, the 3' end or both if a double stranded polynucleotide was used for ligation.

If the adaptor, or the complement of the target polynucleotide, is a synthetic strand, the one or more anchors can be incorporated during the chemical synthesis of the adaptor or complement. For instance, the adaptor or complement can be synthesised using a primer having a reactive group attached to it.

Adenylated polynucleotides are intermediates in ligation reactions, where an adenosine-monophosphate is attached to the 5'-phosphate of the polynucleotide. Various kits are available for generation of this intermediate, such as the 5' DNA Adenylation Kit from NEB. By substituting ATP in the reaction for a modified nucleotide triphosphate, then addition of reactive groups (such as thiols, amines, biotin, azides, etc.) to the 5' of a polynucleotide can be possible. It may also be possible that anchors could be directly added to polynucleotides using a 5' DNA adenylation kit with suitably modified nucleotides (e.g. cholesterol or palmitate).

A common technique for the amplification of sections of genomic DNA is using polymerase chain reaction (PCR). Here, using two synthetic oligonucleotide primers, a number of copies of the same section of DNA can be generated, where for each copy the 5' of each strand in the duplex will be a synthetic polynucleotide. Single or multiple nucleotides can be added to 3' end of single or double stranded DNA by employing a polymerase. Examples of polymerases which could be used include, but are not limited to, Terminal Transferase, Klenow and *E. coli* Poly(A) polymerase). By substituting ATP in the reaction for a modified nucleotide triphosphate then anchors, such as a cholesterol, thiol, amine, azide, biotin or lipid, can be incorporated into double stranded polynucleotides. Therefore, each copy of the amplified polynucleotide will contain an anchor.

Ideally, the polynucleotide is coupled to the membrane without having to functionalize the polynucleotide. This can be achieved by coupling the one or more anchors, such as a polynucleotide binding protein (e.g., polynucleotide unwinding enzyme) or a chemical group, to the membrane and allowing the one or more anchors to interact with the polynucleotide or by functionalizing the membrane. The one or more anchors may be coupled to the membrane by any of the methods described herein. In particular, the one or more anchors may comprise one or more linkers, such as maleimide functionalized linkers. In this embodiment, the polynucleotide is typically RNA, DNA, PNA, TNA or LNA and may be double or single stranded. This embodiment is particularly suited to genomic DNA polynucleotides.

The one or more anchors can comprise any group that couples to, binds to or interacts with single or double stranded polynucleotides, specific nucleotide sequences within the polynucleotide or patterns of modified nucleotides within the polynucleotide, or any other ligand that is present on the polynucleotide.

Suitable binding proteins for use in anchors include, but are not limited to, *E. coli* single stranded binding protein, P5 single stranded binding protein, T4 gp32 single stranded binding protein, the TOPO V dsDNA binding region, human histone proteins, *E. coli* HU DNA binding protein and other archaeal, prokaryotic or eukaryotic single stranded or double stranded polynucleotide (or nucleic acid) binding proteins, including those listed below.

The specific nucleotide sequences could be sequences recognized by transcription factors, ribosomes, endonucleases, topoisomerases or replication initiation factors. The patterns of modified nucleotides could be patterns of methylation or damage.

The one or more anchors can comprise any group which couples to, binds to, intercalates with or interacts with a polynucleotide. The group may intercalate or interact with the polynucleotide via electrostatic, hydrogen bonding or Van der Waals interactions. Such groups include a lysine monomer, poly-lysine (which will interact with ssDNA or dsDNA), ethidium bromide (which will intercalate with dsDNA), universal bases or universal nucleotides (which can hybridize with any polynucleotide) and osmium complexes (which can react to methylated bases). A polynucleotide may therefore be coupled to the membrane using one or more universal nucleotides attached to the membrane. Each universal nucleotide may be coupled to the membrane using one or more linkers. The universal nucleotide preferably comprises one of the following nucleobases: hypoxanthine, 4-nitroindole, 5-nitroindole, 6-nitroindole, formylindole, 3-nitropyrrole, nitroimidazole, 4-nitropyrazole, 4-nitrobenzimidazole, 5-nitroindazole, 4-aminobenzimidazole or phenyl (C6-aromatic ring). The universal nucleotide more preferably comprises one of the following nucleosides: 2'-deoxyinosine, inosine, 7-deaza-2'-deoxyinosine, 7-deaza-inosine, 2-aza-deoxyinosine, 2-aza-inosine, 2-0'-methyl-inosine, 4-nitroindole 2'-deoxyribonucleoside, 4-nitroindole ribonucleoside, 5-nitroindole 2'-deoxyribonucleoside, 5-nitroindole ribonucleoside, 6-nitroindole 2'-deoxyribonucleoside, 6-nitroindole ribonucleoside, 3-nitropyrrole 2'-deoxyribonucleoside, 3-nitropyrrole ribonucleoside, an acyclic sugar analogue of hypoxanthine, nitroimidazole 2'-deoxyribonucleoside, nitroimidazole ribonucleoside, 4-nitropyrazole 2'-deoxyribonucleoside, 4-nitropyrazole ribonucleoside, 4-nitrobenzimidazole 2'-deoxyribonucleoside, 4-nitrobenzimidazole ribonucleoside, 5-nitroindazole 2'-deoxyribonucleoside, 5-nitroindazole ribonucleoside, 4-aminobenzimidazole 2'-deoxyribonucleoside, 4-aminobenzimidazole ribonucleoside, phenyl C-ribonucleoside, phenyl C-2'-deoxyribosyl nucleoside, 2'-deoxynebularine, 2'-deoxyisoguanosine, K-2'-deoxyribose, P-2'-deoxyribose and pyrrolidine. The universal nucleotide more preferably comprises 2'-deoxyinosine. The universal nucleotide is more preferably IMP or dIMP. The universal nucleotide is most preferably dPMP (2'-Deoxy-P-nucleoside monophosphate) or dKMP (N6-methoxy-2, 6-diaminopurine monophosphate).

The one or more anchors may couple to (or bind to) the polynucleotide via Hoogsteen hydrogen bonds (where two nucleobases are held together by hydrogen bonds) or reversed Hoogsteen hydrogen bonds (where one nucleobase is rotated through 1800 with respect to the other nucleobase). For instance, the one or more anchors may comprise one or more nucleotides, one or more oligonucleotides or one or more polynucleotides which form Hoogsteen hydrogen bonds or reversed Hoogsteen hydrogen bonds with the polynucleotide. These types of hydrogen bonds allow a third polynucleotide strand to wind around a double stranded helix and form a triplex. The one or more anchors may couple to (or bind to) a double stranded polynucleotide by forming a triplex with the double stranded duplex.

In this embodiment at least 1%, at least 10%, at least 25%, at least 50% or 100% of the membrane components may be functionalized.

Where the one or more anchors comprise a protein, they may be able to anchor directly into the membrane without further functionalization, for example if it already has an external hydrophobic region which is compatible with the membrane. Examples of such proteins include, but are not limited to, transmembrane proteins, intramembrane proteins and membrane proteins. Alternatively the protein may be expressed with a genetically fused hydrophobic region which is compatible with the membrane. Such hydrophobic protein regions are known in the art.

The one or more anchors are preferably mixed with the polynucleotide before delivery to the membrane, but the one or more anchors may be contacted with the membrane and subsequently contacted with the polynucleotide.

In another aspect the polynucleotide may be functionalized, using methods described above, so that it can be recognized by a specific binding group. Specifically the polynucleotide may be functionalized with a ligand such as biotin (for binding to streptavidin), amylose (for binding to maltose binding protein or a fusion protein), Ni-NTA (for binding to poly-histidine or poly-histidine tagged proteins) or peptides (such as an antigen).

According to a preferred embodiment, the one or more anchors may be used to couple a polynucleotide to the membrane when the polynucleotide is attached to a leader sequence which may thread into the pore. Preferably, the polynucleotide is attached (such as ligated) to a leader sequence which may thread into the pore. Such a leader sequence may comprise a homopolymeric polynucleotide or an abasic region. The leader sequence is typically designed to hybridize to the one or more anchors either directly or via one or more intermediate polynucleotides (or splints). In such instances, the one or more anchors typically comprise a polynucleotide sequence which is complementary to a sequence in the leader sequence or a sequence in the one or more intermediate polynucleotides (or splints). In such instances, the one or more splints typically comprise a polynucleotide sequence which is complementary to a sequence in the leader sequence.

Any of the methods discussed above for coupling polynucleotides to membranes, such as amphiphilic layers, can of course be applied to other polynucleotide and membrane combinations. In some embodiments, an amino acid, peptide, polypeptide or protein is coupled to an amphiphilic layer, such as a triblock copolymer layer or lipid bilayer. Various methodologies for the chemical attachment of such polynucleotides are available. An example of a molecule used in chemical attachment is EDC (1-ethyl-3-[3-dimethylaminopropyl]carbodiimide hydrochloride). Reactive groups can also be added to the 5' of polynucleotides using commercially available kits (Thermo Pierce, Part No. 22980). Suitable methods include, but are not limited to, transient affinity attachment using histidine residues and Ni-NTA, as well as more robust covalent attachment by reactive cysteines, lysines or non-natural amino acids.

Microparticles

A microparticle, typically a bead, may be used to deliver an analyte (e.g., a polynucleotide or polypeptide) to the transmembrane pore. This is described in WO 2016/059375, the content of which is incorporated herein by reference in its entirety. Any number of microparticles can be used in the method of the invention. For instance, the method of the invention may use a single microparticle or 2, 3, 4, 5, 6, 7, 8, 9, 10, 20, 30, 50, 100, 1,000, 5,000, 10,000, 100,000, 500,000 or 1,000,000 or more microparticles. If two or more microparticles are used, the microparticles may be the same. Alternatively, a mixture of different microparticles may be used.

Each microparticle may have one analyte (e.g., a polynucleotide or polypeptide) attached. Alternatively, each microparticle may have two or more analytes (e.g., polynucleotides or polypeptides), such as 3 or more, 4 or more, 5 or more, 6 or more, 7 or more, 8 or more, 9 or more, 10 or more, 20 or more, 30 or more, 50 or more, 100 or more, 500 or more, 1,000 or more, 5,000 or more, 10,000 or more, 100,000 or more, 1000,000 or more or 5000,000 or more analytes (e.g., polynucleotides or polypeptides), attached. A microparticle may be substantially or completed coated or covered with analytes (e.g., polynucleotides or polypeptides). A microparticle may have an analyte (e.g., a polynucleotide or polypeptide) attached over substantially all of, or all of, its surface. A microparticle may be attached to an analyte (e.g., a polynucleotide or polypeptide) via an adaptor. The adaptor may be a Y-adaptor, e.g., as shown in FIG. 36.

Examples of suitable binding moieties include: protein binding tags (streptavidin tags, flag tags, etc.), conjugated attachments (polynucleotides, polymers, biotins, peptides) and amino acids (cysteines, Faz, etc.).

In some embodiments, a polynucleotide may be attached to two or more microparticles.

A microparticle is a microscopic particle whose size is typically measured in micrometers (μm). Microparticles may also be known as microspheres or microbeads. The microparticle may be a nanoparticle. A nanoparticle is a microscopic particle whose size is typically measured in nanometers (nm).

A microparticle typically has a particle size of from about 0.001 μm to about 500 μm. For instance, a nanoparticle may have a particle size of from about 0.01 μm to about 200 μm or about 0.1 μm to about 100 μm. More often, a microparticle has a particle size of from about 0.5 μm to about 100 μm, or for instance from about 1 μm to about 50 μm. The microparticle may have a particle size of from about 1 nm to about 1000 nm, such as from about 10 nm to about 500 nm, about 20 nm to about 200 nm or from about 30 nm to about 100 nm.

A microparticle may be spherical or non-spherical. Spherical microparticles may be called microspheres. Non-spherical particles may for instance be plate-shaped, needle-shaped, irregular or tubular. The term "particle size" as used herein means the diameter of the particle if the particle is spherical or, if the particle is non-spherical, the volume-based particle size. The volume-based particle size is the diameter of the sphere that has the same volume as the non-spherical particle in question.

If two or more microparticles are used in the method, the average particle size of the microparticles may be any of the sizes discussed above, such as from about 0.5 µm to about 500 µm. A population of two or more microparticles preferably has a coefficient of variation (ratio of the standard deviation to the mean) of 10% or less, such as 5% or less or 2% or less.

Any method may be used to determine the size of the microparticle. Suitable methods include, but are not limited to, flow cytometry (see, for example, Chandler et al., J Thromb Haemost. 2011 June; 9(6):1216-24).

The microparticle may be formed from any material. The microparticle is preferably formed from a ceramic, glass, silica, a polymer or a metal. The polymer may be a natural polymer, such as polyhydroxyalkanoate, dextran, polylactide, agarose, cellulose, starch or chitosan, or a synthetic polymer, such as polyurethane, polystyrene, poly(vinyl chloride), silane or methacrylate. Suitable microparticles are known in the art and are commercially available. Ceramic and glass microspheres are commercially available from 3M®. Silica and polymer microparticles are commercially available from EPRUI Nanoparticles & Microspheres Co. Ltd. Microparticles are also commercially available from Polysciences Inc., Bangs Laboratories Inc. and Life Technologies.

The microparticle may be solid. The microparticle may be hollow. The microparticle may be formed from polymer fibers.

The microparticle may be derived from the kit used to extract and isolate the analyte (e.g., polynucleotide or polypeptide).

The surface of the microparticle may interact with and attach the analyte. The surface may naturally interact with the analyte, such as the polynucleotide or polypeptide, without functionalization. The surface of the microparticle is typically functionalized to facilitate attachment of the analyte. Suitable functionalization's are known in the art. For instance, the surface of the microparticle may be functionalized with a polyhistidine-tag (hexa histidine-tag, 6×His-tag, His6 tag or His-Tag®), Ni-NTA, streptavidin, biotin, an oligonucleotide, a polynucleotide (such as DNA, RNA, PNA, GNA, TNA or LNA), carboxyl groups, quaternary amine groups, thiol groups, azide groups, alkyne groups, DIBO, lipid, FLAG-tag (FLAG octapeptide, polynucleotide binding protein (e.g., polynucleotide unwinding enzyme)s (including any of those discussed below), peptides, proteins, antibodies or antibody fragments. The microparticle may also be functionalized with any of the linkers or groups discussed herein.

The microparticle may be functionalized with a molecule or group which specifically binds to the polynucleotide. In this instance, the polynucleotide which will be attached to the microparticle and delivered to the transmembrane pore may be called the target polynucleotide. This allows the microparticle to select or capture the target polynucleotide from a sample containing other polynucleotides. A molecule or group specifically binds to the target polynucleotide if it binds to the target polynucleotide with preferential or high affinity, but does not bind or binds with only low affinity to other or different polynucleotides. A molecule or group binds with preferential or high affinity if it binds with a Kd of $1\times10^{-6}$ M or less, more preferably $1\times10^{-7}$ M or less, $5\times10^{-8}$ M or less, more preferably $1\times10^{-8}$ M or less or more preferably $5\times10^{-9}$ M or less. A molecule or group binds with low affinity if it binds with a Kd of $1\times10^{-6}$ M or more, more preferably $1\times10^{-5}$ M or more, more preferably $1\times10^{-4}$ M or more, more preferably $1\times10^{-3}$ M or more, even more preferably $1\times10^{-2}$ M or more.

Preferably, the molecule or group binds to the target polynucleotide with an affinity that is at least 10 times, such as at least 50, at least 100, at least 200, at least 300, at least 400, at least 500, at least 1000 or at least 10,000 times, greater than its affinity for other polynucleotides. Affinity can be measured using known binding assays, such as those that make use of fluorescence and radioisotopes. Competitive binding assays are also known in the art. The strength of binding between peptides or proteins and polynucleotides can be measured using nanopore force spectroscopy as described in Hornblower et al., Nature Methods. 4: 315-317. (2007).

The microparticle may be functionalized with an oligonucleotide or a polynucleotide which specifically hybridizes to a target polynucleotide or adaptor or which comprises a portion or region which is complementary to a portion or region of the target polynucleotide or adaptor. This allows the microparticle to select or capture the target polynucleotide from a sample containing other polynucleotides.

An oligonucleotide or polynucleotide specifically hybridizes to a target polynucleotide when it hybridizes with preferential or high affinity to the target polynucleotide but does not substantially hybridize, does not hybridize or hybridizes with only low affinity to other polynucleotide. An oligonucleotide or polynucleotide specifically hybridizes if it hybridizes to the target polynucleotide with a melting temperature ($T_m$) that is at least 2° C., such as at least 3° C., at least 4° C., at least 5° C., at least 6° C., at least 7° C., at least 8° C., at least 9° C. or at least 10° C., greater than its $T_m$ for other sequences. More preferably, the oligonucleotide or polynucleotide hybridize to the target polynucleotide with a $T_m$ that is at least 2° C., such as at least 3° C., at least 4° C., at least 5° C., at least 6° C., at least 7° C., at least 8° C., at least 9° C., at least 10° C., at least 20° C., at least 30° C. or at least 40° C., greater than its $T_m$ for other nucleic acids. Preferably, the oligonucleotide or polynucleotide hybridizes to the target polynucleotide with a $T_m$ that is at least 2° C., such as at least 3° C., at least 4° C., at least 5° C., at least 6° C., at least 7° C., at least 8° C., at least 9° C., at least 10° C., at least 20° C., at least 30° C. or at least 40° C., greater than its $T_m$ for a sequence which differs from the target polynucleotide by one or more nucleotides, such as by 1, 2, 3, 4 or 5 or more nucleotides. The oligonucleotide or polynucleotide typically hybridizes to the target polynucleotide with a $T_m$ of at least 90° C., such as at least 92° C. or at least 95° C. $T_m$ can be measured experimentally using known techniques, including the use of DNA microarrays, or can be calculated using publicly available $T_m$ calculators, such as those available over the internet.

Conditions that permit the hybridization are well-known in the art (for example, Sambrook et al., 2001, Molecular Cloning: a laboratory manual, 3rd edition, Cold Spring Harbor Laboratory Press; and Current Protocols in Molecular Biology, Chapter 2, Ausubel et al., Eds., Greene Publishing and Wiley-Interscience, New York (1995)). Hybridization can be carried out under low stringency conditions, for example in the presence of a buffered solution of 30 to 35% formamide, 1 M NaCl and 1% SDS (sodium dodecyl sulfate) at 37° C. followed by a 20 wash in from 1× (0.1650 M Na+) to 2× (0.33 M Na+) SSC (standard sodium citrate) at 50° C. Hybridization can be carried out under moderate stringency conditions, for example in the presence of a buffer solution of 40 to 45% formamide, 1 M NaCl, and 1%

SDS at 37° C., followed by a wash in from 0.5× (0.0825 M Na$^+$) to 1× (0.1650 M Na$^+$) SSC at 55° C. Hybridization can be carried out under high stringency conditions, for example in the presence of a buffered solution of 50% formamide, 1 M NaCl, 1% SDS at 37° C., followed by a wash in 0.1× (0.0165 M Na$^+$) SSC at 60° C.

The polynucleotide may comprise a portion or region which is substantially complementary to a portion or region of the target polynucleotide. The region or portion of the polynucleotide may therefore have 1, 2, 3, 4, 5, 6, 7, 8, 9, 10 or more mismatches across a region of 5, 10, 15, 20, 21, 22, 30, 40 or 50 nucleotides compared with the portion or region in the target polynucleotide.

A portion of region is typically 50 nucleotides or fewer, such as 40 nucleotides or fewer, 30 nucleotides or fewer, 20 nucleotides or fewer, 10 nucleotides or fewer or 5 nucleotides or fewer.

The microparticle is preferably paramagnetic or magnetic. The microparticle preferably comprises a paramagnetic or a superparamagnetic material or a paramagnetic or a superparamagnetic metal, such as iron. Any suitable magnetic microparticle may be used. For instance, magnetic beads commercially available from, for instance, Clontech, Promega, Invitrogen ThermoFisher Scientific and NEB, may be used. In some embodiments, the microparticle comprises a magnetic particle with an organic group such as a metal-chelating group, such as nitrilotriacetic acid (NTA), attached. The organic component may, for instance, comprise a group selected from —C(=O)O—, —C—O—C—, —C(=O)—, —NH—, —C(=O)—NH, —C(=O)—CH$_2$—I, —S(=O)$_2$— and —S—. The organic component may comprise a metal chelating group, such as NTA (nitrilotriacetic acid). Usually, a metal such as gold, iron, nickel or cobalt is also attached to the metal-chelating group. Magnetic beads of this sort are commonly used for capturing His-tagged proteins, but are also suitable for use in the invention.

The microparticle is most preferably a His-Tag Dynabead® which is commercially available from Life Technologies, Mag Strep beads from IBA, Streptavidin magnetic beads from NEB, Solid Phase Reversible Immobilization (SPRI) beads or Agencourt AMPure XP beads from Beckman Coulter or Dynabeads® MyOne™ Streptavidin C1 (ThermoFisher Scientific).

Polynucleotide Binding Protein (e.g., Polynucleotide Unwinding Enzyme)

The methods provided herein use a polymerase to process a polynucleotide such that the by-products of the processing reaction are detected by a nanopore, thereby detecting the addition of a nucleotide by the polymerase to the polynucleotide strand. A polymerase is an example of a polynucleotide binding protein (e.g. a polynucleotide unwinding enzyme).

A polynucleotide binding protein (e.g., polynucleotide unwinding enzyme) is a protein that is capable of binding to the polynucleotide. A polynucleotide binding protein may be capable of controlling movement of the polynucleotide through the pore. It is straightforward in the art to determine whether or not a protein binds to a polynucleotide. The protein typically interacts with and modifies at least one property of the polynucleotide. The protein may modify the polynucleotide by cleaving it to form individual nucleotides or shorter chains of nucleotides, such as mono-, di- or trinucleotides. The moiety may modify the polynucleotide by orienting it or moving it to a specific position, i.e. controlling its movement.

A polynucleotide binding protein (e.g., polynucleotide unwinding enzyme) may be derived from a polynucleotide handling enzyme. A polynucleotide handling enzyme is a polypeptide that is capable of interacting with and modifying at least one property of a polynucleotide. An enzyme may modify the polynucleotide by cleaving it to form individual nucleotides or shorter chains of nucleotides, such as di- or trinucleotides. An enzyme may modify the polynucleotide by orienting it or moving it to a specific position. In some disclosed methods, the polynucleotide handling enzyme does not need to display enzymatic activity as long as it is capable of binding the polynucleotide and controlling its movement through the pore. For instance, in such methods, the enzyme may be modified to remove its enzymatic activity or may be used under conditions which prevent it from acting as an enzyme. Such conditions are discussed in more detail below. In the methods provided herein, the polynucleotide binding protein processes a polynucleotide by adding a nucleotide to the polynucleotide strand and the by-products of the processing reaction are detected by the nanopoire, thereby detecting the addition of a nucleotide to the polynucleotide strand.

Polynucleotide handling enzymes may be derived from a nucleolytic enzyme. Polynucleotide handling enzymes may be derived from a member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31. The enzyme may be any of those disclosed in WO 2010/086603.

Preferably, the polynucleotide handling enzyme is a polymerase. Other polynucleotide handling enzymes include exonucleases, helicases, translocases and topoisomerases, such as gyrases. The polymerase may be PyroPhage® 3173 DNA Polymerase (which is commercially available from Lucigen® Corporation), SD Polymerase (commercially available from Bioron®) or variants thereof. The polymerase is preferably Bst3.0 or Phi29 DNA polymerase or a variant thereof. A topoisomerase may be a member of any of the Moiety Classification (EC) groups 5.99.1.2 and 5.99.1.3.

A polynucleotide handling enzyme may be derived from a helicase. The helicase may be or be derived from a Hel308 helicase, a RecD helicase, such as TraI helicase or a TrwC helicase, a XPD helicase or a Dda helicase. The helicase may be or be derived from Hel308 Mbu, Hel308 Csy Hel308 Tga, Hel308 Mhu, TraI Eco, XPD Mbu or a variant thereof.

The helicase may be any of the helicases, modified helicases or helicase constructs disclosed in WO 2013/057495, WO 2013/098562, WO2013098561, WO 2014/013260, WO 2014/013259, WO 2014/013262 and WO/2015/055981.

A Dda helicase preferably comprises any of the modifications disclosed in WO/2015/055981 and WO 2016/055777.

In some methods disclosed herein, any number of helicases may be used. For instance, 1, 2, 3, 4, 5, 6, 7, 8, 9, 10 or more helicases may be used. In some disclosed methods, different numbers of helicases may be used. Any combination of two or more of the helicases mentioned above may be used. The two or more helicases may be two or more Dda helicases. The two or more helicases may be one or more Dda helicases and one or more TrwC helicases. The two or more helicases may be different variants of the same helicase. The two or more helicases may be preferably attached to one another. The two or more helicases may more preferably be covalently attached to one another. The helicases may be attached in any order and using any method. Preferred helicase constructs for use in such methods are described in WO 2014/013260, WO 2014/013259, WO 2014/013262 and WO2015/055981.

In some embodiments provided herein, the polynucleotide binding protein is a polynucleotide unwinding enzyme. A polynucleotide unwinding enzyme is an enzyme that is capable of unwinding a double-stranded polynucleotide into single stranded. As used herein, a polynucleotide unwinding enzyme may be a polymerase. In some embodiments, the polynucleotide unwinding enzyme is capable of unwinding a double stranded DNA into single strands. Polynucleotide unwinding enzymes may thus possess helicase activity. Examples of polynucleotide unwinding enzymes include, e.g., helicases described herein.

Polynucleotide binding ability can be measured using any method known in the art. For instance, the protein can be contacted with a polynucleotide and its ability to bind to and move along the polynucleotide can be measured. The protein may include modifications that facilitate binding of the polynucleotide and/or facilitate its activity at high salt concentrations and/or room temperature. Proteins may be modified such that they bind polynucleotides (i.e. retain polynucleotide binding ability) but do not function as a helicase (i.e. do not move along polynucleotides when provided with all the necessary components to facilitate movement, (e.g. ATP and $Mg^{2+}$). Such modifications are known in the art. For instance, modification of the $Mg^{2+}$ binding domain in helicases typically results in variants which do not function as helicases. These types of variants may act as molecular brakes.

The enzyme may be covalently attached to the pore. Any method may be used to covalently attach the enzyme to the pore.

In strand sequencing, disclosed herein, a polynucleotide is translocated through a pore either with or against an applied potential. Exonucleases that act progressively or processively on double stranded polynucleotides can be used on the cis side of the pore to feed the remaining single strand through under an applied potential or the trans side under a reverse potential. Likewise, a helicase that unwinds the double stranded DNA can also be used in a similar manner. A polymerase may also be used. There are also possibilities for sequencing applications that require strand translocation against an applied potential, but the DNA must be first "caught" by the enzyme under a reverse or no potential. With the potential then switched back following binding the strand will pass cis to trans through the pore and be held in an extended conformation by the current flow. The single strand DNA exonucleases or single strand DNA dependent polymerases can act as molecular motors to pull the recently translocated single strand back through the pore in a controlled stepwise manner, trans to cis, against the applied potential.

Any helicase may be used in such methods. Helicases may work in two modes with respect to the pore. First, a helicase may move the polynucleotide through the pore with the field resulting from the applied voltage. In this mode the 5' end of the polynucleotide is first captured in the pore, and the helicase moves the polynucleotide into the pore such that it is passed through the pore with the field until it finally translocates through to the trans side of the membrane. Alternatively, a helicase may move the polynucleotide through the pore against the field resulting from the applied voltage. In this mode the 3' end of the polynucleotide is first captured in the pore, and the helicase moves the polynucleotide through the pore such that it is pulled out of the pore against the applied field until finally ejected back to the cis side of the membrane.

Such methods may also be carried out in the opposite direction. The 3' end of a polynucleotide may be first captured in the pore and a helicase may move the polynucleotide into the pore such that it is passed through the pore with the field until it finally translocates through to the trans side of the membrane.

When a helicase is not provided with the necessary components to facilitate movement or is modified to hinder or prevent its movement, it can bind to the polynucleotide and act as a brake slowing the movement of the polynucleotide when it is pulled into the pore by the applied field. In the inactive mode, it does not matter whether the polynucleotide is captured either 3' or 5' down, it is the applied field which pulls the polynucleotide into the pore towards the trans side with the enzyme acting as a brake. When in the inactive mode, the movement control of the polynucleotide by the helicase can be described in a number of ways including ratcheting, sliding and braking. Helicase variants which lack helicase activity can also be used in this way.

In the methods provided herein, the polynucleotide may be contacted with the polynucleotide binding protein (e.g., polynucleotide unwinding enzyme, e.g. polymerase) and the pore in any order. It is preferred that, when the polynucleotide is contacted with the polynucleotide binding protein (e.g., polynucleotide unwinding enzyme, e.g. polymerase) and the pore, the polynucleotide firstly forms a complex with the polynucleotide binding protein (e.g., polynucleotide unwinding enzyme). When the voltage is applied across the pore, the polynucleotide/polynucleotide binding protein (e.g., polynucleotide unwinding enzyme) complex then forms a complex with the pore and controls the movement of the polynucleotide through the pore.

The methods provided herein, which use a polynucleotide binding protein (e.g., polynucleotide unwinding enzyme, e.g. polymerase), are carried out in the presence of free nucleotides or free nucleotide analogues and an enzyme cofactor that facilitates the action of the polynucleotide binding protein (e.g., polynucleotide unwinding enzyme). The free nucleotides may be one or more of any of the individual nucleotides discussed above. The free nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The free nucleotides are preferably selected from AMP, TMP, GMP, CMP, UMP, dAMP, dTMP, dGMP or dCMP. The free nucleotides are preferably adenosine triphosphate (ATP). The enzyme cofactor is a factor that allows the construct to function. The enzyme cofactor is preferably a divalent metal cation. The divalent metal cation is preferably $Mg^{2+}$, $Mn^{2+}$, $Ca^{2+}$ or $Co^{2+}$. The enzyme cofactor is most preferably $Mg^{2+}$.

The nucleotides are preferably labelled. The nucleotides are preferably labelled with an optical label. The nucleotides in the sample are preferably distinguishably labelled according to the type of nucleotides in the sample. For example, if the sample comprises two, three, four or more types of nucleotides then the two, three, four or more types of nucleotides may each comprise a different label such that the two, three, four or more types of nucleotides in the sample are distinguishably labelled. For example, if the sample comprises ATP, CTP, GTP, TTP, UTP, dAPT, dCTP, dGTP, dTTP and/or dUTP, the ATP, CTP, GTP, TTP, UTP, dAPT, dCTP, dGTP, dTTP and/or dUTP are preferably distinguishably labelled. The label is preferably such that the the by-products of the processing reaction by the polymerase are labelled, preferably with an optical label and/or a polymer tag. The polymer tag is preferably charged. The use of polymer tags to detect the by-products of enzyme processing reactions has been previously described e.g by Stranges et al, "*Design and characterization of a nanopore-coupled polymerase for single-molecule DNA sequencing by synthesis on an electrode array*", Proc. Natl. Acad. Sci. USA, 2016 Nov. 1; 113(44): E6749-E6756.

Preferably, the by-products of the processing reaction are thus labelled phosphoate species. The by-products of the processing reaction(s) are thus preferably distinguishably labelled according to the type of nucleotide being added by the polymerase to the polynuceotide strand.

A molecular brake may be any compound or molecule which binds to the polynucleotide and slows the movement of the polynucleotide through a pore. A molecular brake may be any of those discussed above. A molecular brake preferably comprises a compound which binds to the polynucleotide. The compound is preferably a macrocycle. Suitable macrocycles include, but are not limited to, cyclodextrins, calixarenes, cyclic peptides, crown ethers, cucurbiturils, pillararenes, derivatives thereof or a combination thereof. The cyclodextrin or derivative thereof may be any of those disclosed in Eliseev, A. V., and Schneider, H-J. (1994) *J. Am. Chem. Soc.* 116, 6081-6088. The cyclodextrin is more preferably heptakis-6-amino-β-cyclodextrin ($am_7$-βCD), 6-monodeoxy-6-monoamino-β-cyclodextrin ($am_1$-βCD) or heptakis-(6-deoxy-6-guanidino)-cyclodextrin ($gu_7$-βCD).

Membrane

Any membrane may be used in accordance with various aspects described herein Suitable membranes are well-known in the art. The membrane is preferably an amphiphilic layer or a solid state layer.

An amphiphilic layer is a layer formed from amphiphilic molecules, such as phospholipids, which have both hydrophilic and lipophilic properties. The amphiphilic molecules may be synthetic or naturally occurring. Non-naturally occurring amphiphiles and amphiphiles which form a monolayer are known in the art and include, for example, block copolymers (Gonzalez-Perez et al., Langmuir, 2009, 25, 10447-10450). Block copolymers are polymeric materials in which two or more monomer sub-units that are polymerized together to create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic (i.e. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphiphiles. The copolymer may be a triblock, tetrablock or pentablock copolymer. The membrane is preferably a triblock copolymer membrane.

Archaebacterial bipolar tetraether lipids are naturally occurring lipids that are constructed such that the lipid forms a monolayer membrane. These lipids are generally found in extremophiles that survive in harsh biological environments, thermophiles, halophiles and acidophiles. Their stability is believed to derive from the fused nature of the final bilayer. It is straightforward to construct block copolymer materials that mimic these biological entities by creating a triblock polymer that has the general motif hydrophilic-hydrophobic-hydrophilic. This material may form monomeric membranes that behave similarly to lipid bilayers and encompass a range of phase behaviors from vesicles through to laminar membranes. Membranes formed from these triblock copolymers hold several advantages over biological lipid membranes. Because the triblock copolymer is synthesized, the exact construction can be carefully controlled to provide the correct chain lengths and properties required to form membranes and to interact with pores and other proteins.

Block copolymers may also be constructed from sub-units that are not classed as lipid sub-materials; for example a hydrophobic polymer may be made from siloxane or other non-hydrocarbon based monomers. The hydrophilic sub-section of block copolymer can also possess low protein binding properties, which allows the creation of a membrane that is highly resistant when exposed to raw biological samples. This head group unit may also be derived from non-classical lipid head-groups.

Triblock copolymer membranes also have increased mechanical and environmental stability compared with biological lipid membranes, for example a much higher operational temperature or pH range. The synthetic nature of the block copolymers provides a platform to customize polymer based membranes for a wide range of applications.

The membrane is most preferably one of the membranes disclosed in WO2014/064443 or WO2014/064444.

The amphiphilic molecules may be chemically-modified or functionalized to facilitate coupling of the polynucleotide.

The amphiphilic layer may be a monolayer or a bilayer. The amphiphilic layer is typically planar. The amphiphilic layer may be curved. The amphiphilic layer may be supported. The amphiphilic layer may be concave. The amphiphilic layer may be suspended from raised pillars such that the peripheral region of the amphiphilic layer (which is attached to the pillars) is higher than the amphiphilic layer region. This may allow the microparticle to travel, move, slide or roll along the membrane as described above.

Amphiphilic membranes are typically naturally mobile, essentially acting as two dimensional fluids with lipid diffusion rates of approximately $10^{-8}$ cm s-1. This means that the pore and coupled polynucleotide can typically move within an amphiphilic membrane.

The membrane may be a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The lipid bilayer may be any lipid bilayer. Suitable lipid bilayers include, but are not limited to, a planar lipid bilayer, a supported bilayer or a liposome. The lipid bilayer is preferably a planar lipid bilayer. Suitable lipid bilayers are disclosed in WO 2008/102121, WO 2009/077734 and WO 2006/100484.

Methods for forming lipid bilayers are known in the art. Lipid bilayers are commonly formed by the method of Montal and Mueller (Proc. Natl. Acad. Sci. USA., 1972; 69: 3561-3566), in which a lipid monolayer is carried on aqueous solution/air interface past either side of an aperture which is perpendicular to that interface. The lipid is normally added to the surface of an aqueous electrolyte solution by first dissolving it in an organic solvent and then allowing a drop of the solvent to evaporate on the surface of the aqueous solution on either side of the aperture. Once the organic solvent has evaporated, the solution/air interfaces on either side of the aperture are physically moved up and down past the aperture until a bilayer is formed. Planar lipid bilayers may be formed across an aperture in a membrane or across an opening into a recess.

The method of Montal & Mueller is popular because it is a cost-effective and relatively straightforward method of forming good quality lipid bilayers that are suitable for protein pore insertion. Other common methods of bilayer formation include tip-dipping, painting bilayers and patch-clamping of liposome bilayers.

Tip-dipping bilayer formation entails touching the aperture surface (for example, a pipette tip) onto the surface of a test solution that is carrying a monolayer of lipid. Again, the lipid monolayer is first generated at the solution/air interface by allowing a drop of lipid dissolved in organic solvent to evaporate at the solution surface. The bilayer is then formed by the Langmuir-Schaefer process and requires mechanical automation to move the aperture relative to the solution surface.

For painted bilayers, a drop of lipid dissolved in organic solvent is applied directly to the aperture, which is submerged in an aqueous test solution. The lipid solution is spread thinly over the aperture using a paintbrush or an equivalent. Thinning of the solvent leads to formation of a lipid bilayer. However, complete removal of the solvent from the bilayer is difficult and consequently the bilayer formed by this method is less stable and more prone to noise during electrochemical measurement.

Patch-clamping is commonly used in the study of biological cell membranes. The cell membrane is clamped to the end of a pipette by suction and a patch of the membrane becomes attached over the aperture. The method has been adapted for producing lipid bilayers by clamping liposomes which then burst to leave a lipid bilayer sealing over the aperture of the pipette. The method requires stable, giant and unilamellar liposomes and the fabrication of small apertures in materials having a glass surface.

Liposomes can be formed by sonication, extrusion or the Mozafari method (Colas et al. (2007) Micron 38:841-847).

In a preferred embodiment, the lipid bilayer is formed as described in WO 2009/077734. Advantageously in this method, the lipid bilayer is formed from dried lipids. In a most preferred embodiment, the lipid bilayer is formed across an opening as described in WO2009/077734.

A lipid bilayer is formed from two opposing layers of lipids. The two layers of lipids are arranged such that their hydrophobic tail groups face towards each other to form a hydrophobic interior. The hydrophilic head groups of the lipids face outwards towards the aqueous environment on each side of the bilayer. The bilayer may be present in a number of lipid phases including, but not limited to, the liquid disordered phase (fluid lamellar), liquid ordered phase, solid ordered phase (lamellar gel phase, interdigitated gel phase) and planar bilayer crystals (lamellar sub-gel phase, lamellar crystalline phase).

Any lipid composition that forms a lipid bilayer may be used. The lipid composition is chosen such that a lipid bilayer having the required properties, such as surface charge, ability to support membrane proteins, packing density or mechanical properties, is formed. The lipid composition can comprise one or more different lipids. For instance, the lipid composition can contain up to 100 lipids. The lipid composition preferably contains 1 to 10 lipids. The lipid composition may comprise naturally-occurring lipids and/or artificial lipids.

The lipids typically comprise a head group, an interfacial moiety and two hydrophobic tail groups which may be the same or different. Suitable head groups include, but are not limited to, neutral head groups, such as diacylglycerides (DG) and ceramides (CM); zwitterionic head groups, such as phosphatidylcholine (PC), phosphatidylethanolamine (PE) and sphingomyelin (SM); negatively charged head groups, such as phosphatidylglycerol (PG); phosphatidylserine (PS), phosphatidylinositol (PI), phosphatic acid (PA) and cardiolipin (CA); and positively charged headgroups, such as trimethylammonium-Propane (TAP). Suitable interfacial moieties include, but are not limited to, naturally-occurring interfacial moieties, such as glycerol-based or ceramide-based moieties. Suitable hydrophobic tail groups include, but are not limited to, saturated hydrocarbon chains, such as lauric acid (n-Dodecanolic acid), myristic acid (n-Tetradeconoic acid), palmitic acid (n-Hexadecanoic acid), stearic acid (n-Octadecanoic) and arachidic (n-Eicosanoic); unsaturated hydrocarbon chains, such as oleic acid (cis-9-Octadecanoic); and branched hydrocarbon chains, such as phytanoyl. The length of the chain and the position and number of the double bonds in the unsaturated hydrocarbon chains can vary. The length of the chains and the position and number of the branches, such as methyl groups, in the branched hydrocarbon chains can vary. The hydrophobic tail groups can be linked to the interfacial moiety as an ether or an ester. The lipids may be mycolic acid.

The lipids can also be chemically-modified. The head group or the tail group of the lipids may be chemically-modified. Suitable lipids whose head groups have been chemically-modified include, but are not limited to, PEG-modified lipids, such as 1,2-Diacyl-sn-Glycero-3-Phosphoethanolamine-N-[Methoxy(Polyethylene glycol)-2000]; functionalized PEG Lipids, such as 1,2-Distearoyl-sn-Glycero-3 Phosphoethanolamine-N-[Biotinyl(Polyethylene Glycol)2000]; and lipids modified for conjugation, such as 1,2-Dioleoyl-sn-Glycero-3-Phosphoethanolamine-N-(succinyl) and 1,2-Dipalmitoyl-sn-Glycero-3-Phosphoethanolamine-N-(Biotinyl). Suitable lipids whose tail groups have been chemically-modified include, but are not limited to, polymerisable lipids, such as 1,2-bis(10,12-tricosadiynoyl)-sn-Glycero-3-Phosphocholine; fluorinated lipids, such as 1-Palmitoyl-2-(16-Fluoropalmitoyl)-sn-Glycero-3-Phosphocholine; deuterated lipids, such as 1,2-Dipalmitoyl-D62-sn-Glycero-3-Phosphocholine; and ether linked lipids, such as 1,2-Di-O-phytanyl-sn-Glycero-3-Phosphocholine. The lipids may be chemically-modified or functionalised to facilitate coupling of the polynucleotide.

The amphiphilic layer, for example the lipid composition, typically comprises one or more additives that will affect the properties of the layer. Suitable additives include, but are not limited to, fatty acids, such as palmitic acid, myristic acid and oleic acid; fatty alcohols, such as palmitic alcohol, myristic alcohol and oleic alcohol; sterols, such as cholesterol, ergosterol, lanosterol, sitosterol and stigmasterol; lysophospholipids, such as 1-Acyl-2-Hydroxy-sn-Glycero-3-Phosphocholine; and ceramides.

Solid state layers can be formed from both organic and inorganic materials including, but not limited to, microelectronic materials, insulating materials such as $Si_3N_4$, $Al_2O_3$, and SiO, organic and inorganic polymers such as polyamide, plastics such as Teflon® or elastomers such as two-component addition-cure silicone rubber, and glasses. The solid state layer may be formed from graphene. Suitable graphene layers are disclosed in WO 2009/035647. Yusko et al., Nature Nanotechnology, 2011; 6: 253-260 and US Patent Application No. 2013/0048499 describe the delivery of proteins to transmembrane pores in solid state layers without the use of microparticles. The method of the invention may be used to improve the delivery in the methods disclosed in these documents.

The method is typically carried out using (i) an artificial amphiphilic layer comprising a pore, (ii) an isolated, naturally-occurring lipid bilayer comprising a pore, or (iii) a cell having a pore inserted therein. The method is typically carried out using an artificial amphiphilic layer, such as an artificial triblock copolymer layer. The layer may comprise other transmembrane and/or intramembrane proteins as well as other molecules in addition to the pore. Suitable apparatus and conditions are discussed below. The method of the invention is typically carried out in vitro.

The membrane to which the polynucleotide is delivered according to the method of the invention is contained in a liquid. The liquid keeps the membrane "wet" and stops it drying out. The liquid is typically an aqueous solution. The aqueous solution typically has the same density as water. The density of the aqueous solution is typically about 1 $g/cm^3$. The density of the solution may vary depending on temperature and the exact composition of the solution. The aqueous solution typically has a density between about 0.97 and about 1.03 $g/cm^3$.

The membrane typically separates two volumes of aqueous solution. The membrane resists the flow of electrical current between the volumes. The transmembrane pore inserted into the membrane selectively allows the passage of ions across the membrane, which can be recorded as an electrical signal detected by electrodes in the two volumes of aqueous solution. The presence of the target polynucleotide modulates the flow of ions and is detected by observing the resultant variations in the electrical signal.

Array

The membrane is typically part of an array of membranes, wherein each membrane preferably comprises a transmembrane pore. Therefore, the invention provides a method of detecting a target polynucleotide using an array of membranes.

The membrane may be comprised in an apparatus having an array of electrically isolated membranes, each individually addressed using its own electrode, such that the array is equivalent to many individual sensors measuring in parallel from a test sample. The membranes may be relatively densely packed, allowing a large number of membranes to be used for a given volume of test sample. Suitable arrays of membranes and apparatuses are described in the art, for example in WO 2009/077734 and WO2012/042226. WO 2009/077734, for example, discloses a plurality of individually addressable lipid bilayers formed across an array of microwell apertures, each microwell containing an electrode and an aqueous medium in contact with the lipid bilayer.

The apparatus is typically provided to the end user in a 'ready to use' state wherein the membranes and transmembrane pores are pre-inserted. A typical apparatus provided in a 'ready to use' state comprises an array of amphiphilic membranes, each membrane comprising a transmembrane pore and being provided across a well containing a liquid. Such an apparatus and method of making it are disclosed by WO2014/064443. Test liquid to be analyzed is applied to the upper surface of the amphiphilic membranes.

Providing an apparatus in a 'ready to use' state however has additional considerations in that care needs to be taken that the sensor does not dry out, namely that liquid is not lost from the well by passage through the amphiphilic membrane, which may result in a loss of performance or damage the sensor. One solution to address the problem of drying out of the sensor is to provide the device with a buffer liquid over the surface of the amphiphilic membrane such that any evaporation through the surface of the membrane is minimized and the liquids provided on either side of the membrane may have the same ionic strength so as to reduce any osmotic effects. In use the buffer liquid may be removed from the surface of the amphiphilic membrane and a test liquid to be analyzed is introduced to contact the surface.

Some applications may use measurement of electrical properties across the membranes, for example ion current flow. To provide for such measurements, the apparatus may further comprise respective electrodes in each compartment making electrical contact with the volumes comprising polar medium. Other types of measurements may be carried out for example optical measurements such as fluorescence measurements and FET measurements. Optical measurements and electrical measurements may be carried out simultaneously (Heron A J et al., J Am Chem Soc. 2009; 131(5):1652-3).

The apparatus may further comprise a common electrode. The apparatus may further comprise an electrical circuit connected between the common electrode and the respective electrodes in each compartment, the electrical circuit being arranged to take electrical measurements. Such electrical measurements may be dependent on a process occurring at or through the membranes.

The apparatus may comprise a FET array for making measurements of the nanopore array.

Detector

In the methods provided herein, the detector may be selected from (i) a zero-mode waveguide, (ii) a field-effect transistor, optionally a nanowire field-effect transistor; (iii) an AFM tip; (iv) a nanotube, optionally a carbon nanotube; and (v) a nanopore. Preferably, the detector is a nanopore.

Transmembrane Pore

A transmembrane pore is a structure that crosses the membrane to some degree. It permits hydrated ions driven by an applied potential to flow across or within the membrane. The transmembrane pore typically crosses the entire membrane so that hydrated ions may flow from one side of the membrane to the other side of the membrane. However, the transmembrane pore does not have to cross the membrane. It may be closed at one end. For instance, the pore may be a well, gap, channel, trench or slit in the membrane along which or into which hydrated ions may flow.

Any transmembrane pore may be used in the invention. The pore may be biological or artificial. Suitable pores include, but are not limited to, protein pores, polynucleotide pores and solid state pores. The pore may be a DNA origami pore (Langecker et al., Science, 2012; 338: 932-936). The pore may be a motor protein nanopore, e.g., a nanopore that allows the translocation of a double-stranded polynucleotide. In some embodiments, the motor protein nanopore is able to unwind a double stranded polynucleotide. An exemplary motor protein nanopore includes, but is not limited to, a phi29 motor protein nanopore, e.g., as described in Wendell et al. "Translocation of double-stranded DNA through membrane-adapted phi29 motor protein nanopores" *Nat Nanotechnol,* 4 (2009), pp. 765-772. In some embodiments, any nanopore as described or referenced in Feng et al. "Nanopore-based fourth-generation DNA sequencing technology" *Genomics, Proteomics & Bioinformatics* (2015) Volume 13, Issue 1, Pages 4-16, can be used in various aspects described herein.

The transmembrane pore is preferably a transmembrane protein pore. A transmembrane protein pore is a polypeptide or a collection of polypeptides that permits hydrated ions, such as the by-products of processing a polynucleotide with a polymerase, to flow from one side of a membrane to the other side of the membrane. In the present invention, the transmembrane protein pore is capable of forming a pore that permits hydrated ions driven by an applied potential to flow from one side of the membrane to the other. The transmembrane protein pore preferably permits polynucleotides to flow from one side of the membrane, such as a triblock copolymer membrane, to the other. The transmembrane protein pore may allow a polynucleotide, such as DNA or RNA, to be moved through the pore.

The transmembrane protein pore may be a monomer or an oligomer. The pore is preferably made up of several repeating subunits, such as at least 6, at least 7, at least 8, at least 9, at least 10, at least 11, at least 12, at least 13, at least 14, at least 15, or at least 16 subunits. The pore is preferably a hexameric, heptameric, octameric or nonameric pore. The pore may be a homo-oligomer or a hetero-oligomer.

The transmembrane protein pore typically comprises a barrel or channel through which the ions may flow. The subunits of the pore typically surround a central axis and contribute strands to a transmembrane β barrel or channel or a transmembrane α-helix bundle or channel.

The barrel or channel of the transmembrane protein pore typically comprises amino acids that facilitate interaction with nucleotides, polynucleotides or nucleic acids. These amino acids are preferably located near a constriction of the barrel or channel. The transmembrane protein pore typically comprises one or more positively charged amino acids, such as arginine, lysine or histidine, or aromatic amino acids, such as tyrosine or tryptophan. These amino acids typically facilitate the interaction between the pore and nucleotides, polynucleotides or nucleic acids.

Transmembrane protein pores for use in accordance with the invention can be derived from β-barrel pores or α-helix bundle pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smegmatis* porin (Msp), for example MspA, MspB, MspC or MspD, CsgG, outer membrane porin F (OmpF), outer membrane porin G (OmpG), outer membrane phospholipase A and *Neisseria* autotransporter lipoprotein (NalP) and other pores, such as lysenin. α-helix bundle pores comprise a barrel or channel that is formed from α-helices. Suitable α-helix bundle pores include, but are not limited to, inner membrane proteins and α outer membrane proteins, such as WZA and ClyA toxin.

The transmembrane pore may be derived from or based on Msp, α-hemolysin (α-HL), lysenin, CsgG, ClyA, Spl and hemolytic protein fragaceatoxin C (FraC). The transmembrane protein pore is preferably derived from CsgG, more preferably from CsgG from *E. coli* Str. K-12 substr. MC4100. Suitable pores derived from CsgG are disclosed in WO 2016/034591. The transmembrane pore may be derived from lysenin. Suitable pores derived from lysenin are disclosed in WO 2013/153359.

The wild type α-hemolysin pore is formed of 7 identical monomers or sub-units (i.e., it is heptameric). The sequence of one monomer or sub-unit of α-hemolysin-NN is disclosed in, for example, WO2016/059375.

The transmembrane protein pore is preferably derived from Msp, more preferably from MspA. Suitable pores derived from MspA are disclosed in WO 2012/107778.

Any of the proteins described herein, such as the transmembrane protein pores, may be modified to assist their identification or purification, for example by the addition of histidine residues (a his tag), aspartic acid residues (an asp tag), a streptavidin tag, a flag tag, a SUMO tag, a GST tag or a MBP tag, or by the addition of a signal sequence to promote their secretion from a cell where the polypeptide does not naturally contain such a sequence. An alternative to introducing a genetic tag is to chemically react a tag onto a native or engineered position on the pore or construct. An example of this would be to react a gel-shift reagent to a cysteine engineered on the outside of the pore. This has been demonstrated as a method for separating hemolysin heterooligomers (Chem Biol. 1997 July; 4(7):497-505).

The pore may be labelled with a revealing label. The revealing label may be any suitable label which allows the pore to be detected. Suitable labels include, but are not limited to, fluorescent molecules, radioisotopes, e.g. $^{125}$I, $^{35}$S, enzymes, antibodies, antigens, polynucleotides and ligands such as biotin.

Any of the proteins described herein, such as the transmembrane protein pores, may be made synthetically or by recombinant means. For example, the pore may be synthesized by in vitro translation and transcription (IVTT). The amino acid sequence of the pore may be modified to include non-naturally occurring amino acids or to increase the stability of the protein. When a protein is produced by synthetic means, such amino acids may be introduced during production. The pore may also be altered following either synthetic or recombinant production.

Any of the proteins described herein, such as the transmembrane protein pores, can be produced using standard methods known in the art. Polynucleotide sequences encoding a pore or construct may be derived and replicated using standard methods in the art. Polynucleotide sequences encoding a pore or construct may be expressed in a bacterial host cell using standard techniques in the art. The pore may be produced in a cell by in situ expression of the polypeptide from a recombinant expression vector. The expression vector optionally carries an inducible promoter to control the expression of the polypeptide. These methods are described in Sambrook, J. and Russell, D. (2001). Molecular Cloning: A Laboratory Manual, 3rd Edition. Cold Spring Harbor Laboratory Press, Cold Spring Harbor, NY.

The pore may be produced in large scale following purification by any protein liquid chromatography system from protein producing organisms or after recombinant expression. Typical protein liquid chromatography systems include FPLC, AKTA systems, the Bio-Cad system, the Bio-Rad BioLogic system and the Gilson HPLC system.

Measuring Ion Flow

Ion flow through the transmembrane pore may be monitored using an electrical measurement and/or an optical measurement.

The electrical measurement may be a current measurement, an impedance measurement, a tunneling measurement or a field effect transistor (FET) measurement.

The change in ion flow through the transmembrane pore when the by-products of processing of a polypeptide by a polymerase translocate through the pore may be detected as a change in current, resistance or an optical property. The effect measured may be electron tunneling across the transmembrane pore. The effect measured may be a change in potential due to the interaction of the polynucleotide with the transmembrane pore wherein the effect is monitored using localized potential sensor in a FET measurement.

A variety of different types of measurements may be made. This includes without limitation: electrical measurements and optical measurements. A suitable optical method involving the measurement of fluorescence is disclosed by J. Am. Chem. Soc. 2009, 131 1652-1653. Possible electrical measurements include: current measurements, impedance measurements, tunnelling measurements (Ivanov A P et al., Nano Lett. 2011 Jan. 12; 11(1):279-85), and FET measurements (International Application WO 2005/124888). Optical measurements may be combined with electrical measurements (Soni G V et al., Rev Sci Instrum. 2010 January; 81(1):014301). The measurement may be a transmembrane current measurement such as measurement of ionic current flowing through the pore.

Electrical measurements may be made using standard single channel recording equipment as describe in Stoddart D et al., Proc Natl Acad Sci, 12; 106(19):7702-7, Lieberman K R et al, J Am Chem Soc. 2010; 132(50):17961-72, and International Application WO 2000/28312. Alternatively, electrical measurements may be made using a multi-channel system, for example as described in WO 2009/077734 and WO 2011/067559.

The method is preferably carried out with a potential applied across the membrane. The applied potential may be a voltage potential. Alternatively, the applied potential may be a chemical potential. In some embodiments, the applied potential may be driven by osmotic imbalance. An example of this is using a salt gradient across a membrane, such as an amphiphilic layer. A salt gradient is disclosed in Holden et al., J Am Chem Soc. 2007 Jul. 11; 129(27):8650-5. In some instances, the current passing through the pore as a polynucleotide moves with respect to the pore is used to estimate or determine the sequence of the polynucleotide.

Polynucleotide Characterization

In some embodiments of various aspects described herein, the method may involve further characterizing the target polynucleotide. As the target polynucleotide is contacted with the pore, one or more measurements which are indicative of one or more characteristics of the target polynucleotide are taken as the polynucleotide or the by-products of processing of such polynucleotide by a polymerase move with respect to the pore.

The method may involve determining whether or not the polynucleotide is modified. The presence or absence of any modification may be measured. The method preferably comprises determining whether or not the polynucleotide is modified by methylation, by oxidation, by damage, with one or more proteins or with one or more labels, tags or spacers. Specific modifications will result in specific interactions with the pore which can be measured using the methods described below. For instance, methylcytosine may be distinguished from cytosine on the basis of the ion flow through the pore during its interaction with each nucleotide.

Apparatus

The methods may be carried out using any apparatus that is suitable for investigating a membrane/pore system in which a pore is present in a membrane. The method may be carried out using any apparatus that is suitable for transmembrane pore sensing. For example, the apparatus comprises a chamber comprising an aqueous solution and a barrier that separates the chamber into two sections. The barrier typically has an aperture in which the membrane containing the pore is formed. Alternatively the barrier forms the membrane in which the pore is present.

The methods may be carried out using the apparatus described in WO 2008/102120.

A variety of different types of measurements may be made. This includes without limitation: electrical measurements and optical measurements. A suitable optical method involving the measurement of fluorescence is disclosed by J. Am. Chem. Soc. 2009, 131 1652-1653. Possible electrical measurements include: current measurements, impedance measurements, tunnelling measurements (Ivanov A P et al., Nano Lett. 2011 Jan. 12; 11(1):279-85), and FET measurements (International Application WO 2005/124888). Optical measurements may be combined with electrical measurements (Soni G V et al., Rev Sci Instrum. 2010 January; 81(1):014301). The measurement may be a transmembrane current measurement such as measurement of ionic current flowing through the pore.

Electrical measurements may be made using standard single channel recording equipment as describe in Stoddart D et al., Proc Natl Acad Sci, 12; 106(19):7702-7, Lieberman K R et al, J Am Chem Soc. 2010; 132(50):17961-72, and International Application WO 2000/28312. Alternatively, electrical measurements may be made using a multi-channel system, for example as described in International Application WO 2009/077734 and International Application WO 2011/067559.

The method is preferably carried out with a potential applied across the membrane. The applied potential may be a voltage potential. Alternatively, the applied potential may be a chemical potential. An example of this is using a salt gradient across a membrane, such as an amphiphilic layer. A salt gradient is disclosed in Holden et al., J Am Chem Soc. 2007 Jul. 11; 129(27):8650-5. In some instances, the current passing through the pore as the by-products of processing of a polynucleotide by a polymerase move with respect to the pore is used to estimate or determine the sequence of the polynucleotide.

The methods may involve measuring the current passing through the pore as the by-products of processing of a polynucleotide by a polymerase move with respect to the pore. Therefore the apparatus may also comprise an electrical circuit capable of applying a potential and measuring an electrical signal across the membrane and pore. The methods may be carried out using a patch clamp or a voltage clamp. The methods preferably involve the use of a voltage clamp.

The methods of the invention may involve the measuring of a current passing through the pore as the by-products of processing of a polynucleotide by a polymerase move with respect to the pore. Suitable conditions for measuring ionic currents through transmembrane protein pores are known in the art and disclosed in the Example. The method is typically carried out with a voltage applied across the membrane and pore. The voltage used is typically from +5 V to −5 V, such as from +4 V to −4 V, +3 V to −3 V or +2 V to −2 V. The voltage used is typically from −600 mV to +600 mV or −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The methods are typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl), caesium chloride (CsCl) or a mixture of potassium ferrocyanide and potassium ferricyanide is typically used. KCl, NaCl and a mixture of potassium ferrocyanide and potassium ferricyanide are preferred. The charge carriers may be asymmetric across the membrane. For instance, the type and/or concentration of the charge carriers may be different on each side of the membrane.

The salt concentration may be at saturation. The salt concentration may be 3 M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a nucleotide to be identified against the background of normal current fluctuations.

The methods are typically carried out in the presence of a buffer. In the exemplary apparatus discussed above, the buffer is present in the aqueous solution in the chamber. Any buffer may be used in the method of the invention. Typically, the buffer is phosphate buffer. Other suitable buffers are HEPES and Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The methods may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports enzyme function, such as about 37° C.

Free Nucleotides and Co-Factors

The method is carried out in the presence of free nucleotides or free nucleotide analogues and/or an enzyme cofactor that facilitates the action of the polynucleotide binding protein (e.g., polynucleotide unwinding enzyme). The free nucleotides may be one or more of any of the individual nucleotides discussed above. The free nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The free nucleotides are preferably selected from AMP, TMP, GMP, CMP, UMP, dAMP, dTMP, dGMP or dCMP. The free nucleotides are preferably adenosine triphosphate (ATP). The enzyme cofactor is a factor that allows the polynucleotide binding protein (e.g., polynucleotide unwinding enzyme) to function. The enzyme cofactor is preferably a divalent metal cation. The divalent metal cation is preferably $Mg^{2+}$, $Mn^{2+}$, $Ca^{2+}$ or $Co^{2+}$. The enzyme cofactor is most preferably $Mg^{2+}$.

The nucleotides are preferably labelled, preferably with an optical label and/or a polymer tag, as described above.

Kits

The invention also provides a population of adaptors comprising a double stranded barcode sequence, a single stranded leader sequence and a polynucleotide binding protein (e.g., polynucleotide unwinding enzyme, e.g. polymerase) capable of processing the strands of a double stranded polynucleotide, wherein the barcode sequence in each adaptor in the population is unique.

Also disclosed is a kit for use in methods described herein. The kit typically comprises a population of adaptors as described herein. The kit may additionally comprise one or more membrane anchor, a polynucleotide binding protein (e.g., polynucleotide unwinding enzyme) (which may be pre-bound to the adaptors), a ligase, a polymerase and/or free nucleotides or cofactors.

The kit may comprise components of any of the membranes disclosed above, such as an amphiphilic layer or a triblock copolymer membrane. The kit may further comprise a transmembrane pore. Any of the embodiments discussed above with reference to the method of the invention equally apply to the kits.

The kit may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify and/or express polynucleotides, a membrane as defined above or voltage or patch clamp apparatus. Reagents may be present in the kit in a dry state such that a fluid sample is used to resuspend the reagents. The kit may also, optionally, comprise instructions to enable the kit to be used in the method of the invention. The kit may comprise a magnet or an electromagnet. The kit may, optionally, comprise nucleotides.

The following Examples illustrate non-limiting aspects of the application.

EXAMPLES

Example 1

This Example shows that when double-stranded genomic DNA which has single-stranded leader sequences attached to the template and complement strands is contacted with a CsgG nanopore, the template and complement strands translocate through the nanopore sequentially but separately (the template is not joined to complement via a hairpin) under the control of a Dda helicase. An increased sequencing accuracy was observed in comparison to translocation of the same template/complement sequences when joined together by a hairpin.

Materials and Methods

Sample Preparation

Genomic DNA was fragmented as follows. 1 µg of genomic DNA, in 46 µl, was transferred to a Covaris g-TUBE. The g-TUBE was then spun for 1 minute, at room temperature, at the speed for the fragment size required in accordance with the manufacturer's protocol recommendations. The g-TUBE was then inverted and spun for a further 1 minute to collect the fragmented DNA. The fragmented DNA was transferred to a clean 1.5 ml Eppendorf DNA LoBind tube. The success of the fragmentation process was assessed by analyzing 1 µl of sample using an Agilent Bioanalyzer 12000 DNA chip, according to the manufacturer's protocol.

Recovered DNA was treated with NEB's FFPE repair kit, in a 62 µl volume according to the manufacturers protocol, and DNA purified using 1× Agencourt AMPure XP beads before eluting in 46 µl of nuclease free water.

The FFPE repaired DNA was then treated with NEB's Ultra II End-prep module, to add a 5' phosphate and a single dA-nucleotide to each end of the fragmented DNA. The reaction was carried out in a 60 µl volume using 45 µl of FFPE repaired DNA, according to the manufacture's protocol, before being purified using 1× Agencourt AMPure XP beads and eluting in 31 µl of nuclease free water. 1 µl of the recovered end-prepped DNA was quantified using a QuBit fluorimeter.

Figure 3A:
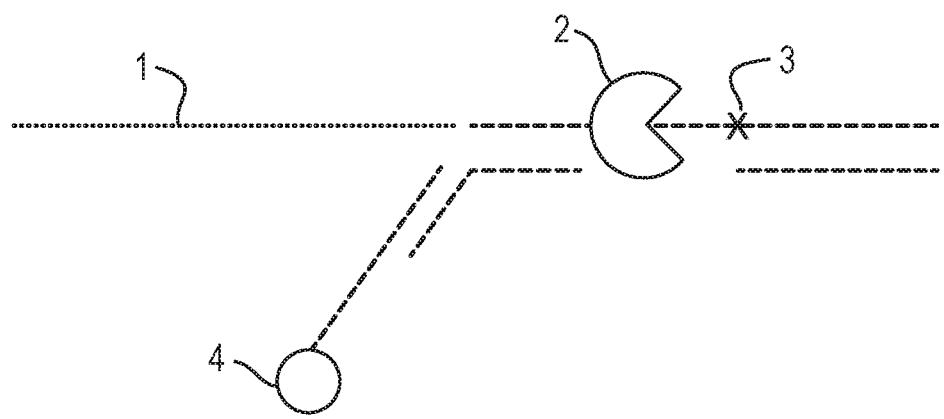
FIGS. 3A-3B illustrate the structure of an enzyme-loaded adaptor according to one embodiment described herein.

Next, 30 µl of end-prepped DNA was added to a clean 1.5 ml Eppendorf DNA LoBind tube. A solution containing adaptors as shown in FIG. 3A with a Dda helicase attached thereto (20 µl of Oxford Nanopore's SQK-LSK108 Adapter Mix which had a Dda helicase attached to each adapter as shown in FIG. 3A (component of the Ligation Sequencing Kit 1D (R9.4) commercially available from Oxford Nanopore Technologies) was then added (this volume of Adapter Mix was optimised for ~350 ng of DNA with a fragment size of greater or equal to 8 kb), followed by 50 µl of NEB's Blunt/TA Ligation Master Mix, before mixing by inversion 5×. The reaction was then left for 10 minutes at room temperature.

To purify the DNA, 40 µl of AMPure XP beads were added to the adapter ligation reaction from the previous step and mixed by 5× inversion. The tube was then incubated on a rotator mixer (Hula mixer) for 5 minutes at room temperature. The tube was then placed on a magnetic rack, and the beads allowed to pellet before the supernatant was removed by pipetting. The tube was removed from the rack before an adapter bead binding buffer (140 µl of Oxford Nanopore's SQK-LSK108 Adapter Bead Binding buffer (component of the Ligation Sequencing Kit 1D (R9.4) commercially available from Oxford Nanopore Technologies) was added. The beads were then resuspended by gentle flicking of the tube. After this the tube was then returned to the magnetic rack and the beads allowed to pellet before the supernatant was removed by pipetting. This step was repeated a second time. After the washing steps the tube was removed from the magnetic rack and the pellet resuspended in an elution buffer (25 µl of Oxford Nanopore's SQK-LSK108 Elution Buffer (component of the Ligation Sequencing Kit 1D (R9.4) commercially available from Oxford Nanopore Technologies). The tube was then incubated for 10 minutes at room temperature and returned to the magnetic rack to pellet the bead. The eluate was removed to a clean 1.5 ml Eppendorf DNA LoBind tube.

Figure 3B:
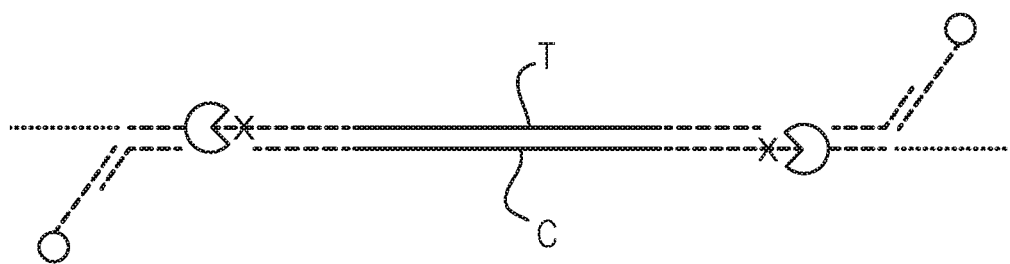

A sequencing reaction mix was then prepared to produce the genomic DNA construct depicted in FIG. 3B. The sequencing reaction mix was prepared by by adding 37.5 µl of RBF and 25.5 µl of LLB, both from Oxford Nanopore's SQK-LSK108 kit (component of the Ligation Sequencing Kit 1D (R9.4) commercially available from Oxford Nanopore Technologies), to 12.0 µl of recovered library.

In order to produce double-stranded genomic DNA with a hairpin joining the template to the complement (see schematic representation of construct in FIG. 1A), a similar procedure to that described above was followed. In the similar procedure, the Oxford Nanopore SQK-LSK102 Adapter Mix and SQK-LSK208 HP Adapter were used (components of the Ligation Sequencing Kit 2D (R9.4) commercially available from Oxford Nanopore Technologies) instead of the of the adapter mix mentioned above and all other steps and components used were the same as mentioned above.

Nanopore Sequencing

Electrical measurements were acquired using an Oxford Nanopore MinION R9.4 flowcell. Double-stranded genomic DNA (either with or without a hairpin joining the template to the complement) was added to the nanopore system. The experiment was run and helicase-controlled DNA movement monitored.

Analysis

Alignment of Events

Alignment of signals was carried out using the method disclosed in WO2016059427. An alignment value of 95% or greater was indicative of the respective events being indicative of the template and its respective complement Analysis of Aligned Signals Subsequent analysis of aligned signal was carried out using the 2D method as described above in order to determine a nucleotide sequence.

Results

Figure 1B:
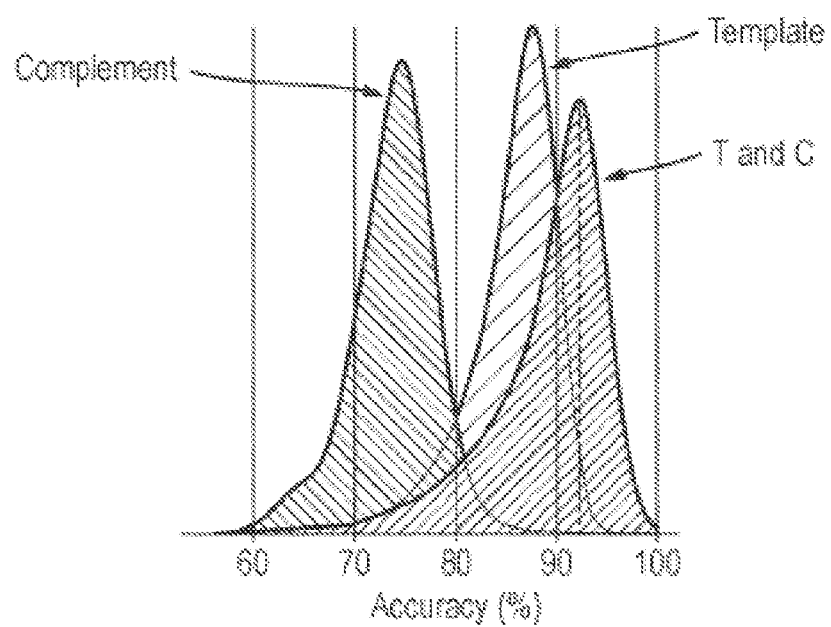
Figure 2A:
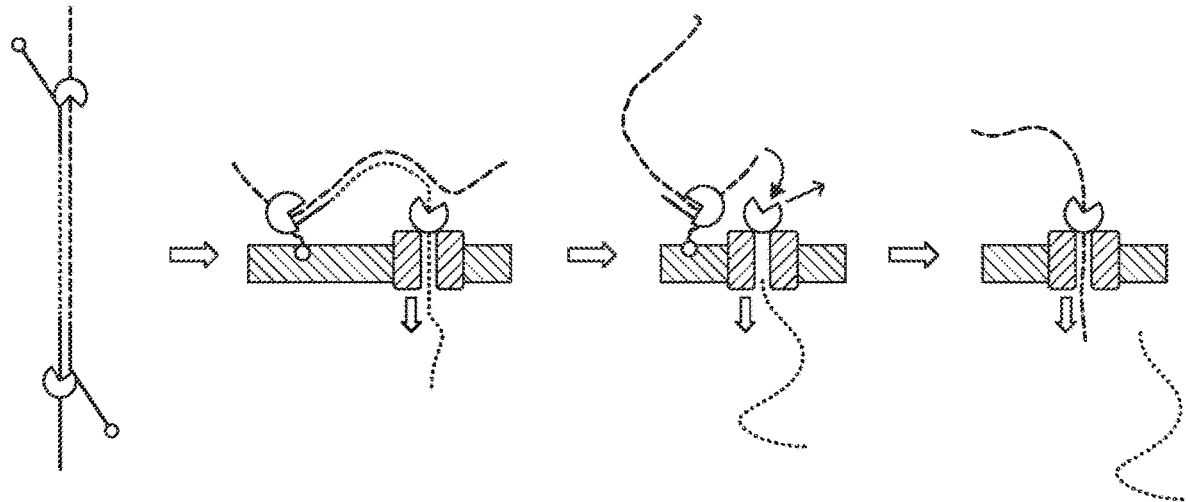
FIGS. 2A-2B illustrate a method of "follow-on" sequencing a double stranded polynucleotide (e.g., DNA) construct without the use of a hairpin according to one method disclosed herein. Both the template and complement polynucleotide (e.g., DNA) strands comprise an adaptor at each end, which adaptor comprises a leader sequence.
Figure 2B:
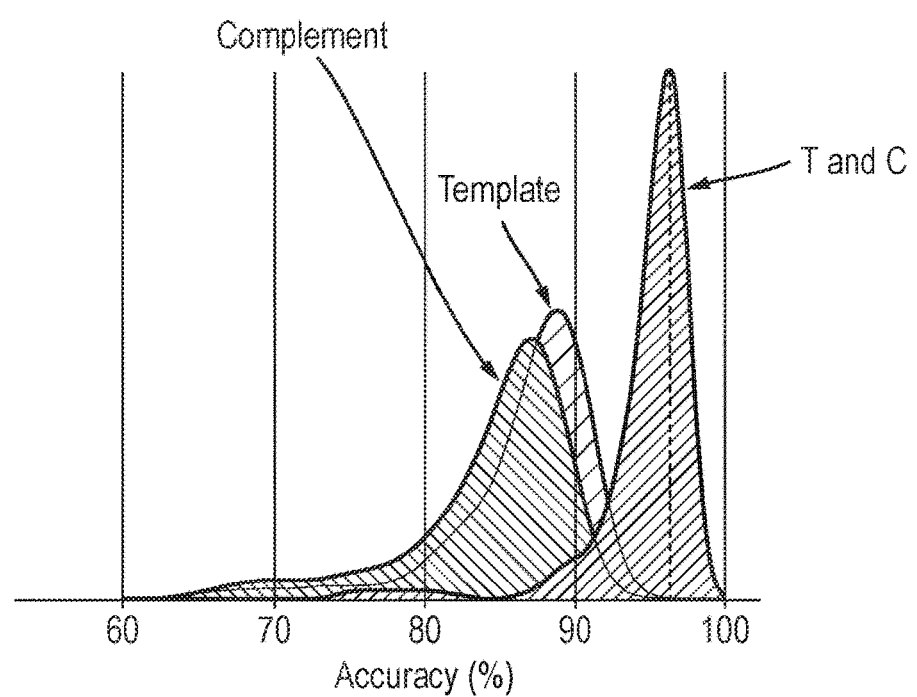

FIG. 1 includes a schematic illustration of a DNA construct which comprises template and complement DNA sequences attached to a Y-adapter and a hairpin translocating through a nanopore (FIG. 1A) under the control of an enzyme, and a graph showing the sequencing accuracy obtained (FIG. 1B). FIGS. 2A and 2B includes a cartoon representation of a DNA construct which comprises template and complement DNA sequences both attached to leader sequences translocating through a nanopore (FIG. 2A) under the control of an enzyme, and a graph showing the sequencing accuracy obtained (FIG. 2B). FIGS. 1B and 2B show peaks illustrating the sequencing accuracy using the template alone, the complement alone and the combined information from the template and complement. By comparing FIGS. 1B and 2B it can clearly be seen that the accuracy of the complement alone increased (from ~75% up to >85%) when the template and the complement were not joined via a hairpin loop, and that the accuracy when the information from the template and the complement was combined also increased when the template and complement were not joined.

Example 2 (Control: Modified Pore, No Binding Site Added to Analyte)

This example describes a method of characterizing a template (first strand captured) and complement (reverse complement of the first strand) of a double stranded polynucleotide when the template and complement are not covalently linked. Identification of the template and complement determined after data analysis as described below are referred in the Examples as "a follow-on pair." In some embodiments, a potential follow-on pair is identified when the pair have >80% overlap occurring within 1 min of each other. In some embodiments, a potential follow-on pair is identified when the follow-on pair occurs immediately, and has a 95-100% overlap.

Template only strands (i.e. those that were not classified as belonging to a follow-on pair) is referred herein to as 'T'. Template strands belonging to a follow-on pair are referred herein to as "$T_n$" and complement strands that belong to a follow-on pair are referred herein to as "$C_n$." "n" can be used to identify the $T_n$ and $C_n$ constituents of a follow-on pair e.g., $T_1$ and $C_1$ are a follow-on pair.

In this example, a control adapter containing a polynucleotide sequence which is not complementary to a pore tag (e.g., a capture polynucleotide) attached to a modified nanopore is used to illustrate the frequency of detecting follow-on pairs using a modified nanopore.

Exemplary Materials and Methods
Ligation of Control Adapter to Genomic DNA

Control Adapter is NB01 (Native Barcode 1) comprises a barcode top strand (SEQ ID NO: 1) and a barcode bottom strand (SEQ ID NO: 2).

```
                                           SEQ ID NO: 1
/5Phos/AAGGTTAACACAAAGACACCGACAACTTTCTTCAGCACCT SEQ ID NO: 2
/5Phos/GGTGCTGAAGAAAGTTGTCGGTGTCTTTGTGTTAACCTTAGC
AAT
```

The ligation of a control adaptor to genomic DNA was carried out following manufactures guidelines using Oxford Nanopore Technologies sequencing kit. 1000 ng of end-repaired and dA-tailed *E. coli* genomic DNA was ligated for 20 minutes at room temperature in 100 μL with 5.5 μL of 640 nM Control Adapter from above in 1× Blunt/TA master mix (NEB M0367L). SPRI purification of the sample was carried out as follows: 40 μL of Agencourt AMPure beads (Beckman Coulter) were added, the sample was mixed by pipette and was incubated for 5 mins at room temperature. 70% ethanol solution was prepared with nuclease free water (Ambion™) and Absolute Ethanol (FisherScientific) and this solution was stored on ice.

The beads were pelleted on a magnetic rack and the supernatant removed. The pelleted beads were washed with 500 μL of the 70% ethanol solution from above, without disturbing the pellet. The supernatant was removed and the pelleted beads were washed again with 500 μL of the 70% ethanol solution. The 70% ethanol solution was removed and the pellet pulsed briefly in a centrifuge before returning to the magnetic rack, the last remnants of 70% ethanol solution were then removed.

The pellet was re-suspended by pipette mixing in 50 μL of nuclease free water (Ambion™) and the sample was left to elute from the beads for 10 minutes on ice. The beads were pelleted and the supernatant containing the sample was removed to a fresh DNA LoBind tube (Eppendorf), this sample will be referred to as the control-adapter-genomic-DNA.

Ligation of Enzyme-Adapter Complex to Control-Adapter-Genomic-DNA

An aliquot of BAM (Barcode Adapter Mix) commercially available from Oxford Nanopore Technologies sequencing kit was thawed on ice. 20 μL of BAM was ligated for 10 minutes at room temperature in 100 μL with 50 μL of the control-adapter-genomic-DNA, 20 μL of NEBNext Quick Ligation Reaction buffer and 10 μL of Quick T4 DNA Ligase (E6056L). SPRI purification 2 was carried out as follows, 40 μL of Agencourt AMPure beads (Beckman Coulter) were then added, the sample was mixed by pipette and was incubated for 5 mins at room temperature. The beads were pelleted on a magnetic rack and the supernatant removed. The pelleted beads were washed with 140 L of an adapter bead binding buffer, the beads were re-suspended in the adaptor bead binding buffer by two successive 180° rotations of the Eppendorf tube on the magnetic rack. The beads were pelleted on a magnetic rack and the supernatant was removed. The pelleted beads were again washed with 140 μL of the buffer, the beads were re-suspended in the buffer by two successive 180° rotations of the Eppendorf tube on the magnetic rack. The beads were pelleted on a magnetic rack and the buffer was removed and the pellet was pulsed briefly in a centrifuge before returning to the magnetic rack, the last remnants of buffer were then removed.

The pellet was re-suspended by pipette mixing in 25 μL of nuclease free water (Ambion™) and this Library was left to elute from the beads for 10 minutes on ice.

Preparation of Tag-Modified Nanopore

Modified CsgG nanopores were prepared to allow conjugation of a pore tag. For example, a CsgG monomer was modified (e.g., by amino acid substitutions) such as a cysteine, a non-natural base, etc. is provided for conjugation of a pore tag. A modified CsgG monomer was prepared using PT7 vector containing the plasmid that encodes amino acid sequence SEQ ID NO: 7 with one or more amino acid substitutions as described herein.

```
SEQ ID NO: 7: amino acid sequence of wild-type
E.coli CsgG without signal sequence (Uniprot
accession number P0AEA2)
CLTAPPKEAARPTLMPRAQSYKDLTHLPAPTGKIFVSVYNIQDETGQFK

PYPASNFSTAVPQSATAMLVTALKDSRWFIPLERQGLQNLLNERKIIRA

AQENGTVAINNRIPLQSLTAANIMVEGSIIGYESNVKSGGVGARYFGIG

ADTQYQLDQIAVNLRVVNVSTGEILSSVNTSKTILSYEVQAGVFRFIDY

QRLLEGEVGYTSNEPVMLCLMSAIETGVIFLINDGIDRGLWDLQNKAER

QNDILVKYRHMSVPPES
```

The plasmid was transformed into BL21 derivative cell line, mutated to replace the endogenous CsgG gene with Kanamycin resistance. Cells were plated out on Agar plates containing Ampicillin (100 μg/ml) and Kanamycin (30 μg/ml) and incubated at 37° C. for 16 hours. A single colony was used to inoculate 100 ml of LB media containing Carbenecillin (100 μg/ml) and Kanamycin (30 μg/ml) and the starter culture was then grown at 37° C./250 rpm for 16 hours. 4×25 ml of the starter culture was used to inoculate 4×500 ml LB containing Carbenecillin (100 μg/ml), Kanamycin (30 μg/ml) 3 mM ATP, 15 mM MgSo4, and 0.5 mM Rhamnose. The culture was grown until the stationary phase was reached and then for an additional 2 hours at 37° C./250 rpm. Glucose was added to 0.2% and the temperature was reduced to 18° C., once cultures were at 18° C. protein expression was induced by the addition of 1% α-Lactose monohydrate. Cultures were incubated at 18° C./250 rpm for 16 hours.

Cells were harvested by centrifugation and subjected to detergent lysis (Bugbuster). Once lysed, the sample was carried forward for initial Strep purification (5 ml HP strep trap), eluted factions were heated to 60° C., spun and supernatant carried forward for qIEX purification (1 ml Hi trap Q HP). Fractions containing the correct protein were pooled, concentrated and carried forward for a final polish on 24 ml Superdex.

An aliquot of the nanopore, above, was modified with a morpholino oligo (SEQ ID NO: 8) as follows:

```
SEQ ID NO: 8: Morpholino oligo supplied by
GeneTools
/5'/-GGAACCTCTCTGACAA/-3'-Pyridyl-Dithio/
```

1.3 µL of 1M DTT (dithiothreitol) was added to 130 µL the nanopore from above which contained approximately 9.75 µg of nanopore, and was left to incubate for 1 hour at room temperature. This sample was buffer exchanged into Reaction Buffer (25 mM Tris, 150 mM NaCl, 2 mM EDTA, 0.1% SDS and 0.1% Brij58, pH 7) using a 0.5 mL 7 MWCO Zeba desalting column (Thermo Fisher Scientific) following the manufacturers guidelines. This sample was again buffer exchanged into Reaction Buffer using a 7 MWCO Zeba desalting column (Thermo Fisher Scientific) following the manufacturers guidelines. A 2 mM stock of Morpholino Oligo (SEQ ID NO: 8) was prepared by dissolving 300 nmol of morpholino oligo supplied by GeneTools in 150 µL of Nuclease free water (Ambion™). This was added to the buffer exchanged sample above to a final concentration of 500 M and left to incubate overnight at room temperature. This is known as modified nanopore.

Electrical Measurements

Electrical measurements were acquired from single modified nanopores inserted in block co-polymer in phosphate buffer (e.g., containing Potassium Ferrocyanide (II) and Potassium Ferricyanide (III), pH 8.0). After achieving a single modified nanopore inserted in the block co-polymer, any excess modified nanopores were removed by rinsing with 2 mL of buffer.

A priming buffer was flowed through the nanopore system. To prepare a sequencing mix, 400 nM Tether (SEQ ID NO: 9), the recovered bead purified Library and library loading beads were mixed in a buffer following the manufacturer's instructions. The sequencing mix was then added to the nanopore system. The experiment was run at −180 mV and helicase-controlled DNA movement monitored.

```
                                    SEQ ID NO: 9
/5Chol-TEG/TT/iSp18//iSp18//iSp18//iSp18/

TTGACCGCTCGCCTC
```

Data Analysis

As DNA strands passing through modified nanopores, changes in the current through the nanopore were measured and collected. The sequences of the strands were then determined using a basecall algorithm, e.g., recurrent neural network (RNN) algorithms, to yield fastq data. The fastq sequence data was subsequently aligned to the reference genome using a sequence alignment tool known in the art.

In order to identify pairs of strands which are mutually complementary (pairs of template and complement strands), the fractional overlaps between strands were calculated. The fractional overlap is defined as the length (in bases) of the contiguous section of bases in the genome that two strands share, normalised by the length (in bases) of the portion of the genome that the two strands straddle (without necessarily overlapping). The maximum fractional overlap for each strand was calculated as the maximum overlap between the strand and all others which passed through the pore within 1 minute of the strand (either before the strand or after it). A high maximum fractional thus indicates that a given strand belonged to a complementary pair (as either template or complement), while a low fractional overlap indicates that the strand did not belong to a complementary pair.

Table 2 shows percents of strands with different maximum fractional overlap values using an unmodified or modified nanopore as described herein

|  | Maximum Fractional Overlap | | | | |
| --- | --- | --- | --- | --- | --- |
|  | 0.0-0.02 | 0.02-0.8 | 0.8-0.9 | 0.9-0.98 | 0.98-1 |
| % Strands using unmodified pore as described in Example 5 | 98.4 | 0.8 | 0.0 | 0.0 | 0.8 |
| % Strands using a modified pore as described in Example 2 | 96.3 | 1.0 | 0.2 | 0.2 | 2.3 |
| % Strands with a modified pore and follow-on adaptor as described in Example 4 | 33.9 | 7.1 | 2.5 | 3.5 | 52.9 |

Results

A helicase, e.g., a Dda helicase such as one described in International PCT Publication No. WO2015/055981, the content of which is incorporated herein by reference in its entirety, was used to control the movement of the polynucleotide through the modified nanopore, e.g., a modified CsgG nanopore as described in International PCT Publication No. WO 2016/034591, the content of which is incorporated herein by reference in its entirety. Table 3 shows the data from Examples 2-5 as described herein. It lists the number of mapped strands (e.g., using the mapping method as known in the art), that were assigned to belong to T, $T_n$ and $C_n$ classifications as described in the data analysis section above. Row 2 of Table 3 below demonstrates the number of T, $T_n$ and $C_n$ strands assigned by the data analysis in the example using the control adapter from Example 2. 2.9% of strands have been classified as follow-on pairs.

In Example 5, where a non-modified nanopore was used, the frequency of follow-on pair was lower (Table 3, row 5), which was only 0.6%. This demonstrates that the use of a tag on a nanopore enhances follow-on events, even when the analyte does not contain the exact sequence. Without wishing to be bound by theory, this is probably because the pore-tag can bind at low efficiency to the exposed ssDNA of the complement (vs. at a defined site)

Example 3 (Modified Pore and Follow-on Adapter Embodiment 1)

This example describes a method of characterizing a template (first strand captured) and complement (reverse complement of the first strand) of a double stranded polynucleotide when the template and complement are not covalently linked. Identification of the template and complement determined after data analysis as described below are referred in the Examples as "a follow-on pair." In some embodiments, a potential follow-on pair is identified when the pair have >80% overlap occurring within 1 min of each other. In some embodiments, a potential follow-on pair is identified when the follow-on pair occurs immediately, and has a 95-100% overlap.

Template only strands (i.e. those that were not classified as belonging to a follow-on pair) is referred herein to as 'T'.

Template strands belonging to a follow-on pair are referred herein to as "$T_n$," and complement strands that belong to a follow-on pair are referred herein to as "$C_n$." "n" can be used to identify the $T_n$ and $C_n$ constituents of a follow-on pair e.g., $T_1$ and $C_1$ are a follow-on pair.

In this example, increased frequency of detecting follow-on pairs is achieved by ligation of a Follow-On Adapter according to one embodiment described herein. As shown in FIGS. 9-10, the adaptor contains a capture polynucleotide sequence within the duplex stem such that the capture polynucleotide sequence is revealed only upon unwinding of the strand. The capture polynucleotide sequence is complementary to a polynucleotide sequence attached to a modified nanopore. In this Example, the capture polynucleotide sequence does not contain spacers, e.g., sp18s, within the duplex stem and such an adaptor generated about 10% follow-on efficiency (i.e., follow-on % to about 10% of all strands).

Materials and Methods
Ligation of Follow-on Adapter to Genomic DNA

One embodiment of the Follow-On Adapter comprises a barcode top strand (SEQ ID NO: 3) and a barcode bottom strand (SEQ ID NO: 4) annealed together at 10 µM and 11 µM respectively in 50 mM HEPES pH 8, 100 mM potassium acetate from 95° C. to 22° C. at 2° C. per minute. The hybridised DNA was known as barcode adapter 2. 6.4 µL of Follow-On Adapter was added to 93.6 µL of 50 mM Tris-HCl pH7.5, 20 mM sodium chloride to make a 640 nM dilution of Follow-On Adapter 1.

SEQ ID NO: 3
/5Phos/GGCGTCTGCTTGGGTGTTTAACCTTTTTGTCAGAGAGGTTCC

AAGTCAGAGAGGTTCCT

SEQ ID NO: 4
/5Phos/GGAACCTCTCTGACTTGGAACCTCTCTGACAAAAAGGTTAAA

CACCCAAGCAGACGCCAGCAAT

The ligation of the follow-on adaptor to genomic DNA was carried out following manufactures guidelines using Oxford Nanopore Technologies sequencing kit. 1000 ng of end-repaired and dA-tailed *E. coli* genomic DNA was ligated for 20 minutes at room temperature in 100 µL with 5.5 µL of 640 nM of Follow-On Adapter from above in 1× Blunt/TA master mix (NEB M0367L). SPRI purification was then carried out as described in Example 2. This sample will be referred to as the follow-on-adapter-genomic-DNA.

Ligation of Enzyme-Adapter Complex to Follow-On-Adapter-Genomic-DNA

An aliquot of BAM (Barcode Adapter Mix) commercially available from Oxford Nanopore Technologies sequencing kit was thawed on ice. 20 µL of BAM was ligated for 10 minutes at room temperature in 100 µL with 50 µL of follow-on-adapter-genomic-DNA, 20 µL of NEBNext Quick Ligation Reaction buffer and 10 µL of Quick T4 DNA Ligase (E6056L). SPRI purification 2 was then carried out as described in Example 2.

Preparation of Tag-Modified Nanopore

The method to prepare a nanopore that is modified to include a polynucleotide sequence that is complementary to the capture polynucleotide sequence of the adaptor was carried out in a similar manner as described in Example 2 above.

Electrical Measurements

The method to measure and acquire electrical measurements as a strand pass through a nanopore was carried out in a similar manner as described in Example 2 above.

Data Analysis

Data processing and analysis of the collected electrical measurements were carried out in a similar manner as described in Example 2 above Results A helicase, e.g., a Dda helicase such as one described in the International PCT Publication No. WO2015/055981, the content of which is incorporated herein by reference in its entirety, was used to control the movement of the polynucleotide through the modified nanopore, e.g., a modified CsgG nanopore as described in the International PCT Publication No. WO 2016/034591, the content of which is incorporated herein by reference in its entirety. Row 3 of Table 3 demonstrates the number of T, $T_n$ and $C_n$ strands assigned by the data analysis in the example using the follow-on adapter as described in this Example. 7.7% of all strands have been classified as follow-on pairs.

Example 4 (Modified Pore and Follow-on Adapter Embodiment 2)

This example describes a method of characterizing a template (first strand captured) and complement (reverse complement of the first strand) of a double stranded polynucleotide when the template and complement are not covalently linked. Identification of the template and complement determined after data analysis as described below are referred in the Examples as "a follow-on pair." In some embodiments, a potential follow-on pair is identified when the pair have >80% overlap occurring within 1 min of each other. In some embodiments, a potential follow-on pair is identified when the follow-on pair occurs immediately, and has a 95-100% overlap.

Template only strands (i.e. those that were not classified as belonging to a follow-on pair) is referred herein to as 'T'. Template strands belonging to a follow-on pair are referred herein to as "$T_n$," and complement strands that belong to a follow-on pair are referred herein to as "$C_n$." "n" can be used to identify the $T_n$ and $C_n$ constituents of a follow-on pair e.g., $T_1$ and $C_1$ are a follow-on pair.

In this example, increased frequency of detecting follow-on pairs is achieved by ligation of Follow-On adapter according to one embodiment described herein. The adaptor contains a capture polynucleotide sequence within the duplex stem such that the capture polynucleotide sequence is revealed only upon unwinding of the strand. The capture polynucleotide sequence is complementary to a polynucleotide sequence attached to a modified nanopore. This adapter also contains a chemistry that enhances the capture efficiency of $C_n$. For example, in this Example, the capture polynucleotide sequence contains spacers, e.g., sp18s, within the duplex stem, and such an adaptor generated about 60% follow-on efficiency (i.e., follow-on % to ~60% of all strands). Without wishing to be bound by theory, this improvement could be due a to a number of reasons, e.g., because enzyme pauses briefly when encountering sp18s giving more time for coupling and thus enhancing the efficiency of hybridization of the capture polynucleotide sequence to the complementary sequence tag on the modified nanopore, and/or because sp18s give more flexibility for coupling geometry, and/or because added length of sp18s is better geometry and displays sequence nearer to a pore-tag (e.g., the orientation of the $C_1$ is altered such that the capture efficiency is improved, and/or T is occluded/stopped from being captured).

Materials and Methods

Ligation of Follow-on Adapter to Genomic DNA

One embodiment of the Follow-On Adapter comprises a barcode top strand (SEQ ID NO: 5) and a barcode bottom strand (SEQ ID NO: 6) annealed together at 10 µM and 11 µM respectively in 50 mM HEPES pH 8, 100 mM potassium acetate from 95° C. to 22° C. at 2° C. per minute. The hybridised DNA was known as barcode adapter 2. 6.4 µL of the Follow-On Adapter was added to 93.6 µL of 50 mM Tris-HCl pH7.5, 20 mM sodium chloride to make a 640 nM dilution of Follow-On Adapter 2.

SEQ ID NO: 5
/5Phos/GGCGTCTGCTTGGGTGTTTAACC/iSp18//iSp18// iSp18//iSp18/TTTTT<u>GTCAGAGAGGTTCCAAGTCAGAGAGGTTCCT</u>

SEQ ID NO: 6
/5Phos/GGAACCTCTCTGACTTGGAACCTCTCTGACAAAAA/iSp18// iSp18//iSp18//iSp18/GGTTAAACACCCAAGCAGACGCCAGCAAT

The ligation of the follow-on adaptor to genomic DNA was carried out following manufactures guidelines using Oxford Nanopore Technologies sequencing kit. 1000 ng of end-repaired and dA-tailed *E. coli* genomic DNA was ligated for 20 minutes at room temperature in 100 L with 5.5 µL of 640 nM of Follow-On Adapter from above in 1× Blunt/TA master mix (NEB M0367L). SPRI purification was then carried out as described in Example 2. This sample will be referred to as the follow-on-adapter-genomic-DNA.

Ligation of Enzyme-Adapter Complex to Follow-On-Adapter-Genomic-DNA

An aliquot of BAM (Barcode Adapter Mix) commercially available from Oxford Nanopore Technologies sequencing kit was thawed on ice. 20 µL of BAM was ligated for 10 minutes at room temperature in 100 µL with 50 µL of follow-on-adapter-genomic-DNA, 20 µL of NEBNext Quick Ligation Reaction buffer and 10 µL of Quick T4 DNA Ligase (E6056L). SPRI purification 2 was then carried out as described in Example 2.

Preparation of Tag-Modified Nanopore

The method to prepare a nanopore that is modified to include a polynucleotide sequence that is complementary to the capture polynucleotide sequence of the adaptor was carried out in a similar manner as described in Example 2 above.

Electrical Measurements

The method to measure and acquire electrical measurements as a strand pass through a nanopore was carried out in a similar manner as described in Example 2 above.

Data Analysis

Data processing and analysis of the collected electrical measurements were carried out in a similar manner as described in Example 2 above.

Results

A helicase, e.g., a Dda helicase such as one described in International PCT Publication No. WO2015/055981, the content of which is incorporated herein by reference in its entirety, was used to control the movement of the polynucleotide through the modified nanopore, e.g., a modified CsgG nanopore as described in International PCT Publication No. WO 2016/034591, the content of which is incorporated herein by reference in its entirety. Row 4 of Table 3 demonstrates the number of T, $T_n$ and $C_n$ strands assigned by the data analysis in the example using the follow-on adapter as described in this Example. 45.1% of strands have been classified as follow-on pairs.

FIGS. 11A-11B show a current trace from the experiment described in this Example. The T, $T_n$ and $C_n$ are labelled to correspond with the data shown in Table 4 below. The data shown in Table 4 below was obtained as described in the data analysis section, and is an example portion of the data summarized in Table 3 for Examples 2, 3 and 4.

Figure 12A:
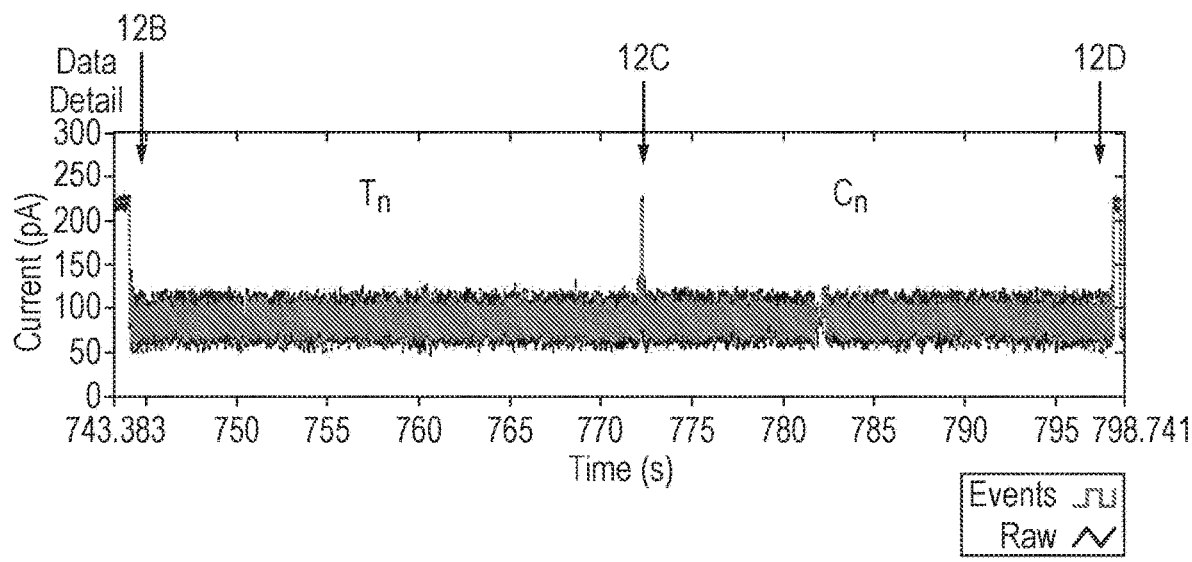
FIGS. 12A-12D show an example section of strand data acquired using one method disclosed herein. The strand data shows the current (pA) vs time (seconds) of electrical data of a single channel on a MinION chip.
Figure 12B:
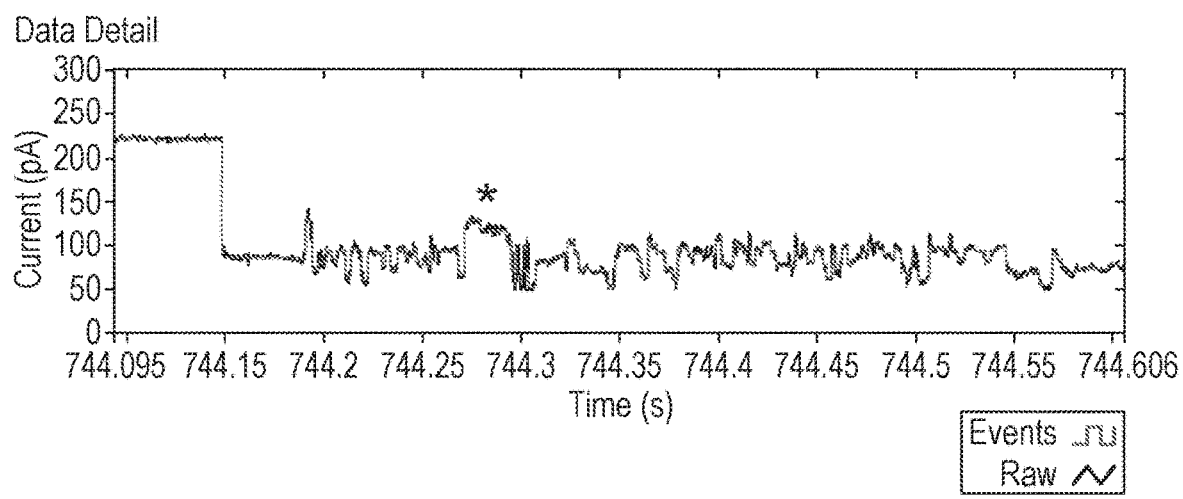
Figure 12C:
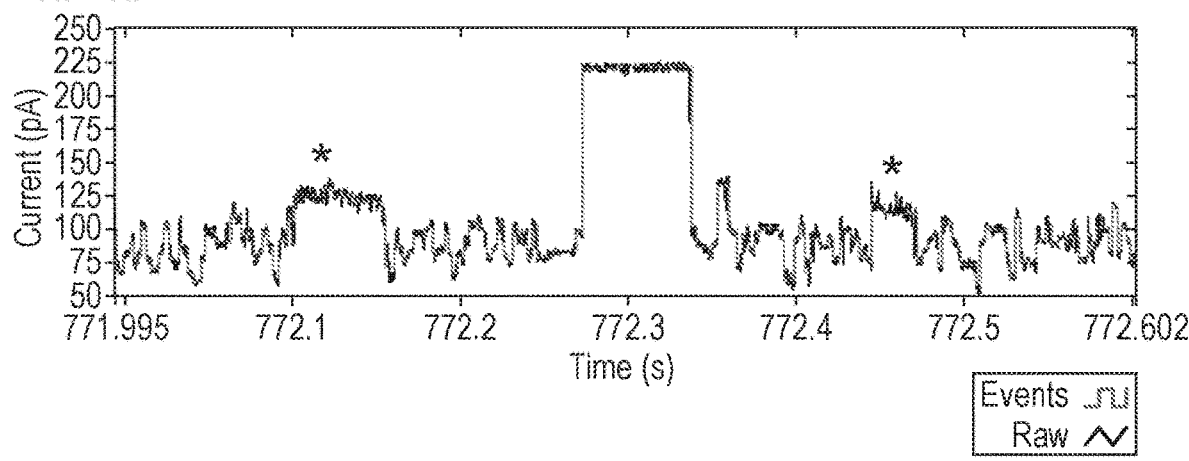
Figure 12D:
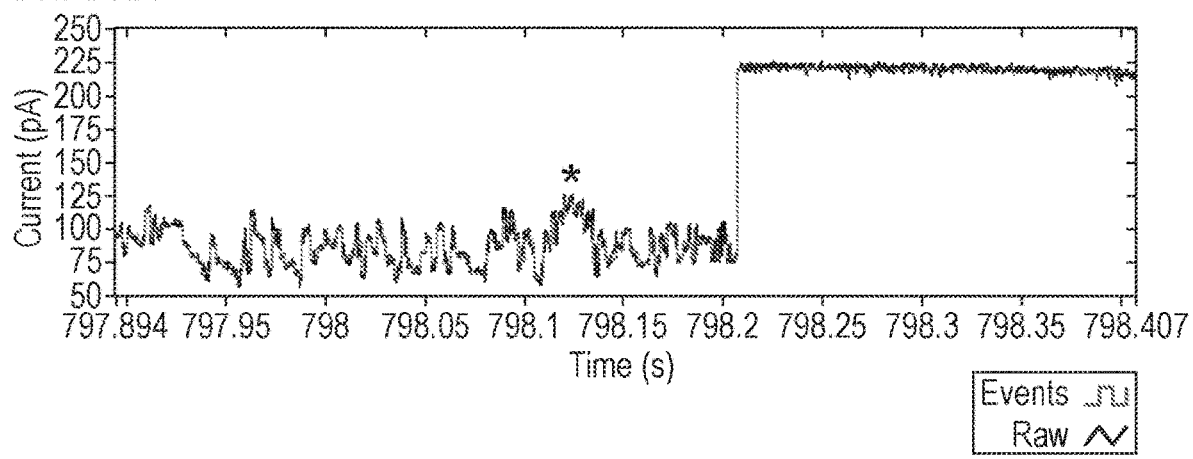
Figure 14:
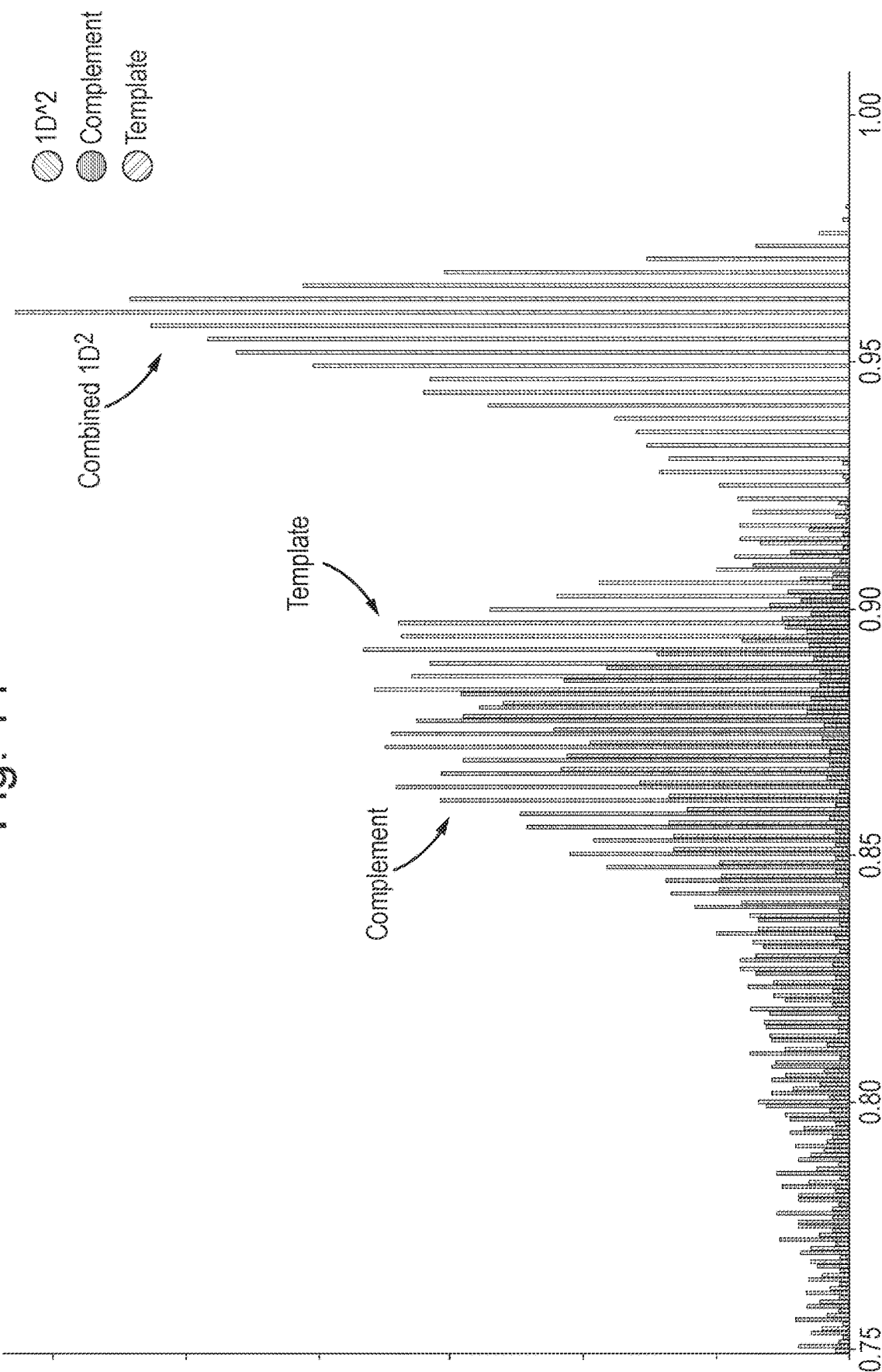
FIG. 14 shows the histograms of the distribution of basecall accuracies of the sequence information (randomly fragmented *E. coli*) obtained from translocation of the template, from translocation of the complement and when the sequence information obtained from translocation of the template and translocation of the complement was combined algorithmically. The sequence information were obtained using the method as illustrated in FIG. 10.

FIGS. 12A-12D show a current trace of the template ($T_n$) and complement ($C_n$) of a follow-on pair polynucleotide as it translocated through the modified nanopore. The nanopore returns to open pore in-between the template and complement being sequenced (see FIG. 12C) in FIG. 12A, illustrating the fact that the template and complement strands are not covalently joined.

SEQ ID NO: 10 and SEQ ID NO: 11 are the sequences derived from the Oxford Nanopore Technologies basecalling RNN algorithms of the polynucleotides from FIGS. 12A to 12D. These can be aligned with high fidelity to demonstrate that the template and complement from a randomly fragmented double stranded polynucleotide fragment were sequenced by the modified nanopore.

In FIGS. 12A-12D, the positions marked with * are the Sp18 spacers found in SEQ ID NO: 5 and SEQ ID NO: 6, the presence of this motif shows that the follow-on adapter as described in this Example was successfully ligated to the polynucleotide, and that the presence of this follow-on adapter greatly enhances the % of follow on pairs (as seen in Table 3).

FIG. 13 shows the "time between strands" in seconds on a logarithmic scale. The label "strand" is used to classify the electrical signal of helicase controlled movement of polynucleotide sequence through the nanopore. This is classified using methods known in the art. Strands are easily split by the return to open-pore. The arrow indicates a pronounced population within the data from Example 4, using the follow-on adapter as described in this Example. This population is indicative of the increased proportion of follow-on pairs, as the time between $T_n$ and $C_n$ is generally shorter than time between either T and T or T and $T_n$ or $C_n$ and T in Examples 2 and 4. This illustrates that follow-on adapter can also be used to increase throughput as time between strands is reduced.

Example 5

This example describes a method of characterizing a template (first strand captured) and complement (reverse complement of the first strand) of a double stranded polynucleotide when the template and complement are not covalently linked. Identification of the template and complement determined after data analysis as described below are referred in the Examples as "a follow-on pair." In some embodiments, a potential follow-on pair is identified when the pair have >80% overlap occurring within 1 min of each other. In some embodiments, a potential follow-on pair is identified when the follow-on pair occurs immediately, and has a 95-100% overlap.

Template only strands (i.e. those that were not classified as belonging to a follow-on pair) is referred herein to as 'T'. Template strands belonging to a follow-on pair are referred herein to as "$T_n$," and complement strands that belong to a follow-on pair are referred herein to as "$C_n$." "n" can be used to identify the $T_n$ and $C_n$ constituents of a follow-on pair e.g., $T_1$ and $C_1$ are a follow-on pair.

In this example, standard components from Oxford Nanopore Technologies sequencing kit were used with the Minion and Flowcell (SpotON Flow Cell comprising an array of nanopores that are not modified to include a pore tag as described herein), to demonstrate the frequency of detecting follow-on pairs in the absence of the modified nanopores and follow-on adapter as described herein.

Materials and Methods

Ligation of Control Adaptor to Genomic DNA

The ligation of the control adaptor (e.g., as described in Example 2) to genomic DNA was carried out following manufactures guidelines using Oxford Nanopore Technologies sequencing kit. 1000 ng of end-repaired and dA-tailed E. coli genomic DNA was ligated for 20 minutes at room temperature in 100 µL with 5.5 µL of 640 nM of Follow-On Adapter from above in 1× Blunt/TA master mix (NEB M0367L). SPRI purification was then carried out as described in Example 2. This sample will be referred to as the follow-on-adapter-genomic-DNA.

Ligation of Enzyme-Adapter Complex to Follow-On-Adapter-Genomic-DNA

An aliquot of BAM (Barcode Adapter Mix) commercially available from Oxford Nanopore Technologies sequencing kit was thawed on ice. 20 µL of BAM was ligated for 10 minutes at room temperature in 100 µL with 50 µL of control-adapter-genomic-DNA, 20 µL of NEBNext Quick Ligation Reaction buffer and 10 µL of Quick T4 DNA Ligase (E6056L). SPRI purification 2 was then carried out as described in Example 2.

Electrical Measurements

The method to measure and acquire electrical measurements as a strand pass through a nanopore was carried out in a similar manner as described in Example 2 above.

Data Analysis

Data processing and analysis of the collected electrical measurements were carried out in a similar manner as described in Example 2 above Results A helicase, e.g., a Dda helicase such as one described in the International PCT Publication No. WO2015/055981, the content of which is incorporated herein by reference in its entirety, was used to control the movement of the polynucleotide through the modified nanopore, e.g., a modified CsgG nanopore as described in International PCT Publication No. WO 2016/034591, the content of which is incorporated herein by reference in its entirety. Row 5 of Table 3 below demonstrates the number of T, $T_n$ and $C_n$ strands assigned by the data analysis in this example. 0.6% of all strands have been classified as follow-on pairs.

TABLE 3

|  | T (Template Only) | $T_n$ (Template) | $C_n$ (Complement) |
|---|---|---|---|
| Example 2 (Control) | 29835 | 448 | 448 |
| Example 3 (Follow-On Adapter 1) | 13179 | 546 | 546 |
| Example 4 (Follow-On Adapter 2) | 23623 | 9707 | 9707 |
| Example 5 | 426384 | 1301 | 1301 |

Table 3 shows the numbers of strands determined to be template only (not followed by its complement pair), template-n (the first strand of a follow-on pair) and complement-n (the reverse complement of a follow-on pair) for Examples 2-5 herein.

TABLE 4

| fast5 | Start/s | End/s | Duration/s | genome_start_pos | genome_end_pos |
|---|---|---|---|---|---|
| 90e5fe72_read_ch241_file335.fast5 | 15678.130 | 15710.975 | 32.846 | 4554265 | 4565926 |
| 90e5fe72_read_ch241_file336.fast5 | 15711.022 | 15739.518 | 28.497 | 4554266 | 4565390 |
| 90e5fe72_read_ch241_file337.fast5 | 15740.340 | 15750.546 | 10.206 | 2273577 | 2277115 |
| 90e5fe72_read_ch241_file338.fast5 | 15750.656 | 15760.139 | 9.483 | 2273617 | 2277156 |
| 90e5fe72_read_ch241_file339.fast5 | 15760.295 | 15780.086 | 19.791 | 919284 | 926128 |
| 90e5fe72_read_ch241_file340.fast5 | 15780.234 | 15796.935 | 16.702 | 919310 | 926054 |
| 90e5fe72_read_ch241_file341.fast5 | 15797.159 | 15824.821 | 27.662 | 1332188 | 1341764 |
| 90e5fe72_read_ch241_file342.fast5 | 15826.033 | 15845.976 | 19.944 | 4382073 | 4386574 |
| 90e5fe72_read_ch241_file343.fast5 | 15846.421 | 15865.318 | 18.897 | 3754934 | 3761744 |
| 90e5fe72_read_ch241_file344.fast5 | 15865.351 | 15881.103 | 15.752 | 3754952 | 3761745 |
| 90e5fe72_read_ch241_file345.fast5 | 15883.544 | 15893.891 | 10.347 | 1569939 | 1573232 |
| 90e5fe72_read_ch241_file346.fast5 | 15901.567 | 15912.124 | 10.557 | 3213966 | 3216413 |
| 90e5fe72_read_ch241_file347.fast5 | 15912.176 | 15921.117 | 8.941 | 3213966 | 3216419 |

| fast5 | Classification | Time between/s | Overlap ratio | overlap_bases |
|---|---|---|---|---|
| 90e5fe72_read_ch241_file335.fast5 | Template 1 | 0.047 | 0.954 | 11124 |
| 90e5fe72_read_ch241_file336.fast5 | Complement1 |  |  |  |
| 90e5fe72_read_ch241_file337.fast5 | Template2 | 0.110 | 0.977 | 3498 |
| 90e5fe72_read_ch241_file338.fast5 | Complement2 |  |  |  |
| 90e5fe72_read_ch241_file339.fast5 | Template3 | 0.148 | 0.985 | 6744 |
| 90e5fe72_read_ch241_file340.fast5 | Complement3 |  |  |  |
| 90e5fe72_read_ch241_file341.fast5 | Template-only | N/A | N/A | N/A |
| 90e5fe72_read_ch241_file342.fast5 | Template-only | N/A | N/A | N/A |
| 90e5fe72_read_ch241_file343.fast5 | Template4 | 0.033 | 0.997 | 6792 |
| 90e5fe72_read_ch241_file344.fast5 | Complement4 |  |  |  |
| 90e5fe72_read_ch241_file345.fast5 | Template-only | N/A | N/A | N/A |
| 90e5fe72_read_ch241_file346.fast5 | Template5 | 0.052 | 0.998 | 2447 |
| 90e5fe72_read_ch241_file347.fast5 | Complement5 |  |  |  |

Table 4 contains the analysis data for the strands shown in FIG. 11, from a single channel (channel 241) of a MinION follow-on run. The table contains columns of:

Fast5=unique filename of the strand, as saved to fast5 output during a MinION run Start=start time of the strand in seconds End=end time of the strand in seconds Duration=duration of strand in seconds Genome_start_pos=after aligning basecalled strand to *E. coli* reference, start location in genomic reference where the section of strand aligned.

Genome_end_pos=after aligning basecalled strand to *E. coli* reference, end location in genomic reference where the section of strand aligned.

Time_between =for pairs, the time between the strands in seconds

Overlap ratio=for pairs, the overlap ratio comparing the alignment overlap (between genome_start_pos and genome_end_pos for each pair)

Pairs are identified by the very short time between strands, and that they overlap when aligned to a reference.

Example 6

This example describes a method of increasing the number of sequenced DNA molecules when low concentrations of DNA are added to a sequencing device.

In this example, this is achieved by generation of a modified DNA-enzyme adapter, which contains a DNA sequence that is complementary to a polynucleotide sequence attached to a modified nanopore. Exemplary adaptors that were used in this Example are illustrated in FIGS. 32A-35.

Exemplary Materials and Methods

Adapter Preparation (Adapter Design A, e.g., as Illustrated in FIG. 32A) A top strand (SEQ ID NO: 12), blocker strand (SEQ ID NO: 13) and a bottom strand (SEQ ID NO: 14) were annealed at 10 μM, 11 μM and 11 μM respectively in 50 mM Hepes, 100 mM KOAc, pH8 (total volume 40 μL), by adjusting the temperature from 95° C. to 22° C. at 2° C. per minute. The annealed strands were mixed with 800 μL of 2.8 μM helicase (e.g., a Dda helicase including wild-type or a mutant thereof as known in the art) and incubated for 5 minutes at room temperature. 10 μL of 8.1 mM Tetramethylazodicarboxamide was added to the solution, and incubated for 35° C. for 1 hour. NaCl was added to result in a final concentration of 500 mM, MgCl2 was added to a final concentration of 10 mM, ATP was added to a final concentration of 1 mM, and the solution was incubated at room temperature for 30 minutes. The sample was purified by HPLC.

SEQ ID NO: 12
/5SpC3//iSpC3//iSpC3//iSpC3//iSpC3//iSpC3//iSpC3// iSpC3//iSpC3//iSpC3//iSpC3//iSpC3//iSpC3//iSpC3// iSpC3//iSpC3//iSpC3//iSpC3//iSpC3//iSpC3//iSpC3// iSpC3//iSpC3//iSpC3//iSpC3//iSpC3//iSpC3//iSpC3// iSpC3//iSpC3/GGCGTCTGCTTGGGTGTTTAACC TTTTTTTTTT/ iSp18/AATGTACTTCGTTCAGTTACGTATTGCT

SEQ ID NO: 13
/5BNA-G//iBNA-G//iBNA-T//iBNA-T//iBNA-A/

AACACCCAAGCAGACGCCTAAGTCAGAGAGGTTCC

SEQ ID NO: 14
/5Phos/GCAAT ACGTAACTGAACGAAGT/iBNA-A//iBNA-meC// iBNA-A//iBNA-T//iBNA-T/TTT GAGGCGAGCGGTCAA

Figure 34A:
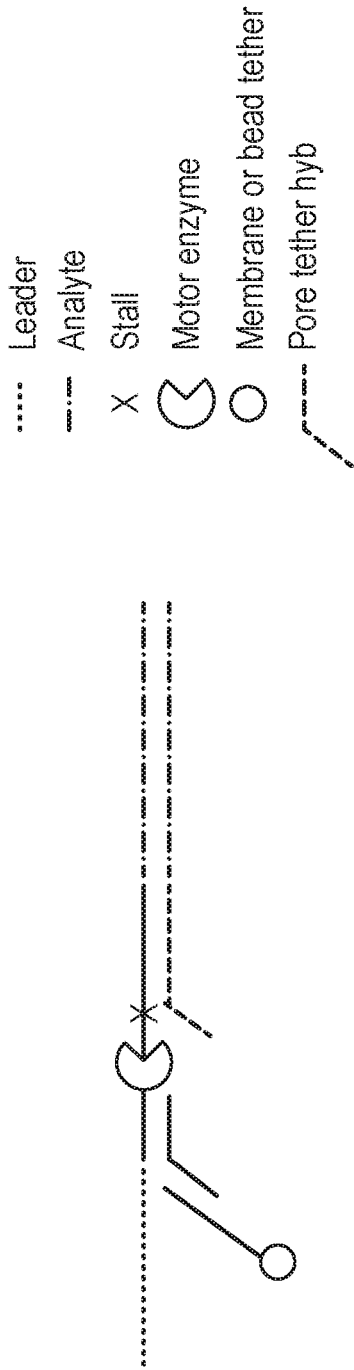
FIG. 34A shows a different embodiment of a Y adapter design, which includes two hybridization sites, one for the pore tether (red) and the other for the membrane or bead tether (blue). In this design the membrane tether is next to the leader sequence.
Figure 34B:
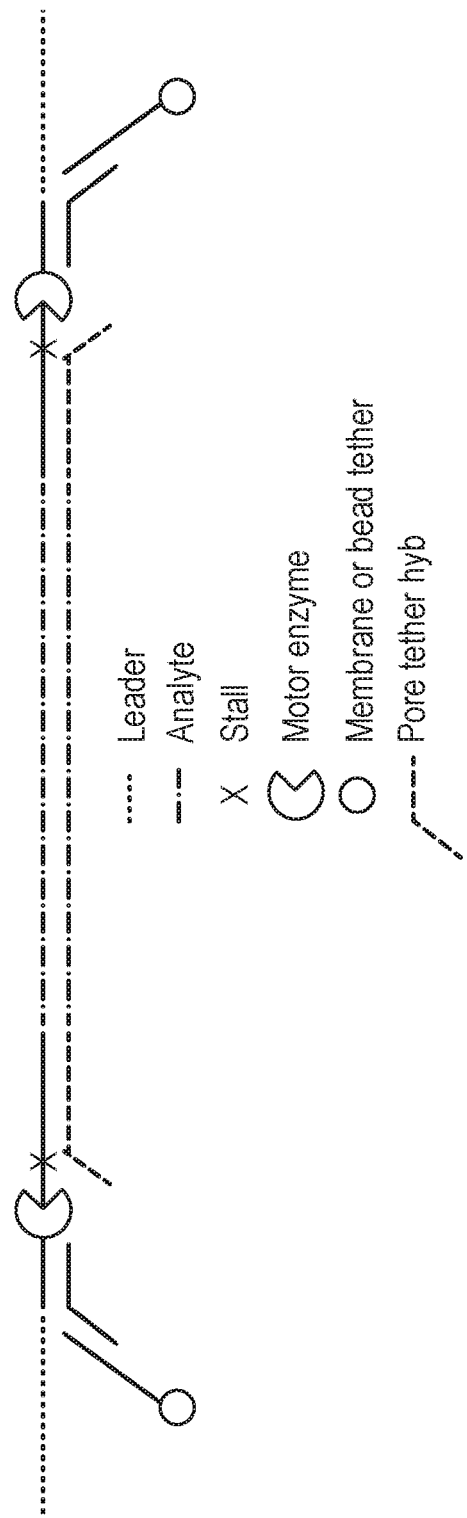
FIG. 34B shows the a ligated analyte, e.g., a double stranded polynucleotide, with a Y adapter on either end.
Figure 35:
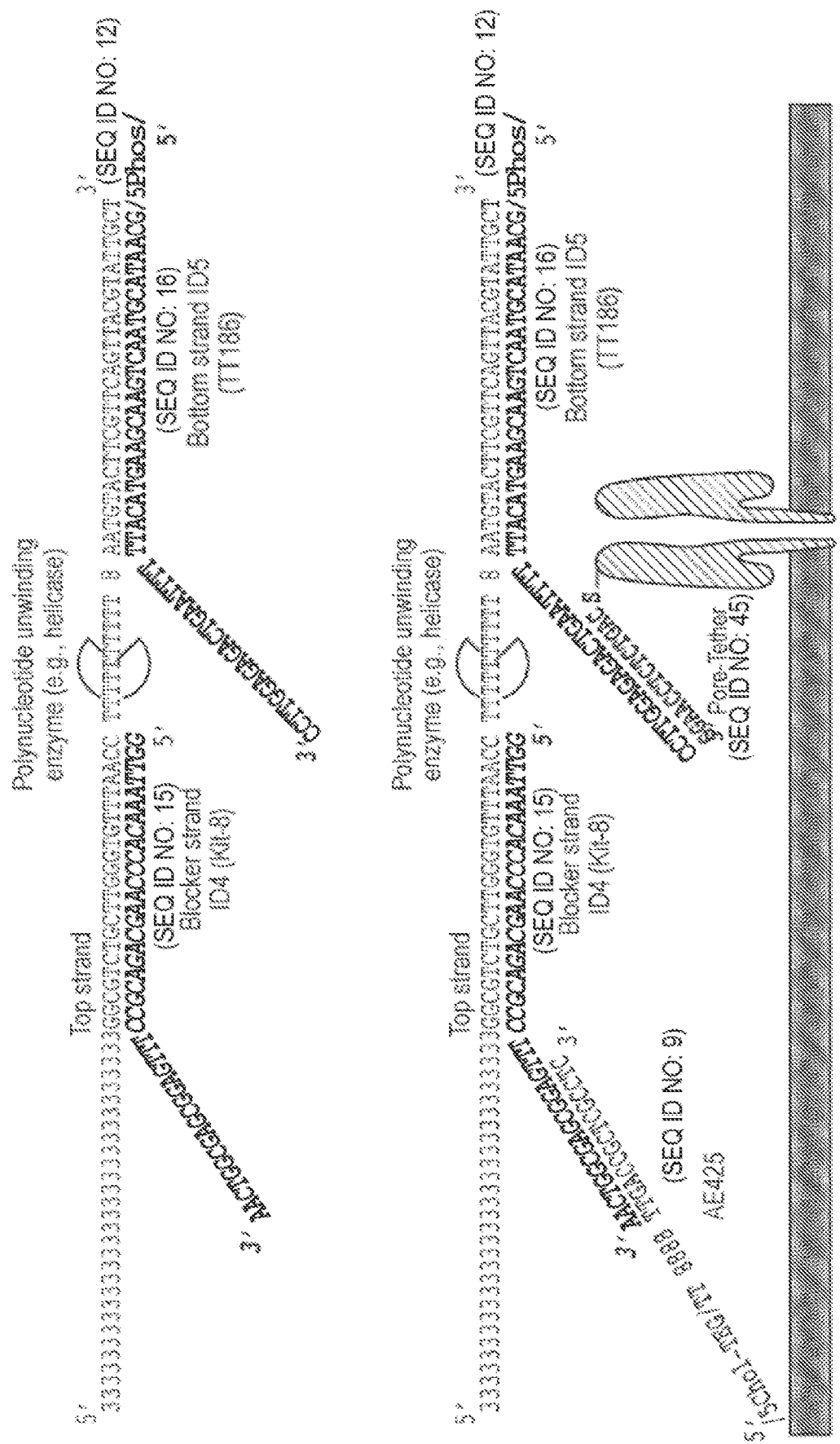
FIG. 35 is a schematic diagram showing example sequences of a Y adapter design illustrated in FIG. 34A.

Adapter Prep (Adapter Design B, e.g., as Illustrated in FIG. 34A)

A top strand (SEQ ID NO: 12), blocker strand (SEQ ID NO: 15) and a bottom strand (SEQ ID NO: 16) were annealed at 10 μM, 11 μM and 11 μM respectively in 50 mM Hepes, 100 mM KOAc, pH8 (total volume 40 μL), by adjusting the temperature from 95° C. to 22° C. at 2° C. per minute. The annealed strands were mixed with 800 μL of 2.8 μM helicase (e.g., a Dda helicase including wild-type or a mutant thereof as known in the art) and incubated for 5 minutes at room temperature. 10 μL of 8.1 mM Tetramethylazodicarboxamide was added to the solution, and incubate for 35° C. for 1 hour. NaCl was added to a final concentration of 500 mM, MgCl$_2$ was added to a final concentration of 10 mM, ATP was added to a final concentration of 1 mM, and the solution was incubated at room temperature for 30 minutes. The sample was purified by HPLC.

SEQ ID NO: 15
GGTTAAACACCCAAGCAGACGCC TTT GAGGCGAGCGGTCAA

SEQ ID NO: 16
/5Phos/GCAAT ACGTAACTGAACGAAGT/iBNA-A//iBNA-meC// iBNA-A//iBNA-T//iBNA-T/TTT TAAGTCAGAGAGGTTCC

Ligation Preparation

Adapter design A was buffer exchanged into 50 mM Tris, 20 mM NaCl, pH8 using 75 μL 7 k MWCO zeba spin columns, using 2 columns with 10 μL per column, and following the manufacturers protocol. The sample was diluted to 2.65 ng/μL, as measured using a Qubit® dsDNA HS Assay Kit. The following components were combined in a 1.5 mL DNA-low-bind tube (supplied by Eppendorf), mixed, and incubated for 10 minutes at room temperature: 11.3 μL adapter (in 50 mM Tris, 20 mM NaCl, pH8, 2.65 ng/μL), 8.7 μL 50 mM Tris, 20 mM NaCl, pH8, 0.9 μL 3.6 kb dA-tailed DNA (40 ng/μL; SEQ ID NO: 26)), 29.1 μL distilled water, and 50 μL TA ligase master mix (supplied by New England Biolabs (UK)).

40 μL of Agencourt AMPure beads (Beckman Coulter) were then added, the sample was mixed by pipette and was incubated for 5 mins at room temperature. The beads were pelleted on a magnetic rack and the supernatant removed. The pelleted beads were washed with 140 μL of an adaptor bead binding buffer, the beads were re-suspended in the the adaptor bead binding buffer by two successive 180° rotations of the Eppendorf tube on the magnetic rack. The beads were pelleted on a magnetic rack and the supernatant removed. The pelleted beads were again washed with 140 μL of the buffer, the beads were re-suspended in the buffer by two successive 180° rotations of the Eppendorf tube on the magnetic rack. The beads were pelleted on a magnetic rack and the buffer was removed and the pellet pulsed briefly in a centrifuge before returning to the magnetic rack, the last remnants of buffer were then removed.

The pellet was re-suspended by pipette mixing in 25 μL of an elution buffer containing Tether (SEQ ID NO: 9), and this Library was left to elute from the beads for 10 minutes on ice.

Pore Modification

Modified CsgG nanopores were prepared to allow conjugation of a pore tag. For example, a CsgG monomer was modified (e.g., by amino acid substitutions) such as a cysteine, a non-natural base, etc. is provided for conjugation of a pore tag. A modified CsgG monomer was prepared using PT7 vector containing the plasmid that encodes amino acid sequence SEQ ID NO: 7 with one or more amino acid substitutions as described herein. The plasmid was transformed into BL21 derivative cell line, mutated to replace the endogenous CsgG gene with Kanamycin resistance. Cells were plated out on Agar plates containing Ampicillin (100 μg/ml) and Kanamycin (30 μg/ml) and incubated at 37° C. for 16 hours. A single colony was used to inoculate 100 ml of LB media containing Carbenecillin (100 μg/ml) and Kanamycin (30 μg/ml) and the starter culture was then grown at 37° C./250 rpm for 16 hours. 4×25 ml of the starter culture was used to inoculate 4 ×500 ml LB containing Carbenecillin (100 μg/ml), Kanamycin (30 μg/ml) 3 mM ATP, 15 mM MgSo4, 0.5 mM Rhamnose. The culture was grown until the stationary phase was reached and then for an additional 2 hours at 37° C./250 rpm. Glucose was added to 0.2% and the temperature was reduced to 18° C., once cultures were at 18° C. protein expression was induced by the addition of 1% α-Lactose monohydrate. Cultures were incubated at 18° C./250 rpm for 16 hours.

Cells were harvested by centrifugation and subjected to detergent lysis (Bugbuster). Once lysed, the sample was carried forward for initial Strep purification (5 ml HP strep trap), eluted factions were heated to 60° C., spun and supernatant carried forward for qIEX purification (1 ml Hi trap Q HP). Fractions containing the correct protein were pooled, concentrated and carried forward for a final polish on 24 ml Superdex.

An aliquot of the Nanopore, above, was modified with a morpholino oligo (SEQ ID NO: 8) as follows. 1.3 μL of 1M DTT (dithiothreitol) was added to 130 μL the nanopore from above which contained approximately 9.75 μg of nanopore, and was left to incubate for 1 hour at room temperature. This sample was buffer exchanged into Reaction Buffer (25 mM Tris, 150 mM NaCl, 2 mM EDTA, 0.1% SDS and 0.1% Brij58, pH 7) using a 0.5 mL 7 MWCO Zeba desalting column (Thermo Fisher Scientific) following the manufacturers guidelines. This sample was again buffer exchanged into Reaction Buffer using a 7 MWCO Zeba desalting column (Thermo Fisher Scientific) following the manufacturers guidelines. A 2 mM stock of morpholino oligonucleotide (SEQ ID NO: 8) was prepared by dissolving 300 nmol of morpholino oligo supplied by GeneTools in 150 μL of Nuclease free water (Ambion™). This was added to the buffer exchanged sample above to a final concentration of 500 μM and left to incubate overnight at room temperature. This is known as modified Nanopore.

Electrical Measurements

Electrical measurements were acquired from single modified nanopores inserted in block co-polymer in buffer (25 mM K Phosphate buffer, 150 mM Potassium Ferrocyanide (II), 150 mM Potassium Ferricyanide (III), pH 8.0). After achieving a single modified nanopore inserted in the block co-polymer, 2 mL of buffer (25 mM K Phosphate buffer, 150 mM Potassium Ferrocyanide (II), and 150 mM Potassium Ferricyanide (III), pH 8.0) was flowed through the system to remove any excess modified nanopores.

A priming buffer was flowed through the nanopore system. To prepare a sequencing mix, a priming buffer, the library (as measured using a Qubit® dsDNA HS Assay Kit) and distilled water were mixed together. The sequencing mix was then added to the nanopore system.

Results

The helicase (e.g., Dda helicase including wild-type or a mutant thereof as known in the art) was used to control the movement of the polynucleotide through the modified nanopore. FIG. 38 shows current traces of polynucleotides as they are translocated through an unmodified nanopore, i.e. this is a system where there is no hybridization of oligonucleotides between the nanopore and the analyte. In this system, the time between strands is evenly distributed around 1 second (see FIG. 40).

FIG. 39 shows current traces of polynucleotides as they are translocated through a nanopore modified with SEQ ID NO: 8, i.e. this is a system that allows hybridization between the nanopore and the analyte. In this system, there are two populations of time between strands (a) evenly distributed around 1 second, and (b) rapid capture of an analyte (<0.1 sec) (see FIG. 40). This indicates that an analyte is hybridized to the pore whilst the pore is sequencing another strand.

Figure 40:
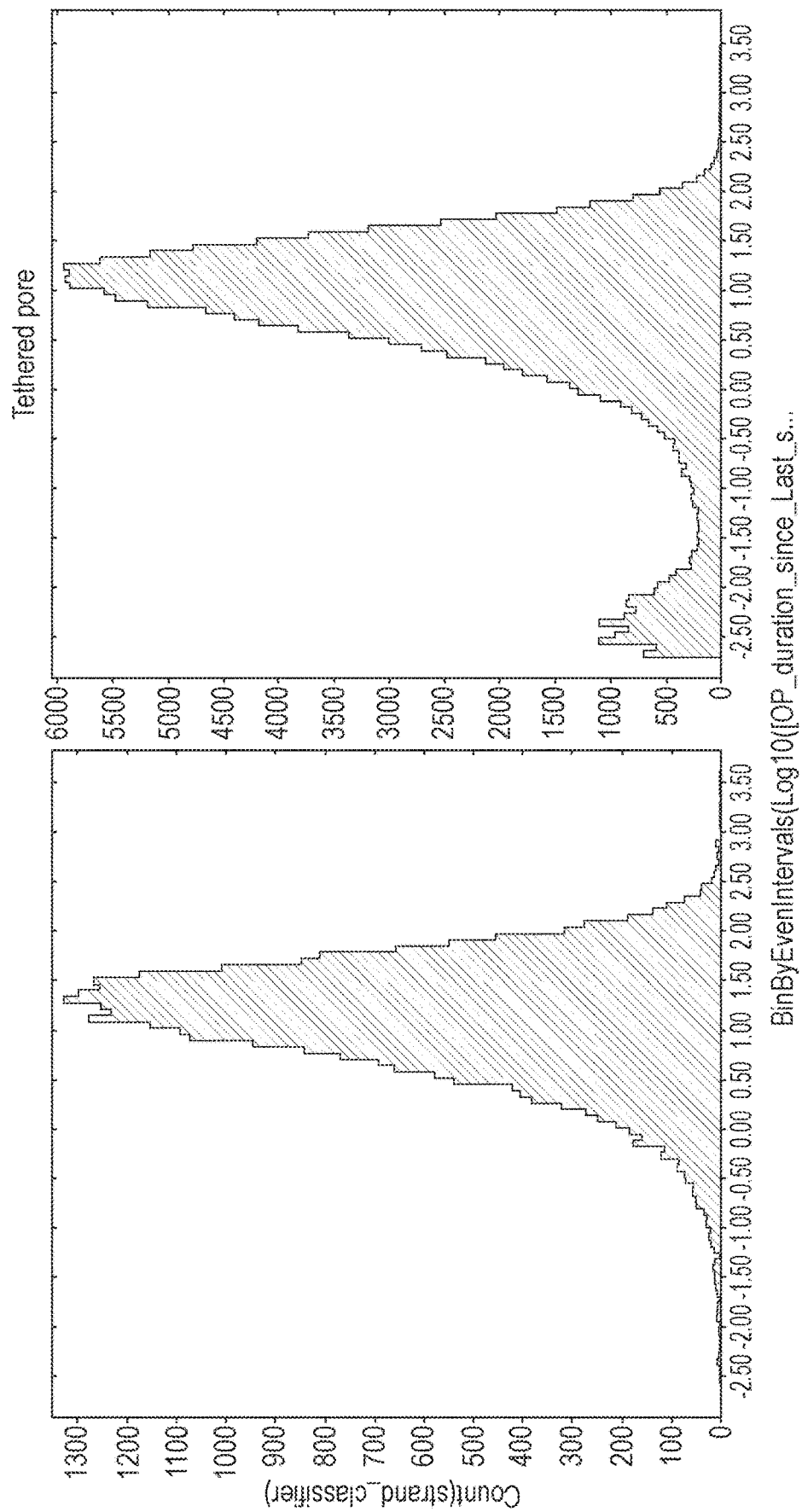
FIG. 40 shows histograms illustrating the time between sequential strands on a log scale. The left graph shows a nanopore (e.g., a CsgG pore) with a single distribution with time between strands greater than 1 second. The right graph shows the time between strands translocating through a tethered pore. This shows two populations, a fast capture population and with a time between strands under 0.1 seconds.
Figure 41:
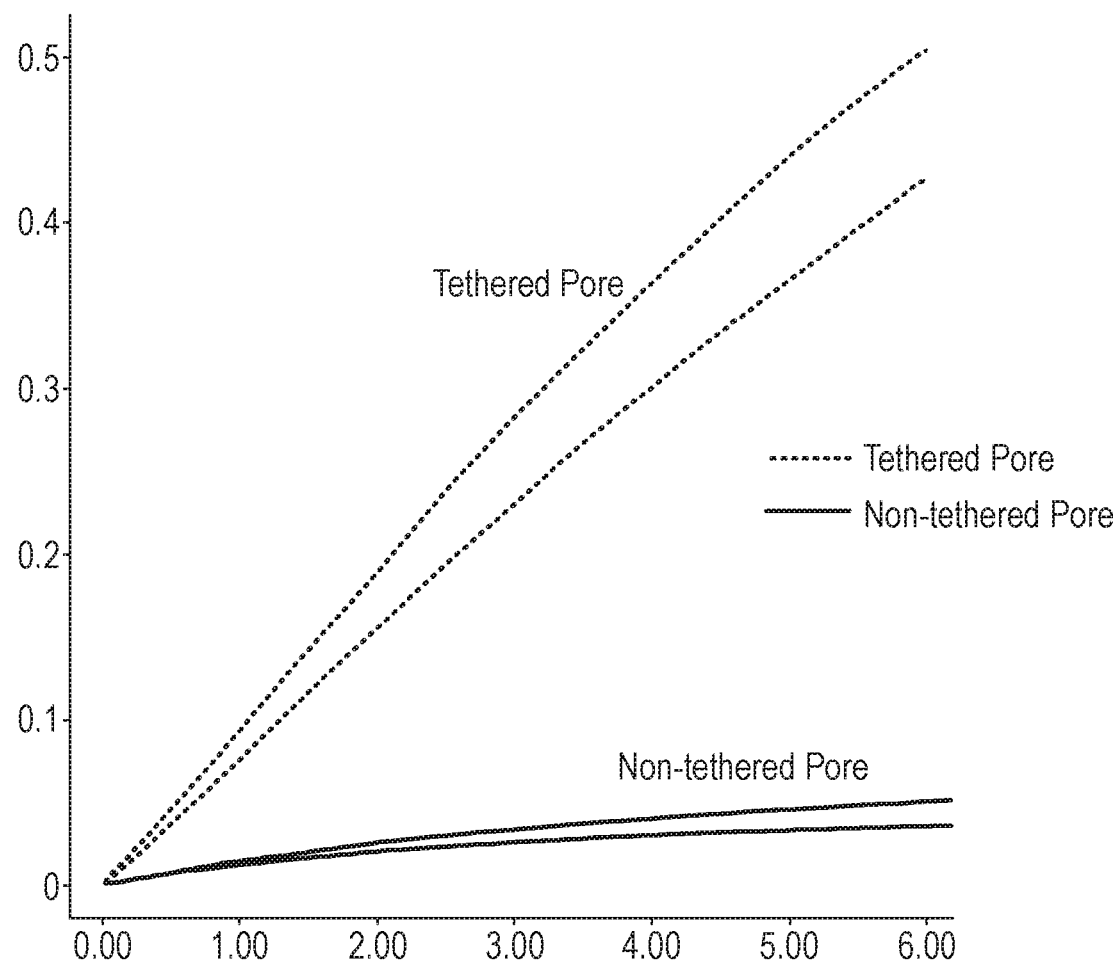
FIG. 41 depicts a graph showing the number of bases sequenced per chip over a 6 hour period from 20 ng input DNA. The red line represents the tethered pore and the blue line shows the non-tethered nanopore.

This difference between the two systems (no hybridization between pore and analyte, vs hybridization between pore and analyte) is summarized in FIG. 40, which shows a histogram of time-between-strands for the two systems. This demonstrates that in the absence of hybridization, only one capture type is observed, and when the analyte can hybridize to the pore, there is an additional capture type, where an analyte is rapidly captured (<0.1 second) after the previous analyte. This reduced time between strands increased the total number of strands sequenced FIG. 41.

Both ends of the analyte are able to tether to the pore.

Example 7

Below is an example protocol for modification of a nanopore (e.g., a CsgG nanopore) to have a pore tag attached to the external surface of the nanopore using pyridyl dithio morpholino Preparation of Tag-Modified Nanopore Modified nanopores (e.g., CsgG nanopores) were prepared to allow conjugation of a pore tag. For example, a CsgG monomer was modified (e.g., by amino acid substitutions) such as a cysteine, a non-natural base, etc. is provided for conjugation of a pore tag. A modified CsgG monomer was prepared using PT7 vector containing the plasmid that encodes amino acid sequence SEQ ID NO: 7 with one or more amino acid substitutions as described herein. The plasmid was transformed into BL21 derivative cell line, mutated to replace the endogenous CsgG gene with Kanamycin resistance. Cells were plated out on Agar plates containing Ampicillin (100 μg/ml) and Kanamycin (30 μg/ml) and incubated at 37° C. for 16 hours. A single colony was used to inoculate 100 ml of LB media containing Carbenecillin (100 μg/ml) and Kanamycin (30 μg/ml) and the starter culture was then grown at 37° C./250 rpm for 16 hours. 4×25 ml of the starter culture was used to inoculate 4×500 ml LB containing Carbenecillin (100 μg/ml), Kanamycin (30 μg/ml) 3 mM ATP, 15 mM MgSo4, and 0.5 mM Rhamnose. The culture was grown until the stationary phase was reached and then for an additional 2 hours at 37° C./250 rpm. Glucose was added to 0.2% and the temperature was reduced to 18° C., once cultures were at 18° C. protein expression was induced by the addition of 1% α-Lactose monohydrate. Cultures were incubated at 18° C./250 rpm for 16 hours.

Cells were harvested by centrifugation and subjected to detergent lysis (Bugbuster). Once lysed, the sample was carried forward for initial Strep purification (5 ml HP strep trap), eluted factions were heated to 60° C., spun and supernatant carried forward for qIEX purification (1 ml Hi trap Q HP). Fractions containing the correct protein were pooled, concentrated and carried forward for a final polish on 24 ml Superdex.

An aliquot of the nanopore, above, was modified with a pore tag such as morpholino oligo (e.g., as shown in SEQ ID NO: 8) as follows. 1.3 µL of 1M DTT (dithiothreitol) was added to 130 µL the nanopore from above which contained approximately 9.75 µg of nanopore, and was left to incubate for 1 hour at room temperature. This sample was buffer exchanged into Reaction Buffer (25 mM Tris, 150 mM NaCl, 2 mM EDTA, 0.1% SDS and 0.1% Brij58, pH 7) using a 0.5 mL 7 MWCO Zeba desalting column (Thermo Fisher Scientific) following the manufacturers guidelines. This sample was again buffer exchanged into Reaction Buffer using a 7 MWCO Zeba desalting column (Thermo Fisher Scientific) following the manufacturers guidelines. A 2 mM stock of pore tag such as morpholino oligonucleotide (e.g., as shown in SEQ ID NO: 8) was prepared in nuclease free water (Ambion™). This was added to the buffer exchanged sample above to a final concentration of 500 µM and left to incubate overnight at room temperature, resulting in modified nanopores.

Figure 27A:
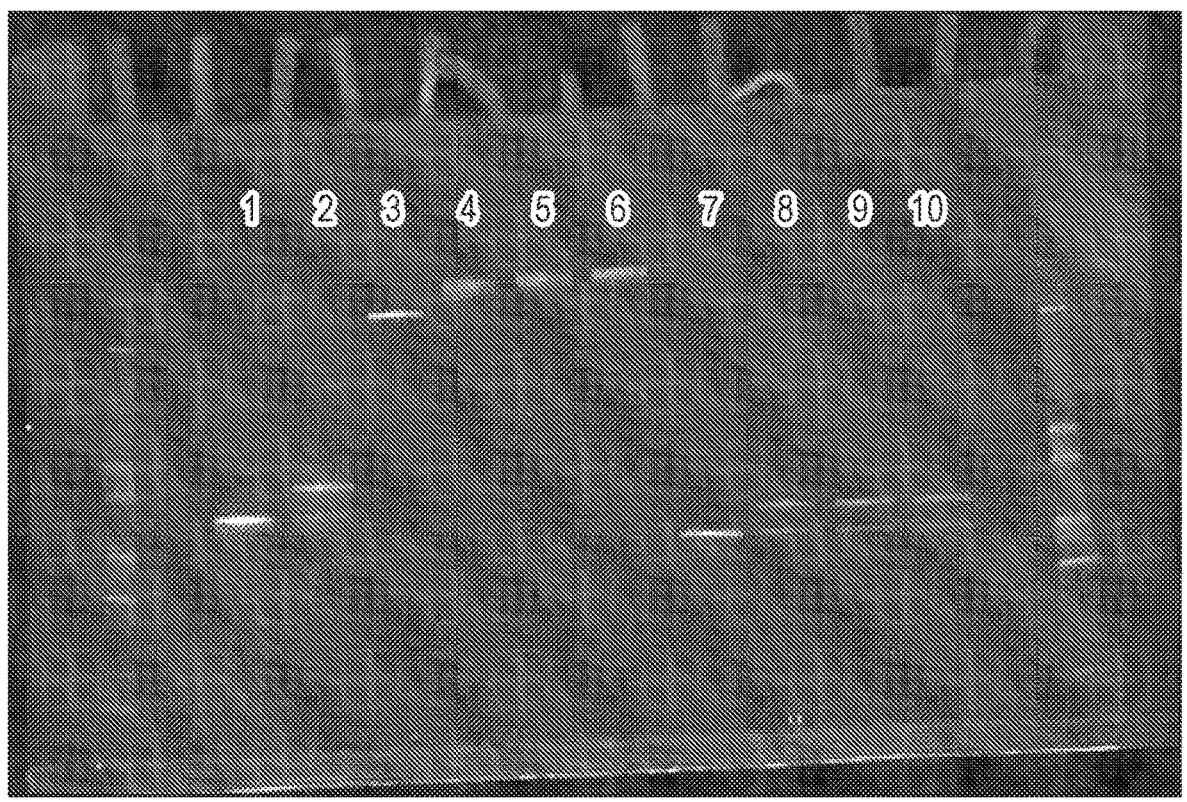
FIG. 27A shows a SYPRO Ruby Protein Gel showing monomers and oligomeric nanopores of CsgG modified with or without morpholino pore tags.

Analysis and Quality Control
SDS-PAGE—Protocol 2 uL of modified & unmodified nanopores were added to 8 uL reaction buffer. The sample was heated to 95° C. for 4 minutes in PCR block to breakdown samples from oligomer into monomer. 10 uL of 2× Laemmli Sample Buffer (65.8 mM Tris-HCL, pH 6.8, 26.3% (w/v) glycerol, 2.1% SDS, 0.01% bromophenol blue) was added to each sample. The samples were run on 4-20% TGX gel at 300 mV for 23 minutes and stained using SYPRO Ruby Protein Gel. The results of the gel are shown in FIG. 27A.

Figure 29:
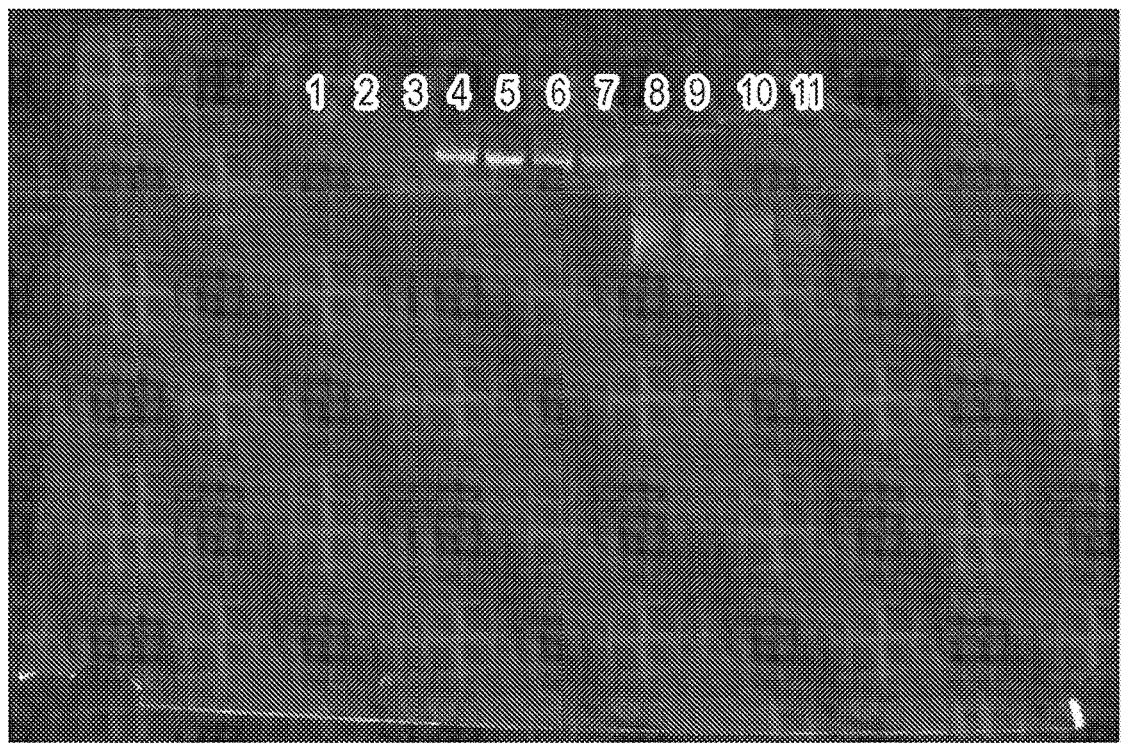
FIG. 29 shows a SYBR Gold Nucleic Acid Gel Stain showing hybridization of an analyte to pyridyl-dithio morpholino modified pore.
Figure 30:
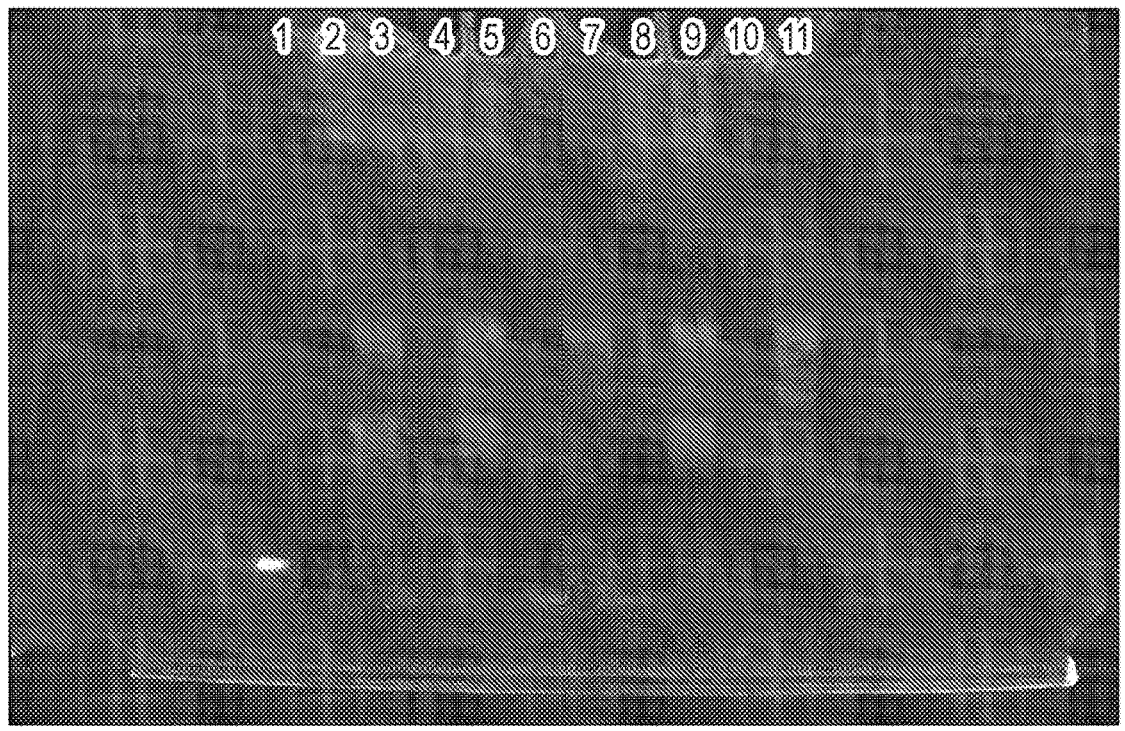
FIG. 30 shows a SYPRO Ruby Protein Gel showing hybridization of an analyte to pyridyl-dithio morpholino modified pore.
Figure 33:
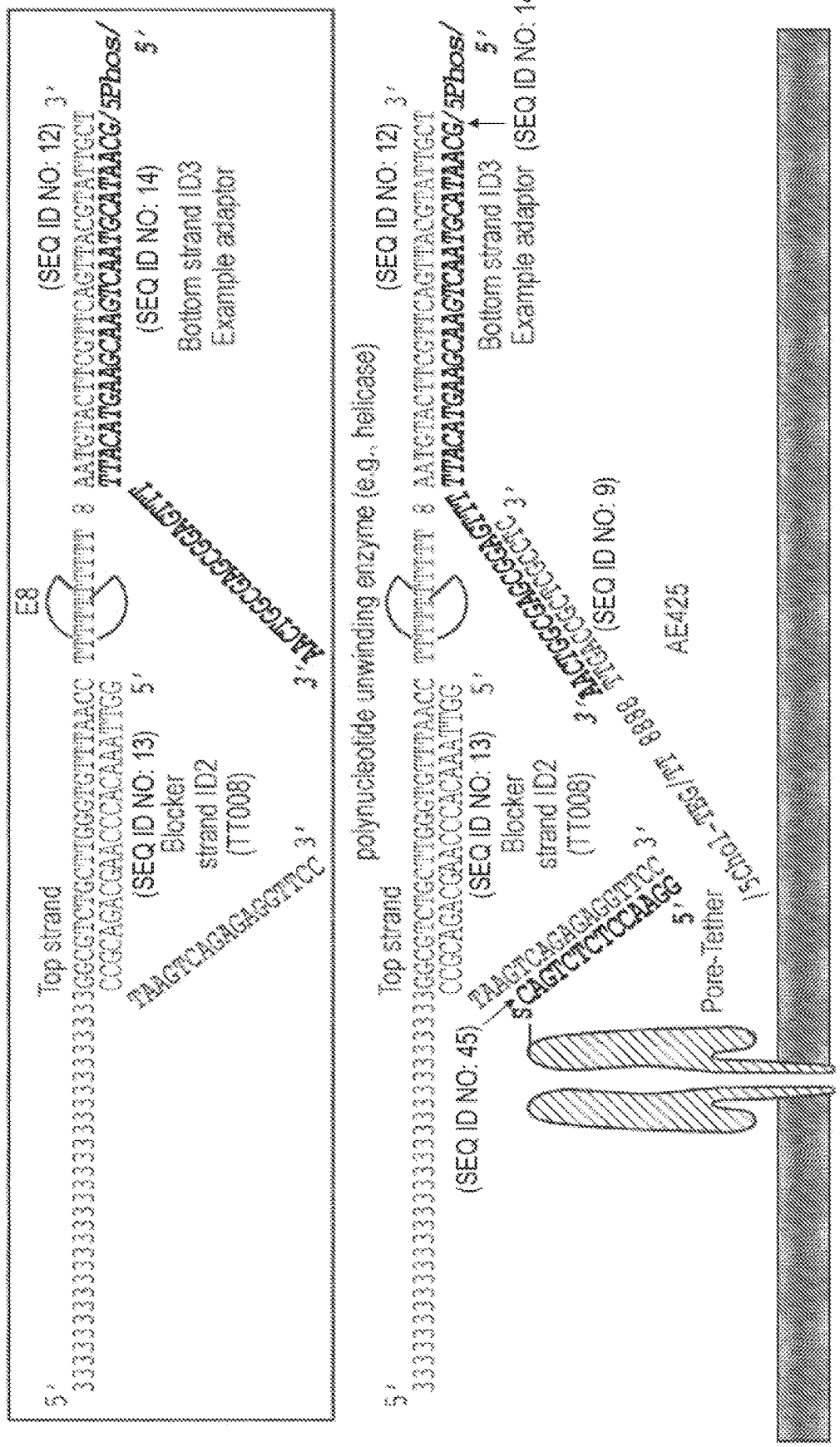
FIG. 33 is a schematic diagram showing example sequences of a Y adapter design illustrated in FIG. 32A.

Hybridization to Pyridyl-Dithio Morpholino Modified Pore—Protocol 10 uL modified nanopore had corresponding fluorescent hybridization sequences added at a 2× excess over the modified nanopore. The sample was made up to a total volume of 20 uL. Each sample was left at room temperature for 1 hour. 5 uL of 5× dyeless loading (50 mM Tris-HCl, pH 8.0, 25% glycerol, 5 mM EDTA) was added. The samples were run on 4-20% TBE gel at 160 mV for 80 mins. The gel was run on a gel scanner for Cy3 fluorescent, was stained using SYBR Gold Nucleic Acid Gel Stain, and was stained using SYPRO Ruby Protein Gel. The results of the gels are shown in FIGS. 28-30.

Example 7

This Example describes a method of characterising a concatenated polynucleotide where the method of attachment used to join the polynucleotides together is click chemistry. In this Example a template (first strand captured) and complement (reverse complement of the first strand) of a first double stranded polynucleotide are characterised using a nanopore when the template and complement are not covalently linked. As the template and complement are separated, a sequence complementary to a pore tether in a follow-on adapter ligated to the first double stranded poly-nucleotide is exposed in the complement and the complement binds to a pore tether attached to the nanopore. A concatenation adapter is also ligated to the first double stranded polynucleotide so that the complementary strand can be concatenated to a second double stranded polynucleotide.

Materials and Methods
Ligation of Follow-on Adapter to Genomic DNA

The Follow-On Adapter comprises a barcode top strand (SEQ ID NO: 17) and a barcode bottom strand (SEQ ID NO: 18) annealed together at 10 µM and 11 µM respectively in 50 mM HEPES pH 8, 100 mM potassium acetate from 95° C. to 22° C. at 2° C. per minute. The hybridised DNA was known as Follow-On Adapter. 6.4 µL of Follow-On Adapter was added to 93.6 µL of 50 mM Tris-HCl pH7.5, 20 mM sodium chloride to make a 640 nM dilution of Follow-On Adapter.

```
SEQ ID NO: 17: follow-on adapter top strand
/5Phos/TAACGAGGTTGTTTCTATCTCGGCGTCTGCTTGGGTGTTTAA CC/iSp18//iSp18//iSp18//iSp18/

TTTTTGTCAGAGAGGTTCCAAGTCAGAGAGGTTCCT

SEQ ID NO: 18: follow-on adapter bottom strand
/5Phos/GGAACCTCTCTGACTTGGAACCTCTCTGACAAAAA/ iSp18//iSp18//iSp18//iSp18/GGTTAAACACCCAAGCAGACGC

CGAGATAGAAACAACCCATCAGATTGTGTTTGTTAGTCGCT/iSp18// iSp18//iSp18//iSp 18/AGCGACTAACAAACACAATCTGATG/

DBCO/
```

The ligation of the follow-on adaptor to genomic DNA was carried out following manufacturer's guidelines using Oxford Nanopore Technologies sequencing kit. 1000 ng of end-repaired and dA-tailed E. coli genomic DNA was ligated for 20 minutes at room temperature in 100 L with 5.5 µL of 640 nM of Follow-On Adapter from above in 1× Blunt/TA master mix (NEB M0367L). SPRI purification of the sample was carried out as described in Example 2. This sample will be referred to as the follow-on-adapter-genomic-DNA.

Ligation of Concatenation Enzyme-Adapter Complex to Follow-On-Adapter-Genomic-DNA A leader strand (SEQ ID NO: 19), a blocker strand (SEQ ID NO: 20) and a bottom strand (SEQ ID NO: 21) were annealed at 5.5 uM, 6 uM and 6 uM respectively in 50 mM HEPES pH 8, 100 mM potassium acetate from 95° C. to 22° C. at 2° C. per minute. The hybridised DNA was known as concatenation enzyme-adapter complex.

```
SEQ ID NO: 19: Concatenation sequencing adapter
top strand
/Azide/GGTTGTTTCTATCTC/iSpC3//iSpC3//iSpC3// iSpC3//iSpC3//iSpC3//iSpC3//iSpC3//iSpC3// iSpC3//iSpC3//iSpC3//iSpC3//iSpC3//iSpC3/

GGCGTCTGCTTGGGTGTTTAACCTTTTTTTTTT/iSp18/

AATGTACTTCGTTCAGTTACGT
```

-continued

SEQ ID NO: 20: Concatenation sequencing adapter
blocker strand
GGTTAAACACCCAAGCAGACGCCTTTGAGGCGAGCGGTCAA SEQ ID NO: 21: Concatenation sequencing adapter
bottom strand
/5Phos/TCGTTAACGTAACTGAACGAAGT/iBNA-A//iBNAmeC//iBNA-A//iBNA-T//iBNA-T/

An aliquot of T4 Dda-(E94C/F98W/C109A/C136A/ A360C) (SEQ ID NO: 51 with mutations E94C/F98W/ C109A/C136A/A360C and then (ΔM1)G1G2 (where (ΔM1) G1G2=deletion of M1 and then addition G1 and G2) was thawed on ice before 50 µl was buffer exchanged into 50 mM HEPES pH 8, 100 mM potassium acetate, 2 mM EDTA through a 0.5 ml Zeba column, according to the manufacturer's instructions. The recovered protein was quantified using the A280 nm value and adjusted to 0.25 mg ml-1 using the same buffer.

27 µl of buffer exchanged protein was mixed with 3 µl of concatenation enzyme-adapter complex in a DNA low bind eppendorf and left to incubate for 10 mins at 35° C. 0.37 µl of 8.1 mM TMAD was then added and the sample was left to incubate for 60 mins at 35° C. 30 µl of 50 mM HEPES pH 8, 1 M NaCl, 2 mM MgCl2, 2 mM rATP was then added and left for a further 20 mins at room temperature.

222 µl of Agencourt AMPure beads (Beckman Coulter) were added and the sample incubated for 5 mins at room temperature on a rotator. The beads were pelleted on a magnetic rack and the supernatant removed. While still on the magnetic rack the beads were washed with 500 µl of 50 mM Tris pH 7.5, 2.5 M NaCl, 20% PEG 8,000, turning through 360o to bathe the pellet on the rack. The wash buffer was removed and the pellet pulsed briefly in a centrifuge before returning to the magnetic rack to remove the last remnants of solution. The pellet was resuspended in 30 µl of 50 mM Tris pH 7.5, 20 mM NaCl for 5 mins at room temperature before being placed on a magnetic rack to recover the purified adapter which was known as preloaded concatenation enzyme-adapter complex.

20 µL of preloaded concatenation enzyme-adapter complex was ligated for 10 minutes at room temperature in 100 µL with 50 µL of the follow-on-adapter-genomic-DNA, 20 PL of NEBNext Quick Ligation Reaction buffer and 10 µL of Quick T4 DNA Ligase (E6056L). SPRI purification was carried out as follows, 40 µL of Agencourt AMPure beads (Beckman Coulter) were then added, the sample was mixed by pipette and was incubated for 5 mins at room temperature. The beads were pelleted on a magnetic rack and the supernatant removed. The pelleted beads were washed with 140 µL of an adapter bead binding buffer, the beads were re-suspended in the adaptor bead binding buffer by two successive 180° rotations of the Eppendorf tube on the magnetic rack. The beads were pelleted on a magnetic rack and the supernatant was removed. The pelleted beads were again washed with 140 µL of the buffer, the beads were re-suspended in the buffer by two successive 180° rotations of the Eppendorf tube on the magnetic rack. The beads were pelleted on a magnetic rack and the buffer was removed and the pellet was pulsed briefly in a centrifuge before returning to the magnetic rack, the last remnants of buffer were then removed.

The pellet was re-suspended by pipette mixing in 25 µL of nuclease free water (Ambion™) and this Library was left to elute from the beads for 10 minutes on ice.

Preparation of Tag-Modified Nanopore

The method to prepare a nanopore that is modified to include a polynucleotide sequence that is complementary to the capture polynucleotide sequence of the adaptor was carried out in a similar manner as described in Example 2 above.

Electrical Measurements

The method to measure and acquire electrical measurements as a strand pass through a nanopore was carried out in a similar manner as described in Example 2 above.

Data Analysis

As DNA strands passing through modified nanopores, changes in the current through the nanopore were measured and collected. The sequences of the strands were then determined using a basecall algorithm, e.g., recurrent neural network (RNN) algorithms, to yield fastq data. The fastq sequence data was subsequently aligned to the reference genome using a sequence alignment tool known in the art.

Example 8

This Example describes a method of characterising and concatenating double stranded target polynucleotides, where the method of attachment is non-covalent. The complement strand of the first double stranded target polynucleotide recruits a second double stranded target polynucleotide and brings it into a local concentration to the pore. In turn, as the first complement strand is sequenced the recruited second double stranded target polynucleotide becomes dehybridised from the complement strand and instead hybridises to a pore tether, in a similar manner to that which occurs in the Example 2. This enables the first and second (and subsequent, third, fourth, fifth, etc, etc,) double stranded target polynucleotides to follow one another through the pore with minimal time between strands. This is especially useful when the concentration of double strand target polynucleotides is low as the second target polynucleotide can be recruited while the first is being sequenced.

The analyte is prepared in the same manner as described in Example 7, but using SEQ ID NOs: 5, 6, 22, 15 and 23, rather than SEQ ID NOs: 17-21. All other procedures, reagents and conditions are the same as described in Example 7.

SEQ ID NO: 5: Follow-on adapter top strand
/5Phos/GGCGTCTGCTTGGGTGTTTAACC/iSp18//iSp18// iSp18//iSp18/TTTTTGTCAGAGAGGTTCCAAGTCAGAGAGGTTCCT

SEQ ID NO: 6: Follow-on adapter bottom strand
/5Phos/GGAACCTCTCTGACTTGGAACCTCTCTGACAAAAA/ iSp18//iSp18//iSp18//iSp18/GGTTAAACACCCAAGCAGACGC

CAGCAAT

SEQ ID NO: 22: Fishing adapter top strand
/5SpC3//iSpC3//iSpC3//iSpC3//iSpC3//iSpC3// iSpC3//iSpC3//iSpC3//iSpC3//iSpC3//iSpC3// iSpC3//iSpC3//iSpC3/TTGTCAGAGAGGTTCC/iSpC3// iSpC3//iSpC3//iSpC3//iSpC3//iSpC3//iSpC3// iSpC3//iSpC3//iSpC3//iSpC3//iSpC3//iSpC3// iSpC3//iSpC3/GGCGTCTGCTTGGGTGTTTAACCTTTTTTTTTT// iSp18/AATGTACTTCGTTCAGTTACGT

-continued

SEQ ID NO: 15: Fishing adapter blocker strand
GGTTAAACACCCAAGCAGACGCCTTTGAGGCGAGCGGTCAA SEQ ID NO: 23: Fishing adapter bottom strand
/5Phos/ACGTAACTGAACGAAGT/iBNA-A//iBNA-meC// iBNA-A//iBNA-T//iBNA-T/

Example 9

This is another Example that describes a method of characterising and concatenating double stranded target polynucleotides, where the method of attachment is non-covalent. This method is carried out exactly as for Example 8 but uses a different tether to SEQ ID NO: 9. The two component fishing tether provides a second hybridisation site for the follow-on sequences and for the pore tether, to increase the proportion of events seen.

When forming the sequencing mix, SEQ ID NO: 9 is replaced with 400 nM of annealed SEQ ID NO: 24 and SEQ ID NO: 25. All other procedures, reagents and conditions are the same as described in Example 8.

SEQ ID NO: 24: Fishing tether top strand
TTGTCAGAGAGGTTCCTTTTTTTTTTTTTTTTTTTTTTTTTTTTT

TTTTTGGTTGTTTCTGTTGGTGCTGATATTGCTTTTTTGACCGCTCGCC

TC

SEQ ID NO: 25: Fishing tether bottom strand
GCAATATCAGCACCAACAGAAACAACCTT/iSp18//iSp18// iSp18//iSp18//iSp18//iSp18/TT/3CholTEG/

Example 10

This Example describes a method of characterising and concatenating many double stranded target polynucleotides, where the method of attachment is non-covalent. The complement strand of the first double stranded target polynucleotide recruits a many other double stranded target polynucleotides and concentrates them in the vicinity of the pore. This provides a higher local concentration around the pore than in the general bulk solution and so double stranded target polynucleotides follow one another through the open pore with minimal time between strands. This is especially useful when the concentration of double strand target polynucleotides is low. This Example is carried out as for Example 8. However, rather than annealing SEQ ID NO: 9 a tether consisting of an oligo coupled to a single stranded binding protein is used.

As the template strand of the first double strand target polynucleotide is sequenced the complement strand is released into solution as ssDNA. The single stranded binding proteins of the other double stranded target polynucleotides are able to bind to the ssDNA. As part of the follow-on process, as the complement strand is sequenced the 3' of the complement strand is drawn back towards the pore. The single stranded binding proteins on the ssDNA complement strand are displaced from the complement strand when they encounter the motor protein controlling movement of the complement through the pore and so are deposited around the pore increasing the local concentration.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

The invention claimed is:

1. A method of characterizing a polynucleotide, the method comprising:
   (i) combining in a solution:
      a) a construct comprising a double-stranded polynucleotide, having a template strand and a complement strand, wherein the template strand and the complement strand are not covalently linked, with
      b) a detector disposed in a membrane, wherein at least one tag that binds to the complement strand is conjugated to the detector; and
      c) a polymerase and nucleotides;
   (ii) processing the template strand using the polymerase to produce a product and by-products, the product comprising a third polynucleotide strand complementary to the template strand, wherein as the template strand of the double-stranded polynucleotide is processed, the complement strand becomes bound to the detector via the at least one tag conjugated to the detector; and
   (iii) detecting the by-products through addition of each nucleotide to the third polynucleotide strand by the polymerase.

2. A method according to claim 1, wherein after processing of the template strand by the polymerase, the complement strand of the construct is processed by a polymerase and the by-products of the processing of the complement strand are detected by the detector.

3. A method according to claim 1, further comprising identifying a nucleotide sequence of the template strand based on the detecting in (iii).

4. A method according to claim 1, wherein each type of nucleotide in the solution is distinguishably labelled according to the type of nucleotide.

5. A method according to claim 4, wherein each type of nucleotide in the solution is distinguishably labelled with optical labels and/or polymer tags.

6. A method according to claim 1, wherein the by-products of the processing in (ii) are sequentially released as nucleotides are sequentially added by the polymerase to the polynucleotide strand.

7. A method according to claim 6, wherein the by-products of the processing step are labelled phosphate species.

8. A method according claim 1, wherein the detector is selected from (i) a zero-mode waveguide, (ii) a field-effect transistor; (iii) an AFM tip; (iv) a nanotube; and (v) a nanopore.

9. A method according to claim 1, wherein an adapter is attached to one or both of the two ends of the double-stranded polynucleotide prior to processing of the construct by the polymerase.

10. A method according to claim 1, wherein the detector is a nanopore and the polymerase is provided within the lumen of the nanopore.

11. A method according to claim 1, wherein the detector is a nanopore and the at least one tag that binds to the complement strand is conjugated to an outer rim of the nanopore.

12. A method according to claim 1, wherein processing of the template strand by the polymerase reveals a portion of the complement strand for hybridization with the tag.

13. A method according to claim 1, wherein an adapter comprising a duplex stem and a first single strand extending from the duplex stem is attached to at least one end of the double-stranded polynucleotide such that the first single strand of the adaptor is contiguous with the complement strand.

14. A method according to claim 1, wherein the detector is a nanopore, wherein step (ii) comprises applying a potential difference across the nanopore so as to permit the by-products of the processing reaction to enter the nanopore;

and the potential difference is maintained across the nanopore for a sufficient period of time so as to permit translocation of at least a portion of the by-products of the processing reaction through the nanopore.

15. The method according to claim 1, further comprising
determining a sequence of the template strand based on changes measured in a property indicative of the by-products of the processing of the template strand by the polymerase,
determining a sequence of the complement strand based on changes measured in a property indicative of the by-products of the processing of the complement strand by a polymerase, and
comparing the sequence of the template strand with the sequence of the complement strand to establish a sequence of the polynucleotide.

16. A method according to claim 1, wherein detecting the by-products of the processing involves measuring a property indicative of the by-products of the processing; and
wherein the polynucleotide is characterized based on a measured property of the by-products of the processing.

17. A method according to claim 16, wherein the detector is a nanopore and the solution is ionic and the measured property is ion current flow through the nanopore and the polynucleotide is characterized based on the change in ionic current flow through the nanopore measured as the by-products of the processing translocate through the nanopore.

* * * * *